US012751973B2

(12) United States Patent
Yao et al.

(10) Patent No.: US 12,751,973 B2
(45) **Date of Patent: *Oct. 6, 2026**

(54) BISPECIFIC CHIMERIC ANTIGEN RECEPTORS TARGETING CD20 AND BCMA

(71) Applicant: ABELZETA INC., Rockville, MD (US)

(72) Inventors: Yihong Yao, Rockville, MD (US); Jiaqi Huang, Rockville, MD (US); Shigui Zhu, Rockville, ME (US); Xin Yao, Rockville, MD (US); Xiaobing Luo, Rockville, MD (US); Yutian Wei, Rockville, MD (US)

(73) Assignee: ABELZETA INC., Rockville, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/006,633

(22) Filed: Dec. 31, 2024

(65) Prior Publication Data

US 2025/0136707 A1 May 1, 2025

Related U.S. Application Data

(63) Continuation of application No. PCT/US2024/022317, filed on Mar. 29, 2024.

(60) Provisional application No. 63/509,371, filed on Jun. 21, 2023, provisional application No. 63/493,495, filed on Mar. 31, 2023.

(51) Int. Cl.

| | |
|---|---|
| ***A61K 35/17*** | (2025.01) |
| ***A61K 40/11*** | (2025.01) |
| ***A61K 40/15*** | (2025.01) |
| ***A61K 40/31*** | (2025.01) |
| ***A61K 40/42*** | (2025.01) |
| ***A61P 35/00*** | (2006.01) |
| ***A61P 37/02*** | (2006.01) |
| ***A61P 37/06*** | (2006.01) |
| ***C07K 16/28*** | (2006.01) |
| ***C12N 5/0783*** | (2010.01) |

(52) U.S. Cl.

CPC ............. *A61K 35/17* (2013.01); *A61K 40/11* (2025.01); *A61K 40/15* (2025.01); *A61K 40/31* (2025.01); *A61K 40/4202* (2025.01); *A61K 40/4215* (2025.01); *A61K 40/4221* (2025.01); *A61K 40/4224* (2025.01); *A61P 35/00* (2018.01); *A61P 37/02* (2018.01); *A61P 37/06* (2018.01); *C07K 16/2878* (2013.01); *C07K 16/2887* (2013.01); *C12N 5/0636* (2013.01); *A61K 2239/13* (2023.05); *A61K 2239/21* (2023.05); *A61K 2239/22* (2023.05); *A61K 2239/29* (2023.05); *C07K 2317/31* (2013.01); *C07K 2317/53* (2013.01); *C07K 2317/622* (2013.01); *C07K 2319/03* (2013.01); *C12N 2510/00* (2013.01)

(58) Field of Classification Search

None

See application file for complete search history.

(56) References Cited

U.S. PATENT DOCUMENTS

| | | | |
|---|---|---|---|
| 5,350,674 | A | 9/1994 | Boenisch et al. |
| 5,399,346 | A | 3/1995 | Anderson et al. |
| 5,580,859 | A | 12/1996 | Felgner et al. |
| 5,585,362 | A | 12/1996 | Wilson et al. |
| 5,589,466 | A | 12/1996 | Felgner et al. |
| 6,074,841 | A | 6/2000 | Gearing et al. |
| 6,326,193 | B1 | 12/2001 | Liu et al. |
| 6,410,319 | B1 | 6/2002 | Raubitschek et al. |
| 7,446,179 | B2 | 11/2008 | Jensen et al. |
| 7,462,352 | B2 | 12/2008 | Hansen et al. |
| 7,910,098 | B2 | 3/2011 | Fuh et al. |
| 8,287,864 | B2 | 10/2012 | Goldenberg et al. |
| 8,329,181 | B2 | 12/2012 | Martin et al. |
| 8,361,744 | B2 | 1/2013 | Marrichi et al. |
| 8,410,250 | B2 | 4/2013 | Ashkenazi et al. |
| 8,486,397 | B2 | 7/2013 | Bagri et al. |
| 8,529,902 | B2 | 9/2013 | Teeling et al. |
| 8,597,652 | B2 | 12/2013 | Fuh et al. |
| 8,735,098 | B2 | 5/2014 | Marrichi et al. |
| 8,778,340 | B2 | 7/2014 | Dupont et al. |
| 8,906,682 | B2 | 12/2014 | June et al. |
| 8,911,993 | B2 | 12/2014 | June et al. |
| 8,916,381 | B1 | 12/2014 | June et al. |

(Continued)

FOREIGN PATENT DOCUMENTS

| | | |
|---|---|---|
| CN | 101544694 A | 9/2009 |
| CN | 103562225 A | 2/2014 |

(Continued)

OTHER PUBLICATIONS

Nakagawa et al. "*Staphylococcus aureus* Virulent PSMa Peptides Induce Keratinocyte Alarmin Release to Orchestrate IL-17-Dependent Skin Inflammation", Cell Host & Microbe 2017; 22, 667-677. [16 pages].

(Continued)

*Primary Examiner* — Brad Duffy

(74) *Attorney, Agent, or Firm* — LEASON ELLIS LLP

(57) ABSTRACT

The present disclosure provides bispecific chimeric antigen receptors targeting CD20 and BCMA. The CAR may comprise an scFv targeting CD20 and an scFv targeting BCMA, a hinge region, a transmembrane domain, a co-stimulatory region, and a cytoplasmic signaling domain. The chimeric antigen receptors can be used to treat autoimmune disorders or cancer.

12 Claims, 22 Drawing Sheets

Specification includes a Sequence Listing.

(56) References Cited

U.S. PATENT DOCUMENTS

| | | | | |
|---|---|---|---|---|
| 8,921,537 | B2 | 12/2014 | Fuh et al. | |
| 8,956,611 | B2 | 2/2015 | Abelzela | |
| 8,975,071 | B1 | 3/2015 | June et al. | |
| 9,101,584 | B2 | 8/2015 | June et al. | |
| 9,102,720 | B2 | 8/2015 | Bagri et al. | |
| 9,102,760 | B2 | 8/2015 | June et al. | |
| 9,102,761 | B2 | 8/2015 | June et al. | |
| 9,139,863 | B2 | 9/2015 | Corn et al. | |
| 9,150,664 | B2 | 10/2015 | Kufer | |
| 9,161,977 | B2 | 10/2015 | Ashkenazi et al. | |
| 9,226,961 | B2 | 1/2016 | Gokarn et al. | |
| 9,327,035 | B2 | 5/2016 | Fuh et al. | |
| 9,328,156 | B2 | 5/2016 | June et al. | |
| 9,358,250 | B2 | 6/2016 | Ashkenazi et al. | |
| 9,447,194 | B2 | 9/2016 | Jensen | |
| 9,464,140 | B2 | 10/2016 | June et al. | |
| 9,481,728 | B2 | 11/2016 | June et al. | |
| 9,499,623 | B2 | 11/2016 | Ashkenazi et al. | |
| 9,499,629 | B2 | 11/2016 | June et al. | |
| 9,518,123 | B2 | 12/2016 | June et al. | |
| 9,540,445 | B2 | 1/2017 | June et al. | |
| 9,592,240 | B2 | 3/2017 | Howard et al. | |
| 9,598,500 | B2 | 3/2017 | Kufer | |
| 9,662,354 | B2 | 5/2017 | Hyde et al. | |
| 9,717,731 | B2 | 8/2017 | Buggy et al. | |
| 9,765,342 | B2 | 9/2017 | Kochenderfer | |
| 9,777,059 | B2 | 10/2017 | Fuh et al. | |
| 9,834,590 | B2 | 12/2017 | Campana et al. | |
| 9,919,061 | B2 | 3/2018 | McDonagh et al. | |
| 10,000,571 | B2 | 6/2018 | Ashkenazi et al. | |
| 10,010,611 | B2 | 7/2018 | Gokarn et al. | |
| 10,189,903 | B2 | 1/2019 | Jensen | |
| 10,208,120 | B2 | 2/2019 | Yin et al. | |
| 10,221,245 | B2 | 3/2019 | Brogdon et al. | |
| 10,227,416 | B2 | 3/2019 | Marrichi et al. | |
| 10,287,356 | B2 | 5/2019 | Ashkenazi et al. | |
| 10,435,694 | B2 | 10/2019 | Reilly et al. | |
| 10,442,867 | B2 | 10/2019 | Orentas et al. | |
| 10,493,139 | B2 | 12/2019 | Wu et al. | |
| 10,501,539 | B2 | 12/2019 | Schneider et al. | |
| 10,507,219 | B2 | 12/2019 | Gilbert | |
| 10,525,083 | B2 | 1/2020 | Brannetti et al. | |
| 10,533,055 | B2 | 1/2020 | Chen et al. | |
| 10,603,380 | B2 | 3/2020 | Wilzius | |
| 10,639,329 | B2 | 5/2020 | Dropulic et al. | |
| 10,689,445 | B2 | 6/2020 | Kowanetz et al. | |
| 10,736,918 | B2 | 8/2020 | Jensen et al. | |
| 10,767,184 | B2 | 9/2020 | Kochenderfer | |
| 10,815,487 | B2 | 10/2020 | Kochenderfer | |
| 10,815,488 | B2 | 10/2020 | Kochenderfer | |
| 10,829,556 | B2 | 11/2020 | Jensen | |
| 10,844,387 | B2 | 11/2020 | Kochenderfer | |
| 10,876,123 | B2 | 12/2020 | Kochenderfer | |
| 10,881,641 | B2 | 1/2021 | Murali et al. | |
| 10,900,042 | B2 | 1/2021 | Kochenderfer | |
| 10,925,966 | B2 | 2/2021 | Wurth | |
| 10,934,363 | B2 | 3/2021 | Fan | |
| 10,955,422 | B2 | 3/2021 | Plavina | |
| 11,066,457 | B2 | 7/2021 | Yao et al. | |
| 11,066,709 | B2 | 7/2021 | Klijn et al. | |
| 11,091,546 | B2 | 8/2021 | Young et al. | |
| 11,147,886 | B2 | 10/2021 | Ng et al. | |
| 11,173,179 | B2 | 11/2021 | Ma et al. | |
| 11,207,339 | B2 | 12/2021 | Lobb et al. | |
| 11,207,349 | B2 | 12/2021 | Yao et al. | |
| 11,241,485 | B2 | 2/2022 | Suri et al. | |
| 11,279,767 | B2 | 3/2022 | Bourgon et al. | |
| 11,299,544 | B2 | 4/2022 | Chen et al. | |
| 11,300,570 | B2 | 4/2022 | Fabrizio et al. | |
| 11,359,204 | B2 | 6/2022 | Kochenderfer | |
| 11,370,833 | B2 | 6/2022 | Le et al. | |
| 11,377,660 | B2 | 7/2022 | Kochenderfer | |
| 11,390,872 | B2 | 7/2022 | Reilly et al. | |
| 11,401,333 | B2 | 8/2022 | Ashkenazi et al. | |
| 11,402,382 | B2 | 8/2022 | Ashkenazi et al. | |
| 11,406,692 | B2 | 8/2022 | Poma et al. | |
| 11,439,665 | B2 | 9/2022 | Yao et al. | |
| 11,472,858 | B2 | 10/2022 | Yao et al. | |
| 11,473,151 | B2 | 10/2022 | Guan et al. | |
| 11,513,122 | B2 | 11/2022 | Klein et al. | |
| 11,530,269 | B2 | 12/2022 | Kowanetz et al. | |
| 11,535,671 | B2 | 12/2022 | Hegde et al. | |
| 11,608,369 | B2 | 3/2023 | Yao et al. | |
| 11,618,778 | B2 | 4/2023 | Yao et al. | |
| 11,633,430 | B2 | 4/2023 | Yao et al. | |
| 11,639,387 | B2 | 5/2023 | Jensen | |
| 11,643,447 | B2 | 5/2023 | Schreiber et al. | |
| 11,655,452 | B2 | 5/2023 | Ma et al. | |
| 11,666,642 | B2 | 6/2023 | Suri et al. | |
| 11,690,908 | B2 | 7/2023 | Williams et al. | |
| 11,754,573 | B2 | 9/2023 | Morgan et al. | |
| 11,767,366 | B1 | 9/2023 | Russell et al. | |
| 11,768,203 | B2 | 9/2023 | Chaudhary et al. | |
| 11,795,195 | B2 | 10/2023 | Ban et al. | |
| 11,802,144 | B2 | 10/2023 | Wesselhoeft et al. | |
| 11,834,506 | B2 | 12/2023 | Chang et al. | |
| 11,840,575 | B2 | 12/2023 | Zhang et al. | |
| 11,857,628 | B2 | 1/2024 | Poma et al. | |
| 11,859,252 | B2 | 1/2024 | Klijn et al. | |
| 11,905,528 | B2 | 2/2024 | Ma et al. | |
| 11,913,075 | B2 | 2/2024 | Regev et al. | |
| 11,970,542 | B2 | 4/2024 | Green et al. | |
| 11,994,512 | B2 | 5/2024 | Mead et al. | |
| 11,999,802 | B2 | 6/2024 | Bradner et al. | |
| 12,018,093 | B2 | 6/2024 | Ban et al. | |
| 12,060,424 | B2 | 8/2024 | Yang et al. | |
| 12,078,638 | B2 | 9/2024 | Hegde et al. | |
| 12,091,459 | B2 | 9/2024 | Jensen | |
| 12,104,177 | B2 | 10/2024 | Russell et al. | |
| 12,161,714 | B2 | 12/2024 | Williams et al. | |
| 12,180,484 | B2 | 12/2024 | Kochenderfer | |
| 12,180,517 | B2 | 12/2024 | Shah et al. | |
| 12,183,434 | B2 | 12/2024 | Khan et al. | |
| 12,269,859 | B2 | 4/2025 | Chaudhary | |
| 12,305,186 | B2 | 5/2025 | Chaudhary | |
| 12,311,022 | B2 * | 5/2025 | Yao | C07K 14/7051 |
| 12,318,457 | B2 | 6/2025 | Qin et al. | |
| 12,331,128 | B2 | 6/2025 | Chang et al. | |
| 12,383,601 | B2 | 8/2025 | Abujoub et al. | |
| 12,384,847 | B2 | 8/2025 | Chang et al. | |
| 12,398,377 | B2 | 8/2025 | Russell et al. | |
| 12,448,432 | B2 | 10/2025 | Yao et al. | |
| 12,458,667 | B2 | 11/2025 | Yao et al. | |
| 12,473,363 | B2 | 11/2025 | Capon | |
| 12,479,923 | B2 | 11/2025 | Chen et al. | |
| 2004/0167319 | A1 | 8/2004 | Teeling | |
| 2009/0148447 | A1 | 6/2009 | Ledbetter | |
| 2011/0091473 | A1 | 4/2011 | Golab et al. | |
| 2013/0004480 | A1 | 1/2013 | Parren | |
| 2013/0224205 | A1 | 8/2013 | Hofmeister et al. | |
| 2013/0273055 | A1 | 10/2013 | Borges et al. | |
| 2014/0093454 | A1 | 4/2014 | Teeling et al. | |
| 2014/0105915 | A1 | 4/2014 | Algate | |
| 2014/0154253 | A1 | 6/2014 | Ng | |
| 2015/0038684 | A1 | 2/2015 | Jensen | |
| 2015/0051266 | A1 | 2/2015 | Kochenderfer | |
| 2015/0306141 | A1 | 10/2015 | Jensen et al. | |
| 2016/0152723 | A1 | 6/2016 | Chen et al. | |
| 2016/0158359 | A1 | 6/2016 | Gilbert | |
| 2016/0333108 | A1 | 11/2016 | Forman et al. | |
| 2016/0362472 | A1 | 12/2016 | Bitter et al. | |
| 2017/0226216 | A1 | 8/2017 | Morgan | |
| 2017/0267756 | A1 | 9/2017 | Riddell et al. | |
| 2017/0275382 | A1 | 9/2017 | Poma et al. | |
| 2017/0296623 | A1 | 10/2017 | Juillerat et al. | |
| 2017/0355767 | A1 | 12/2017 | Engelberts et al. | |
| 2017/0368098 | A1 | 12/2017 | Chen | |
| 2018/0002435 | A1 | 1/2018 | Sasu et al. | |
| 2018/0044415 | A1 | 2/2018 | Escarpe | |
| 2018/0085401 | A1 | 3/2018 | Wu et al. | |
| 2018/0118823 | A1 | 5/2018 | Thompson et al. | |
| 2018/0125892 | A1 | 5/2018 | Brannetti | |
| 2018/0142034 | A1 | 5/2018 | Chang | |
| 2018/0142035 | A1 | 5/2018 | Lobb | |

(56) References Cited

U.S. PATENT DOCUMENTS

2018/0153977 A1 6/2018 Wu et al.
2018/0230225 A1 8/2018 Fan
2018/0243341 A1 8/2018 June et al.
2018/0258391 A1 9/2018 June et al.
2018/0355052 A1 12/2018 Orentas et al.
2018/0355318 A1 12/2018 Delaney et al.
2019/0106501 A1 4/2019 Press
2019/0107537 A1 4/2019 Chaudhary
2019/0112380 A1 4/2019 Chaudhary
2019/0119382 A1 4/2019 Jensen
2019/0135940 A1 5/2019 Brogdon et al.
2019/0144515 A1 5/2019 Sievers et al.
2019/0169289 A1 6/2019 Young et al.
2019/0321404 A1 10/2019 Fan et al.
2020/0002400 A1 1/2020 Yao et al.
2020/0024312 A1 1/2020 Poma et al.
2020/0040096 A1 2/2020 Forman et al.
2020/0078405 A1 3/2020 Jensen et al.
2020/0093861 A1 3/2020 Klein et al.
2020/0109210 A1 4/2020 Orentas et al.
2020/0215108 A1 7/2020 Jensen
2020/0216534 A1 7/2020 Devila
2020/0246382 A1 8/2020 Perez et al.
2020/0261501 A1 8/2020 Quigley et al.
2020/0283729 A1 9/2020 Loew et al.
2020/0289517 A1 9/2020 He
2020/0306375 A1 10/2020 Lobb et al.
2020/0308223 A1 10/2020 Chang
2020/0362048 A1* 11/2020 Wei .................... C07K 16/2878
2020/0371091 A1 11/2020 Pruteanu-Malinici et al.
2021/0000870 A1 1/2021 Jin et al.
2021/0137977 A1 5/2021 Chaudhary
2021/0140967 A1 5/2021 Kowanetz et al.
2021/0290673 A1 9/2021 Yao et al.
2021/0290676 A1 9/2021 Chaudhary
2021/0301015 A1 9/2021 Tseng
2021/0301023 A1 9/2021 Wu et al.
2021/0338729 A1 11/2021 Ma et al.
2021/0369781 A1 12/2021 Brentjens et al.
2021/0388100 A1 12/2021 Satpayev et al.
2022/0064595 A1 3/2022 Wang et al.
2022/0073623 A1 3/2022 Kowanetz
2022/0135678 A1 5/2022 Chaudhary
2022/0202864 A1 6/2022 Zhang et al.
2022/0241327 A1 8/2022 Ma et al.
2022/0249568 A1 8/2022 Yao et al.
2022/0251152 A1 8/2022 Carbonneau et al.
2022/0259284 A1 8/2022 Schebesta et al.
2022/0267398 A1 8/2022 Ols et al.
2022/0281943 A1 9/2022 Bluestone et al.
2022/0281945 A1 9/2022 Yao et al.
2022/0288244 A1 9/2022 Ludwig et al.
2022/0332786 A1 10/2022 Li et al.
2022/0340640 A1 10/2022 Yao et al.
2022/0348633 A1 11/2022 Ma et al.
2022/0363764 A1 11/2022 Chen et al.
2022/0370606 A1 11/2022 Chen et al.
2022/0403001 A1 12/2022 Suri et al.
2022/0403035 A1 12/2022 Anlahr et al.
2023/0026259 A1 1/2023 Suri et al.
2023/0036065 A1 2/2023 Mccreedy et al.
2023/0053305 A1 2/2023 Wei et al.
2023/0074800 A1 3/2023 Berger et al.
2023/0081117 A1 3/2023 Oakes et al.
2023/0084763 A1 3/2023 Chen et al.
2023/0104705 A1 4/2023 Yao et al.
2023/0114854 A1 4/2023 Song et al.
2023/0140802 A1 5/2023 Chaudhary
2023/0159641 A1 5/2023 Kowanetz et al.
2023/0190811 A1 6/2023 Ostertag et al.
2023/0201258 A1 6/2023 Pu et al.
2023/0210953 A1 7/2023 Mumm
2023/0212255 A1 7/2023 Yao et al.
2023/0212319 A1 7/2023 Chaudhary
2023/0220115 A1 7/2023 Capon
2023/0220116 A1 7/2023 Capon
2023/0227917 A1 7/2023 Gasser et al.
2023/0228739 A1 7/2023 Naj et al.
2023/0242613 A1 8/2023 Yao et al.
2023/0248825 A1 8/2023 Das et al.
2023/0266324 A1 8/2023 Klein et al.
2023/0272040 A1 8/2023 Zhou et al.
2023/0277622 A1 9/2023 Ma et al.
2023/0278974 A1 9/2023 Royo et al.
2023/0302051 A1 9/2023 Ma et al.
2023/0331806 A1 10/2023 Wesselhoeft
2023/0332104 A1 10/2023 Estevez et al.
2023/0357436 A1 11/2023 Frost et al.
2023/0392210 A1 12/2023 Muller et al.
2024/0000839 A1 1/2024 Yao et al.
2024/0059732 A1 2/2024 Ban et al.
2024/0059798 A1 2/2024 Xu et al.
2024/0060135 A1 2/2024 Liu et al.
2024/0075142 A1 3/2024 Schneider et al.
2024/0082304 A1 3/2024 Wang et al.
2024/0082404 A1 3/2024 Poma et al.
2024/0115605 A1 4/2024 Yao et al.
2024/0131156 A1 4/2024 Valamehr et al.
2024/0133885 A1 4/2024 Chaudhary
2024/0139243 A1 5/2024 Yao et al.
2024/0150471 A1 5/2024 Faber
2024/0150712 A1 5/2024 Roskamp et al.
2024/0156864 A1 5/2024 Dotti et al.
2024/0158526 A1 5/2024 Capon
2024/0166753 A1 5/2024 Chang et al.
2024/0166755 A1 5/2024 Chaudhary
2024/0190967 A1 6/2024 Hedge et al.
2024/0197783 A1 6/2024 Dipierro et al.
2024/0200146 A1 6/2024 Klijn et al.
2024/0228636 A1 7/2024 Sasu et al.
2024/0245758 A1 7/2024 Genkin et al.
2024/0285762 A1 8/2024 Maldonado et al.
2024/0287472 A1 8/2024 Russell et al.
2024/0350632 A1 10/2024 Ma et al.
2024/0368282 A1 11/2024 Schlegel et al.
2024/0377400 A1 11/2024 Moscat-Guillen et al.
2024/0384007 A1 11/2024 Bradner et al.
2024/0390496 A1 11/2024 Chaudhary
2024/0415890 A1 12/2024 Lum et al.
2025/0052759 A1 2/2025 Kowanetz et al.
2025/0061965 A1 2/2025 Khan et al.
2025/0084169 A1 3/2025 Capon
2025/0092160 A1 3/2025 Capon
2025/0093359 A1 3/2025 Kowanetz et al.
2025/0122529 A1 4/2025 Matias et al.
2025/0134962 A1 5/2025 He et al.
2025/0136707 A1 5/2025 Yao et al.
2025/0161481 A1 5/2025 Lu et al.
2025/0163153 A1 5/2025 Yang et al.
2025/0164494 A1 5/2025 Kowanetz et al.
2025/0177522 A1 6/2025 Dupont et al.
2025/0180562 A1 6/2025 Mariathasan
2025/0186496 A1 6/2025 Maus et al.
2025/0197475 A1 6/2025 Smith et al.
2025/0236647 A1 7/2025 Schnepp et al.
2025/0242018 A1 7/2025 Kyratsous et al.
2025/0243285 A1 7/2025 June et al.
2025/0255958 A1 8/2025 Saha et al.
2025/0255985 A1 8/2025 Kong et al.
2025/0262243 A1 8/2025 Yao et al.
2025/0281611 A1 9/2025 Schlegel et al.
2025/0282842 A1 9/2025 Uppal et al.
2025/0302876 A1 10/2025 Agarwal
2025/0304679 A1 10/2025 Li et al.
2025/0304687 A1 10/2025 Li et al.
2025/0306027 A1 10/2025 Fabrizio et al.
2025/0326823 A1 10/2025 Li et al.
2025/0326860 A1 10/2025 Du et al.

(56) References Cited

U.S. PATENT DOCUMENTS

| | | | |
|---|---|---|---|
| 2025/0327807 | A1 | 10/2025 | Chaudhary |
| 2025/0333695 | A1 | 10/2025 | Ellebrecht et al. |

FOREIGN PATENT DOCUMENTS

| | | | |
|---|---|---|---|
| CN | 104114578 | A | 10/2014 |
| CN | 104379179 | A | 2/2015 |
| CN | 105384825 | A | 3/2016 |
| CN | 106163547 | A | 11/2016 |
| CN | 106795217 | A | 5/2017 |
| CN | 107827989 | A | 3/2018 |
| CN | 107847583 | A | 3/2018 |
| CN | 108026510 | A | 5/2018 |
| CN | 108348620 | A | 7/2018 |
| CN | 109423495 | A | 3/2019 |
| CN | 109562126 | A | 4/2019 |
| CN | 109575143 | A | 4/2019 |
| CN | 110372796 | A | 10/2019 |
| CN | 110606893 | A | 12/2019 |
| CN | 111727373 | A | 9/2020 |
| CN | 111886012 | A | 11/2020 |
| CN | 112390891 | A | 2/2021 |
| CN | 112501125 | A | 3/2021 |
| CN | 112608387 | A | 4/2021 |
| CN | 112689516 | A | 4/2021 |
| CN | 113056283 | A | 6/2021 |
| CN | 105874061 | B | 8/2021 |
| CN | 113286874 | A | 8/2021 |
| CN | 105408473 | B9 | 9/2021 |
| CN | 113402612 | A | 9/2021 |
| CN | 113498353 | A | 10/2021 |
| CN | 113684185 | A | 11/2021 |
| CN | 116390746 | A | 7/2023 |
| CN | 117120077 | A | 11/2023 |
| CN | 117241824 | A | 12/2023 |
| CN | 117357637 | A | 1/2024 |
| CN | 108884459 | B | 4/2024 |
| CN | 117866991 | A | 4/2024 |
| CN | 118450901 | A | 8/2024 |
| CN | 118524843 | A | 8/2024 |
| CN | 118853581 | A | 10/2024 |
| CN | 119998452 | A | 5/2025 |
| CN | 120093911 | A | 6/2025 |
| CN | 112795594 | B | 9/2025 |
| CN | 120752259 | A | 10/2025 |
| JP | 2014520088 | A | 8/2014 |
| JP | 2014534242 | A | 12/2014 |
| JP | 2015504306 | A | 2/2015 |
| JP | 2015092865 | A | 5/2015 |
| JP | 2017513478 | A | 6/2017 |
| JP | 2017522882 | A | 8/2017 |
| JP | 2017538710 | A | 12/2017 |
| JP | 2018508215 | A | 3/2018 |
| JP | 2020509077 | A | 3/2020 |
| JP | 2021509009 | A | 3/2021 |
| JP | 2021520185 | A | 8/2021 |
| JP | 2023503163 | A | 1/2023 |
| KR | 1020140105757 | A | 9/2014 |
| WO | 0023573 | A2 | 4/2000 |
| WO | 0129058 | A1 | 4/2001 |
| WO | 0196584 | A2 | 12/2001 |
| WO | 2012088461 | A2 | 6/2012 |
| WO | 2012163805 | A1 | 12/2012 |
| WO | 2013072406 | A1 | 5/2013 |
| WO | 2013123061 | A1 | 8/2013 |
| WO | 2016014576 | A1 | 1/2016 |
| WO | 2016014789 | A2 | 1/2016 |
| WO | 2016059622 | A2 | 4/2016 |
| WO | 2016079332 | A1 | 5/2016 |
| WO | 2016097231 | A2 | 6/2016 |
| WO | 2016120216 | A1 | 8/2016 |
| WO | 2016138034 | A1 | 9/2016 |
| WO | 2016139487 | A1 | 9/2016 |
| WO | 2016166521 | A1 | 10/2016 |
| WO | 2016166630 | A1 | 10/2016 |
| WO | 2016168773 | A2 | 10/2016 |
| WO | 2016179319 | A1 | 11/2016 |
| WO | 2017025038 | A1 | 2/2017 |
| WO | 2017072716 | A1 | 5/2017 |
| WO | 2017172981 | A2 | 10/2017 |
| WO | 2017210617 | A2 | 12/2017 |
| WO | 2017211900 | A1 | 12/2017 |
| WO | 2018028647 | A1 | 2/2018 |
| WO | 2018075813 | A1 | 4/2018 |
| WO | 2018121604 | A1 | 7/2018 |
| WO | 2018145649 | A1 | 8/2018 |
| WO | 2018151836 | A1 | 8/2018 |
| WO | 2018231759 | A1 | 12/2018 |
| WO | 2019067805 | A1 | 4/2019 |
| WO | 2019079569 | A1 | 4/2019 |
| WO | 2019108900 | A1 | 6/2019 |
| WO | 2019112899 | A2 | 6/2019 |
| WO | 2019126724 | A1 | 6/2019 |
| WO | 2019126748 | A1 | 6/2019 |
| WO | 2019128952 | A1 | 7/2019 |
| WO | 2019129177 | A1 | 7/2019 |
| WO | 2019149743 | A1 | 8/2019 |
| WO | 2019196713 | A1 | 10/2019 |
| WO | 2019232503 | A1 | 12/2019 |
| WO | 2019241315 | A1 | 12/2019 |
| WO | 2020006216 | A1 | 1/2020 |
| WO | 2020010110 | A1 | 1/2020 |
| WO | 2020010235 | A1 | 1/2020 |
| WO | 2020025596 | A1 | 2/2020 |
| WO | 2020028444 | A1 | 2/2020 |
| WO | 2020029774 | A1 | 2/2020 |
| WO | 2020037066 | A1 | 2/2020 |
| WO | 2020051493 | A1 | 3/2020 |
| WO | 2020061796 | A1 | 4/2020 |
| WO | 2020072536 | A1 | 4/2020 |
| WO | 2020117526 | A1 | 6/2020 |
| WO | 2020150702 | A1 | 7/2020 |
| WO | 2020151752 | A1 | 7/2020 |
| WO | 2020185632 | A1 | 9/2020 |
| WO | 2020191316 | A1 | 9/2020 |
| WO | 2020210398 | A1 | 10/2020 |
| WO | 2020219742 | A1 | 10/2020 |
| WO | 2020227515 | A1 | 11/2020 |
| WO | 2020252404 | A1 | 12/2020 |
| WO | 2020252405 | A1 | 12/2020 |
| WO | 2021011919 | A1 | 1/2021 |
| WO | 2021050601 | A1 | 3/2021 |
| WO | 2021071962 | A1 | 4/2021 |
| WO | 2021077117 | A1 | 4/2021 |
| WO | 2021080920 | A1 | 4/2021 |
| WO | 2021178430 | A1 | 9/2021 |
| WO | 2021184673 | A1 | 9/2021 |
| WO | 2021188599 | A1 | 9/2021 |
| WO | 2021223707 | A1 | 11/2021 |
| WO | 2021263085 | A1 | 12/2021 |
| WO | 2021263205 | A1 | 12/2021 |
| WO | 2022076910 | A1 | 4/2022 |
| WO | 2022098925 | A1 | 5/2022 |
| WO | 2022119923 | A1 | 6/2022 |
| WO | 2022120334 | A1 | 6/2022 |
| WO | 2022164886 | A2 | 8/2022 |
| WO | 2022178367 | A2 | 8/2022 |
| WO | 2022187289 | A1 | 9/2022 |
| WO | 2022187906 | A1 | 9/2022 |
| WO | 2022216514 | A1 | 10/2022 |
| WO | 2022216624 | A1 | 10/2022 |
| WO | 2023279112 | A1 | 1/2023 |
| WO | 2023028657 | A1 | 3/2023 |
| WO | 2023049918 | A1 | 3/2023 |
| WO | 2023070059 | A1 | 4/2023 |
| WO | 2023081754 | A1 | 5/2023 |
| WO | 2023081901 | A1 | 5/2023 |
| WO | 2023129937 | A1 | 7/2023 |
| WO | 2023192321 | A1 | 10/2023 |
| WO | 2023196980 | A1 | 10/2023 |
| WO | 2023196994 | A1 | 10/2023 |
| WO | 2023240050 | A1 | 12/2023 |
| WO | 2023240169 | A1 | 12/2023 |
| WO | 2023240212 | A1 | 12/2023 |

(56) References Cited

FOREIGN PATENT DOCUMENTS

| | | | |
|---|---|---|---|
| WO | 2024006931 | A1 | 1/2024 |
| WO | 2024007020 | A1 | 1/2024 |
| WO | 2024040194 | A1 | 2/2024 |
| WO | 2024040195 | A1 | 2/2024 |
| WO | 2024044743 | A1 | 2/2024 |
| WO | 2024059834 | A1 | 3/2024 |
| WO | 2024102954 | A1 | 5/2024 |
| WO | 2024103017 | A1 | 5/2024 |
| WO | 2024121379 | A1 | 6/2024 |
| WO | 2024148337 | A1 | 7/2024 |
| WO | 2024163738 | A1 | 8/2024 |
| WO | 2024173607 | A1 | 8/2024 |
| WO | 2024183750 | A1 | 9/2024 |
| WO | 2024206884 | A1 | 10/2024 |
| WO | 2024220099 | A1 | 10/2024 |
| WO | 2024220152 | A1 | 10/2024 |
| WO | 2024220650 | A1 | 10/2024 |
| WO | 2024229100 | A1 | 11/2024 |
| WO | 2024240112 | A1 | 11/2024 |
| WO | 2024251242 | A1 | 12/2024 |
| WO | 2024254774 | A1 | 12/2024 |
| WO | 2024258863 | A1 | 12/2024 |
| WO | 2024259279 | A1 | 12/2024 |
| WO | 2025000037 | A1 | 1/2025 |
| WO | 2025019834 | A1 | 1/2025 |
| WO | 2025029810 | A1 | 2/2025 |
| WO | 2025049821 | A1 | 3/2025 |
| WO | 2025049961 | A1 | 3/2025 |
| WO | 2025067205 | A1 | 4/2025 |
| WO | 2025096824 | A1 | 5/2025 |
| WO | 2025101938 | A1 | 5/2025 |
| WO | 2025106626 | A1 | 5/2025 |
| WO | 2025113557 | A1 | 6/2025 |
| WO | 2025146143 | A1 | 7/2025 |
| WO | 2025149068 | A1 | 7/2025 |
| WO | 2025159236 | A1 | 7/2025 |
| WO | 2025174770 | A1 | 8/2025 |
| WO | 2025176853 | A1 | 8/2025 |
| WO | 2025194170 | A1 | 9/2025 |
| WO | 2025212973 | A1 | 10/2025 |
| WO | 2025213573 | A1 | 10/2025 |
| WO | 2025214498 | A1 | 10/2025 |
| WO | 2025218739 | A1 | 10/2025 |
| WO | 2025229499 | A1 | 11/2025 |
| WO | 2025235727 | A1 | 11/2025 |
| WO | 2025235738 | A1 | 11/2025 |
| WO | 2025250751 | A1 | 12/2025 |

OTHER PUBLICATIONS

NCBI Accession AMZ04820, 2016, 1 page.
NCBI Accession ANS59202, 2016, 1 page.
Panka et al. "Variable region framework differences result in decreased or increased affinity of variant anti-digoxin antibodies", Proc Natl Acad Sci USA 1988; 85(9):3080-4. [5 pages].
Parker et al. "Single-Cell Analyses Identify Brain Mural Cells Expressing CD19 as Potential Off-Tumor Targets for CAR-T Immunotherapies", Cell. 2020; 183(1):126-142.e17 [35 pages].
Patel et al. "Expanding the Role of CAR-T Cell Therapy to Systemic Lupus Erythematosus" , (2020) EMJ Hematology, 8(1): 105-12. [8 pages].
Pavlasova et al. "The regulation and function of CD20: an "enigma" of B-cell biology and targeted therapy", Haematologica, 105(6), 1494-1506 (2020). [13 pages].
Pisetsky et al. "New insights into the role of antinuclear antibodies in systemic lupus erythematosus", Nat. Rev. Rheumatol. 16, 565-579 (2020) [32 pages].
Qin et al. "Anti-BCMA CAR T-cell therapy CT103A in relapsed or refractory AQP4-IgG seropositive neuromyelitis optica spectrum disorders: phase 1 trial interim results", Sig Transduct Target Ther 8, 5 (2023).
Qu et al. "Phase 1 study of C-CAR088, a novel humanized anti-BCMA CAR T-cell therapy in relapsed/ refractory multiple myeloma", J Immunother Cancer. 2022; 10(9):e005145 [12 pages].
Ramos et al. "CAR-T Cell Therapy for Lymphoma", Annu. Rev. Med. 2016; 67: 165-183. [22 pages].
Riaz et al. "Anti-CD19 and anti-CD20 CAR-modified T cells for B-cell malignancies: a systematic review and meta-analysis", Immunotherapy (2017) 9(12), 979-993. [16 pages].
Rosenberg et al. "Use of Tumor-Infiltrating Lymphocytes and Interleukin-2 in the Immunotherapy of Patients with Metastatic Melanoma", New Eng. J. of Med. 319: 1676 (1988). [5 pages].
Rubtsov et al. "Toll-like receptor 7 (TLR7)-driven accumulation of a novel CD11c B-cell population is important for the development of autoimmunity", Blood, 2011; 118(5):1305-15 [11 pages].
Rudikoff et al. "Single amino acid substitution altering antigen-binding specificity", Proc Natl Acad Sci USA 1982;79 (6): 1979-83. [5 pages].
Rufener et al. "Preserved Activity of CD20-Specific Chimeric Antigen Receptor-A Expressing T Cells in the Presence of Rituximab" , Cancer Immunology Research, 4(6), 2016, pp. 509-519. [12 pages].
Ryan et al. "Antibody targeting of B-cell maturation antigen on malignant plasma cells", Mol Cancer Ther 2007; 6(11): 3009-3018. [11 pages].
Salmon. "Arming T cells against B cells in systemic lupus erythematosus", Nat. Med. 28, 2009-2010 (2022). [2 pages].
Sela-Culang et al. "The structural basis of antibody-antigen recognition", Front Immunol. 2013;4:302. [13 pages].
Shah et al. "Bispecific anti-CD20, anti-CD19 CART cells for relapsed B cell malignancies: a phase 1 dose escalation and expansion trial", Nat Med. 2020; 26(10):1569-1575. [19 pages].
Sharei et al. "A vector-free microfluidic platform for intracellular delivery", PNAS (2013) 110(6): 2082-2087 [6 pages].
Shetty et al. "Liver sinusoidal endothelial cells—gatekeepers of hepatic immunity", Nat Rev Gastroenterol Hepatol. 2018; 15(9): 555-567. [13 pages].
Tai et al. "Role of B-cell-activating factor in adhesion and growth of human multiple myeloma cells in the bone marrow microenvironment", Cancer research. 2006; 66(13):6675-82 [8 pages].
Taubmann et al. "Long term safety and efficacy of CAR-T cell treatment in refractory systemic lupus erythematosus—data from the first seven patients", Annals of the Rheumatic Diseases, OP0141, p. 93 (2023) [2 pages].
Teeling et al. "The Biological Activity of Human CD20 Monoclonal Antibodies Is Linked to Unique Epitopes on CD20", J Immunol 2006; 177: 362-371. [10 pages].
Teeling et al. "Characterization of new human CD20 monoclonal antibodies with potent cytolytic activity against non-Hodgkin lymphomas", (2004) Blood 104: 1793-1800. [8 pages].
Till et al. "Adoptive immunotherapy for indolent non-Hodgkin lymphoma and mantle cell lymphoma using genetically modified autologous CD20-specific T cells", (2008) Blood112(6): 2261-2271. [11 pages].
Till et al. "CD20-specific adoptive immunotherapy for lymphoma using a chimeric antigen receptor with both CD28 and 4-1BB domains: pilot clinical trial results", Blood (2012) 119(17): 3940-3950 [11 pages].
Ui-Tei et al. "Sensitive assay of RNA interference in Drosophila and Chinese hamster cultured cells using firefly luciferase gene as target", FEBS Letters 479 (2000): 79-82. [4 pages].
Wang et al. "Human autoimmune diseases: a comprehensive update", J. Intern. Med. 2015, 278(4):369-95 [27 pages].
Wang et al. "IL-21 drives expansion and plasma cell differentiation of autoreactive CD11c(hi)T-bet(+) B cells in SLE", Nat. Commun. 9, 1758 (2018).
Wark et al. "Latest technologies for the enhancement of antibody affinity", Adv Drug Deliv Rev. 2006; 58 (5-6):657-70. [14 pages].
Wong et al. "Structural requirements for a specificity switch and for maintenance of affinity using mutational analysis of a phage-displayed anti-arsonate antibody of Fab heavy chain first complementarity-determining region", J Immunol. 1998; 160(12):5990-7. [8 pages].
Wriggers et al. "Control of Protein Functional Dynamics by Peptide Linkers", Current Trends in Peptide Science (2005) 80(6): 736-746 [11 pages].

(56) References Cited

OTHER PUBLICATIONS

Wu et al. "Multimerization of a chimeric anti-CD20 single-chain Fv-Fc fusion protein is mediated through variable domain exchange", Protein Eng. (2001) 14(12): 1025-1033. [9 pages].
Zhang et al. "Treatment of CD20-directed Chimeric Antigen Receptor-modified T cells in patients with relapsed or refractory B-cell non-Hodgkin lymphoma: an early phase IIa trial report", (2016) Signal Transduction and Targeted Therapy 1: 16002; p. 1-10. [9 pages].
Zhou et al. The efficacy and safety of anti-CD19/CD20 chimeric antigen receptor-T cells immunotherapy in relapsed or refractory B-cell malignancies: a meta-analysis, BMC Cancer. 2018; 18(1):929, 13 pages.
Dorner et al. "Mechanisms of B cell autoimmunity in SLE", Arthritis Res. Ther. 13, 243 (2011) [12 pages].
Lee et al. "B cell depletion therapies in autoimmune disease: advances and mechanistic insights", Nat. Rev. Drug Discov. 20, 179-199 (2021) [21 pages].
Chavez et al. "CAR T-cell therapy for B-cell lymphomas: clinical trial results of available products", Ther Adv Hematol. 2019; 10:2040620719841581. [20 pages].
Martyniszyn et al. "CD20-CD19 Bispecific CART Cells for the Treatment of B-Cell Malignancies", Hum Gene Ther. 2017; 28(12):1147-1157. [11 pages].
Schneider et al. "A tandem CD19/CD20 Car lentiviral vector drives on-target and off-target antigen modulation in leukemia cell lines", Journal for Immuno Therapy of Cancer. 2017; 5:42. [17 pages].
Tong et al. "Optimized tandem CD19/CD20 CAR-engineered T cells in refractory/relapsed B-cell lymphoma", Blood. 2020; 136(14):1632-1644. [13 pages].
Wang et al. "Effective response and delayed toxicities of refractory advanced diffuse large B-cell lymphoma treated by CD20-directed chimeric antigen receptor-modified T cells", (2014) Clinical Immunology 155: 160-175. [16 pages].
Watanabe et al. "Target antigen density governs the efficacy of anti-CD20-CD28-CD3ζ chimeric antigen receptor-modified effector CD8+ T cells", J Immunol. 2015; 194(3):911-20. [10 pages].
Zah et al. "T Cells Expressing CD19/CD20 Bispecific Chimeric Antigen Receptors Prevent Antigen Escape by Malignant B Cells", Cancer Immunol Res. 2016; 4(6):498-508. [15 pages].
Zah et al. " Addendum: T Cells Expressing CD19/CD20 Bispecific Chimeric Antigen Receptors Prevent Antigen Escape by Malignant B Cells", Cancer Immunol Res. 2016;4(7):639-41. [3 pages].
Zhu et al. "Closed-system manufacturing of CD19 and dual-targeted CD20/19 chimeric antigen receptor T cells using the CliniMACS Prodigy device at an academic medical center", Cytotherapy. 2018; 20(3):394-406. [14 pages].
Jensen et al. "CD20 is a molecular target for scFvFc:zeta receptor redirected T-cells: implications for cellular immunotherapy of CD20 malignancy", (1998) Biology of Blood and Marrow Transplant, 4: 75-83. [9 pages].
U.S. Appl. No. 19/003,301, filed Dec. 27, 2024.
U.S. Appl. No. 19/005,160, filed Dec. 30, 2024.
Ataca et al. "Chimeric Antigen Receptor T Cell Therapy in Hematology", Turk J Hematol 2015; 32:285-294. [10 pages].
Belovezhec. Design and Comparative Analysis of CD20-Specific Chimeric Antigen Receptors. Proceedings of XIV International Conference of Students, Graduate Students and Young Scientists "Perspectives in Fundamental Sciences" Apr. 25-28, 2017. vol. 4: Biology and Basic Medical Sciences p. 22-24 (with translation/abstract). [6 pages].
Berahovich et al. "CAR-T Cells Based on Novel BCMA Monoclonal Antibody Block Multiple Myeloma Cell Growth", Cancers, vol. 10, No. 9, 2018:323 [16 pages].
Bernabei et al. "PD-1 Inhibitor Combinations As Salvage Therapy for Relapsed/Refractory Multiple Myeloma (MM) Patients Progressing after Bcma-Directed Car T Cells", Blood, vol. 132 (Supplement 1), Nov. 29, 2018 (Nov. 29, 2018), p. 1973 [4 pages].
Bhoj et al. "Persistence of long-lived plasma cells and humoral immunity in individuals responding to CD19-directed CAR T-cell therapy", Blood 128, 360-370 (2016) [12 pages].
Budde et al. "Combining a CD20 Chimeric Antigen Receptor and an Inducible Caspase 9 Suicide Switch to Improve the Efficacy and Safety of T Cell Adoptive Immunotherapy for Lymphoma", PLoS One, vol. 8, No. 12, 2013, pp. 1-10 [10 pages].
Cao et al. "Efficiency and safety of autologous chimeric antigen receptor T-cells therapy used for patients with lymphoma", (2019) Medicine 98: 42(e17506) [8 pages].
Casan et al. "Anti-CD20 monoclonal antibodies: reviewing a revolution", (2018) Human Vaccines & Immunotherapeutics 14(12): 2820-2841. [23 pages].
Chow et al. "Outcomes of patients with large B-cell lymphomas and progressive disease following CD19-specific CART-cell therapy", (2019) Am. J. Hematol. 94(8): E209-E213. [7 pages].
Chuda et al. "Ofatumumab: A Novel Anti-CD20Monoclonal Antibody for the Treatment of Chronic Lymphocytic Leukemia", Current Drug Therapy, 2012, 7, 281-289. [9 pages].
Dogan et al. "B-cell maturation antigen expression across hematologic cancers: a systematic literature review", Blood Cancer J. 10, 73 (2020) [13 pages].
Dondelinger et al. "Understanding the Significance and Implications of Antibody Numbering and Antigen-Binding Surface/Residue Definition", Front Immunol, Oct. 2018; 9:2278. [15 pages].
Dotti et al., Design and development of therapies using chimeric antigen receptor-expressing T cells, Immunol Rev. 2014, 257(1):107-126 [35 pages].
Du et al. "Structure of the Fab fragment of therapeutic antibody Ofatumumab provides insights into the recognition mechanism with CD20", Mol Immunol. 2009; 46(11-12):2419-23.
Feng et al. "Overview of anti-BCMA CAR-T immunotherapy for multiple myeloma and relapsed/refractory multiple myeloma", Scandinavian Journal of Immunology, vol. 92, No. 2, 2020, pp. 109-119. [11 pages].
Fesnak et al., Engineered T Cells: The Promise and Challenges of Cancer Immunotherapy, Nature Reviews Cancer, vol. 16, No. 9, 2016, pp. 566-581 (in 2 parts).
Gen Bank Accession AA022134.1 (2005) [2 pages].
GenBank Accession No. AKH40187, Version AKH40187.1, GenBank, Jul. 28, 2015. [4 pages].
Ghafouri et al. "CD19/CD20 bispecific chimeric antigen receptor (CAR) in naive/memory T-cells for the treatment of relapsed or refractory B-cell lymphomas", Cancer Res., Jul. 1, 2021; 81(13):Abstract CT007. [5 pages].
HALLEK. "Chronic lymphocytic leukemia: 2017 update on diagnosis, risk stratification, and treatment", (2017) Am J Hematol. 92: 946-965. [20 pages].
Hamdy et al. "Sheep red blood cells armed with anti-CD20 single-chain variable fragments (scFvs) fused to a glycosylphosphatidylinositol (GPI) anchor: a strategy to target CD20-positive tumor cells", (2005) J. Immunol. Methods 297 (1-2): 109-124. [16 pages].
Hao et al. "A B-cell subset uniquely responsive to innate stimuli accumulates in aged mice", Blood, 2011; 118(5):1294-304 [11 pages].
International Search Report and Written Opinion of PCT/US2024/022317, mailed Jul. 30, 2024. [10 pages].
International Search Report and Written Opinion of PCT/CN2019/081064, mailed Jul. 3, 2019. [18 pages].
International Search Report and Written Opinion of PCT/US21/61410, mailed Mar. 30, 2022. [11 pages].
International Search Report and Written Opinion of PCT/CN2018/075867, mailed May 9, 2018.
International Search Report and Written Opinion of PCT/US22/13875, mailed Jul. 8, 2022 [10 pages].
Jabbour et al. "Monoclonal antibodies in acute lymphoblastic leukemia", Blood 2015; 125(26): 4010-4016. [7 pages].
Jenks et al. "Distinct Effector B Cells Induced by Unregulated Toll-like Receptor 7 Contribute to Pathogenic Responses in Systemic Lupus Erythematosus", Immunity 49, 725-739 e726 (2018) [35 pages].

(56) References Cited

OTHER PUBLICATIONS

Jensen et al. "Design and implementation of adoptive therapy with chimeric antigen receptor-modified T cells", Immunol Rev. (2014) 257(1):127 [32 pages].
Jonnalagadda et al. "Chimeric Antigen Receptors With Mutated IgG4 Fc Spacer Avoid Fc Receptor Binding and Improve T Cell Persistence and Antitumor Efficacy", Molecular Therapy 2015; vol. 23 no. 4, 757-768. [12 pages].
Korycka-Wolowiec et al. "Ofatumumabfor treating chronic lymphocytic leukemia: a safety profile", Expert Opinion on Drug Safety 2015; 14(12): 1945-1959. [15 pages].
Krumbholz et al. "B cells and antibodies in multiple sclerosis pathogenesis and therapy", Nature reviews Neurology, 2012, 8(11): 613-23. [11 pages].
Ku et al. "Tumour cell surface antigen targeted therapies in B-cell lymphomas: Beyond rituximab", Blood Reviews, vol. 31, No. 1, 2016, pp. 23-35 [13 pages].
Kunik et al. "Structural consensus among antibodies defines the antigen binding site", PLoS Comput Biol. 2012; 8(2): e1002388. [12 pages].
Kussie et al. "A single engineered amino acid substitution changes antibody fine specificity", J. Immunol. 1994; 152(1): 146-52. [7 pages].
Lee et al. "The future is now: chimeric antigen receptors as new targeted therapies for childhood cancer", Clin. Cancer Res. (2012) 18(10):2780 [19 pages].
Lin. "Ofatumumab: a novel monoclonal anti CD20 antibody", (2010) Pharmacogenomics and Personalized Medicine 3: 51-59. [9 pages].
Lin et al. "Preclinical evaluation of CD8+ anti-BCMA mRNA CAR T-cells for treatment of multiple myeloma", Leukemia. 2021, 35(3): 752-76 [21 pages].
Liu et al. "Fine mapping of the antigen-antibody interaction of scFv215, a recombinant antibody inhibiting RNA polymerase II from Drosophila melanogaster", J Mol Recognit. Mar.-Apr. 1999; 12(2):103-11. [9 pages].
Lopez-Atalya et al. "Development and Maintenance of the Brain's Immune Toolkit: Microglia and Non-Parenchymal Brain Macrophages", Dev Neurobiol. 2018; 78(6): 561-579. [19 pages].
Lulla et al. "The Use of Chimeric Antigen Receptor T Cells in Patients with Non-Hodgkin Lymphoma", (2018) Clinical Advances in Hematology & Oncology, 16(5): 375-386. [21 pages].
Mackensen et al. "Anti-CD19 Car T cell therapy for refractory systemic lupus erythematosus", Nat. Med. 28, 2124-2132 (2022). [20 pages].
Madduri et al. "CARTITUDE-1:Phase 1 b/2 Study of Ciltacabtagene Autoleucel, a B-Cell Maturation Antigen-Directed Chimeric Antigen Receptor T Cell Therapy, in Relapsed/Refractory Multiple Myeloma", 62nd ASH Annual Meeting and Exposition, Dec. 5-8, 2020: Blood, vol. 136, Supplement 1, pp. 22-25. [5 pages].
Mailankody. "Orvacabtagene autoleucel (orva-cel), a B-cell maturation antigen (BCMA)-directed CAR T cell therapy for patients (pts) with relapsed/refractory multiple myeloma (RRMM): update of the phase 1/2 EVOLVE study (NCT03430011)", Journal of Clinical Oncology, 2020, 38(15) suppl., Abstract 8504. [5 pages].
Metelo et al. "Allogeneic Anti-Bcma CAR-T Cells Show Tumour Specific Killing Against Primary Multiple Myeloma Cells from Different Genomic Sub-Groups", Blood, vol. 134, 2019: 1834 [3 pages].
Morgan et al. "Unraveling B cell trajectories at single cell resolution", Trends Immunol. 43, 210-229 (2022) [20 pages].
Munshi et al. "Idecabtagene vicleucel (ide-cel; bb2121), a BCMA-targeted CAR T-cell therapy, in patients with relapsed and refractory multiple myeloma (RRMM): Initial KarMMa results", Journal of Clinical Oncology, 2020, 38(15) suppl., Abstract 8503. [4 pages].
U.S. Appl. No. 19/348,065, filed Oct. 2, 2025. [113 pages].
U.S. Appl. No. 19/356,548, filed Oct. 13, 2025. [114 pages].
U.S. Appl. No. 19/356,595, filed Oct. 13, 2025 [112 pages].

* cited by examiner

BISPECIFIC CHIMERIC ANTIGEN RECEPTORS TARGETING CD20 AND BCMA

CROSS REFERENCE TO RELATED APPLICATIONS

The present application is a Continuation Applications of PCT/US2024/022317 (filed on Mar. 29, 2024), which claims priority to U.S. Provisional Patent Application Nos. 63/493,495 (filed on Mar. 31, 2023) and 63/509,371 (filed on Jun. 21, 2023), each of which is hereby incorporated by reference in its entirety.

INCORPORATION-BY-REFERENCE OF SEQUENCE LISTING

The application contains a sequence listing which has been submitted electronically in XML format and is hereby incorporated by reference in its entirety. Said XML copy, created on Mar. 26, 2024, is named 11299_011840-US4_SL.xml and is 168,342 bytes in size.

FIELD OF THE INVENTION

The present disclosure relates to the field of immunotherapy, and more particularly to bispecific chimeric antigen receptors (CARs) targeting CD20 and BCMA.

BACKGROUND

Autoimmune diseases are conditions caused by the immune system's response to the body itself, resulting in damage to its own tissues. These are typically divided into two main categories: systemic autoimmune diseases, such as systemic lupus erythematosus (SLE), rheumatoid arthritis, and systemic vasculitis; and organ-specific autoimmune diseases, such as autoimmune hepatitis and type I diabetes. Most autoimmune diseases are difficult to cure and often require long-term or lifelong medication. Treatment primarily involves corticosteroids and immunosuppressants, greatly impacting the patient's quality of life and presenting a significant unmet clinical need (Wang et al., Human autoimmune diseases: a comprehensive update, J. Intern. Med. 2015, 278(4):369-95).

The etiology of autoimmune diseases is unclear. In patients, abnormal activation of humoral immunity occurs, leading to the production of a large number of antibodies against self-antigens. These combine to form pathogenic immune complexes, which then deposit locally and cause inflammatory reactions. B cells play an important role in the pathogenesis of autoimmune diseases, promoting the occurrence of autoimmune diseases through various mechanisms such as producing autoantibodies, releasing cytokines, and presenting autoantigens. Autoantibodies, as a key factor, can bind with autoantigens to form immune complexes, which can activate innate immune system cells to produce type I interferon and other pro-inflammatory cytokines resulting in organ damage. Therefore, the depletion or removal of lymphocytes has become a potential treatment strategy.

SLE is a prototypic autoimmune disease that is known to be associated with polyclonal B-cell hyperreactivity (Dorner et al., Mechanisms of B cell autoimmunity in SLE, Arthritis Res. Ther. 13, 243 (2011)). As such, one of the immunological hallmarks of SLE is the production of antinuclear antibodies (ANAs), which can mediate SLE pathogenesis by binding to respective autoantigens, resulting in deposition of immune complexes and induction of inflammation and organ damage (for example, lupus nephritis) (Salmon, J. E., Arming T cells against B cells in systemic lupus erythematosus, Nat. Med. 28, 2009-2010 (2022)). There are two main types of ANAs: anti-DNA antibodies and antibodies recognizing RNA-binding proteins (RBP) (Pisetsky et al., New insights into the role of antinuclear antibodies in systemic lupus erythematosus, Nat. Rev. Rheumatol. 16, 565-579 (2020)). In patients with SLE, the sources of autoantibodies include not only B cells but also a subset of plasma cells termed long-lived plasma cells (LLPCs). While the anti-DNA antibodies are produced by naïve B cells that transition to memory B cells and plasmablasts, which maintain high level expression of CD19 and CD20 on the cell surface, the anti-RBP antibodies are produced by LLPCs, which may lose surface expression of CD19 and CD20, but are positive for B-cell maturation antigen (BCMA), a cell surface protein expressed on all mature plasma cells (Dogan et al., B-cell maturation antigen expression across hematologic cancers: a systematic literature review. Blood Cancer J. 10, 73 (2020); Morgan et al., Unraveling B cell trajectories at single cell resolution, Trends Immunol. 43, 210-229 (2022)). Recent studies demonstrated that a CD11c$^{hi}$T-bet$^{+}$ B cell subset is expanded in human SLE and serves as precursors of autoantibody producing plasma cells. This B cell subset displays high expression of CD19 and CD20 and corresponds to the autoreactive, murine age-associated B cells (autoreactive B cells or ABCs; the term may be used to represent human CD11c$^{hi}$T-bet$^{+}$ B cells) (Jenks et al., Distinct Effector B Cells Induced by Unregulated Toll-like Receptor 7 Contribute to Pathogenic Responses in Systemic Lupus Erythematosus, Immunity 49, 725-739 e726 (2018); Wang et al., IL-21 drives expansion and plasma cell differentiation of autoreactive CD11c(hi)T-bet(+) B cells in SLE, Nat. Commun. 9, 1758 (2018)). In addition to autoantibody production, B cells also participate in the pathogenesis of SLE and other autoimmune diseases by secreting cytokines and acting as antigen-presenting cells. Therefore, depleting B cells in patients with SLE can be an effective therapy for this life-threatening disease.

B cell depletion could be achieved by administration of monoclonal antibodies against B cell surface markers. Although the anti-CD20 antibody rituximab was successful in early open-label trials in SLE, it failed to meet its primary end points in two randomized controlled trials (Lee et al., B cell depletion therapies in autoimmune disease: advances and mechanistic insights, Nat. Rev. Drug Discov. 20, 179-199 (2021)). Other antibodies targeting CD19 (obexelimab) were also tested in SLE. Although patients receiving obexelimab sustained their level of disease inactivity despite steroid withdrawal in initial studies, phase II clinical trials, failed to meet their primary end points (Lee et al., B cell depletion therapies in autoimmune disease: advances and mechanistic insights, Nat. Rev. Drug Discov. 20, 179-199 (2021)).

One promising approach to achieve B cell depletion is adoptive transfer of CAR-T cells. CAR-T cells are genetically engineered T lymphocytes that, in the absence of major histocompatibility complex (MHC), can recognize specific antigens on target cells, proliferate, and generate cytotoxic immune responses. In a recent study, compassionate-use of CD19 CAR-T therapy in 5 patients with refractory SLE led to deep depletion of B cells and drug-free remission, suggesting that CAR-T cell transfer is feasible, tolerable, and highly effective in SLE (Mackensen et al., Anti-CD19 CAR T cell therapy for refractory systemic lupus erythematosus, Nat. Med. 28, 2124-2132 (2022)).

There is still an urgent need to develop methods to effectively treat autoimmune diseases.

SUMMARY

The present disclosure provides for a bispecific chimeric antigen receptor (CAR), comprising: (i) an anti-CD20 antigen-binding region which comprises a light chain variable region ($V_L$1) and a heavy chain variable region ($V_H$1), wherein $V_L$1 comprises three complementarity determining regions (CDRs), CDR1, CDR2 and CDR3, having amino acid sequences about 80% to about 100% identical to the amino acid sequences set forth in SEQ ID NO: 130, SEQ ID NO: 131, SEQ ID NO: 132, respectively, and wherein $V_H$1 comprises three CDRs, CDR1, CDR2 and CDR3, having amino acid sequences about 80% to about 100% identical to the amino acid sequences set forth in SEQ ID NO: 127, SEQ ID NO: 128, SEQ ID NO: 129, respectively; and (ii) an anti-BCMA antigen-binding region which comprises a light chain variable region ($V_L$2) and a heavy chain variable region ($V_H$2), wherein $V_L$2 comprises three complementarity determining regions (CDRs), CDR1, CDR2 and CDR3, having amino acid sequences about 80% to about 100% identical to the amino acid sequences set forth in SEQ ID NO: 134, SEQ ID NO: 136, SEQ ID NO: 138, respectively, and wherein $V_H$2 comprises three CDRs, CDR1, CDR2 and CDR3, having amino acid sequences about 80% to about 100% identical to the amino acid sequences set forth in SEQ ID NO: 141, SEQ ID NO: 143, SEQ ID NO: 145, respectively.

The present disclosure provides for a bispecific chimeric antigen receptor (CAR), comprising: (i) an anti-CD20 antigen-binding region which comprises a light chain variable region ($V_L$1) and a heavy chain variable region ($V_H$1); and (ii) an anti-BCMA antigen-binding region which comprises a light chain variable region ($V_L$2) and a heavy chain variable region ($V_H$2).

In one embodiment, $V_L$1 is located at the N-terminus of $V_H$1. In one embodiment, $V_H$1 is located at the N-terminus of $V_L$1. In one embodiment, $V_L$2 is located at the N-terminus of $V_H$2. In one embodiment, $V_H$2 is located at the N-terminus of $V_L$2.

In certain embodiments, $V_L$1 and $V_H$1 have amino acid sequences about 80% to about 100% identical to amino acid sequences set forth in SEQ ID NO: 4 and SEQ ID NO: 8, respectively.

In certain embodiments, $V_L$2 and $V_H$2 have amino acid sequences about 80% to about 100% identical to amino acid sequences set forth in SEQ ID NO: 12 and SEQ ID NO: 16, respectively.

The anti-CD20 antigen-binding region may be a single-chain variable fragment (scFv) that specifically binds CD20. The anti-BCMA antigen-binding region may be a scFv that specifically binds BCMA.

The bispecific CAR may further comprise one or more of the following: (a) a signal peptide, (b) a hinge region, (c) a transmembrane domain, (d) a co-stimulatory region, and (e) a cytoplasmic signaling domain.

The hinge region may comprise a hinge region of IgG4, CD8, CD28, CD137, or combinations thereof.

The transmembrane domain may comprise a transmembrane domain of CD8, CD28, CD3F, CD45, CD4, CD5, CD9, CD16, CD22, CD33, CD37, CD64, CD80, CD86, CD134, CD137, CD154, or combinations thereof.

The co-stimulatory region may comprise a co-stimulatory region of 4-1BB (CD137), CD28, OX40, CD2, CD7, CD27, CD30, CD40, CD70, CD134, PD1, Dap10, CDS, ICAM-1, LFA-1 (CD11a/CD18), ICOS (CD278), NKG2D, GITR, TLR2, or combinations thereof.

The cytoplasmic signaling domain may comprise a cytoplasmic signaling domain of CD3ζ.

The present disclosure provides for a bispecific CAR comprising (or having) an amino acid sequence about 80% to about 100% identical to the amino acid sequence set forth in SEQ ID NO:26, SEQ ID NO:40, SEQ ID NO:54, SEQ ID NO:68, SEQ ID NO:84, SEQ ID NO:98, SEQ ID NO:112, or SEQ ID NO:126.

Also encompassed by the present disclosure is an immune cell expressing the bispecific CAR. The immune cell may be a T cell or a natural killer (NK) cell.

The present disclosure provides for a nucleic acid encoding the bispecific CAR.

The present disclosure provides for a vector comprising the present nucleic acid encoding the bispecific CAR.

The present disclosure provides for a pharmaceutical composition comprising the bispecific CAR, the immune cell, the nucleic acid, or the vector.

The present disclosure also provides for a method of treating an autoimmune disorder. The method may comprise administering the immune cell, or the pharmaceutical composition, to a subject in need thereof.

The autoimmune disorder may be systemic lupus erythematosus (SLE) (e.g., lupus nephritis), systemic vasculitis, systemic sclerosis, inflammatory myopathy (e.g., polymyositis, dermatomyositis, or inclusion-body myositis), systemic scleroderma, multiple sclerosis, myasthenia gravis, a myositis autoantibody-driven disease, or neuromyelitis optica.

The autoimmune disorder may be polymyositis, dermatomyositis, or inclusion-body myositis. The autoimmune disorder may be lupus nephritis.

The present disclosure also provides for a method of treating a cancer. The method may comprise administering the immune cell, or the pharmaceutical composition, to a subject in need thereof.

The cancer may be a hematologic cancer. The cancer may be a B-cell malignancy. The cancer may be Hodgkin's lymphoma, non-Hodgkin's lymphoma, leukemia, and/or multiple myeloma. The cancer may be acute myeloid leukemia (AML), multiple myeloma (MM), chronic lymphocytic leukemia (CLL), chronic myelogenous leukemia, acute lymphoblastic leukemia (ALL), diffuse large B cell lymphoma (DLBCL), or combinations thereof.

The immune cell may be allogeneic or autologous.

BRIEF DESCRIPTION OF THE DRAWINGS

FIG. 3A shows the levels of IFN-γ secreted by the TOB1 to TOB4 CAR-T cells in the cell culture supernatant. FIG. 3B shows the levels of IFN-γ secreted by the TOBL1 to TOBL4 CAR-T cells in the cell culture supernatant. FIG. 3C: TOBL1 to TOBL4 showed high level IFN-γ release when co-cultured with target cells naturally expressing CD20 and BCMA. MM.1S is a BCMA-positive multiple myeloma (MM) cell line; RAJI is CD20 positive and BCMA positive.

(FIG. 5A: TOB1 to TOB4; FIG. 5B: TOBL1 to TOBL4) by RTCA assays.

FIG. 6A shows the structures of C-CAR168 (TOBL1 which is an anti-CD20/BCMA CAR), anti-CD20 CAR (C-CAR066), and anti-BCMA CAR (C-CAR088). FIG. 6B shows the release of IFN-γ after the CAR-T cells were co-cultured with CD20-positive and/or BCMA-positive target cells. FIG. 6C shows the cytotoxicity of the CAR-T cells targeting CD20 and/or BCMA, at different E:T ratios.

FIG. 7A: Generation of C-CAR168 CAR-T cells. The lower panels show the CAR positive rate of C-CAR168 CAR-T cells prepared from the peripheral blood of 3 healthy donors. FIG. 7B: Differentiation of ABCs. The lower panels show that the proportion of ABC subpopulations increased significantly after induction of differentiation of autologous B cells. FIG. 7C: Cytolysis of ABC-enriched B cells by C-CAR168 at different E:T ratios.

FIGS. 8A-8B: C-CAR168 scFv-RabFc binding specificity in the membrane protein array. FIG. 8C: Flow cytometry detection of expression of ITGB2-ITGAM and ITGB2-ITGAL in 293T cells. FIG. 8D (left panel): Flow cytometric detection of the proportion of 4-1BB-positive cells. FIG. 8D (right panel): Flow cytometry detection of IFN-γ concentrations in the co-culture supernatants.

FIG. 9A: C-CAR168 significantly inhibited the growth of A549-CD20 cells in B-NDG tumor bearing mice. Left panel: tumor growth curve of each group during the experiment; right panel: average tumor weight of animals in each group at Day 42. *: P<0.001, compared to the vehicle control group. FIG. 9B: C-CAR168 significantly inhibited the growth of human multiple myeloma MM.1S tumor cells in B-NDG tumor bearing mice. Left panel: tumor growth curve of each group during the experiment; right panel: average tumor weight of animals in each group at Day 28. *: P<0.001, compared to the vehicle control group. FIG. 9C: Images of the A549-CD20 tumors of the animals in each group at Day 42. "/" indicates that the animal was dead. The blank box indicates that no tumor tissue was collected. FIG. 9D: Images of MM.1S tumors of the animals in each group at Day 28. The blank box indicates that no tumor tissue was collected. FIGS. 9E-9G: C-CAR168 significantly inhibited the growth of K562-CD20-BCMA tumor cells in B-NDG tumor bearing mice. FIG. 9E: Tumor growth curve of each group during the experiment. FIG. 9F: The survival rate curve of each group during the experimental period. FIG. 9G: Images of tumors of animals in each group at Day 28. "/" indicates that the animal was dead. The blank box indicates that no tumor tissue was collected.

FIG. 10A: T cells from eight SLE patients were successfully transduced by lentiviral vectors encoding C-CAR168 and expressed the anti-CD20/BCMA CAR. FIG. 10B: C-CAR168 CAR-T cells generated from the SLE patient samples showed robust activity (IFN-γ release) against target cells expressing CD20 and BCMA. K562 is negative for both CD20 and BCMA; MM.1S is a multiple myeloma cell line which is BCMA-positive. FIG. 10C: C-CAR168 CAR-T cells generated from the SLE patient samples showed robust activity (e.g., IFN-γ release) against pan B cells isolated from the SLE patients. FIG. 10D: Pan B cells isolated from the SLE patients were recognized and lysed by autologous C-CAR168 cells.

DETAILED DESCRIPTION

Figure 1:
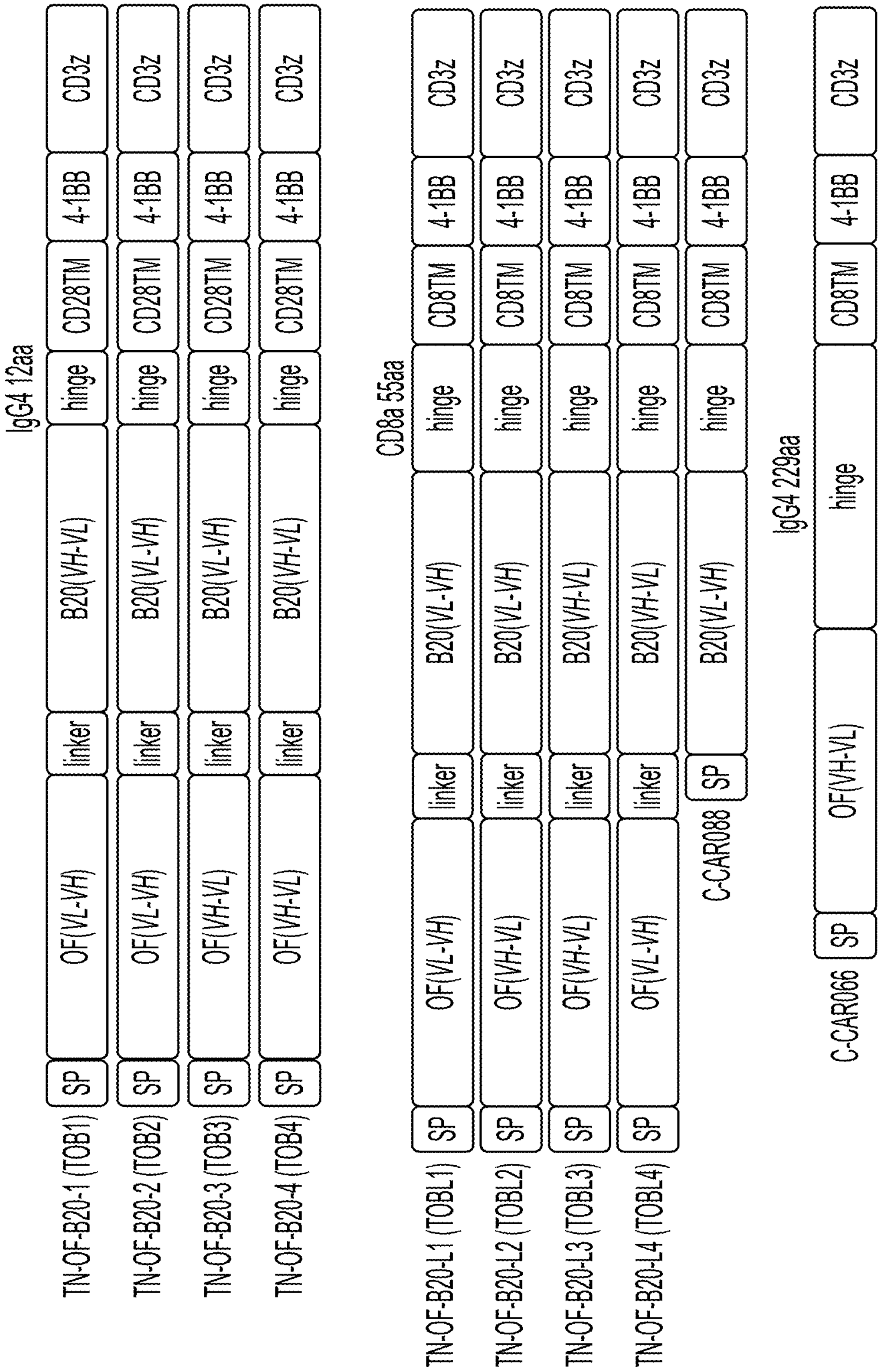
FIG. 1 shows the structures of the combined chimeric antigen receptors targeting CD20 and BCMA. The structures of the CARs include a signal peptide (SP), an anti-CD20 scFv (OF), a linker (linker-2), an anti-BCMA scFv (B20), a hinge region, a transmembrane domain, a co-stimulatory region, and a cytoplasmic signaling domain (CD3ζ). A short IgG4 hinge (12 aa) and a CD28 transmembrane domain are included in TOB1 to TOB4; a CD8a hinge and a CD8a transmembrane domain are included in TOBL1 to TOBL4. Four combinations of orientations of $V_H$ and $V_L$ in the two scFv sequences are included in the two groups of CARs (TOB1-4 and TOBL1-4). TOBL1 is also named C-CAR168.

The present disclosure provides a chimeric antigen receptor (CAR) that targets both CD20 and BCMA. The CAR may comprise a signal peptide, an anti-CD20 scFv, an anti-BCMA scFv, a hinge region, a transmembrane domain, a co-stimulatory region, and a cytoplasmic signaling domain. The present CARs can be used to treat autoimmune diseases or cancer.

B-cell maturation antigen (BCMA), also known as TNFRSF17 or CD269, is a member of the tumor necrosis factor receptor family. It serves as an important receptor for B-cell activating factor (BAFF), along with TACI and BAFF-R, and participates in the regulation of B lymphocyte differentiation and maturation. BCMA is a type III transmembrane protein, specifically expressed in B cells, especially in plasmablasts and differentiated mature plasma cells.

CD20, which is a B-cell membrane marker, also known as B1, is a transmembrane glycoprotein encoded by the MS4A gene. CD20 plays an important role in the development, proliferation, activation, differentiation, and malignant transformation of B cells through the regulation of transmembrane $Ca^{2+}$ conductance.

The present disclosure provides for a bispecific chimeric antigen receptor (CAR). The bispecific CAR may comprise: (i) an anti-CD20 antigen-binding region which comprises a light chain variable region ($V_L1$) and a heavy chain variable region ($V_H1$); and (ii) an anti-BCMA antigen-binding region which comprises a light chain variable region ($V_L2$) and a heavy chain variable region ($V_H2$).

The present bispecific chimeric antigen receptor (CAR) may comprise: (i) an anti-CD20 antigen-binding region which comprises a light chain variable region ($V_L1$) and a heavy chain variable region ($V_H1$) having amino acid sequences about 80% to about 100%, about 85% to about 100%, about 90% to about 100%, or about 95% to about 100%, identical to the amino acid sequences set forth in SEQ ID NO: 4 and SEQ ID NO: 8, respectively; and (ii) an anti-BCMA antigen-binding region which comprises a light chain variable region ($V_L2$) and a heavy chain variable region ($V_H2$) having amino acid sequences about 80% to about 100%, about 85% to about 100%, about 90% to about 100%, or about 95% to about 100%, identical to the amino acid sequences set forth in SEQ ID NO: 12 and SEQ ID NO: 16, respectively.

The present disclosure provides for a bispecific chimeric antigen receptor (CAR). The bispecific CAR may comprise: (i) an anti-CD20 antigen-binding region which comprises a light chain variable region ($V_L1$) and a heavy chain variable region ($V_H1$), and (ii) an anti-BCMA antigen-binding region which comprises a light chain variable region ($V_L2$) and a heavy chain variable region ($V_H2$). $V_L1$ may comprise three complementarity determining regions (CDRs), CDR1, CDR2 and CDR3, having amino acid sequences about 80% to about 100%, about 85% to about 100%, about 90% to about 100%, or about 95% to about 100%, identical to the amino acid sequences set forth in SEQ ID NO: 130, SEQ ID NO: 131, SEQ ID NO: 132, respectively. $V_H1$ may comprise three CDRs, CDR1, CDR2 and CDR3, having amino acid sequences about 80% to about 100%, about 85% to about 100%, about 90% to about 100%, or about 95% to about 100%, identical to the amino acid sequences set forth in SEQ ID NO: 127, SEQ ID NO: 128, SEQ ID NO: 129, respectively. $V_L2$ may comprise three complementarity determining regions (CDRs), CDR1, CDR2 and CDR3, having amino acid sequences about 80% to about 100%, about 85% to about 100%, about 90% to about 100%, or about 95% to about 100%, identical to the amino acid sequences set forth in SEQ ID NO: 134, SEQ ID NO: 136, SEQ ID NO: 138, respectively. $V_H2$ may comprise three CDRs, CDR1, CDR2 and CDR3, having amino acid sequences about 80% to about 100%, about 85% to about 100%, about 90% to about 100%, or about 95% to about 100%, identical to the amino acid sequences set forth in SEQ ID NO: 141, SEQ ID NO: 143, SEQ ID NO: 145, respectively.

In certain embodiments, $V_L1$ is located at the N-terminus of $V_H1$. In certain embodiments, $V_H1$ is located at the N-terminus of $V_L1$. In certain embodiments, $V_H2$ is located at the N-terminus of $V_L2$. In certain embodiments, $V_L2$ is located at the N-terminus of $V_H2$. In one embodiment, $V_L1$ is located at the N-terminus of $V_H1$; $V_L2$ is located at the N-terminus of $V_H2$.

In certain embodiments, $V_L1$ and $V_H1$ have amino acid sequences about 80% to about 100% identical to amino acid sequences set forth in SEQ ID NO: 4 and SEQ ID NO: 8, respectively.

In certain embodiments, $V_L2$ and $V_H2$ have amino acid sequences about 80% to about 100% identical to amino acid sequences set forth in SEQ ID NO: 12 and SEQ ID NO: 16, respectively.

In certain embodiments, the antigen-binding region that specifically binds CD20 is located at the N-terminus of the antigen-binding region that specifically binds BCMA. In certain embodiments, the antigen-binding region that specifically binds BCMA is located at the N-terminus of the antigen-binding region that specifically binds CD20.

The anti-CD20 antigen-binding region may be a single-chain variable fragment (scFv) that specifically binds CD20. The anti-BCMA antigen-binding region may be a scFv that specifically binds BCMA. In certain embodiments, the scFv that specifically binds CD20 is located at the N-terminus of the scFv that specifically binds BCMA. In certain embodiments, the scFv that specifically binds BCMA is located at the N-terminus of the scFv that specifically binds CD20.

The bispecific CAR may further comprise one or more of the following: (a) a signal peptide or SP (or a leader sequence), (b) a hinge region, (c) a transmembrane domain, (d) a co-stimulatory region, and (e) a cytoplasmic signaling domain.

The present bispecific CARs may comprise, from N-terminus to C-terminus, a signal peptide, an anti-CD20 scFv, an anti-BCMA scFv, a hinge region, a transmembrane domain, and a co-stimulatory region, and a cytoplasmic signaling domain.

The signal peptide may comprise a signal peptide of (or may be derived from) CD8, CD28, GM-CSF, CD4, CD137, or combinations thereof. In one embodiment, the signal peptide is a signal peptide of (or is derived from) CD8.

In one embodiment, the signal peptide comprises an amino acid sequence about 80% to about 100%, about 85% to about 100%, about 90% to about 100%, or about 95% to about 100%, identical to the amino acid sequence set forth in SEQ ID NO: 2.

The hinge region may comprise a hinge region of (or may be derived from) IgG4, CD8, CD28, CD137, or combinations thereof, wildtype or mutants.

In one embodiment, the hinge region is a hinge region of (or is derived from) IgG4. In one embodiment, the hinge region comprises an amino acid sequence about 80% to about 100%, about 85% to about 100%, about 90% to about 100%, or about 95% to about 100%, identical to the amino acid sequence set forth in SEQ ID NO: 78.

In one embodiment, the hinge region is a hinge region of (or is derived from) CD8a. In one embodiment, the hinge region comprises an amino acid sequence about 80% to about 100%, about 85% to about 100%, about 90% to about 100%, or about 95% to about 100%, identical to the amino acid sequence set forth in SEQ ID NO: 18.

The transmembrane domain may comprise a transmembrane domain of (or may be derived from) CD8, CD28, CD3F, CD45, CD4, CD5, CD9, CD16, CD22, CD33, CD37, CD64, CD80, CD86, CD134, CD137, CD154, or combinations thereof.

In one embodiment, the transmembrane domain is a transmembrane domain of (or is derived from) CD8. In one embodiment, the transmembrane domain comprises an amino acid sequence about 80% to about 100%, about 85% to about 100%, about 90% to about 100%, or about 95% to about 100%, identical to the amino acid sequence set forth in SEQ ID NO: 20.

In one embodiment, the transmembrane domain is a transmembrane domain of (or is derived from) CD28. In one embodiment, the transmembrane domain comprises an amino acid sequence about 80% to about 100%, about 85% to about 100%, about 90% to about 100%, or about 95% to about 100%, identical to the amino acid sequence set forth in SEQ ID NO: 80.

The co-stimulatory region may comprise a co-stimulatory region of (or may be derived from) 4-1BB (CD137), CD28, OX40, CD2, CD7, CD27, CD30, CD40, CD70, CD134, PD1, Dap10, CDS, ICAM-1, LFA-1 (CD11a/CD18), ICOS (CD278), NKG2D, GITR, TLR2, or combinations thereof.

In one embodiment, the co-stimulatory region is a co-stimulatory region of (or is derived from) 4-1BB. In one embodiment, the co-stimulatory region comprises an amino acid sequence about 80% to about 100%, about 85% to about 100%, about 90% to about 100%, or about 95% to about 100%, identical to the amino acid sequence set forth in SEQ ID NO: 22.

The cytoplasmic signaling domain may comprise a cytoplasmic signaling domain of (or may be derived from) CD3ζ. In one embodiment, the cytoplasmic signaling domain comprises an amino acid sequence about 80% to about 100%, about 85% to about 100%, about 90% to about 100%, or about 95% to about 100%, identical to the amino acid sequence set forth in SEQ ID NO: 24.

The present CAR may comprise a linker (linker-1) between $V_L$ and $V_H$ of the anti-CD20 antigen-binding region. In one embodiment, the linker (linker-1) comprises an amino acid sequence about 80% to about 100%, about 85% to about 100%, about 90% to about 100%, or about 95% to about 100%, identical to the amino acid sequence set forth in SEQ ID NO:6.

The present CAR may comprise a linker (linker-2) between the anti-CD20 antigen-binding region and the anti-BCMA antigen-binding region. In one embodiment, the linker (linker-2) comprises an amino acid sequence about 80% to about 100%, about 85% to about 100%, about 90% to about 100%, or about 95% to about 100%, identical to the amino acid sequence set forth in SEQ ID NO:10.

The present CAR may comprise a linker (linker-3) between $V_L$ and $V_H$ of the anti-BCMA antigen-binding region. In one embodiment, the linker (linker-3) comprises an amino acid sequence about 80% to about 100%, about 85% to about 100%, about 90% to about 100%, or about 95% to about 100%, identical to the amino acid sequence set forth in SEQ ID NO:14.

In one embodiment, the bispecific CAR comprises, from N-terminus to C-terminus, (a) an anti-CD20 antigen-binding region with a light chain variable region ($V_L1$) and a heavy chain variable region ($V_H1$) of those of ofatumumab, (ii) an anti-BCMA antigen-binding region with a light chain variable region ($V_L2$) and a heavy chain variable region ($V_H2$) of those of the BCMA-20 antibody, (iii) a hinge region having an amino acid sequence set forth in SEQ ID NO:18, (iv) a transmembrane domain having an amino acid sequence set forth in SEQ ID NO:20, (v) a co-stimulatory region having an amino acid sequence set forth in SEQ ID NO:22, and (vi) a cytoplasmic signaling domain having an amino acid sequence set forth in SEQ ID NO:24.

In one embodiment, the bispecific CAR comprises, from N-terminus to C-terminus, (a) an anti-CD20 antigen-binding region with a light chain variable region ($V_L1$) and a heavy chain variable region ($V_H1$) having amino acid sequences set forth in SEQ ID NO:4 and SEQ ID NO:8, respectively, (ii) an anti-BCMA antigen-binding region with a light chain variable region ($V_L2$) and a heavy chain variable region ($V_H2$) having amino acid sequences set forth in SEQ ID NO:12 and SEQ ID NO:16, respectively, (iii) a hinge region having an amino acid sequence set forth in SEQ ID NO:18, (iv) a transmembrane domain having an amino acid sequence set forth in SEQ ID NO:20, (v) a co-stimulatory region having an amino acid sequence set forth in SEQ ID NO:22, and (vi) a cytoplasmic signaling domain having an amino acid sequence set forth in SEQ ID NO:24.

In one embodiment, the bispecific CAR comprises, from N-terminus to C-terminus, (a) an anti-CD20 antigen-binding region with a light chain variable region ($V_L1$) and a heavy chain variable region ($V_H1$) of those of ofatumumab, (ii) an anti-BCMA antigen-binding region with a light chain variable region ($V_L2$) and a heavy chain variable region ($V_H2$) of those of BCMA-20, (iii) a hinge region having an amino acid sequence set forth in SEQ ID NO:78, (iv) a transmembrane domain having an amino acid sequence set forth in SEQ ID NO:80, (v) a co-stimulatory region having an amino acid sequence set forth in SEQ ID NO:22, and (vi) a cytoplasmic signaling domain having an amino acid sequence set forth in SEQ ID NO:24.

In one embodiment, the bispecific CAR comprises, from N-terminus to C-terminus, (a) an anti-CD20 antigen-binding region with a light chain variable region ($V_L1$) and a heavy chain variable region ($V_H1$) having amino acid sequences set forth in SEQ ID NO:4 and SEQ ID NO:8, respectively, (ii) an anti-BCMA antigen-binding region with a light chain variable region ($V_L2$) and a heavy chain variable region ($V_H2$) having amino acid sequences set forth in SEQ ID NO:12 and SEQ ID NO:16, respectively, (iii) a hinge region having an amino acid sequence set forth in SEQ ID NO:78, (iv) a transmembrane domain having an amino acid sequence set forth in SEQ ID NO:80, (v) a co-stimulatory region having an amino acid sequence set forth in SEQ ID NO:22, and (vi) a cytoplasmic signaling domain having an amino acid sequence set forth in SEQ ID NO:24.

In certain embodiments, $V_L1$ is located at the N-terminus of $V_H1$. In certain embodiments, $V_H1$ is located at the N-terminus of $V_L1$. In certain embodiments, $V_H2$ is located at the N-terminus of $V_L2$. In certain embodiments, $V_L2$ is located at the N-terminus of $V_H2$. In one embodiment, $V_L1$ is located at the N-terminus of $V_H1$; $V_L2$ is located at the N-terminus of $V_H2$.

In certain embodiments, the bispecific CAR comprises an amino acid sequence about 80% to about 100%, about 85% to about 100%, about 90% to about 100%, or about 95% to about 100%, identical to the amino acid sequence set forth in SEQ ID NO:26, SEQ ID NO:40, SEQ ID NO:54, SEQ ID NO:68, SEQ ID NO:84, SEQ ID NO:98, SEQ ID NO:112, or SEQ ID NO:126.

In certain embodiments, the bispecific CAR may have an amino acid sequence set forth in SEQ ID NO:26, SEQ ID NO:40, SEQ ID NO:54, SEQ ID NO:68, SEQ ID NO:84, SEQ ID NO:98, SEQ ID NO:112, or SEQ ID NO:126.

The present bispecific CAR may be encoded by a nucleic acid having a nucleotide sequence about 80% to about 100%, about 85% to about 100%, about 90% to about 100%, or about 95% to about 100%, identical to the nucleotide sequence set forth in SEQ ID NO:25, SEQ ID NO:39, SEQ ID NO:53, SEQ ID NO:67, SEQ ID NO:83, SEQ ID NO:97, SEQ ID NO:111, or SEQ ID NO:125.

The present bispecific CAR may be encoded by a nucleic acid having a nucleotide sequence set forth in SEQ ID NO:25, SEQ ID NO:39, SEQ ID NO:53, SEQ ID NO:67, SEQ ID NO:83, SEQ ID NO:97, SEQ ID NO:111, or SEQ ID NO: 125.

The present disclosure provides for an immune cell expressing or comprising the present bispecific CAR. The immune cell may be a T cell or a natural killer (NK) cell.

The present disclosure provides an immune cell, comprising the vector or the nucleic acid encoding the present CAR (e.g., integrated into its genome). The cell may be an isolated cell. The cell may be a genetically engineered cell. The cell may be a mammalian cell. In one embodiment, the cell is a CAR-T cell and/or a CAR-NK cell.

Also encompassed by the present disclosure is a nucleic acid encoding the present chimeric antigen receptor (e.g., the present bispecific CAR).

The present nucleic acid may comprise a nucleotide sequence about 80% to about 100%, about 85% to about 100%, about 90% to about 100%, or about 95% to about 100%, identical to the nucleotide sequence set forth in SEQ ID NO:25, SEQ ID NO:39, SEQ ID NO:53, SEQ ID NO:67, SEQ ID NO:83, SEQ ID NO:97, SEQ ID NO:111, or SEQ ID NO:125.

The present nucleic acid may comprise a nucleotide sequence set forth in SEQ ID NO:25, SEQ ID NO:39, SEQ ID NO:53, SEQ ID NO:67, SEQ ID NO:83, SEQ ID NO:97, SEQ ID NO:111, or SEQ ID NO: 125.

The present disclosure provides for a vector comprising the present nucleic acid. The vector may comprise DNA or RNA. The vector may be a plasmid, virus vector, transposon, or combinations thereof. The vector may comprise a DNA virus or a retroviral vector. The vector may be a lentiviral vector, an adenoviral vector, an adeno-associated viral vector, or combinations thereof. In one embodiment, the vector is a lentiviral vector.

The present disclosure also provides for a pharmaceutical composition, comprising the present chimeric antigen receptor (e.g., the present bispecific CAR), the present immune cell, the present nucleic acid, or the present vector. The pharmaceutical composition may further comprise a pharmaceutically acceptable carrier, diluent or excipient. The pharmaceutical composition may be a liquid preparation.

The pharmaceutical composition may comprise the present immune cells at a concentration ranging from about $1\times10^3$ cells/mL to about $1\times10^8$ cells/mL, or from about $1\times10^4$ cells/mL to about $1\times10^7$ cells/mL.

The present disclosure also provides for a method of treating an autoimmune disease/disorder. The present disclosure provides for a method of treating cancer. The method may comprise administering the present immune cell or present pharmaceutical composition to a subject in need thereof.

The immune cell may be allogeneic or autologous.

The autoimmune disorder may be systemic lupus erythematosus (SLE) (e.g., lupus nephritis), systemic sclerosis (SSc), inflammatory myopathy (e.g., polymyositis, dermatomyositis, or inclusion-body myositis), systemic scleroderma, multiple sclerosis, or neuromyelitis optica (NMO).

The cancer may be a hematologic cancer. The cancer may be a B-cell malignancy. The cancer may be Hodgkin's lymphoma, non-Hodgkin's lymphoma, leukemia, and/or multiple myeloma. The cancer may be acute myeloid leukemia (AML), multiple myeloma (MM), chronic lymphocytic leukemia (CLL), chronic myelogenous leukemia, acute lymphoblastic leukemia (ALL), diffuse large B cell lymphoma (DLBCL), or combinations thereof.

The present disclosure provides a method for preparing an immune cell (e.g., a CAR-T cell) expressing the chimeric antigen receptor, where the method comprises: transducing the present nucleic acid molecule or the present vector into an immune cell (e.g., a T cell or NK cell), thereby obtaining the immune cell expressing the chimeric antigen receptor (e.g., the CAR-T cell).

The present disclosure provides a chimeric antigen receptor (CAR), wherein the structure of the chimeric antigen receptor may be shown in formula I:

SP-scFv1-linker2-scFv2-H-TM-C-CSD (I), where, each "-" is independently a linker peptide or a peptide bond; SP is an optional signal peptide; H is an optional hinge region; TM is a transmembrane domain; C is a co-stimulatory region; CSD is a cytoplasmic signaling domain; one of scFv1 and scFv2 is an anti-CD20 antigen binding region, and the other is an anti-BCMA antigen binding region.

In one embodiment, scFv1 is an anti-CD20 antigen binding region, and scFv2 is an anti-BCMA antigen binding region. In another embodiment, scFv1 is an anti-BCMA antigen binding region, and scFv2 is an anti-CD20 antigen binding region.

The structure of the anti-CD20 antigen binding region may be as shown in formula A or B as below:

$V_{H1}$-$V_{L1}$ (A);

$V_{L1}$-$V_{H1}$ (B)

wherein $V_{H1}$ is an anti-CD20 antibody heavy chain variable region; $V_{L1}$ is an anti-CD20 antibody light chain variable region; and "-" is a linker peptide or a peptide bond.

In one embodiment, the present CAR has an anti-CD20 antigen binding region (or domain) with a structure as shown in formula B.

In certain embodiments, the amino acid sequence of $V_{L1}$ is shown in SEQ ID NO: 4, and the amino acid sequence of $V_{H1}$ is shown in SEQ ID NO: 8.

$V_{L1}$ and $V_{H1}$ may be linked with a linker peptide (linker 1 or linker-1). Linker-1 may have the sequence set forth in SEQ ID NO: 6.

The structure of the anti-BCMA antigen binding region may be as shown in formula C or D as below:

$V_{L2}$-$V_{H2}$ (C);

$V_{H2}$-$V_{L2}$ (D)

where $V_{L2}$ is an anti-BCMA antibody light chain variable region; $V_{H2}$ is an anti-BCMA antibody heavy chain variable region; and "-" is a linker peptide or a peptide bond.

In one embodiment, the present CAR has an anti-BCMA antigen binding domain with a structure as shown in formula C.

In certain embodiments, the amino acid sequence of the $V_{L2}$ is shown in SEQ ID NO: 12, and the amino acid sequence of the $V_{H2}$ is shown in SEQ ID NO: 16.

$V_L2$ and $V_{H2}$ may be linked with a linker peptide (linker 3 or linker-3). Linker-3 may have the sequence set forth in SEQ ID NO: 14.

In another embodiment, the structure of the chimeric antigen receptor is shown in formula II as below:

SP-$V_{L1}$-$V_{H1}$-linker2-$V_{L2}$-$V_{H2}$-H-TM-C-CSD (II)

In one embodiment, linker 2 (or linker-2) has the sequence set forth in SEQ ID NO: 10.

In certain embodiments, the anti-CD20 antigen-binding region includes a light chain variable region ($V_L$) comprising an amino acid sequence at least or about 70%, at least or about 75%, at least or about 80%, at least or about 85%, at least or about 90%, at least or about 95%, at least or about 99%, at least or about 81%, at least or about 82%, at least or about 83%, at least or about 84%, at least or about 85%, at least or about 86%, at least or about 87%, at least or about 88%, at least or about 89%, at least or about 90%, at least or about 91%, at least or about 92%, at least or about 93%, at least or about 94%, at least or about 95%, at least or about 96%, at least or about 97%, at least or about 98%, at least or about 99%, or about 100% identical to the amino acid sequence set forth in SEQ ID NO: 4.

In certain embodiments, the anti-CD20 antigen-binding region includes a heavy chain variable region ($V_H$) comprising an amino acid sequence at least or about 70%, at least or about 75%, at least or about 80%, at least or about 85%, at least or about 90%, at least or about 95%, at least or about 99%, at least or about 81%, at least or about 82%, at least or about 83%, at least or about 84%, at least or about 85%, at least or about 86%, at least or about 87%, at least or about 88%, at least or about 89%, at least or about 90%, at least or about 91%, at least or about 92%, at least or about 93%, at least or about 94%, at least or about 95%, at least or about 96%, at least or about 97%, at least or about 98%, at least or about 99%, or about 100% identical to the amino acid sequence set forth in SEQ ID NO: 8.

In certain embodiments, the anti-BCMA antigen-binding region includes a light chain variable region ($V_L$) comprising an amino acid sequence at least or about 70%, at least or about 75%, at least or about 80%, at least or about 85%, at least or about 90%, at least or about 95%, at least or about 99%, at least or about 81%, at least or about 82%, at least or about 83%, at least or about 84%, at least or about 85%, at least or about 86%, at least or about 87%, at least or about 88%, at least or about 89%, at least or about 90%, at least or about 91%, at least or about 92%, at least or about 93%, at least or about 94%, at least or about 95%, at least or about 96%, at least or about 97%, at least or about 98%, at least or about 99%, or about 100% identical to the amino acid sequence set forth in SEQ ID NO: 12.

In certain embodiments, the anti-BCMA antigen-binding region includes a heavy chain variable region ($V_H$) comprising an amino acid sequence at least or about 70%, at least or about 75%, at least or about 80%, at least or about 85%, at least or about 90%, at least or about 95%, at least or about 99%, at least or about 81%, at least or about 82%, at least or about 83%, at least or about 84%, at least or about 85%, at least or about 86%, at least or about 87%, at least or about 88%, at least or about 89%, at least or about 90%, at least or about 91%, at least or about 92%, at least or about 93%, at least or about 94%, at least or about 95%, at least or about 96%, at least or about 97%, at least or about 98%, at least or about 99%, or about 100% identical to the amino acid sequence set forth in SEQ ID NO: 16.

A light chain variable region ($V_L$) of the anti-CD20 antigen-binding region can comprise one, two, or three complementarity determining regions (CDRs), CDR1, CDR2 and CDR3, that are at least or about 70%, at least or about 75%, at least or about 80%, at least or about 85%, at least or about 90%, at least or about 95%, at least or about 99%, at least or about 81%, at least or about 82%, at least or about 83%, at least or about 84%, at least or about 85%, at least or about 86%, at least or about 87%, at least or about 88%, at least or about 89%, at least or about 90%, at least or about 91%, at least or about 92%, at least or about 93%, at least or about 94%, at least or about 95%, at least or about 96%, at least or about 97%, at least or about 98%, at least or about 99%, or about 100%, identical to CDR1, CDR2 and CDR3 as set forth in position 24-34, position 50-56, position 89-97 of SEQ ID NO:4, respectively (the CDRs of a light chain variable region of the Ofatumumab antibody).

A light chain variable region ($V_L$) of the anti-CD20 antigen-binding region can comprise one, two, or three complementarity determining regions (CDRs), CDR1, CDR2 and CDR3, that are at least or about 70%, at least or about 75%, at least or about 80%, at least or about 85%, at least or about 90%, at least or about 95%, at least or about 99%, at least or about 81%, at least or about 82%, at least or about 83%, at least or about 84%, at least or about 85%, at least or about 86%, at least or about 87%, at least or about 88%, at least or about 89%, at least or about 90%, at least or about 91%, at least or about 92%, at least or about 93%, at least or about 94%, at least or about 95%, at least or about 96%, at least or about 97%, at least or about 98%, at least or about 99%, or about 100%, identical to CDR1, CDR2 and CDR3 as set forth in SEQ ID NO: 130, SEQ ID NO: 131, SEQ ID NO: 132, respectively (the CDRs of a light chain variable region of the Ofatumumab antibody).

A heavy chain variable region ($V_H$) of the anti-CD20 antigen-binding region can comprise one, two, or three complementarity determining regions (CDRs), CDR1, CDR2 and CDR3, that are at least or about 70%, at least or about 75%, at least or about 80%, at least or about 85%, at least or about 90%, at least or about 95%, at least or about 99%, at least or about 81%, at least or about 82%, at least or about 83%, at least or about 84%, at least or about 85%, at least or about 86%, at least or about 87%, at least or about 88%, at least or about 89%, at least or about 90%, at least or about 91%, at least or about 92%, at least or about 93%, at least or about 94%, at least or about 95%, at least or about 96%, at least or about 97%, at least or about 98%, at least or about 99%, or about 100%, identical to CDR1, CDR2 and CDR3 as set forth in position 30-35, position 50-66, position 99-111 of SEQ ID NO:8, respectively (the CDRs of a heavy chain variable region of the Ofatumumab antibody).

A heavy chain variable region ($V_H$) of the anti-CD20 antigen-binding region can comprise one, two, or three complementarity determining regions (CDRs), CDR1, CDR2 and CDR3, that are at least or about 70%, at least or about 75%, at least or about 80%, at least or about 85%, at least or about 90%, at least or about 95%, at least or about 99%, at least or about 81%, at least or about 82%, at least or about 83%, at least or about 84%, at least or about 85%, at least or about 86%, at least or about 87%, at least or about 88%, at least or about 89%, at least or about 90%, at least or about 91%, at least or about 92%, at least or about 93%, at least or about 94%, at least or about 95%, at least or about 96%, at least or about 97%, at least or about 98%, at least or about 99%, or about 100%, identical to CDR1, CDR2 and CDR3 as set forth in SEQ ID NO: 127, SEQ ID NO: 128, SEQ ID NO: 129, respectively (the CDRs of a heavy chain variable region of the Ofatumumab antibody).

In certain embodiments, a light chain variable region ($V_L$) of the anti-CD20 antigen-binding region includes three CDRs, CDR1, CDR2 and CDR3, that are identical to CDR1, CDR2 and CDR3 as set forth in position 24-34, position 50-56, position 89-97 of SEQ ID NO: 4, respectively (CDRs of a light chain variable region of the Ofatumumab antibody), and a heavy chain variable region ($V_H$) of the anti-CD20 antigen-binding region includes three CDRs that are identical to CDR1, CDR2 and CDR3 as set forth in position 30-35, position 50-66, position 99-111 of SEQ ID NO: 8 (CDRs of a heavy chain variable region of the Ofatumumab antibody).

In certain embodiments, a light chain variable region ($V_L$) of the anti-CD20 antigen-binding region includes three CDRs, CDR1, CDR2 and CDR3, that are identical to CDR1, CDR2 and CDR3 as set forth in SEQ ID NO: 130, SEQ ID NO: 131, SEQ ID NO: 132, respectively (the CDRs of a light chain variable region of the Ofatumumab antibody), and a heavy chain variable region ($V_H$) of the anti-CD20 antigen-binding region includes three CDRs that are identical to CDR1, CDR2 and CDR3 as set forth in SEQ ID NO: 127, SEQ ID NO: 128, SEQ ID NO: 129, respectively (the CDRs of a heavy chain variable region of the Ofatumumab antibody).

A light chain variable region ($V_L$) of the anti-BCMA antigen-binding region can comprise one, two, or three complementarity determining regions (CDRs), CDR1, CDR2 and CDR3, that are at least or about 70%, at least or about 75%, at least or about 80%, at least or about 85%, at least or about 90%, at least or about 95%, at least or about 99%, at least or about 81%, at least or about 82%, at least or about 83%, at least or about 84%, at least or about 85%, at least or about 86%, at least or about 87%, at least or about 88%, at least or about 89%, at least or about 90%, at least or about 91%, at least or about 92%, at least or about 93%, at least or about 94%, at least or about 95%, at least or about 96%, at least or about 97%, at least or about 98%, at least or about 99%, or about 100%, identical to CDR1, CDR2 and CDR3 as set forth position 24-34, position 50-56, position 89-97 of SEQ ID NO: 12, respectively (the CDRs of a light chain variable region of the BCMA-20 antibody).

A light chain variable region ($V_L$) of the anti-BCMA antigen-binding region can comprise one, two, or three complementarity determining regions (CDRs), CDR1, CDR2 and CDR3, that are at least or about 70%, at least or about 75%, at least or about 80%, at least or about 85%, at least or about 90%, at least or about 95%, at least or about 99%, at least or about 81%, at least or about 82%, at least or about 83%, at least or about 84%, at least or about 85%, at least or about 86%, at least or about 87%, at least or about 88%, at least or about 89%, at least or about 90%, at least or about 91%, at least or about 92%, at least or about 93%, at least or about 94%, at least or about 95%, at least or about 96%, at least or about 97%, at least or about 98%, at least or about 99%, or about 100%, identical to CDR1, CDR2 and CDR3 as set forth SEQ ID NO: 134, SEQ ID NO: 136, SEQ ID NO: 138, respectively (the CDRs of a light chain variable region of the BCMA-20 antibody).

A heavy chain variable region ($V_H$) of the anti-BCMA antigen-binding region can comprise one, two, or three complementarity determining regions (CDRs), CDR1, CDR2 and CDR3, that are at least or about 70%, at least or about 75%, at least or about 80%, at least or about 85%, at least or about 90%, at least or about 95%, at least or about 99%, at least or about 81%, at least or about 82%, at least or about 83%, at least or about 84%, at least or about 85%, at least or about 86%, at least or about 87%, at least or about 88%, at least or about 89%, at least or about 90%, at least or about 91%, at least or about 92%, at least or about 93%, at least or about 94%, at least or about 95%, at least or about 96%, at least or about 97%, at least or about 98%, at least or about 99%, or about 100%, identical to CDR1, CDR2 and CDR3 as set forth in position 31-35, position 50-66, position 99-110 of SEQ ID NO: 16, respectively (the CDRs of a heavy chain variable region of the BCMA-20 antibody).

A heavy chain variable region ($V_H$) of the anti-BCMA antigen-binding region can comprise one, two, or three complementarity determining regions (CDRs), CDR1, CDR2 and CDR3, that are at least or about 70%, at least or about 75%, at least or about 80%, at least or about 85%, at least or about 90%, at least or about 95%, at least or about 99%, at least or about 81%, at least or about 82%, at least or about 83%, at least or about 84%, at least or about 85%, at least or about 86%, at least or about 87%, at least or about 88%, at least or about 89%, at least or about 90%, at least or about 91%, at least or about 92%, at least or about 93%, at least or about 94%, at least or about 95%, at least or about 96%, at least or about 97%, at least or about 98%, at least or about 99%, or about 100%, identical to CDR1, CDR2 and CDR3 as set forth in SEQ ID NO: 141, SEQ ID NO: 143, SEQ ID NO: 145, respectively (the CDRs of a heavy chain variable region of the BCMA-20 antibody).

In certain embodiments, a light chain variable region ($V_L$) of the anti-BCMA antigen-binding region includes three CDRs, CDR1, CDR2 and CDR3, that are identical to CDR1, CDR2 and CDR3 as set forth position 24-34, position 50-56, position 89-97 of SEQ ID NO: 12, respectively (CDRs of a light chain variable region of the BCMA-20 antibody), and a heavy chain variable region ($V_H$) of the anti-BCMA antigen-binding region includes three CDRs, CDR1, CDR2 and CDR3, that are identical to CDR1, CDR2 and CDR3 as set forth in position 31-35, position 50-66, position 99-110 of SEQ ID NO: 16, respectively (CDRs of a heavy chain variable region of the BCMA-20 antibody).

In certain embodiments, a light chain variable region of the anti-BCMA antigen-binding region includes three CDRs, CDR1, CDR2 and CDR3, that are identical to CDR1, CDR2 and CDR3 as set forth SEQ ID NO: 134, SEQ ID NO: 136, SEQ ID NO: 138, respectively (CDRs of a light chain variable region ($V_L$) of the BCMA-20 antibody), and a heavy chain variable region ($V_H$) of the anti-BCMA antigen-binding region includes three CDRs, CDR1, CDR2 and CDR3, that are identical to CDR1, CDR2 and CDR3 as set forth in SEQ ID NO: 141, SEQ ID NO: 143, SEQ ID NO: 145, respectively (CDRs of a heavy chain variable region of the BCMA-20 antibody).

In certain embodiments, in the present CAR, the antigen binding domain targeting CD20 comprises a light chain variable domain $V_L$ (SEQ ID NO: 4) and a heavy chain variable domain $V_H$ (SEQ ID NO: 8) derived from the Ofatumumab antibody.

The light chain variable domain $V_L$ derived from the Ofatumumab (OF) antibody may have the below sequence:

(SEQ ID NO: 4)
EIVLTQSPATLSLSPGERATLSCRASQSVSSYLAWYQQKPGQAPRLLIYD ASNRATGIPARFSGSGSGTDFTLTISSLEPEDFAVYYCQQRSNWPITFGQ GTRLEIK

OF-VL-CDR1: SEQ ID NO: 4, position 24-34. The sequence of OF-VL-CDR1 is:

(SEQ ID NO: 130)
RASQSVSSYLA.

OF-VL-CDR2: SEQ ID NO: 4, position 50-56. The sequence of OF-VL-CDR2 is:

(SEQ ID NO: 131)
DASNRAT.

OF-VL-CDR3: SEQ ID NO: 4, position 89-97. The sequence of OF-VL-CDR3 is:

(SEQ ID NO: 132)
QQRSNWPIT.

The heavy chain variable domain $V_H$ derived from the Ofatumumab antibody may have the below sequence:

(SEQ ID NO: 8)
EVQLVESGGGLVQPGRSLRLSCAASGFTFNDYAMHWVRQAPGKGLEWVST ISWNSGSIGYADSVKGRFTISRDNAKKSLYLQMNSLRAEDTALYYCAKDI QYGNYYYGMDVWGQGTTVTVSS

OF-VH-CDR1: SEQ ID NO: 8, position 30-35. The sequence of OF-VH-CDR1 is:

(SEQ ID NO: 127)
NDYAMH.

OF-VH-CDR2: SEQ ID NO: 8, position 50-66. The sequence of OF-VH-CDR2 is:

(SEQ ID NO: 128)
TISWNSGSIGYADSVKG.

OF-$V_H$-CDR3: SEQ ID NO: 8, position 99-111. The sequence of OF-VH-CDR3 is:

(SEQ ID NO: 129)
DIQYGNYYYGMDV.

In certain embodiments, the antigen-binding domain targeting BCMA in the present CAR comprises a light chain variable domain $V_L$ (SEQ ID NO: 12) and a heavy chain variable domain $V_H$ (SEQ ID NO: 16) derived from the BCMA-20 (B20) antibody.

The light chain variable domain $V_L$ derived from the BCMA-20 antibody may have the below sequence:

```
                                        (SEQ ID NO: 12)
DIQMTQSPSSLSASVGDRVTITCRASQGISNYLNWYQQKPGKAPKPLIYY

TSNLQSGVPSRFSGSGSGTDYTLTISSLQPEDFATYYCMGQTISSYTFGQ

GTKLEIK
```

B20-VL-CDR1: SEQ ID NO: 12, position 24-34. The sequence of B20-VL-CDR1 is:

```
                                        (SEQ ID NO: 134)
RASQGISNYLN.
```

B20-VL-CDR2: SEQ ID NO: 12, position 50-56. The sequence of B20-VL-CDR2 is:

```
                                        (SEQ ID NO: 136)
YTSNLQS.
```

B20-VL-CDR3: SEQ ID NO: 12, position 89-97. The sequence of B20-VL-CDR3 is:

```
                                        (SEQ ID NO: 138)
MGQTISSYT.
```

The heavy chain variable domain $V_H$ derived from the BCMA-20 antibody may have the below sequence:

```
                                        (SEQ ID NO: 16)
EVQLVESGGGLVQPGGSLRLSCAASGFTFSNFDMAWVRQAPGKGLVWVSS

ITTGADHAIYADSVKGRFTISRDNAKNTLYLQMNSLRAEDTAVYYCVRHG

YYDGYHLFDYWGQGTLVTVSS
```

B20-VH-CDR1: SEQ ID NO: 16, position 31-35. The sequence of B20-VH-CDR1 is:

```
                                        (SEQ ID NO: 141)
NFDMA.
```

B20-VH-CDR2: SEQ ID NO: 16, position 50-66. The sequence of B20-VH-CDR2 is:

```
                                        (SEQ ID NO: 143)
SITTGADHAIYADSVKG.
```

B20-VH-CDR3: SEQ ID NO: 16, position 99-110. The sequence of B20-VH-CDR3 is:

```
                                        (SEQ ID NO: 145)
HGYYDGYHLFDY.
```

The signal peptide may be the signal peptide of CD8, having the following sequence:

```
                                        (SEQ ID NO: 2)
MALPVTALLLPLALLLHAARP
```

The linker between $V_L$ and $V_H$ (or $V_H$ and $V_L$) of the anti-CD20 scFv (linker-1) may have the following sequence: GSTSGGGSGGGSGGGGSS (SEQ ID NO:6)

The linker between the anti-CD20 scFv and the anti-BCMA scFv (linker-2) may have the following sequence: GGGGS (SEQ ID NO:10)

The linker between $V_L$ and $V_H$ (or $V_H$ and $V_L$) of the anti-BCMA scFv (linker-3) may have the following sequence: GGGGSGGGGSGGGGS (SEQ ID NO:14)

The hinge region between the extracellular region (antigen-binding domain) and the transmembrane domain may be derived from IgG4, CD8 (CD8a), CD28, CD137, or combinations thereof.

The hinge region may be derived from CD8a which has the following sequence:

```
                                        (SEQ ID NO: 18)
FVPVFLPAKPTTTPAPRPPTPAPTIASQPLSLRPEACRPAAGGAVHTRGL

DFACD
```

The hinge region may be derived from IgG4 which has the following sequence:

```
                                        (SEQ ID NO: 78)
ESKYGPPCPPCP
```

The transmembrane domain may be derived from CD8 (CD8TM) which has the following sequence: IYIWAPLAGTCGVLLLSLVITLYC (SEQ ID NO:20)

The transmembrane domain may be derived from CD28 (CD28TM) which has the following sequence: MFWVLVVVGGVLACYSLLVTVAFIIFWV (SEQ ID NO:80)

The co-stimulatory region may be derived from 4-1BB which has the following sequence:

```
                                        (SEQ ID NO: 22)
KRGRKKLLYIFKQPFMRPVQTTQEEDGCSCRFPEEEEGGCEL
```

The cytoplasmic signaling domain may be derived from CD3ζ which has the following sequence:

```
                                        (SEQ ID NO: 24)
RVKFSRSADAPAYQQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR
```

Chimeric Antigen Receptors (CARs)

The terms "chimeric antigen receptor," or alternatively "CAR", are used interchangeably throughout and refer to a recombinant polypeptide construct comprising, e.g., an extracellular antigen binding domain, a transmembrane domain and an intracellular domain. Lee et al., *Clin. Cancer Res.* (2012) 18(10):2780; Jensen et al., *Immunol Rev.* (2014) 257(1):127. In one embodiment, the stimulatory molecule is the zeta chain associated with the T cell receptor complex. In one aspect, the cytoplasmic signaling domain further comprises one or more functional signaling domains derived from at least one costimulatory molecule. The costimulatory molecule may also be 4-1BB (i.e., CD137), CD27 and/or CD28 or fragments of those molecules. In another aspect, the CAR comprises a chimeric fusion protein comprising an extracellular antigen recognition domain, a transmembrane domain and an intracellular signaling domain comprising a functional signaling domain derived from a stimulatory molecule. The CAR may comprise a chimeric fusion protein comprising an extracellular antigen recognition domain, a transmembrane domain and an intracellular signaling domain comprising a functional signaling domain derived from a co-stimulatory molecule and a functional signaling domain derived from a stimulatory molecule. Alternatively, the CAR may comprise a chimeric fusion protein comprising an extracellular antigen recognition domain, a transmembrane domain and an intracellular signaling domain comprising two functional signaling domains derived from one or more co-stimulatory molecule(s) and a functional signaling domain derived from a stimulatory molecule. The CAR may also comprise a chimeric fusion protein comprising an extracellular antigen recognition domain, a transmembrane domain and an intracellular signaling domain comprising at least two functional signaling domains derived from one or more co-stimulatory molecule(s) and a functional signaling domain derived from a stimulatory molecule. The antigen-binding region of the CAR may contain any antigen-binding antibody fragment. The antibody fragment can comprise one or more CDRs, the variable region (or portions thereof), the constant region (or portions thereof), or combinations of any of the foregoing.

The term “zeta” or alternatively “zeta chain”, “CD3-zeta” or “TCR-zeta” may be the protein provided as GenBank accession numbers NP_932170, NP_000725, or XP_011508447; or the equivalent residues from a non-human species, e.g., mouse, rodent, monkey, ape and the like, and a “zeta stimulatory domain” or alternatively a “CD3-zeta stimulatory domain” or a “TCR-zeta stimulatory domain” may be the amino acid residues from the cytoplasmic domain of the zeta chain that are sufficient to functionally transmit an initial signal necessary for T cell activation.

A chimeric receptor may refer to a non-naturally occurring molecule that can be expressed on the surface of a host cell and comprises an antigen-binding fragment that binds to an antigen. In addition to the antigen-binding fragment, the chimeric receptor may further comprise one or more of a hinge region, a transmembrane domain, at least one co-stimulatory region, and a cytoplasmic signaling domain. In some embodiments, the chimeric antigen receptor comprises from N terminus to C terminus, an antigen-binding region (or fragment), a hinge region, a transmembrane domain, and a cytoplasmic signaling domain. In some embodiments, the chimeric antigen receptor further comprises at least one co-stimulatory region. Thus, the chimeric antigen receptor may comprise from N terminus to C terminus, an antigen-binding region (or fragment), a hinge region, a transmembrane domain, a co-stimulatory region, and a cytoplasmic signaling domain.

In some embodiments, the chimeric antigen receptors comprise a hinge region, which may be located between the antigen-binding region and a transmembrane domain. The hinge region may contain about 10-200 amino acids, e.g., 15-150 amino acids, 20-100 amino acids, or 30-60 amino acids. In some embodiments, the hinge region may be of about 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 110, 120, 130, 140, 150, 160, 170, 180, 190, or 200 amino acids in length. The hinge region may contain 0-300 amino acids, 2 amino acids to 100 amino acids, 5 amino acids to 80 amino acids, 10 amino acids to 60 amino acids, 10 amino acids to 15 amino acids, 20 amino acids to 80 amino acids, 30 amino acids to 70 amino acids, 40 amino acids to 60 amino acids, 50 amino acids to 60 amino acids, or 30 amino acids to 60 amino acids.

In some embodiments, the hinge region is a hinge domain of a naturally occurring protein. Hinge domains of any protein known in the art to comprise a hinge domain are compatible for use in the chimeric antigen receptors. In some embodiments, the hinge domain is of CD8α or CD28α. In some embodiments, the hinge domain is a portion of the hinge domain of CD8a, e.g., a fragment containing at least 15 (e.g., 20, 25, 30, 35, or 40) consecutive amino acids of the hinge domain of CD8α or CD28α.

Hinge domains of antibodies, such as an IgG, IgA, IgM, IgE, or IgD antibody, are also compatible for use in the chimeric antigen receptors. In some embodiments, the hinge region is the hinge domain that joins the constant domains CH1 and CH2 of an antibody. In some embodiments, the hinge region is of an antibody and comprises the hinge domain of the antibody and one or more constant regions of the antibody. In some embodiments, the hinge region comprises the hinge domain of an antibody and the CH3 constant region of the antibody. In some embodiments, the hinge region comprises the hinge domain of an antibody and the CH2 and CH3 constant regions of the antibody. In some embodiments, the antibody is an IgG, IgA, IgM, IgE, or IgD antibody. In some embodiments, the antibody is an IgG antibody. In some embodiments, the antibody is an IgG1, IgG2, IgG3, or IgG4 antibody. In some embodiments, the hinge region comprises the hinge region and the CH2 and CH3 constant regions of an IgG4 antibody. In some embodiments, the hinge region comprises the hinge region and the CH3 constant region of an IgG4 antibody.

The hinge region may be a non-naturally occurring peptide. In some embodiments, the hinge region between the extracellular antigen-binding domain and the transmembrane domain is a peptide linker, such as a (GlyxSer)n (or (GxS)n) linker, wherein x and n, independently can be an integer between 3 and 12, including 3, 4, 5, 6, 7, 8, 9, 10, 11, 12, or more.

Additional peptide linkers that may be used in a hinge region of the chimeric receptors described herein are known in the art. See, e.g., Wriggers et al. *Current Trends in Peptide Science* (2005) 80(6): 736-746 and PCT Publication WO 2012/088461.

In some embodiments, the chimeric antigen receptors may comprise a transmembrane domain. The transmembrane domain can be in any form known in the art. Transmembrane domains compatible for use in the chimeric antigen receptors may be obtained from a naturally occurring protein. Alternatively, the transmembrane domain may be a synthetic, non-naturally occurring protein segment, e.g., a hydrophobic protein segment that is thermodynamically stable in a cell membrane.

In some embodiments, the transmembrane domain is that of CD8a. In some embodiments, the transmembrane domain is that of CD28. In some embodiments, the transmembrane domain is that of ICOS.

In some embodiments, the chimeric antigen receptors comprise one or more costimulatory regions. A co-stimulatory region may be at least a portion of a protein that mediates signal transduction within a cell to induce an immune response, such as an effector function. The co-stimulatory region of the chimeric antigen receptor can be from a protein which transduces a signal and modulates responses mediated by immune cells, such as T cells, natural killer (NK) cells, macrophages, neutrophils, or eosinophils.

In some embodiments, the chimeric antigen receptor comprises one or more than one (at least 2, 3, 4, or more) co-stimulatory region. In some embodiments, the chimeric antigen receptor comprises more than one co-stimulatory region obtained from different proteins. In some embodiments, the chimeric antigen receptor does not comprise a co-stimulatory region.

Examples of co-stimulatory regions for use in the chimeric antigen receptors can be a domain from co-stimulatory proteins, including, without limitation, CD27, CD28, 4-1BB, OX40, CD30, Cd40, PD-1, ICOS, lymphocyte function-associated antigen-1 (LFA-1), CD2, CD7, LIGHT, NKG2C, B7-H3. In some embodiments, the co-stimulatory region is derived from 4-1BB, CD28, or ICOS. In some embodiments, the co-stimulatory region is derived from CD28 and the chimeric antigen receptor comprises a second co-stimulatory region from 4-1BB or ICOS. In some embodiments, the co-stimulatory region is a fusion domain comprising more than one co-stimulatory region or portions of more than one co-stimulatory region. In some embodiments, the costimulatory region is a fusion of costimulatory regions from CD28 and ICOS.

In some embodiments, the chimeric antigen receptors comprise a cytoplasmic signaling domain. Any cytoplasmic signaling domain can be used in the chimeric antigen receptors described herein. A cytoplasmic signaling domain may relay a signal, such as interaction of an extracellular ligand-binding domain with its ligand, to stimulate a cellular response, such as inducing an effector function of the cell (e.g., cytotoxicity).

The chimeric antigen receptors can be prepared by routine methods, such as recombinant technology. Methods for preparing the chimeric antigen receptors may involve generation of a nucleic acid that encodes a polypeptide comprising each of the domains of the chimeric antigen receptors, including the antigen-binding fragment and optionally, the hinge region, the transmembrane domain, at least one co-stimulatory region, and the cytoplasmic signaling domain. In some embodiments, nucleic acids encoding each of the components of the chimeric antigen receptor are joined together using recombinant technology. Sequences of each of the components (e.g., domains) can be joined directly or indirectly (e.g., using a nucleic acid sequence encoding a peptide linker) to form a nucleic acid sequence encoding the chimeric antigen receptor, using methods such as PCR amplification or ligation. Alternatively, the nucleic acid encoding the chimeric antigen receptor may be synthesized. In some embodiments, the nucleic acid is DNA. In other embodiments, the nucleic acid is RNA.

In one embodiment, the present CAR, from the N-terminus to C-terminus, comprises a signal peptide (also known as leader sequence), an antigen recognition sequence (antigen-binding domain), a hinge region, a transmembrane domain, a co-stimulatory region, and a cytoplasmic signaling domain (e.g., a CD3zeta signaling region ((chain portion)).

Bispecificity means that the CAR can specifically bind two different antigens. The bispecific CAR may generate an immune response by binding to one antigen or both antigens.

As used herein, the terms "CAR-T cell", "CAR-T", "CART", "CART cell" may refer to the T cell that expresses the present CAR targeting both CD20 and BCMA.

Immune Cells Expressing Chimeric Antigen Receptors

The present disclosure also provides immune cells expressing the present CAR. Recognition of a target cell having the antigen(s) on its cell surface by the antigen-binding fragment of the chimeric antigen receptor may transduce an activation signal to the signaling domain(s) (e.g., co-stimulatory region and/or the cytoplasmic signaling domain) of the chimeric antigen receptor, which may activate an effector function in the immune cell expressing the chimeric antigen receptor.

The chimeric antigen receptor can be introduced into a suitable immune cell for expression via conventional technology. In some embodiments, the immune cells are T cells, such as primary T cells or T cell lines. Alternatively, the immune cells can be natural killer (NK) cells, such as established NK cell lines (e.g., NK-92 cells). In some embodiments, the immune cells are T cells that express CD8 ($CD8^+$) or CD8 and CD4 ($CD8^+/CD4^+$). In some embodiments, the T cells are T cells of an established T cell line, for example, Jurkat cells.

Primary T cells may be obtained from any source, such as peripheral blood mononuclear cells (PBMCs), bone marrow, tissues such as spleen, lymph node, thymus, or tumor tissue. In some embodiments, the population of immune cells is derived from a human patient having an autoimmune disorder or cancer (e.g., hematopoietic malignancy), such as from the bone marrow or from PBMCs obtained from the patient. In some embodiments, the population of immune cells is derived from a healthy donor. In some embodiments, the immune cells are obtained from the subject to whom the immune cells expressing the chimeric antigen receptors will be subsequently administered. Immune cells that are administered to the same subject from which the cells were obtained are referred to as autologous cells, whereas immune cells that are obtained from a subject who is not the subject to whom the cells will be administered may be referred to as allogeneic cells.

The type of immune cells desired may be expanded within the population of cells obtained by co-incubating the cells with stimulatory molecules, for example, anti-CD3 and anti-CD28 antibodies may be used for expansion of T cells.

To construct the immune cells that express the chimeric antigen receptors described herein, vectors for stable or transient expression of the chimeric antigen receptor may be constructed via conventional methods as described herein and introduced into immune cells. For example, nucleic acids encoding the chimeric antigen receptors may be cloned into a suitable vector, such as a viral vector.

In certain embodiments, immune cells (e.g., T cells) are transduced with lentiviral vectors (LVs) encoding the present CAR. The transduced immune cells (e.g., T cells) can target CD20 and BCMA, synergistically activate the T cells, and induce T cell-mediated immune responses.

In one embodiment, in the present method, T cells from an autologous patient (or an allogeneic donor) are isolated, activated and genetically modified to generate CAR-T cells expressing the present CAR, and then administered to the patient. CAR-T cells can replicate in vivo resulting in long-term persistence. In addition, the CAR-mediated immune response may be part of an adoptive immunotherapy approach in which the anti-CD20/BCMA CAR-T cells elicit an immune response against cells expressing CD20 and/or BCMA.

In certain embodiments, cells are isolated from a mammal (e.g., a human) and genetically modified (i.e., transduced or transfected in vitro) with a vector expressing a CAR disclosed herein. The CAR-modified cells can be administered to a mammalian recipient to provide a therapeutic benefit. The mammalian recipient may be a human. The CAR-modified cell can be autologous with respect to the recipient. Alternatively, the cells can be allogeneic, syngeneic or xenogeneic with respect to the recipient.

The methods of preparing immune cells expressing the present chimeric antigen receptors may comprise activating and/or expanding the immune cells ex vivo. Activating an immune cell means stimulating an immune cell into an activated state in which the cell may be able to perform effector functions (e.g., cytotoxicity). Methods of activating an immune cell will depend on the type of the immune cell used for expression of the chimeric antigen receptors. Expanding immune cells may involve any method that results in an increase in the number of cells expressing chimeric antigen receptors, for example, allowing the cells to proliferate or stimulating the cells to proliferate. In some embodiments, the cells expressing the chimeric receptors described herein are activated and/or expanded ex vivo prior to administration to a subject.

The CAR-expressing immune cells may also serve as a vaccine for ex vivo immunization and/or in vivo therapy in a mammal. In addition to using a cell-based vaccine in terms of ex vivo immunization, the present disclosure also provides compositions and methods for in vivo immunization to elicit an immune response directed against an antigen in a patient. Preferably, the mammal is a human. With respect to ex vivo immunization, one or more of the following may occur in vitro prior to administering the cell into a mammal: i) expanding the cells, ii) introducing a nucleic acid encoding a CAR to the cells, and/or iii) cryopreservation of the cells.

Vectors

The present disclosure provides a nucleic acid encoding the present CAR. The present disclosure also provides vectors comprising the present nucleic acid.

The vectors include, but are not limited to, a plasmid, a phagemid, a phage derivative, a virus, and a cosmid.

The vector may be a viral vector. Viruses, which are useful as vectors comprise, but are not limited to, retroviruses, adenoviruses, adeno-associated viruses, herpes viruses, and lentiviruses. In certain embodiments, the present vector is a retroviral vector such as a lentiviral vector. In some embodiments, the vectors for expression of the chimeric antigen receptors are retroviruses. In some embodiments, the vectors for expression of the chimeric antigen receptors are lentiviruses. In some embodiments, the vectors for expression of the chimeric antigen receptors are adeno-associated viruses.

A variety of promoters can be used for expression of the chimeric receptors, including, without limitation, cytomegalovirus (CMV) intermediate early promoter, a viral LTR such as the Rous sarcoma virus LTR, HIV-LTR, HTLV-1 LTR, Maloney murine leukemia virus (MMLV) LTR, myeoloproliferative sarcoma virus (MPSV) LTR, spleen focus-forming virus (SFFV) LTR, the simian virus 40 (SV40) early promoter, herpes simplex tk virus promoter, elongation factor 1-alpha (EF1-α) promoter with or without the EF1-α intron. Additional promoters for expression of the chimeric receptors include any constitutively active promoter in an immune cell. Alternatively, any regulatable promoter (e.g., inducible promoters) may be used, such that its expression can be modulated within an immune cell.

The vector can be introduced into a cell, e.g., mammalian, bacterial, yeast, or insect cell, by any method in the art. For example, the vector can be transferred into a cell by physical, chemical, or biological means.

Physical methods for introducing a polynucleotide into a cell comprise calcium phosphate precipitation, lipofection, particle bombardment, microinjection, electroporation, and the like. See, for example, Sambrook et al. (2001, Molecular Cloning: A Laboratory Manual, Cold Spring Harbor Laboratory, New York).

Biological methods for introducing a polynucleotide of interest into a cell comprise the use of DNA and RNA vectors. Viral vectors can be derived from retroviruses, lentiviruses, poxviruses, herpes simplex virus I, adenoviruses and adeno-associated viruses, and the like.

Chemical means for introducing a polynucleotide into a host cell comprise colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In some embodiments, the vector (nucleic acid) encoding the chimeric antigen receptor is a DNA vector and may be electroporated to immune cells (see, e.g., Till, et al. Blood (2012) 119(17): 3940-3950). In some embodiments, the vector (nucleic acid) encoding the chimeric antigen receptor is an RNA molecule, which may be electroporated to immune cells.

Any of the vectors comprising a nucleic acid that encodes a chimeric antigen receptor described herein is also within the scope of the present disclosure. Such a vector may be delivered into host cells such as immune cells by a suitable method. Methods of delivering vectors to immune cells are well known in the art and may include DNA, RNA, or transposon electroporation, transfection reagents such as liposomes or nanoparticles to delivery DNA, RNA, or transposons; delivery of DNA, RNA, or transposons or protein by mechanical deformation (see, e.g., Sharei et al. PNAS (2013) 110(6): 2082-2087); or viral transduction. In some embodiments, the vectors for expression of the chimeric receptors are delivered to cells by viral transduction.

In examples in which the vectors encoding chimeric antigen receptors are introduced to the host cells using a viral vector, viral particles that are capable of infecting the immune cells and carry the vector may be produced by any method known in the art. The viral particles are harvested from the cell culture supernatant and may be isolated and/or purified prior to contacting the viral particles with the immune cells.

Pharmaceutical Compositions

The present disclosure provides a pharmaceutical composition comprising the present immune cells, the present CAR, the present nucleic acid, or the present vector. The present pharmaceutical composition may further comprise a pharmaceutically acceptable carrier, diluent or excipient. In one embodiment, the preparation is a liquid preparation. In one embodiment, the concentration of the immune cells (e.g., CAR-T cells) in the preparation is $1\times10^3$-$1\times10^8$ cells/mL, or $1\times10^4$-$1\times10^7$ cells/mL.

Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. In some embodiments, the effective amount alleviates, relieves, ameliorates, improves, reduces the symptoms, or delays the progression of a disease or disorder in the subject. In some embodiments, the subject is a mammal. In some embodiments, the subject is a human.

Pharmaceutically acceptable carriers, including buffers, are well known in the art, and may comprise phosphate, citrate, and other organic acids; antioxidants including ascorbic acid and methionine; preservatives; low molecular weight polypeptides; proteins, such as serum albumin, gelatin, or immunoglobulins; amino acids; hydrophobic polymers; monosaccharides; disaccharides; and other carbohydrates; metal complexes; and/or non-ionic surfactants. See, e.g. Remington: The Science and Practice of Pharmacy 20th Ed. (2000) Lippincott Williams and Wilkins, Ed. K. E. Hoover.

The present pharmaceutical composition may be delivered to a cell by contacting the cell with the present pharmaceutical composition.

The present pharmaceutical composition may be delivered/administered to a subject by any route, including, without limitation, intravenous, intracerebroventricular (ICV) injection, intracisternal injection or infusion, oral, transdermal, ocular, intraperitoneal, subcutaneous, implant, sublingual, subcutaneous, intramuscular, rectal, mucosal, ophthalmic, intrathecal, intra-articular, intra-arterial, sub-arachinoid, bronchial and lymphatic administration. The present pharmaceutical composition may be administered parenterally or systemically. The present composition may be administered locally. The pharmaceutical composition may be formulated for intravenous administration.

The administration of the present compositions may be carried out in any convenient manner, including by aerosol inhalation, injection, ingestion, transfusion, implantation or transplantation. The compositions may be administered to a patient subcutaneously, intradermaliy, intratumorally, intranodally, intramedullary, intramuscularly, by intravenous (i.v.) injection, or intraperitoneally. In one embodiment, the compositions are administered to a subject (e.g., a patient) by intradermal or subcutaneous injection. In another embodiment, the compositions are administered by i.v. injection. The compositions may be injected directly into a tumor, lymph node, or site of disorder.

The present immune cells or pharmaceutical composition may be delivered/administered to a subject via intravenous, intramuscular, subcutaneous, intraperitoneal, spinal or other parenteral administration, such as by injection or infusion.

The present pharmaceutical compositions may be administered in a manner appropriate to the disease to be treated (or prevented). The quantity and frequency of administration will be determined by such factors as the condition of the patient, and the type and severity of the patient's disease, although appropriate dosages may be determined by clinical trials.

When "an effective amount", "a therapeutically effective amount", or "a therapeutic amount" is indicated, the precise amount of the compositions to be administered can be determined by a physician with consideration of individual differences in age, weight, tumor size, extent of infection or metastasis, and condition of the patient (subject). A pharmaceutical composition comprising the immune cells may be administered at a dosage of $10^4$ to $10^9$ cells/kg body weight, or $10^5$ to $10^6$ cells/kg body weight, including all integer values within those ranges. The compositions may also be administered multiple times at these dosages. The cells can be administered by using infusion techniques that are commonly known in immunotherapy (see, e.g., Rosenberg et al, New Eng. J. of Med. 319: 1676, 1988). The optimal dosage and treatment regime for a particular patient can readily be determined by one skilled in the art of medicine by monitoring the patient for signs of disease and adjusting the treatment accordingly.

The dosage of the above treatments to be administered to a patient may vary with the precise nature of the condition being treated and the recipient of the treatment. The scaling of dosages for patient administration can be performed according to art-accepted practices. In one embodiment, $1\times10^6$ to $1\times10^{10}$ of the immune cells (e.g., CAR-T cells) can be administered to a patient by means of, for example, intravenous infusion for each treatment or each course of treatment.

Conditions to be Treated

The present CAR, immune cells or pharmaceutical composition may be used to treat an autoimmune disease/disorder, or to treat cancer or tumor.

In certain embodiments, the present anti-CD20/BCMA bispecific CAR targets both B cells and plasma cells, which may reduce/eradicate autoimmune antibodies. In certain embodiments, the present anti-CD20/BCMA bispecific CAR may reduce/deplete B cells, plasmablasts, and/or long-lived plasma cells (LLPCs) to reduce/eradiate autoantibody production.

The present disclosure provides for a method of treating an autoimmune disease/disorder. The method may comprise administering the CAR, immune cells or pharmaceutical composition to a subject in need thereof.

The autoimmune disorder may be systemic lupus erythematosus (SLE), lupus nephritis (LN), systemic sclerosis (SSc), CREST syndrome (calcinosis, Raynaud's syndrome, esophageal dysmotility, sclerodactyl, and telangiectasia), opsoclonus, inflammatory myopathy (e.g., polymyositis, dermatomyositis, and inclusion-body myositis), myositis autoantibody-driven diseases, systemic scleroderma, primary biliary cirrhosis, celiac disease (e.g., gluten sensitive enteropathy), dermatitis herpetiformis, Miller-Fisher Syndrome, acute motor axonal neuropathy (AMAN), multifocal motor neuropathy with conduction block, autoimmune hepatitis, antiphospholipid syndrome, Wegener's granulomatosis, microscopic polyangiitis, Churg-Strauss syndrome, rheumatoid arthritis, chronic autoimmune hepatitis, scleromyositis, myasthenia gravis (MG), Lambert-Eaton myasthenic syndrome, Hashimoto's thyroiditis, Graves' disease, Paraneoplastic cerebellar degeneration, Stiff person syndrome, limbic encephalitis, Isaacs Syndrome, Sydenham's chorea, pediatric autoimmune neuropsychiatric disease associated with Streptococcus (PANDAS), encephalitis, diabetes mellitus type 1, neuromyelitis optica (NMO), chronic inflammatory bowel disease, Hashimoto's disease, organ transplant rejection, and/or neuromyelitis optica spectrum disorder (NMOSD).

The autoimmune disorder may be pernicious anemia, Addison's disease, psoriasis, inflammatory bowel disease (IBD), psoriatic arthritis, Sjögren's syndrome, lupus erythematosus (e.g., discoid lupus erythematosus, drug-induced lupus erythematosus, and neonatal lupus erythematosus), multiple sclerosis, and/or reactive arthritis.

The autoimmune disorder may be polymyositis, dermatomyositis, multiple endocrine failure, Schmidt's syndrome, autoimmune uveitis, adrenalitis, thyroiditis, autoimmune thyroid disease, gastric atrophy, chronic hepatitis, lupoid hepatitis, atherosclerosis, presenile dementia, demyelinating diseases, subacute cutaneous lupus erythematosus, hypoparathyroidism, Dressler's syndrome, autoimmune thrombocytopenia, idiopathic thrombocytopenic purpura, hemolytic anemia, pemphigus vulgaris, pemphigus, alopecia arcata, pemphigoid, scleroderma, progressive systemic sclerosis, adult onset diabetes mellitus (e.g., type II diabetes), male and female autoimmune infertility, ankylosing spondolytis, ulcerative colitis, Crohn's disease, sprue, mixed connective tissue disease, polyarteritis nedosa, systemic necrotizing vasculitis, juvenile onset rheumatoid arthritis, glomerulonephritis, atopic dermatitis, atopic rhinitis, Goodpasture's syndrome, Chagas' disease, sarcoidosis, rheumatic fever, asthma, recurrent abortion, antiphospholipid syndrome, farmer's lung, erythema multiforme, post cardiotomy syndrome, Cushing's syndrome, autoimmune chronic active hepatitis, bird-fancier's lung, allergic disease, allergic encephalomyelitis, toxic epidermal necrolysis, alopecia, Alport's syndrome, alveolitis, allergic alveolitis, fibrosing alveolitis, interstitial lung disease, erythema nodosum, pyoderma gangrenosum, transfusion reaction, leprosy, malaria, leishmaniasis, trypanosomiasis, Takayasu's arteritis, polymyalgia rheumatica, temporal arteritis, schistosomiasis, giant cell arteritis, ascariasis, aspergillosis, Sampter's syndrome, eczema, lymphomatoid granulomatosis, Behcet's disease, Caplan's syndrome, Kawasaki's disease, dengue, endocarditis, endomyocardial fibrosis, endophthalmitis, erythema elevatum et diutinum, erythroblastosis fetalis, eosinophilic faciitis, Shulman's syndrome, Felty's syndrome, filariasis, cyclitis, chronic cyclitis, heterochronic cyclitis, Fuch's cyclitis, IgA nephropathy, Henoch-Schonlein purpura, graft versus host disease, transplantation rejection, human immunodeficiency virus infection, echovirus infection, cardiomyopathy, Alzheimer's disease, parvovirus infection, rubella virus infection, post vaccination syndromes, congenital rubella infection, Hodgkin's and non-Hodgkin's lymphoma, renal cell carcinoma, multiple myeloma, Eaton-Lambert syndrome, relapsing polychondritis, malignant melanoma, cryoglobulinemia, Waldenstrom's macroglobulemia, Epstein-Barr virus infection, mumps, Evan's syndrome, and/or autoimmune gonadal failure.

The autoimmune diseases also include, e.g., acute disseminated encephalomyelitis, alopecia areata, antiphospholipid syndrome, autoimmune hepatitis, autoimmune myocarditis, autoimmune pancreatitis, autoimmune polyendocrine syndromesautoimmune uveitis, inflammatory bowel disease (Crohn's disease, ulcerative colitis), type I diabetes mellitus (e.g., juvenile onset diabetes), multiple sclerosis, scleroderma, ankylosing spondylitis, sarcoid, pemphigus vulgaris, pemphigoid, psoriasis, myasthenia gravis, systemic lupus erythematosus, rheumatoid arthritis, juvenile arthritis, psoriatic arthritis, Behcet's syndrome, Reiter's disease, Berger's disease, dermatomyositis, polymyositis, antineutrophil cytoplasmic antibody-associated vasculitides (e.g., granulomatosis with polyangiitis (also known as Wegener's granulomatosis), microscopic polyangjitis, and Churg-Strauss syndrome), scleroderma, Sjogren's syndrome, anti-glomerular basement membrane disease (including Goodpasture's syndrome), dilated cardiomyopathy, primary biliary cirrhosis, thyroiditis (e.g., Hashimoto's thyroiditis, Graves' disease), transverse myelitis, allergies, arthritis, fibromyalgia, fibromytosis, lupus, vitiligo, and Guillane-Barre syndrome.

The autoimmune diseases include inflammatory bowel disease (IBD), ulcerative colitis, Crohn's disease, sprue, autoimmune arthritis, rheumatoid arthritis, Type I diabetes, multiple sclerosis, graft vs. host disease following bone marrow transplantation, osteoarthritis, juvenile chronic arthritis, Lyme arthritis, psoriatic arthritis, reactive arthritis, spondy loarthropathy, systemic lupus erythematosus, insulin dependent diabetes mellitus, thyroiditis, asthma, psoriasis, dermatitis scleroderma, atopic dermatitis, graft versus host disease, acute or chronic immune disease associated with organ transplantation, sarcoidosis, atherosclerosis, disseminated intravascular coagulation, Kawasaki's disease, Grave's disease, nephrotic syndrome, chronic fatigue syndrome, Wegener's granulomatosis, Henoch-Schoenlejn purpurea, microscopic vasculitis of the kidneys, chronic active hepatitis, uveitis, septic shock, toxic shock syndrome, sepsis syndrome, cachexia, acquired immunodeficiency syndrome, acute transverse myelitis, Huntington's chorea, Parkinson's disease, Alzheimer's disease, stroke, primary biliary cirrhosis, hemolytic anemia, polyglandular deficiency type I syndrome and polyglandular deficiency type II syndrome, Schmidt's syndrome, adult (acute) respiratory distress syndrome, alopecia, alopecia areata, seronegative arthopathy, arthropathy, Reiter's disease, psoriatic arthropathy, chlamydia, yersinia and salmonella associated arthropathy spondyloarhopathy, atheromatous disease/arteriosclerosis, atopic allergy, food allergies, autoimmune bullous disease, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, myalgic encephalitis/Royal Free Disease, chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, Hepatitis C, common varied immunodeficiency (common variable hypogammaglobulinaemia), dilated cardiomyopathy, fibrotic lung disease, cryptogenic fibrosing alveolitis, postinflammatory interstitial lung disease, interstitial pneumonitis, connective tissue disease associated interstitial lung disease, mixed connective tissue disease associated lung disease, systemic sclerosis associated interstitial lung disease, rheumatoid arthritis associated interstitial lung disease, systemic lupus erythematosus associated lung disease, dermatomyositis/polymyositis associated lung disease, Sjogren's disease associated lung disease, ankylosing spondy litis associated lung disease, vasculitic diffuse lung disease, haemosiderosis associated lung disease, drug-induced interstitial lung disease, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycemia, type B insulin resistance with acanthosis nigricans, hypoparathyroidism, acute immune disease associated with organ transplantation, chronic immune disease associated with organ transplantation, osteoarthrosis, primary sclerosing cholangitis, idiopathic leucopenia, autoimmune neutropenia, renal disease NOS, glomerulonephritides, microscopic vasulitis of the kidneys, discoid lupus, erythematosus, male infertility idiopathic or NOS, sperm autoimmunity, multiple sclerosis (all subtypes), insulindependent diabetes mellitus, sympathetic ophthalmia, pulmonary hypertension secondary to connective tissue disease, Goodpasture's syndrome, pulmonary manifestation of polyarteritis nodosa, acute rheumatio fever, rheumatoid spondylitis, Still's disease, systemic sclerosis, Takayasu's disease/arteritis, autoimmune thrombocytopenia, idiopathic thrombocytopenia, autoimmune thyroid disease, hyperthyroidism, goitrous autoimmune hypothyroidism (Hashimoto's disease), atrophic autoimmune hypothyroidism, primary myxoedema, phacogenic uveitis, primary vasculitis, vitiligo, allergic rhinitis (pollen allergies), anaphylaxis, pet allergies, latex allergies, drug allergies, allergic rhinoconjuctivitis, eosinophilic esophagitis, hypereosinophilic syndrome, eosinophilic gastroenteritis cutaneous lupus erythematosus, eosinophilic esophagitis, hypereosinophilic syndrome, and eosinophilic gastroenteritis.

The autoimmune disorder may be an inflammatory muscle disease. Inflammatory myopathies are a group of diseases that involve chronic muscle inflammation, muscle weakness, and in some cases, muscle pain. The four main types of chronic, or long-term, inflammatory myopathy are: polymyositis, which affects skeletal muscles (the type involved in body movement) on both sides of the body; dermatomyositis, which causes progressive muscle weakness; inclusion body myositis, which is characterized by slow, progressive muscle weakness and muscle shrinking and loss of muscle; and necrotizing autoimmune myopathy, which involves muscle weakness in the upper and lower body.

In another embodiment, the autoimmune disease is an autoimmune disease caused by overexpression of B cells (such as lupus erythematosus).

Also encompassed by the present disclosure is a method of treating cancer. The method may comprise administering the CAR, immune cells or pharmaceutical composition to a subject in need thereof.

The present disclosure provides chimeric antigen receptors for treating CD20-positive diseases such as B cell lymphoma.

The cancer may be a BCMA-positive malignancy. The cancer may be multiple myeloma (MM), or plasma cell leukemia.

The cancer may be a hematologic cancer. The cancer may be a plasma-cell malignancy. The cancer may be a B-cell malignancy. The B-cell malignancy may be acute lymphocytic leukemia (ALL), chronic lymphocytic leukemia (CLL), B-cell acute lymphoblastic leukemia (B-ALL), B-cell leukemia, or B cell lymphoma.

The cancer may be Hodgkin's lymphoma, non-Hodgkin's lymphoma, leukemia, and/or multiple myeloma (MM).

The cancer may be acute myeloid leukemia (AML), multiple myeloma (MM), chronic lymphocytic leukemia (CLL), chronic myelogenous leukemia, acute lymphoblastic leukemia (ALL), diffuse large B cell lymphoma (DLBCL), or a combination thereof.

Diseases that may be treated using the present CAR, immune cells or pharmaceutical composition include CD20-positive tumors and diseases, e.g., caused by excessive B cells (such as autoimmune diseases, for example, lupus erythematosus, etc.). CD20-positive tumors may include CD20-positive non-solid tumors (such as hematological cancer, for example, leukemias and lymphomas) or solid tumors. Tumors or cancers to be treated with present CAR, immune cells or pharmaceutical composition include, but are not limited to, carcinoma, blastoma, and sarcoma, and leukemia or lymphoid malignancies, benign and malignant tumors, and malignancies e.g., sarcomas, carcinomas, gastric cancer, peritoneal metastasis of gastric cancer, liver cancer, renal cancer, lung cancer, small intestine cancer, bone cancer, prostate cancer, colorectal cancer, breast cancer, large intestine cancer, cervical cancer, ovarian cancer, lymphoma, nasopharyngeal carcinoma, adrenal tumor, bladder tumor, non-small cell lung cancer (NSCLC), glioma, endometrial cancer, and melanomas. Adult tumors/cancers and pediatric tumors/cancers are included.

Hematologic cancers are cancers of the blood or bone marrow. Examples of hematological (or hematogenous) cancers include leukemias, e.g., acute leukemias (such as acute lymphocytic leukemia, acute myelocytic leukemia, acute myelogenous leukemia and myeloblasts, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

The cancer may be a solid tumor. Solid tumors can be benign or malignant. Different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, mesothelioma, malignant lymphoma, pancreatic cancer and ovarian cancer.

Kits

Also within the scope of the present disclosure are kits for use of the present CARs, immune cells, nucleic acids, vectors or pharmaceutical compositions. Such kits may include one or more containers comprising the present CARs, immune cells, nucleic acids, vectors or pharmaceutical compositions.

In some embodiments, the kit can comprise instructions for use in any of the methods described herein. The included instructions can comprise a description of administration of the pharmaceutical composition to a subject to achieve the intended activity in a subject. The kit may further comprise a description of selecting a subject suitable for treatment based on identifying whether the subject is in need of the treatment. In some embodiments, the instructions comprise a description of administering the pharmaceutical compositions to a subject who is in need of the treatment.

The instructions relating to the use of the pharmaceutical compositions generally include information as to dosage, dosing schedule, and route of administration for the intended treatment. The containers may be unit doses, bulk packages (e.g., multi-dose packages) or sub-unit doses.

The kits provided herein are in suitable packaging. Suitable packaging includes, but is not limited to, vials, bottles, jars, flexible packaging, and the like.

The following examples of specific aspects for carrying out the present disclosure are offered for illustrative purposes only, and are not intended to limit the scope of the present disclosure in any way.

Example 1 Construction of Anti-CD20/BCMA CARs

We prepared eight bispecific CARs having the anti-CD20 scFv and anti-BCMA scFv in the same order (i.e., anti-CD20 scFv ("OF") followed by anti-BCMA scFv ("B20")), but with different $V_H/V_L$ orders and having different hinge regions and/or transmembrane domains: TOB1-4 and TOBL1-4, where TOBL1 is C-CAR168 (FIG. 1).

The anti-CD20/BCMA CAR-T cells were prepared using apheresis from healthy donors. Specifically, PBMCs were isolated from the venous blood of healthy donors by density gradient centrifugation. On day 0, PBMCs were activated in a cell culture flask previously coated with CD3 monoclonal antibody (OKT3) and Retronectin (TAKARA). The medium was GT-551 cell culture medium containing 1% human albumin and 300 U/mL recombinant human interleukin 2 (IL-2). On day 3, activated PBMCs were transduced with lentiviral vectors encoding the anti-CD20/BCMA CARs.

Figure 2:
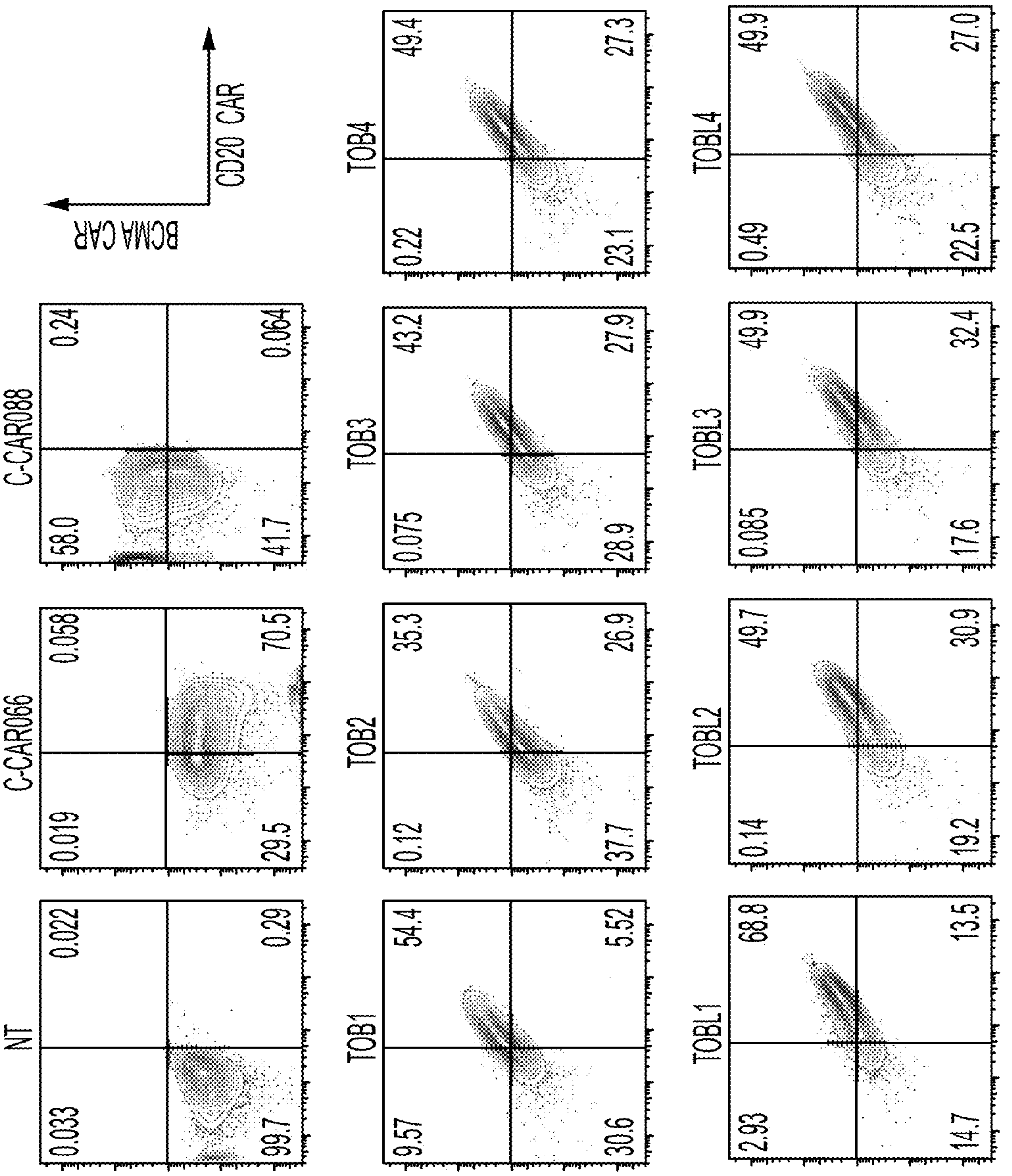
FIG. 2 shows the expression level of anti-CD20 and anti-BCMA CARs on the surface of the T cells.
Figure 3A:
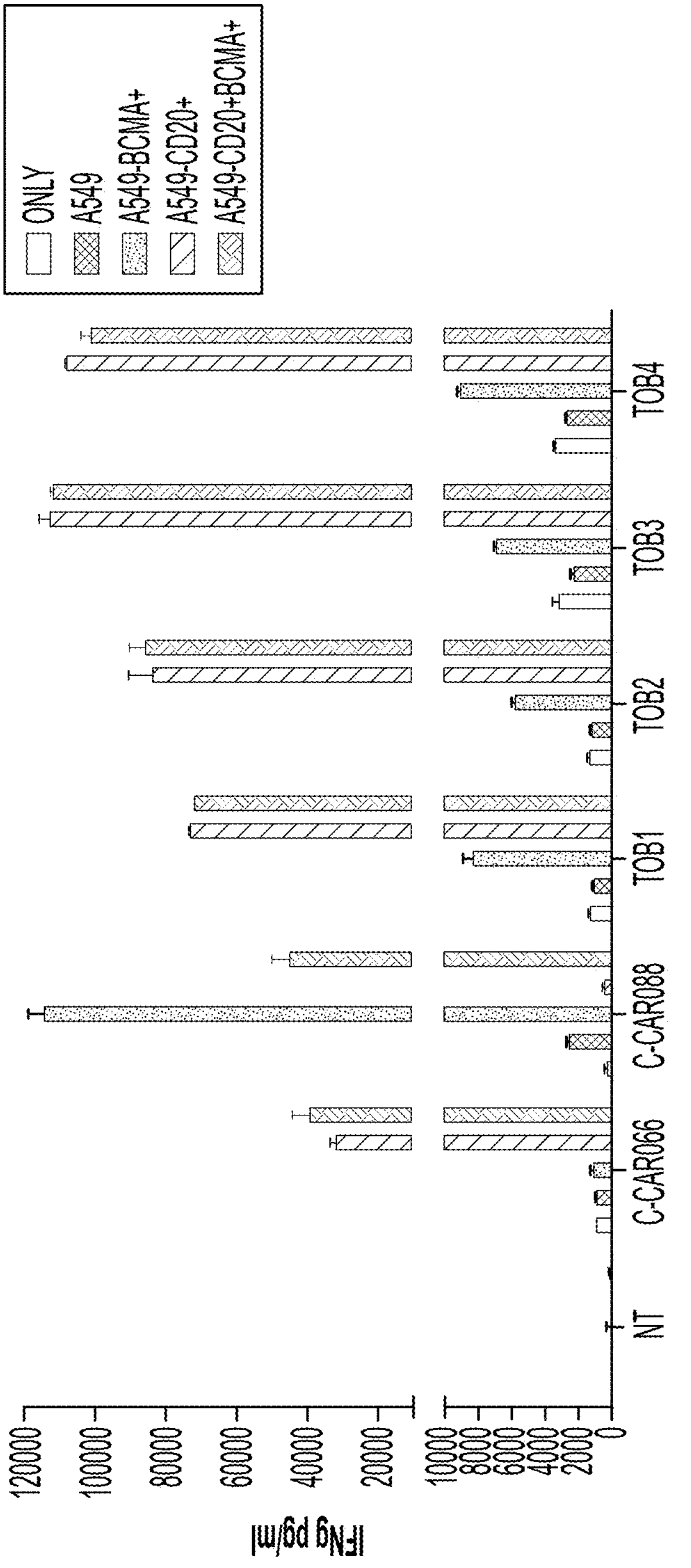
FIGS. 3A-3C show the levels of IFN-γ secreted by the activated CAR-T cells in vitro in the cell culture supernatant.
Figure 3B:
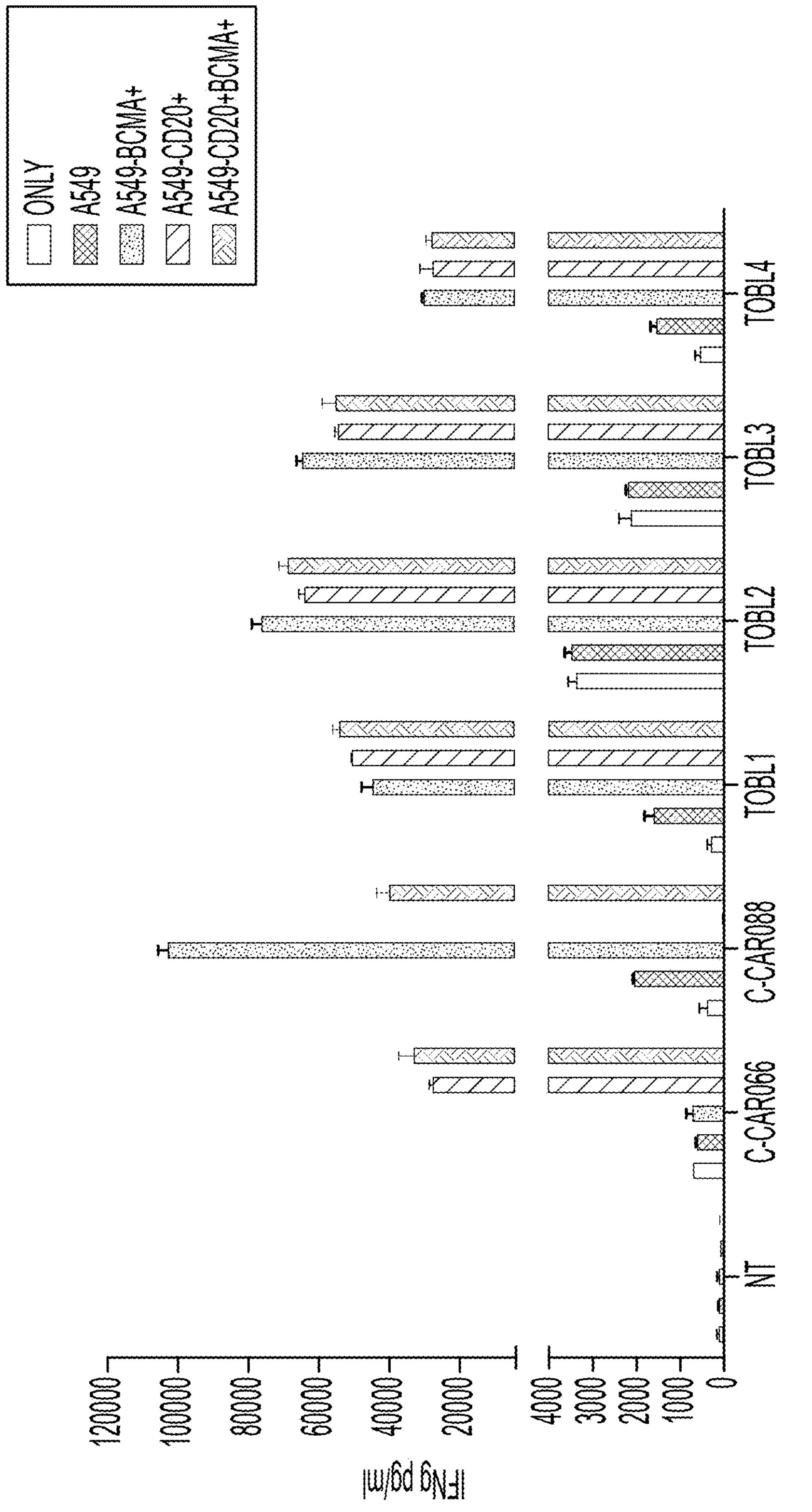
Figure 3C:
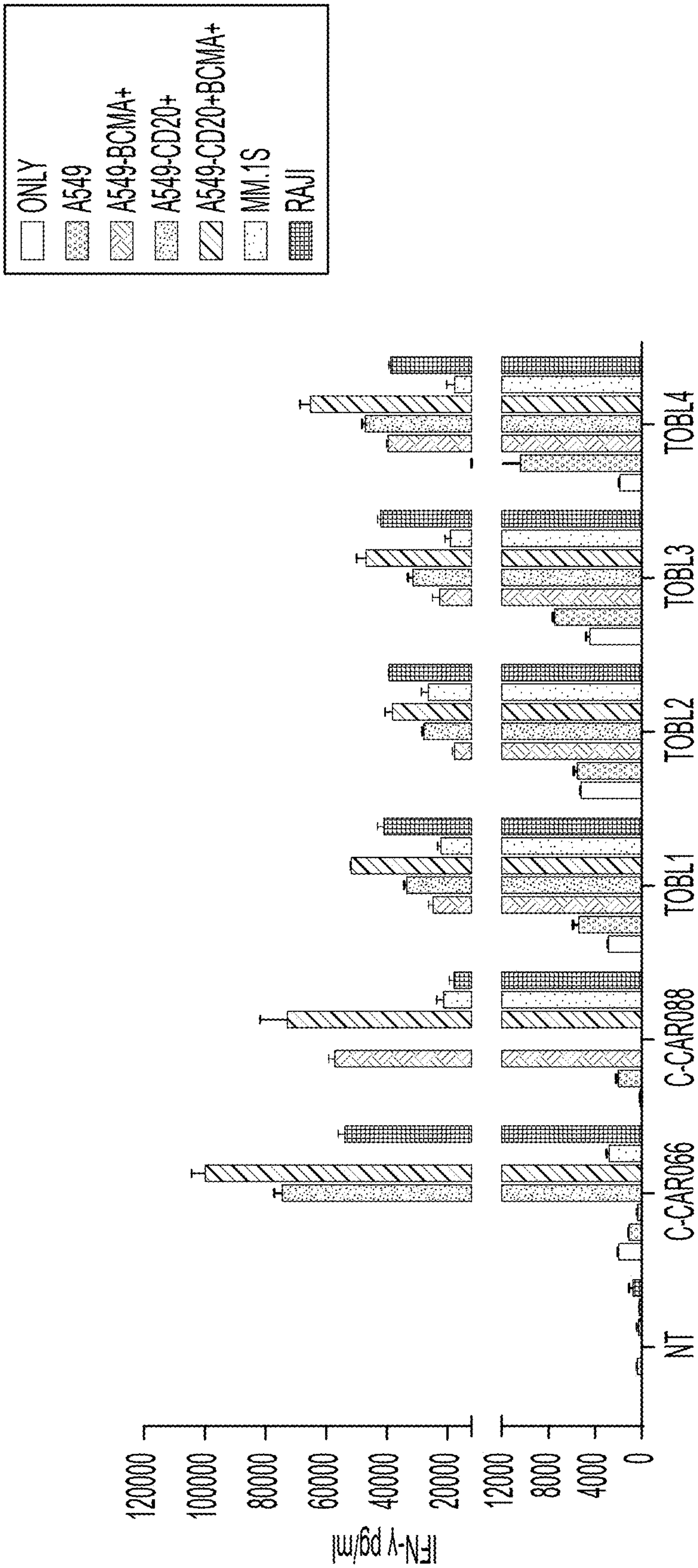

FIG. 2 shows the expression levels of the anti-CD20 and anti-BCMA CARs on the surface of the T cells. The expression levels of anti-BCMA CARs were detected by flow cytometry using BCMA-Fc fusion protein; the expression levels of anti-CD20 CARs were detected by flow cytometry using antibody specific to OF scFv.

Example 2 Antigen-Specific Activation of Anti-CD20/BCMA CAR-T Cells In Vitro

Antigen-specific activation of the anti-CD20/BCMA CAR-T was evaluated by assaying IFN-γ release and CD137 expression when the CAR-T cells were co-cultured with target cells. Target cells ("T") included CD20-positive A549-CD20+ tumor cells, BCMA-positive A549-BCMA+ tumor cells, CD20 and BCMA double positive A549-CD20+ BCMA+ tumor cells, Raji cells, MM.1S cells, and double negative A549 tumor cells. Effector cells ("E") are the anti-CD20/BCMA CAR-T cells.

PBMCs were isolated from the venous blood of healthy donors by density gradient centrifugation. On day 0, PBMCs were activated in a cell culture flask previously coated with CD3 monoclonal antibody (OKT3) and Retronectin (TAKARA). The medium was GT-551 cell culture medium containing 1% human albumin and 300 U/mL recombinant human interleukin 2 (IL-2). On day 3, activated PBMCs were transduced with lentiviral vectors encoding the anti-CD20/BCMA CARs. Starting from day 6, the CAR-T cells can be taken for activity assays.

IFNγ release was assayed using the CAR-T cells cultured for 7 days. $1\times10^5$ of CAR-T cells were cultured with CD20-positive A549-$CD20^+$ tumor cells, BCMA-positive A549-BCMA+ tumor cells, CD20 and BCMA double positive A549-$CD20^+$ BCMA+ tumor cells, double negative A549 tumor cells, or without tumor cells (NT), in 200 μl of medium for 18 h with an E:T ratio of 1:1. Then the levels of IFN-γ secreted in the cell culture supernatant were detected by ELISA.

Expression levels of CD137 were assayed using the CAR-T cells cultured for 7 days. $1\times10^5$ of CAR-T cells were cultured with CD20-positive A549-CD20+ tumor cells, BCMA-positive A549-BCMA+ tumor cells, CD20 and BCMA double positive A549-CD20+BCMA+ tumor cells, double negative A549 tumor cells, or without tumor cells, in 200 μl of medium for 18 h with an E:T ratio of 1:1. Then the expression levels of CD137 on the surface of the CAR-T cells were detected by flow cytometry.

The IFNγ release results are shown in FIGS. 3A-3C and FIG. 6B. After co-culturing the CAR-T cells with A549 cells expressing CD20 and/or BCMA antigens, anti-CD20 CAR-T (C-CAR066) cells can specifically recognize CD20 single-positive or CD20/BCMA double-positive target cells and release IFN-γ. Similarly, anti-BCMA CAR-T (C-CAR088) cells can specifically recognize BCMA single-positive or CD20/BCMA double-positive target cells to release IFN-γ. Only anti-CD20/BCMA CAR-T (TOB1-4 and TOBL1-4, where TOBL1 is C-CAR168) cells can recognize CD20 single-positive, BCMA single-positive and CD20/BCMA double-positive target cells, as well as release high levels of IFN-γ. TOB1 to TOB4 CAR-T cells showed high IFN-γ release when co-cultured with CD20 positive targets cells, but lower reactivity to BCMA single positive target cells. TOBL1 to TOBL4 CAR-T cells showed high IFN-γ release when co-cultured with CD20 positive targets and BCMA positive target cells. TOBL1 to TOBL4 CAR-T cells showed high IFN-γ release when co-cultured with target cells naturally expressing CD20 and BCMA.

Figure 4A:
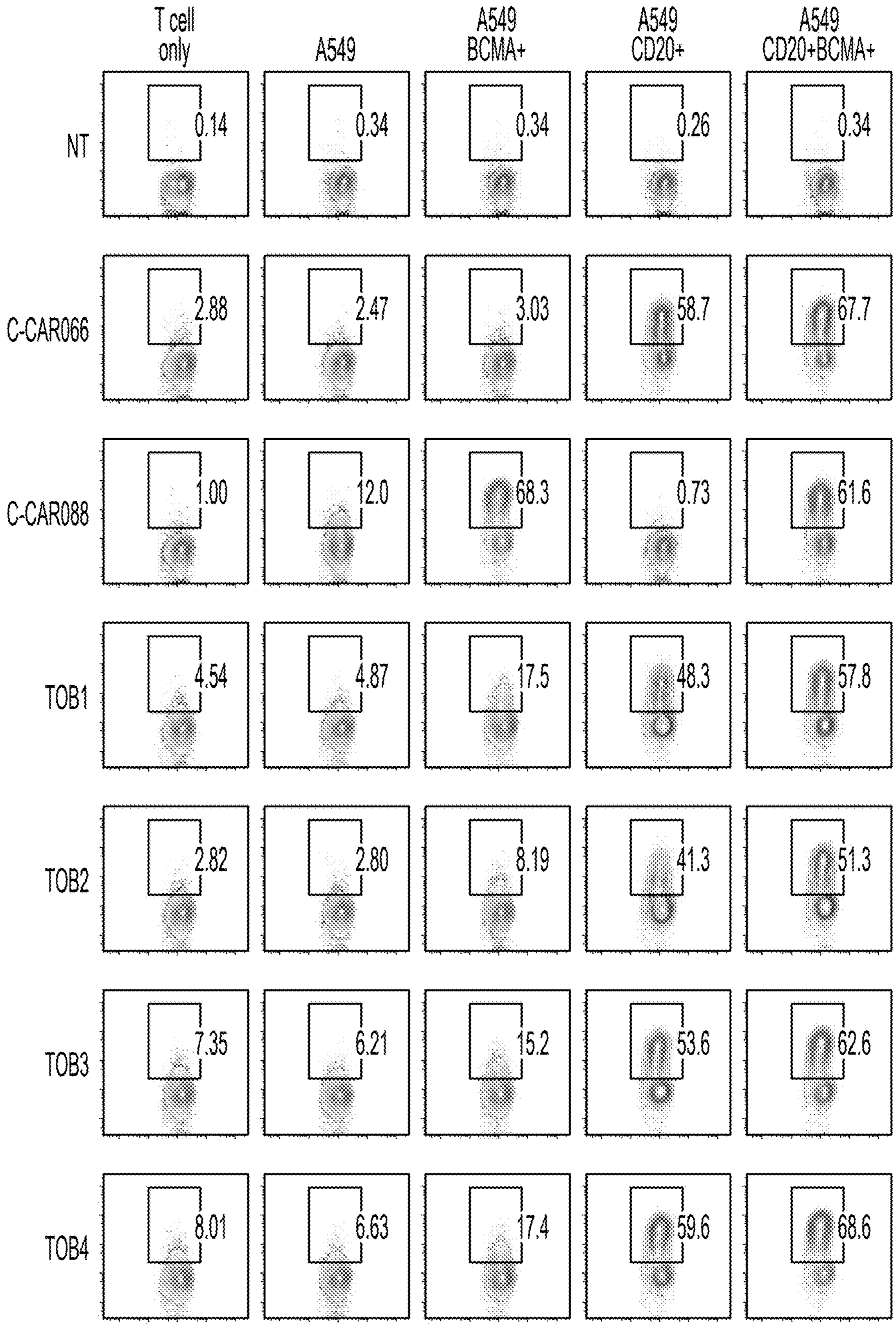
FIGS. 4A-4B show the expression levels of CD137 on the surface of the activated CAR-T cells.
Figure 4B:
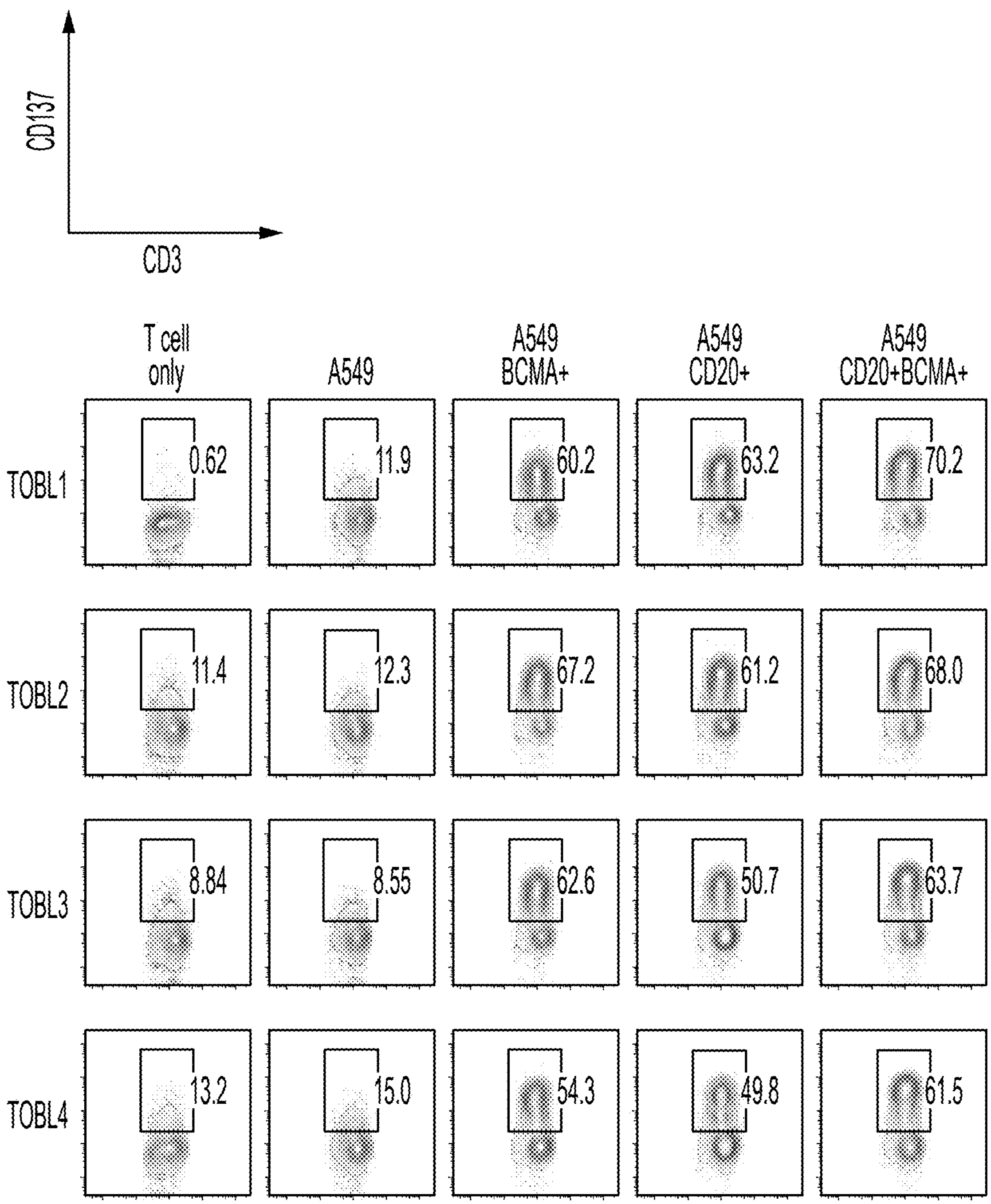

The flow cytometry results showed that the anti-CD20/BCMA CAR-T cells were activated by a variety of CD20/BCMA single-positive or double-positive cells and up-regulated the expression level of CD137 (FIGS. 4A and 4B).

Example 3 Cytotoxicity of Anti-CD20/BCMA CAR-T Cells In Vitro

The anti-CD20/BCMA CAR-T cells were co-cultured with target cells at E:T ratios of 0:1, 0.25:1, 0.5:1, 1:1, 2:1 and 4:1, respectively. Real-Time Cell Analysis (RTCA) label-free technology was used to evaluate the cytotoxicity of the CAR-T cells on target cells.

Figure 5A:
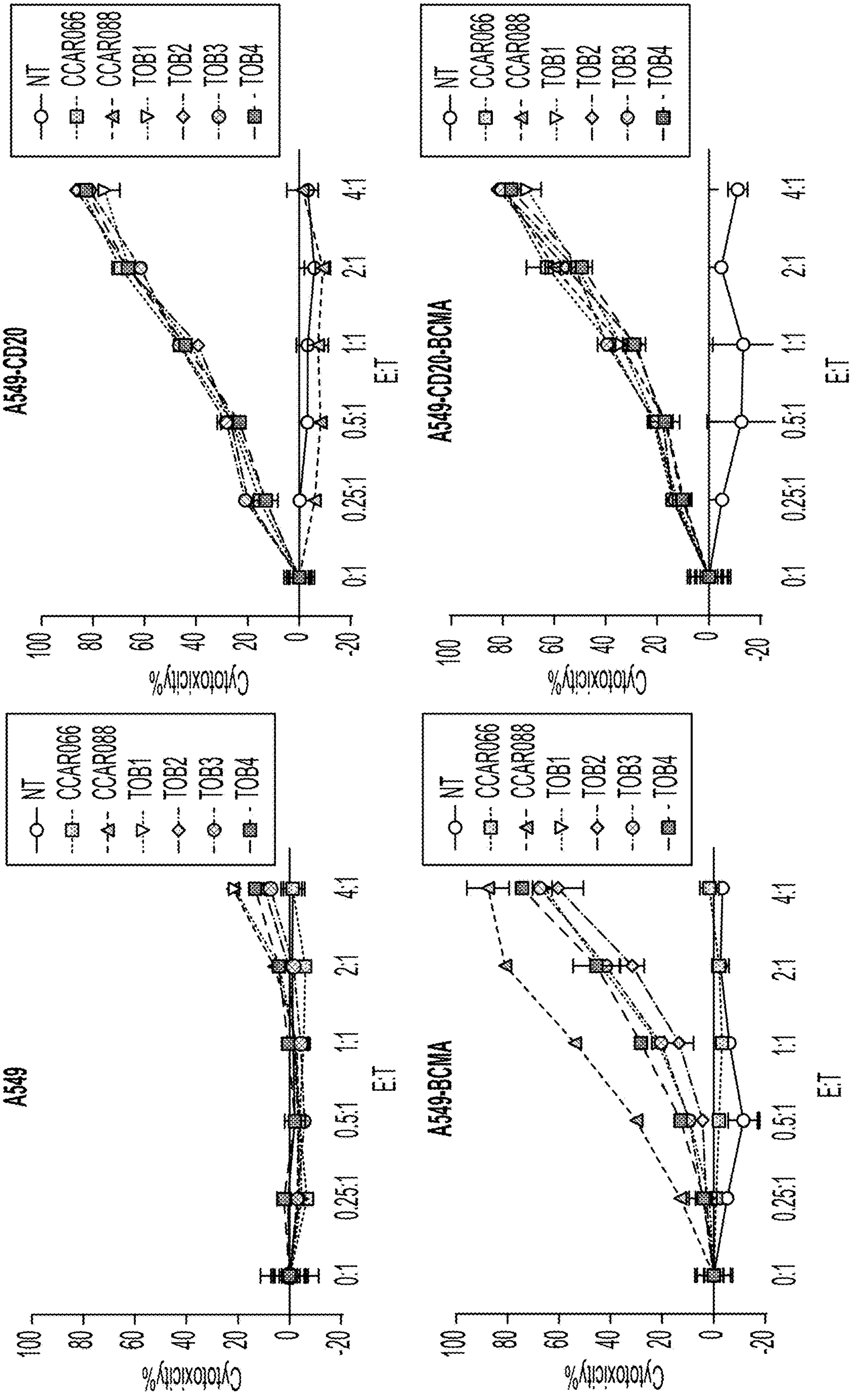
FIGS. 5A-5B show the in vitro cytotoxicity of CAR-Ts cells
Figure 5B:
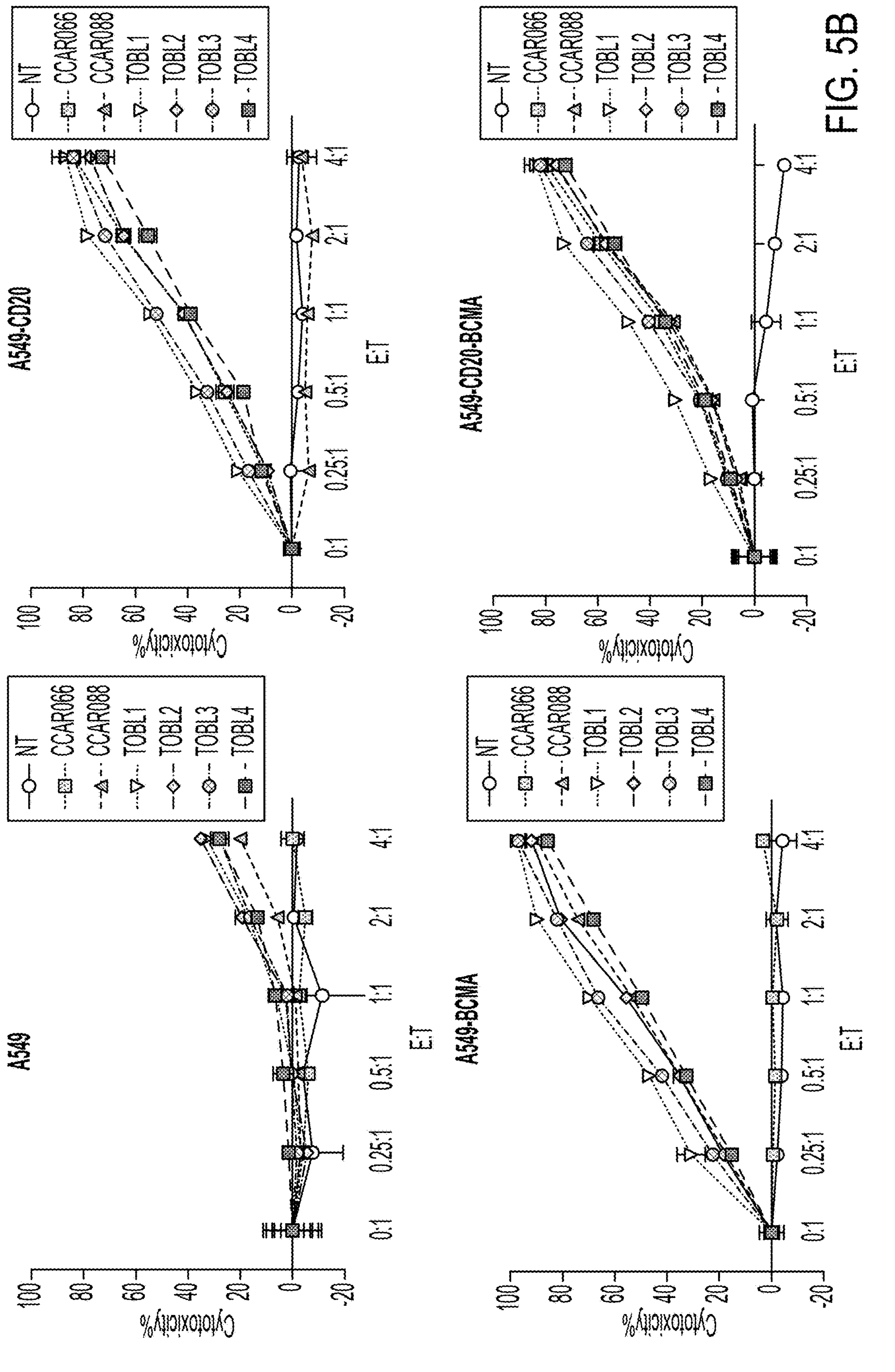
Figure 6A:
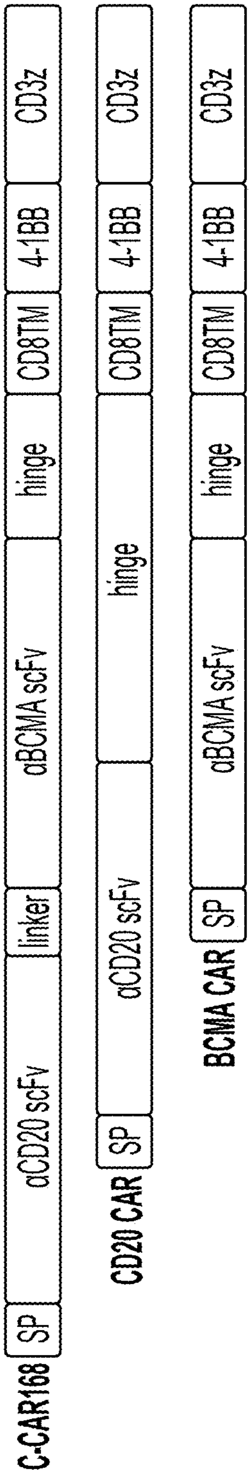
FIGS. 6A-6C: C-CAR168 shows robust potency against CD20+ and BCMA+ cells in vitro.
Figure 6B:
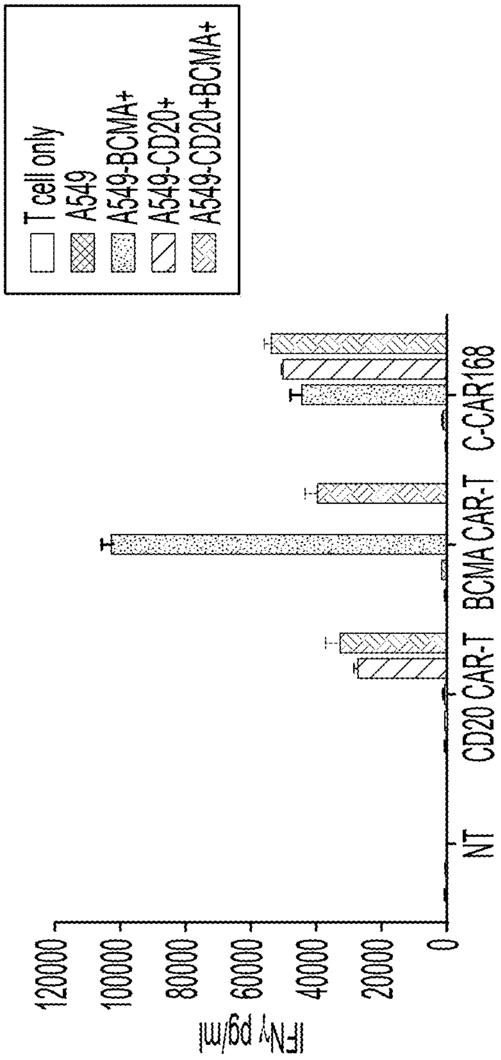
Figure 6C:
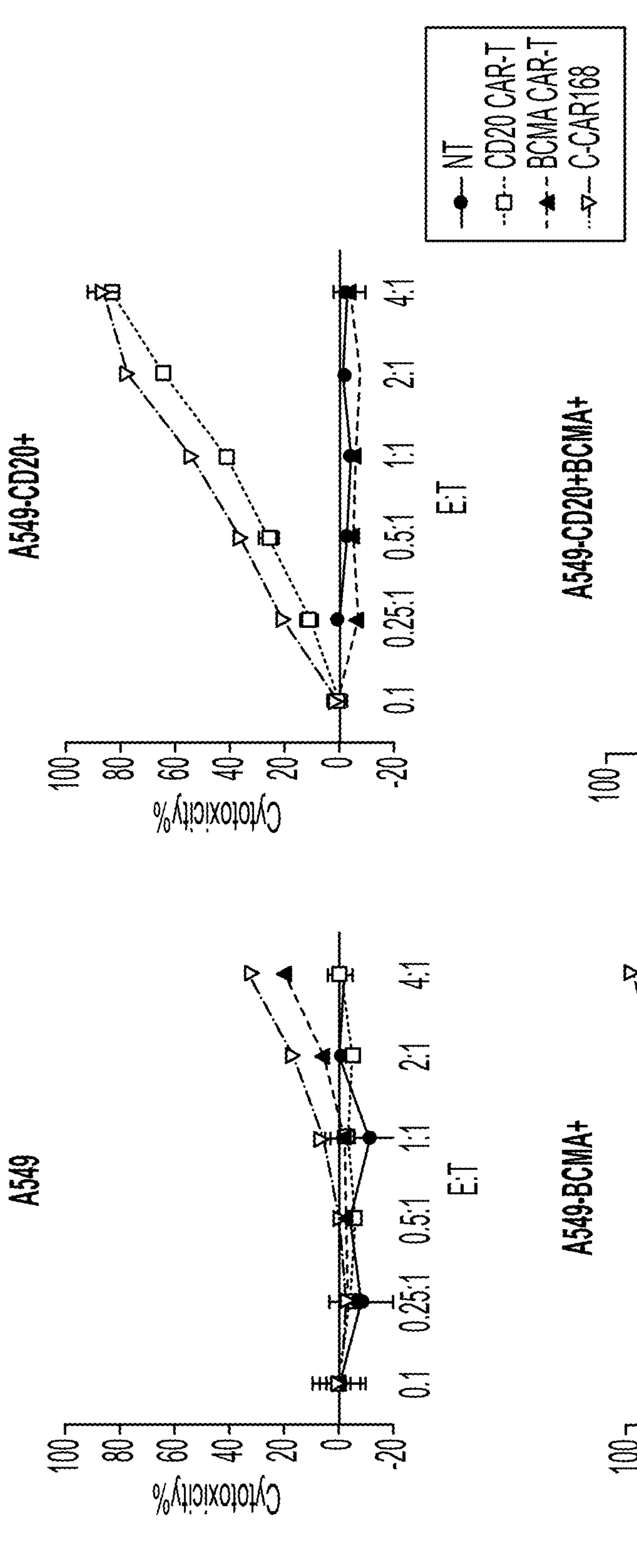

The results show that the anti-CD20/BCMA CAR-T cells effectively killed CD20/BCMA single-positive or double-positive tumor cells in vitro (A549-CD20+, A549-BCMA+, A549-BCMA+CD20+), while they had no effect on A549 cells which do not express CD20 or BCMA (FIGS. 5A-5B, FIG. 6C). Their killing ability was comparable to the anti-CD20 and anti-BCMA monospecific CAR-T cells, with all being dose-dependent (FIGS. 5A-5B, FIG. 6C). The TOBL1 to TOBL4 CAR-T cells (FIG. 5B) showed high cytotoxicity to CD20-positivie and BCMA-positive target cells. The TOB1 to TOB4 CAR-T cells (FIG. 5A) showed lower cytotoxicity to BCMA single positive target cells (compared to anti-BCMA CAR which is C-CAR088).

Example 4 Cytotoxicity of Anti-CD20/BCMA CAR-T Cells on Autoreactive B Cells In Vitro Recent studies have shown that in patients with systemic lupus erythematosus (SLE), the proportion of $CD11c^{hi}T$-$bet^+$ B cell subsets is significantly increased, and is closely related to the production of autoantibodies and the patient's clinical manifestations. Autoantibodies are characteristics of reactive B cells (see, Distinct Effector B Cells Induced by Unregulated Toll-like Receptor 7 Contribute to Pathogenic Responses in Systemic Lupus Erythematosus, Immunity, 2018, 16; 49(4):725-739.e6. IL-21 drives expansion and plasma cell differentiation of autoreactive CD11chiT-bet+ B cells in SLE, Nat. Commun. 2018; 9(1):1758). This subset of cells is enriched with age in some animal models of autoimmune diseases and in the peripheral blood of patients with rheumatoid arthritis, so they are also called age-associated B cells (ABCs) (see, Toll-like receptor 7 (TLR7)-driven accumulation of a novel $CD11c^+$ B-cell population is important for the development of autoimmunity. Blood, 2011; 118(5):1305-15. A B-cell subset uniquely responsive to innate stimuli accumulates in aged mice, Blood, 2011; 118(5):1294-304).

TLR7 activation plays a role in the accumulation of autoreactive B cells and the production of autoantibodies in autoimmune diseases. One of the consequences of aberrant TLR7 activation is the accumulation of autoreactive B cells, or age-associated B cells (ABCs). ABCs are B cells that recognize self-antigens and have the potential to produce autoantibodies, which can target and damage the body's own tissues. Wang et al., Nature Communications, (2018) 9:1758.

Figure 7A:
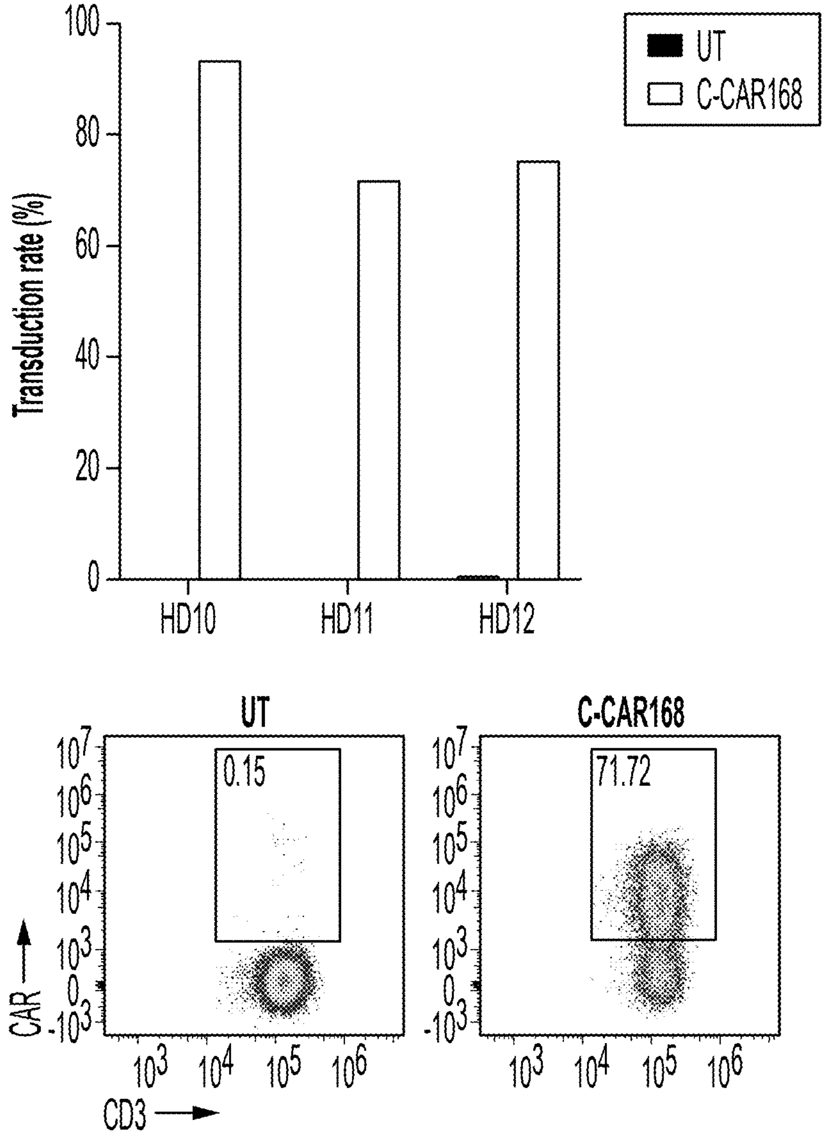
FIGS. 7A-7C: Cytotoxicity of C-CAR168 on ABC-enriched B cells in vitro.
Figure 7B:
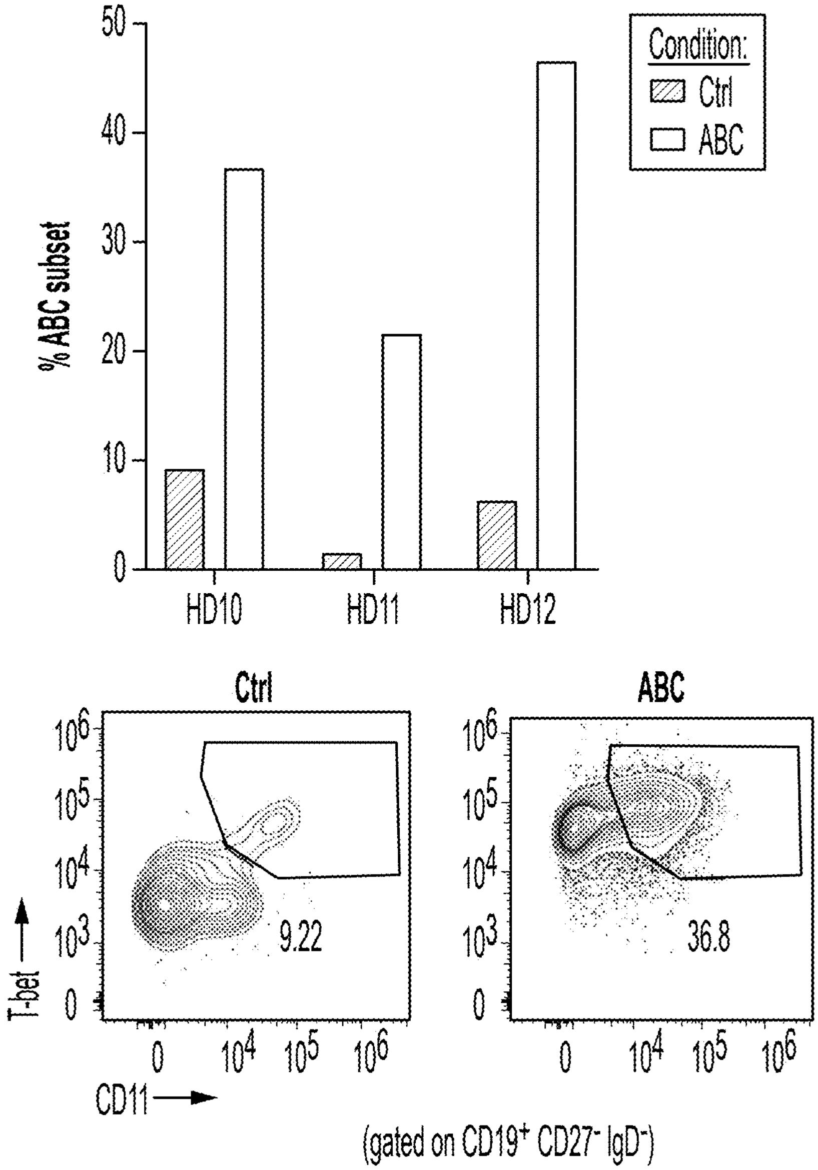
Figure 7C:
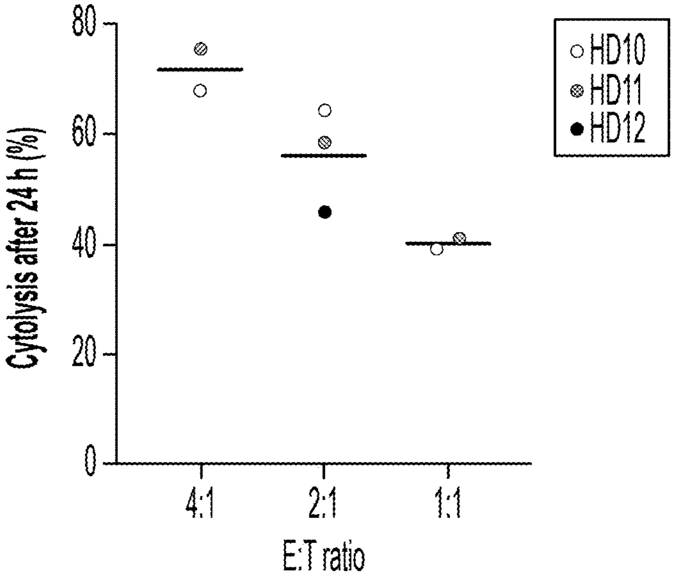

In order to verify that the anti-CD20/BCMA CAR-T cells also have the ability to eliminate ABCs, we prepared C-CAR168 (TOBL1) CAR-T cells from the peripheral blood of three healthy human donors (HD10, HD11 and HD12). We also isolated autologous B cells from the PBMCs of heathy donors and induced their differentiation in vitro to obtain ABC-enriched autologous B cells which were then used as target cells to perform cytotoxicity experiments. After co-culture for 2 to 4 hours, C-CAR168 CAR-T cells derived from different donors showed apparent cytotoxicity effects on the ABC-enriched autologous B cells at different E:T ratios compared with control T cells without CAR transduction (FIGS. 7A-7C).

C-CAR168 can target both CD20+ B cells and BCMA+ plasma cells, which can provide superior duration of response in autoimmune diseases. The results show C-CAR168 CAR-T cells can eliminate ABC cells efficiently.

In Vitro ABC Differentiation

PBMCs from healthy donors were isolated by gradient centrifugation using Ficoll and cryopreserved. On the day of ABC differentiation, pan B cells were first isolated from thawed PBMC by human B cell isolation kit (Miltenyi Biotec; negative selection, e.g., non-B cells were labeled and depleted) according to the manufacturer's instructions. B cells were then seeded in 96-well plates with 200 μl RPMI complete medium and stimulated with TLR7 ligand R848, CD40L, BAFF, IL-2, Goat Anti-Human IgA+IgG+IgM (H+L), IL-21, and IFN-γ for 3 days. Cell medium was exchanged every day by replenishing with the complete medium and stimulation cocktail. The induction of ABCs was confirmed by FACS analysis. Antibodies for FACS staining included live/dead dye, anti-human CD19, CD38, CD27, IgD, CD11c, CD21, and T-bet.

Cytotoxicity Assay

After differentiation, the ABC-enriched B cells were cocultured with C-CAR168 or non-transduced (NT) T cells at the indicated E:T ratios. After 24 hours, cells were stained with the LIVE/DEAD Fixable Aqua Dead Cell Stain (Invitrogen) to determine their viability, along with anti-CD19 and anti-CD3 antibodies to distinguish B and T cells. Cytotoxicity was determined by the depletion of the percentage of viable $CD19^+$ cells. The cytolysis of B cells was calculated by the following formula: Percentage of lysis (%) (1−(viable $CD19^+$ cell fraction of the C-CAR168 coculture/viable $CD19^+$ cell fraction of UT coculture))×100. See, Lin et al., Preclinical evaluation of $CD8^+$ anti-BCMA mRNA CAR T-cells for treatment of multiple myeloma. Leukemia. 2021, 35(3): 752-763.

Example 5 Inhibitory Effect of Anti-CD20/BCMA CAR-T Cells on Tumor Cells in Mice C-CAR168 Effectively Inhibited the Growth of CD20 Single Positive and BCMA Single Positive Tumor Cells in Tumor-Bearing Mice The in vivo cytotoxicity effect of the anti-CD20/BCMA CAR-T cells on CD20 or BCMA single-positive cells was evaluated by mouse subcutaneous tumor model established using tumor cell lines expressing either CD20 (A549-CD20) or BCMA (MM.1S).

6-8 weeks female B-NDG mice were subcutaneously inoculated with A549-CD20 (CD20+) or MM.1S (BCMA+) cells. When the average tumor volume reached 100 $mm^3$, C-CAR168 CAR-T cells were administered via the tail vein at the dosage of 3-5×$10^6$ CAR-T cells/mouse. During the experiment, the tumor volume of the mice treated with the C-CAR168 CAR-T cells continued to decrease. At the end of the experiment, the tumor weight of the C-CAR168 groups was significantly lower than that of the vehicle control group. C-CAR168 cells showed strong cytotoxicity towards CD20-positive and BCMA-positive target cells in vivo.

Figure 9A:
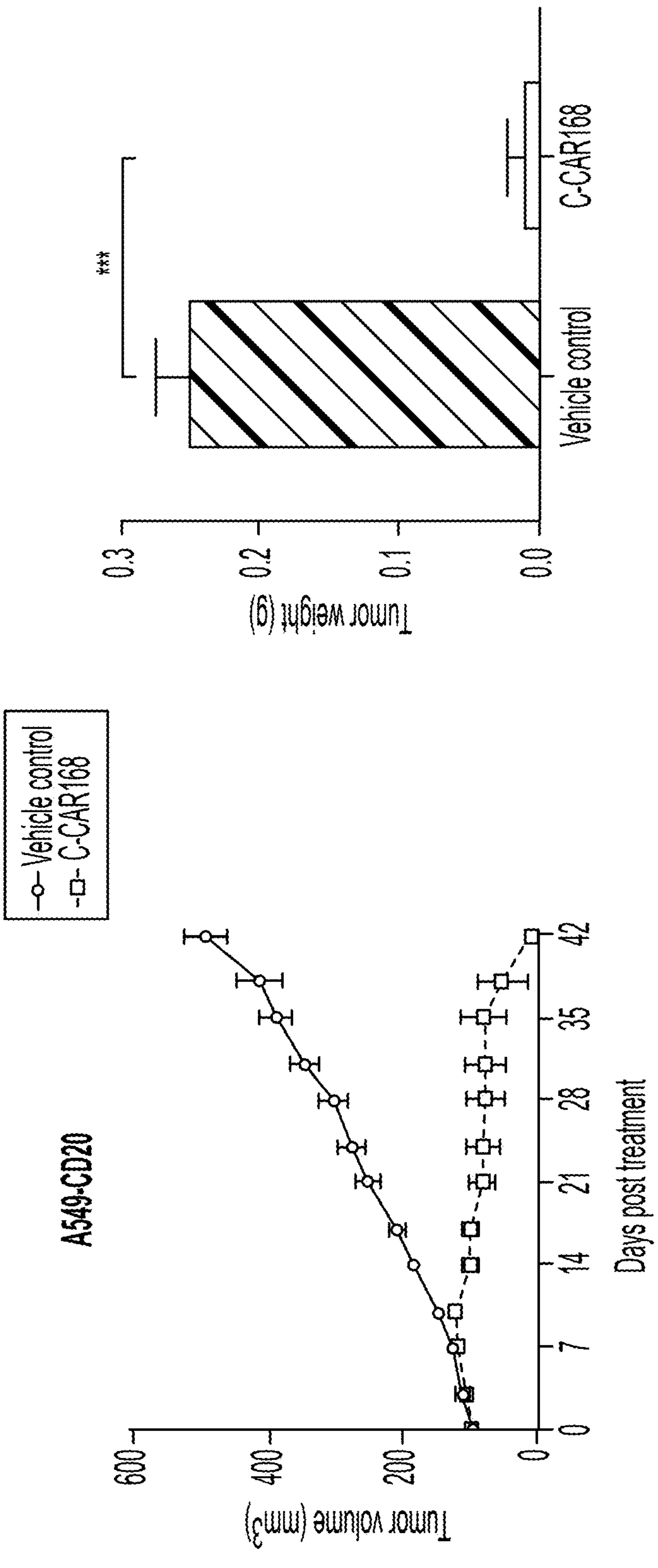
FIGS. 9A-9G: In vivo cytotoxicity of C-CAR168 in tumor-bearing mice.

Specifically, female B-NDG (NOD.Cg-$Prkdc^{scid}$ $Il2rg^{tm1\,Vst}$/Vst) mice were subcutaneously inoculated with 5×$10^6$ A549-CD20 cells/animal. When the average tumor volume reached about 100 $mm^3$, 20 animals were selected and randomly divided into 2 groups (vehicle control group vs. C-CAR168 group), with 10 animals in each group. A single dose of a vehicle control or C-CAR168 (3×$10^6$ CAR-T cells/animal) was administered to the mice by tail vein injection. After administration, the average tumor volume in the vehicle control group continued to increase, reaching 494.16±31.5 $mm^3$ on Day 42, with an average tumor weight of 0.254±0.025 g. The average tumor volumes in the C-CAR168 group began to decrease from Day 10. By Day 42, the average tumor volumes were 10.02±7.04 $mm^3$ (FIG. 9A, left panel), and the tumor weights were 0.013±0.01 g, with significant differences compared to the vehicle control group (P<0.001) (FIG. 9A, right panel). The tumor growth inhibition rates calculated based on tumor weight were 94.88%. The results show that C-CAR168 can significantly inhibit the growth of CD20-positive target cells in vivo.

Figure 9B:
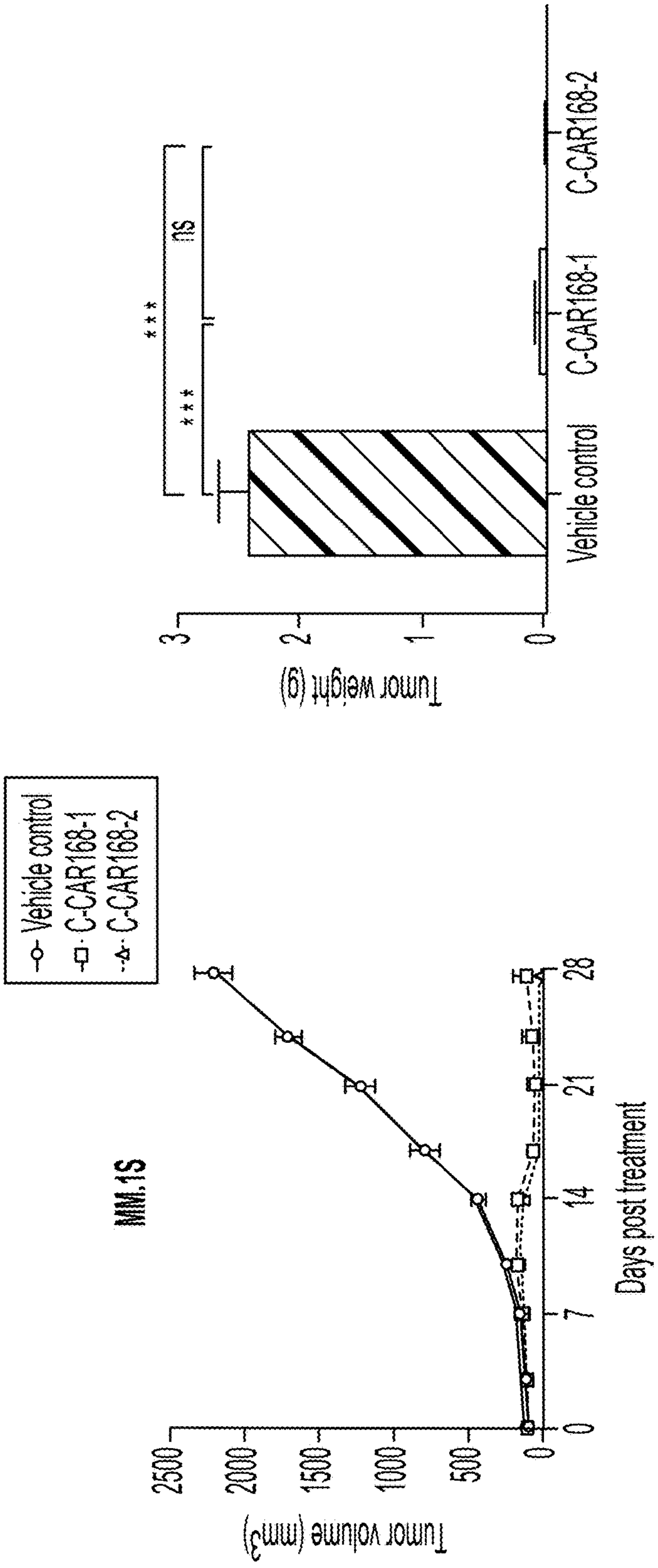
Figure 9C:
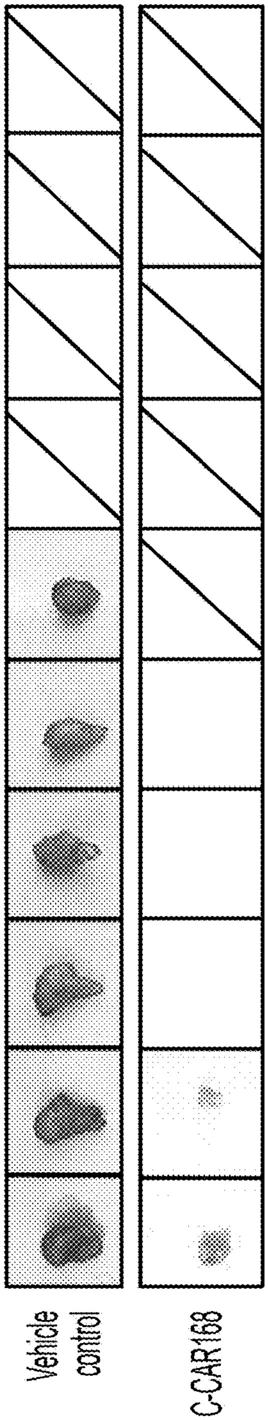
Figure 9D:
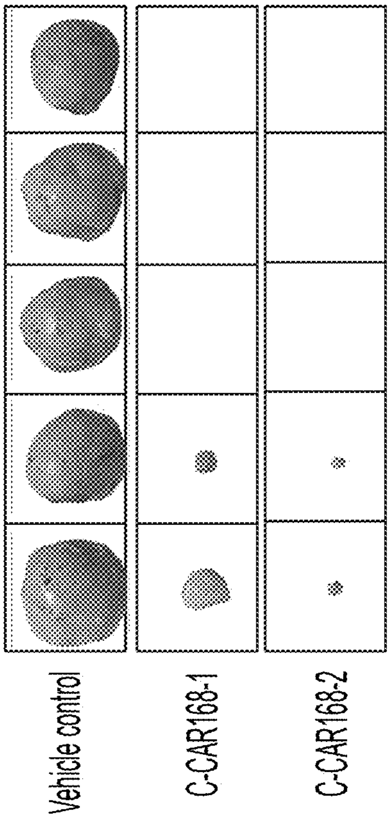

To evaluate the in vivo effects of C-CAR168 on BCMA single positive target cells and compare in vivo efficacy of different batches of C-CAR168, 20 female B-NDG (NOD.CB17-$Prkdc^{scid}Il2rg^{tm1}$/Bcgen) mice were subcutaneously inoculated with 5×$10^6$ MM.1S cells/animal. When the average tumor volume reached about 100 $mm^3$, 15 animals were selected and randomly divided into 3 groups (a vehicle control group vs. two C-CAR168 groups), with 5 animals in each group. Each mouse was dosed once by tail vein injection. For C-CAR168, the dosage was 5×$10^6$ CAR-T cells/animal. After administration, the average tumor volume in the vehicle control group continued to increase, reaching 2220.86±117.35 $mm^3$ on Day 28, with a tumor weight of 2.409±0.216 g. The average tumor volumes in the C-CAR168-1 and C-CAR168-2 groups began to decrease from Day 10 (FIG. 9B, left panel). By Day 28, the average tumor volumes were 109.2±88.92 $mm^3$ and 9.07±5.58 $mm^3$, respectively, and the tumor weights were 0.041±0.034 g and 0.003±0.002 g, respectively (FIG. 9B, right panel), with significant differences compared to the vehicle control group, (P<0.001, P<0.001). The tumor growth inhibition rates calculated based on tumor weight were 98.30% and 99.88%, respectively. There was no significant difference between the two batches of C-CAR168. The results show that a single intravenous administration of 5×$10^6$ C-CAR168 CAR-T cells/mouse was well tolerated in B-NDG tumor-bearing mice, and C-CAR168 can significantly inhibit the growth of BCMA-positive target cells in vivo.

C-CAR168 Effectively Inhibited the Growth of CD20 and BCMA Double Positive Tumor Cells in Tumor-Bearing Mice To evaluate the in vivo anti-tumor effects of C-CAR168, 65 female B-NDG (NOD.CB17-$Prkdc^{scid}Il2rg^{tm1}$/Bcgen) mice were subcutaneous inoculated with 1×$10^6$ K562-CD20-BCMA cells/animal. When the average tumor volume reached about 100 $mm^3$, 50 animals were selected and randomly divided into 5 groups: vehicle control group, T cell control group, C-CAR168 low-dose group (1×$10^6$ CAR-T cells/mouse), medium-dose group (5×$10^6$ CAR-T cells/mouse) and high-dose group (10×$10^6$ CAR-T cells/mouse). The T cell control group were injected with non-transduced T cells from the same donor as C-CAR168, and the dose was consistent with the total T cell number in the C-CAR168 high-dose group. Each mouse was dosed once by tail vein injection.

Figure 9E:
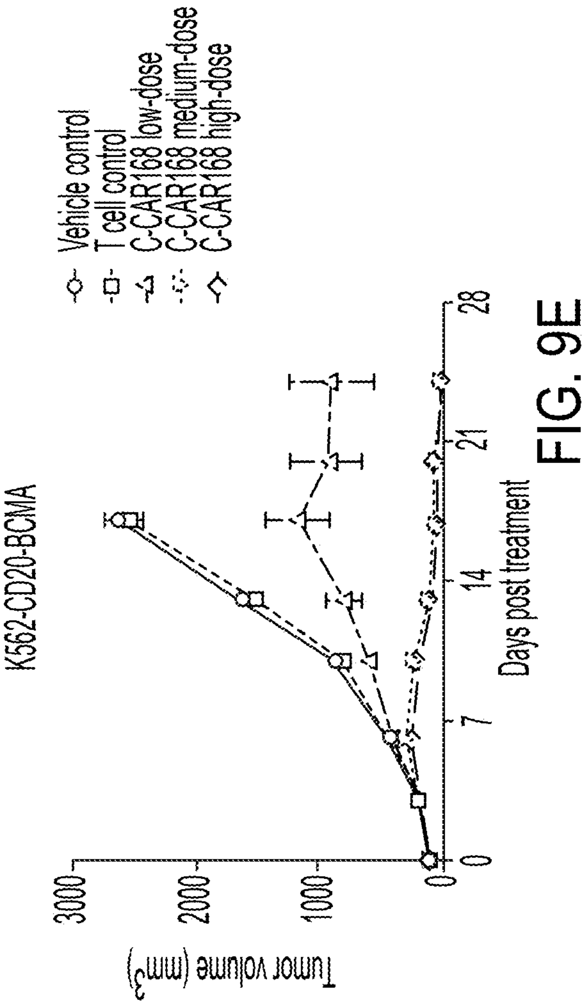
Figure 9F:
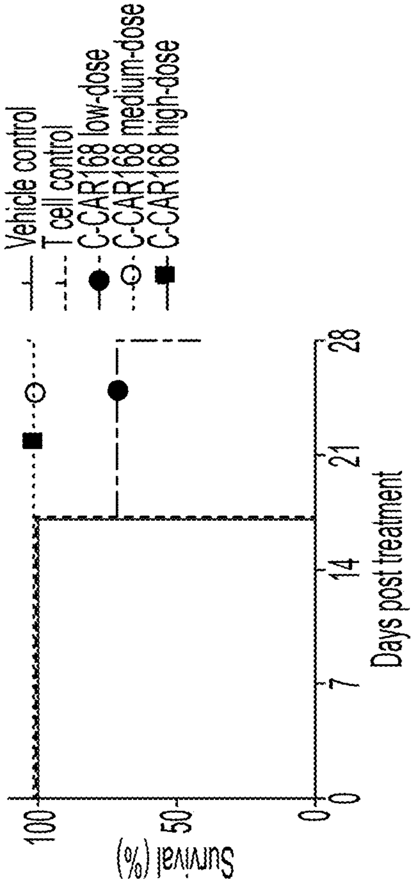
Figure 9G:
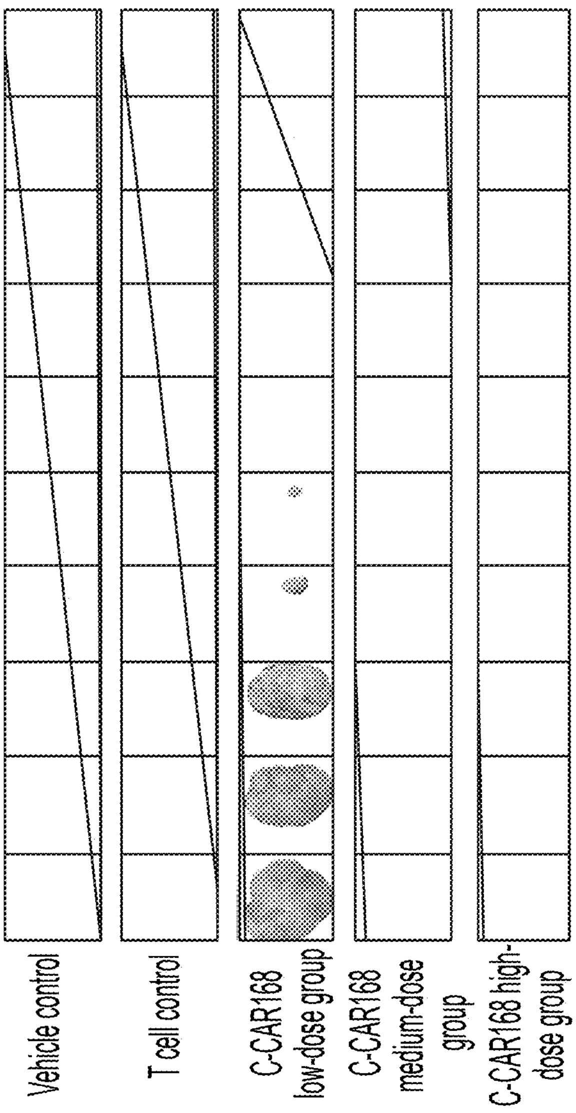

During the experiment, the mean tumor volume of the animals in the vehicle control group and T cell control group continued to increase, and the mean tumor volume was 2628.78±117.32 $mm^3$ and 2536.23±97.80 $mm^3$, respectively at Day 17. The tumor volume in the C-CAR168 low-dose group continued to increase, although after 10 days of administration, the tumor volume was significantly lower than that in the vehicle control group and T cell control group. The average tumor volume of the C-CAR168 medium-dose group and high-dose group began to decline on Day 6. The C-CAR168 low-dose, medium-dose, and high-dose groups showed dose-dependent reductions in tumor, with tumor growth inhibition rates being 55.47%, 97.75%, and 98.01%, respectively on Day 17. No tumor tissues were observed in the C-CAR168 medium-dose and high-dose groups on Day 28 (FIG. 9E). FIG. 9F shows the survival rate curve of each group during the experimental period. Although all animals in the vehicle control group and T cell control group were dead around Day 17, all mice in the C-CAR168 medium-dose and high-dose groups were alive.

In summary, a single intravenous administration of $1\times10^6$, $5\times10^6$ or $10\times10^6$ C-CAR168 CAR-T cells/mouse was well tolerated in B-NDG tumor bearing mice, and C-CAR168 significantly inhibited the growth of K562-CD20-BCMA tumor cells in a dose-dependent manner.

Example 6 Antigen Specificity of Anti-CD20/BCMA CARs

In the membrane protein array, genetic engineering methods are used to construct the full-length cDNA sequences of human membrane proteins into expression vectors, which are then transiently transfected into HEK293T cells and arranged into an array by using microfluidic technology or chip printing technology. It is a high-throughput screening technology for studying the interaction between test substances and membrane proteins.

To examine the affinity and specificity of the anti-CD20/BCMA CARs, we used a membrane protein array assay to evaluate the risk of off-target binding between the antigen-binding domain of C-CAR168 and 5220 human cell membrane proteins.

Figure 8A:
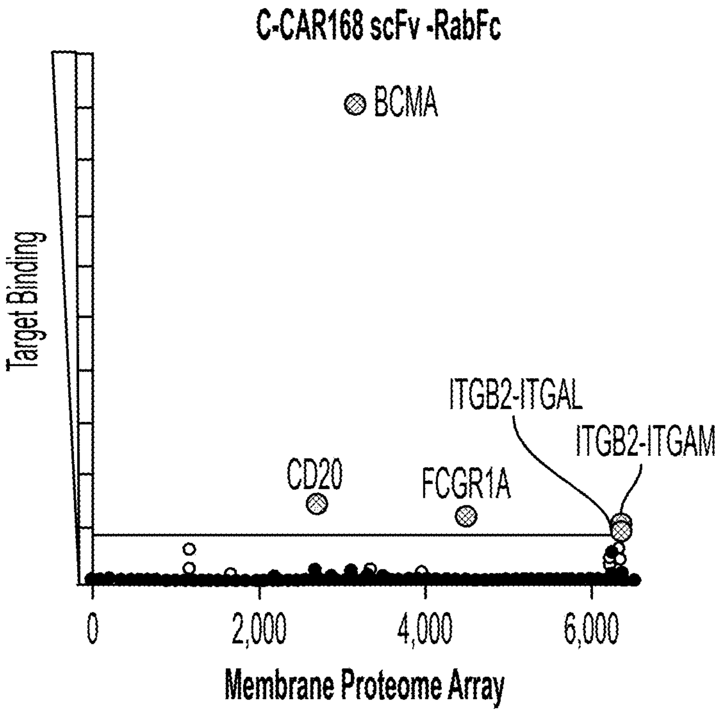
FIGS. 8A-8D: C-CAR168 bears no cross-reactivity against human membrane proteome.
Figure 8B:
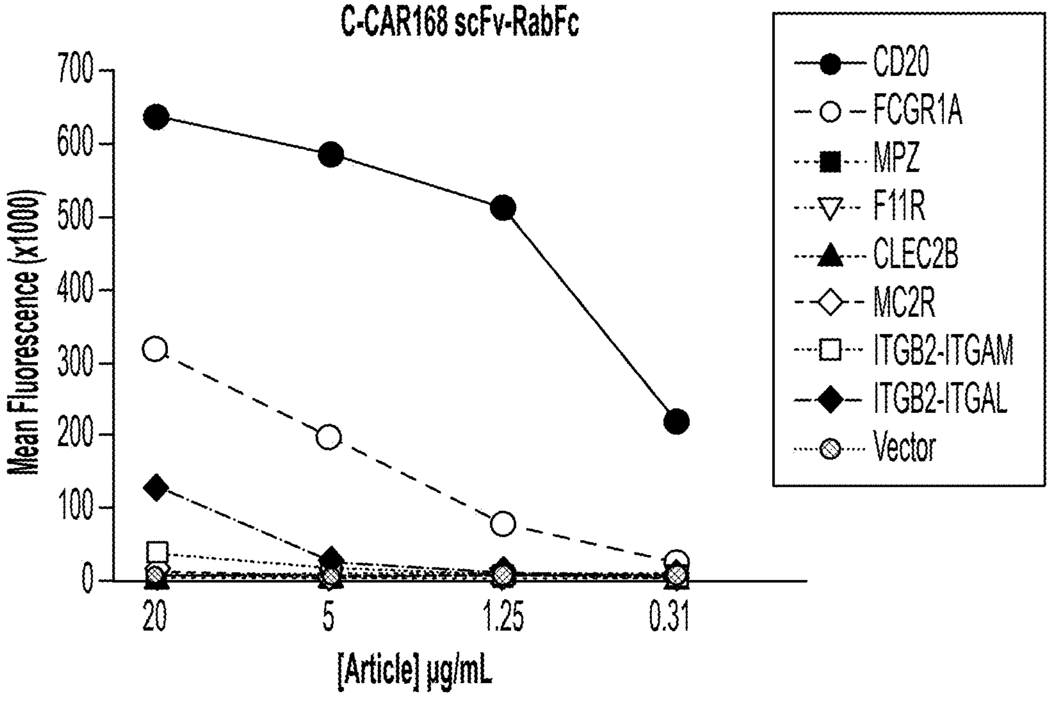
Figure 8C:
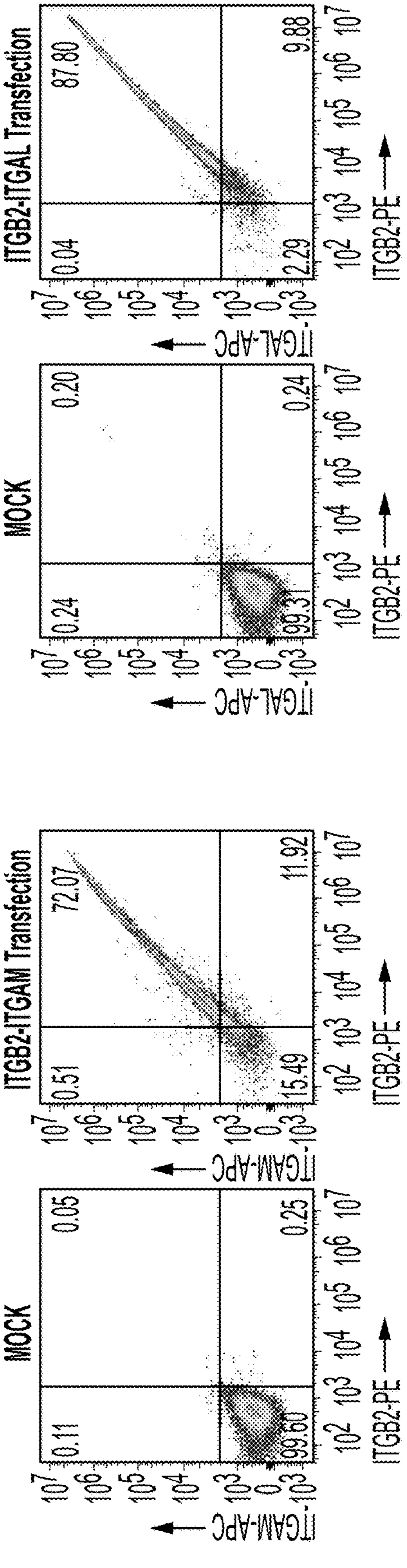

A chimeric rabbit monoclonal antibody, C-CAR168 scFv-RabFc, was generated by linking the anti-CD20 scFv (e.g., derived from the Ofatumumab mAb) and the anti-BCMA scFv (e.g., derived from the BCMA-20 mAb) in frame with a rabbit IgG Fc region. The chimeric antibody was added at a concentration of 20 μg/mL to the HEK293T cell array transiently transfected with 5220 membrane proteins. Flow cytometry results show that C-CAR168 scFv-RabFc bound strongly to human CD20 and BCMA (FIG. 8A). The average fluorescence intensity of its binding to CD20 and BCMA in flow cytometry was about 60-fold and 110-fold of that of the negative control group, respectively (FIG. 8B). In addition to CD20 and BCMA, C-CAR168 scFv-RabFc showed specific binding to FCGR1A (FIG. 8B), and the average fluorescence intensity was 2.5 times that of the negative control group. This is mainly due to the binding between FCGR1A and the rabbit-derived Fc of the recombinant protein; so there is no relevant risk in clinical applications. C-CAR168 scFv-RabFc showed weak binding to ITGB2-ITGAM and ITGB2-ITGAL heterodimers, and the average fluorescence intensity was 2 to 3 times that of the negative control group. For other proteins discovered in the preliminary screening (MPZ, F11R, CLEC2B and MC2R), the average fluorescence intensity binding to C-CAR168 scFv-RabFc did not change with concentration. At the concentrations of 20 μg/mL and 5 μg/mL, it did not exceed 2 times that of the negative control group, so the possibility of these proteins binding specifically to C-CAR168 scFv was low or minimal.

To test whether ITGB2-ITGAM and ITGB2-ITGAL heterodimers expressed on the cell membrane can be recognized by C-CAR168 CAR-T cells to activate downstream events, C-CAR168 was co-cultured with 293T cells transfected with ITGB2-ITGAM or ITGB2-ITGAL. Expression of CD137 on C-CAR168 CAR-T cells, as well the levels of IFN-γ, TNF-α, IL-2 and other cytokines in the cell culture supernatant, were essayed. 293T cells transfected with empty vector were used as negative control, and 293T cells transfected with CD20 and BCMA were used as positive control.

CD137 (4-1BB) is a cell surface marker for antigen-specific activation of T cells. The antigen-specific activation of CAR-T cells can be assessed by detecting the up-regulation of CD137 expression on the cell surface. The experiment found that after three batches of C-CAR168 cells were co-cultured with cells expressing CD20 and BCMA, the proportion of 4-1BB-positive cells increased compared with non-transduced T cells ("NT"). After co-culturing with those expressing ITGB2-ITGAM and ITGB2-ITGAL, the proportion of 4-1BB positive cells was not significantly different from that in the non-transduced T cell group ("NT") (FIG. 8D, left panel), indicating that C-CAR168 does not bind specifically to ITGB2-ITGAM or ITGB2-ITGAL in vitro.

Figure 8D:
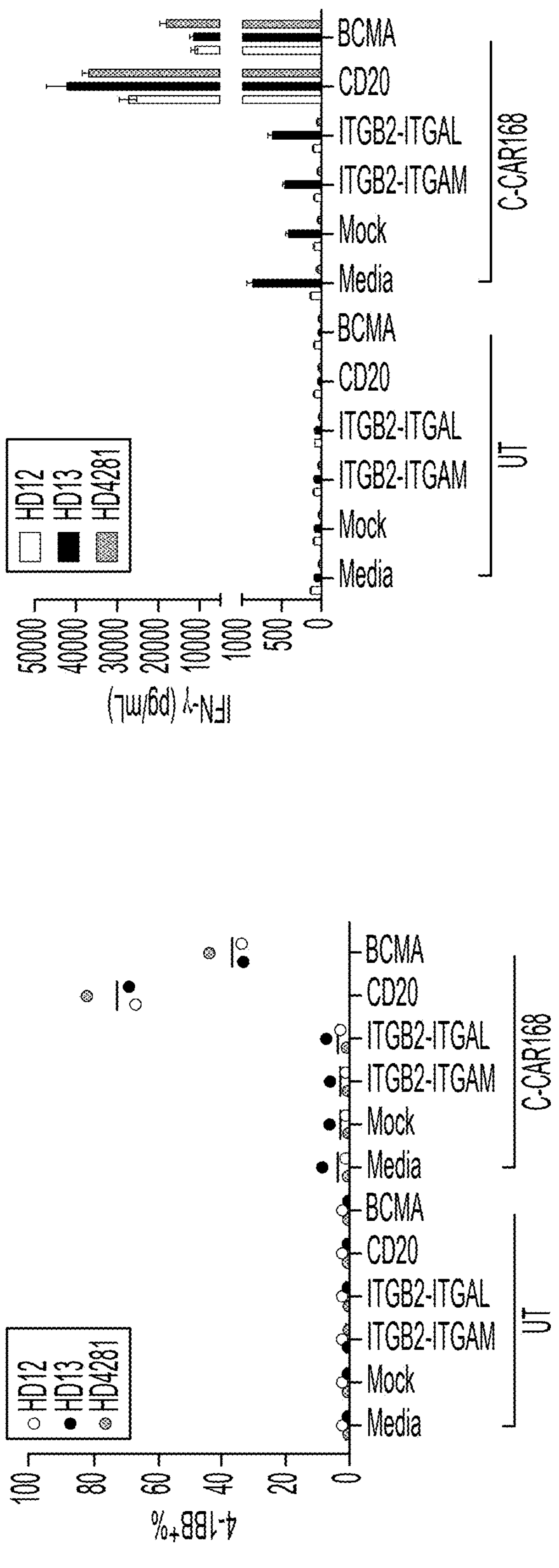

Cytokines in the cell culture supernatant were assayed, and the results showed that C-CAR168 CAR-T cells secreted high levels of IFN-γ when co-cultured with cells expressing CD20 or BCMA. When co-cultured with cells expressing ITGB2-ITGAM or ITGB2-ITGAL, compared with non-transduced T cells, the concentrations of IFN-γ in the supernatant did not increase significantly (FIG. 8D, right panel). The results further showed that C-CAR168 did not specifically recognize ITGB2-ITGAM and ITGB2-ITGAL in vitro.

In summary, the membrane protein array and in vitro co-culture results show that the antigen-binding domain of C-CAR168 binds strongly to human CD20 and BCMA, and has no other non-specific binding sites. The membrane protein array study identified that C-CAR168 has no cross-reactivity against membrane proteome except weak binding to two heterocomplexes.

Example 7 C-CAR168 Shows Robust Potency Against Autologous B Cells from SLE Patients To study CAR-T therapies for the treatment of autoimmune diseases, such as SLE, we evaluated the efficiency of the CAR-T cells to deplete autoreactive B cells. We will also study the efficacy of the CAR-T cells on remission and survival of a lupus model.

Efficiency of C-CAR168 to Eliminate Pan B Cells from Lupus Patients In Vitro

10~15 mL of peripheral blood samples from eight patients with SLE were collected. The patients had different activity and autoantibody profile, displayed different organ damage (patients with lupus nephritis were preferable), and underwent different treatment, to represent the heterogenous nature of lupus patients. Patients who recently received B cell depleting antibodies were excluded.

Figure 10A:
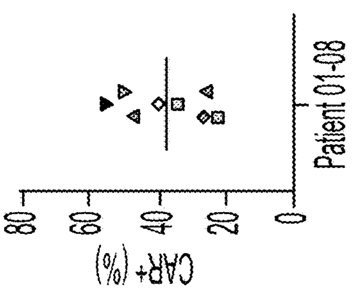
FIGS. 10A-10D: C-CAR168 shows robust potency in vitro against autologous B cells from SLE patients.

For each sample, part of the blood was used to isolate T cells for CAR-T production, and the remaining blood was used to isolate pan B cells as target for a cytolytic assay. T cells isolated from eight SLE patients were transduced by lentiviral vectors encoding C-CAR168 and tested for CAR expression. T cell samples from 8 SLE patent samples were successfully transduced and expanded well for function assays (FIG. 10A).

Figure 10B:
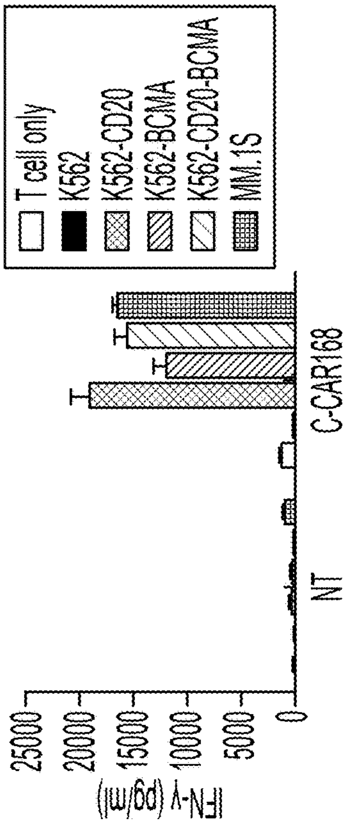

C-CAR168 CAR-T cells generated from 8 patient samples, or non-transduced (NT) T cells, were co-cultured with target cell lines expressing CD20 or/and BCMA. K562 is negative for both CD20 and BCMA; MM.1S is a multiple myeloma cell line which is BCMA-positive. After 24 hours, co-culture supernatants were collected for ELISA (enzyme-linked immunosorbent assay) to assess the IFN-γ levels. Result from one representative sample of 8 patients is shown in FIG. 10B. Thus, C-CAR168 cells generated from SLE patient samples showed robust activity against target cells expressing CD20 and BCMA.

Figure 10C:
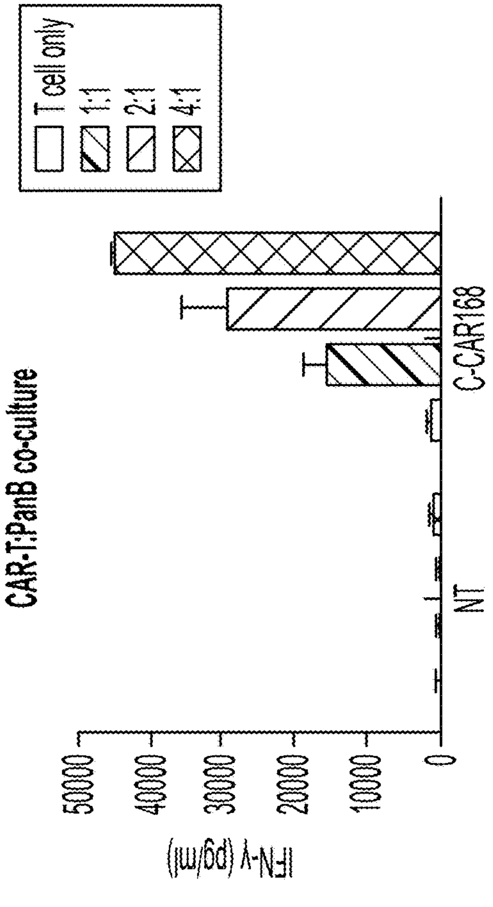
Figure 10D:
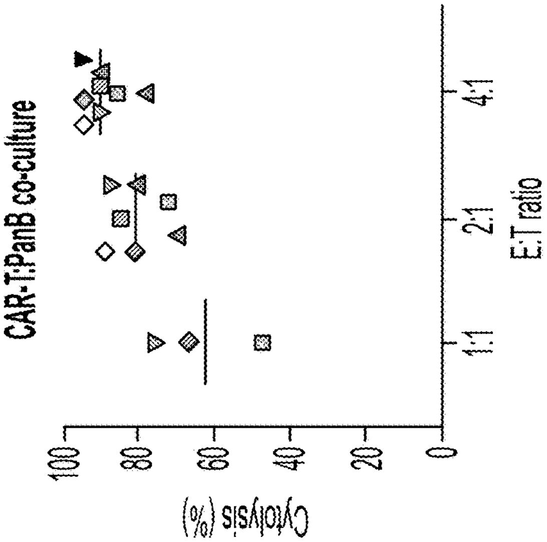

Isolated pan B cells isolated from 8 patient samples were co-cultured with autologous C-CAR168 CAR-T cells, or non-transduced (NT) T cells, at the indicated E:T (effector to target) ratios. After 24 hours, co-culture supernatants were collected for ELISA to assess the IFN-γ levels. Cytotoxicity was determined by fluorescence-activated cell sorting (FACS) and calculation of the depletion of the percentage of viable CD19+ pan B cells. The cytolysis of B cells was calculated by the following formula: Percentage of lysis (%)=(1−(viable CD19+ cell fraction of the C-CAR168 coculture/viable CD19+ cell fraction of UT coculture))×100. Results from one representative sample of 8 patients are shown in FIGS. 10C and 10D. Pan B cells isolated from 8 SLE patient samples were recognized and lysed by autologous C-CAR168 cells. The results confirmed the efficiency of C-CAR168 CAR-T cells to deplete peripheral B cells from lupus patients in the in vitro setting.

Efficiency of the CAR-T to Eliminate ABCs from Lupus Patients In Vitro

The efficiency of the CAR-T to eliminate ABCs, the essential subset of pathogenic B cells, from lupus patients in vitro will be studied.

Blood samples or PBMCs from lupus patients will be processed for ABCs differentiation and CAR-T production as well as functional analysis.

The study will confirm the efficiency of the CAR-T cells to deplete ABCs from lupus patients in the in vitro setting.

Efficiency of the CAR-T to Deplete B Cells and the Therapeutic Efficacy In Vivo

The efficiency of the CAR-T to deplete B cells and its therapeutic efficacy will be evaluated in vivo with a humanized mouse model of SLE. $CD34^+$ stem cell humanized mice will be obtained. 2 or more mice will be sacrificed to collect spleens with aseptic technique. T cells will then be isolated from the spleens for CAR-T production. The remaining mice will be used to induce the onset of lupus disease, and upon successful induction, mice will be divided into groups to receive CAR-T or control treatment (for example, non-transduced T cells). Blood samples will be obtained from the mice periodically to monitor the persistence of CAR-T cells, as well as efficiency of B cell depletion (including ABCs) by FACS. The sera samples will be used to measure the titers of various autoantibodies. Urine samples will also be routinely collected to measure the levels of proteinuria. At the end of the study, or in case an animal dies early (presumably in control group), tissues will be collected for histology, for example, to examine the deposition of immune complex in the kidney and the severity of nephritis. The presence of B cells or plasma cells in diseased tissue will also be examined. Survival curves will be generated to compare the effect of CAR-T versus control treatment.

REFERENCES

Bhoj, V. G. et al. Persistence of long-lived plasma cells and humoral immunity in individuals responding to CD19-directed CAR T-cell therapy. *Blood* 128, 360-370 (2016).

Taubmann et al. Long term safety and efficacy of CAR-T cell treatment in refractory systemic lupus erythematosus—data from the first seven patients. Annals of the Rheumatic Diseases, OP0141, page 93 (2023).

Qin, C., Tian, D S., Zhou, L Q. et al. Anti-BCMA CAR T-cell therapy CT103A in relapsed or refractory AQP4-IgG seropositive neuromyelitis optica spectrum disorders: phase 1 trial interim results. Sig Transduct Target Ther 8, 5 (2023).

Tai et al. Role of B-cell-activating factor in adhesion and growth of human multiple myeloma cells in the bone marrow microenvironment. Cancer research. 2006; 66(13):6675-82.

Pavlasova et al. (2020). The regulation and function of CD20: an “enigma” of B-cell biology and targeted therapy. Haematologica, 105(6), 1494-1506.

Krumbholz et al. B cells and antibodies in multiple sclerosis pathogenesis and therapy [J]. Nature reviews Neurology, 2012, 8(11): 613-23.

Parker et al., Single-Cell Analyses Identify Brain Mural Cells Expressing CD19 as Potential Off-Tumor Targets for CAR-T Immunotherapies. Cell. 2020 Oct. 1; 183 (1):126-142.e17.

Qu et al. Phase 1 study of C-CAR088, a novel humanized anti-BCMA CAR T-cell therapy in relapsed/refractory multiple myeloma. J Immunother Cancer. 2022 September; 10(9):e005145.

The structures of the anti-CD20/BCMA CARs, TOB1-4 and TOBL1-4, are shown in Table 1.

TABLE 1

| Anti-CD20/BCMA CAR | scFv VH/VL order | CAR structure |
|---|---|---|
| TN-OF-B20-L1 (TOBL1, or C-CAR168) | OF($V_L$-$V_H$)-B20($V_L$-$V_H$) | SP-OF $V_L$-linker 1-OF $V_H$-linker 2-B20 $V_L$-linker 3-B20$V_H$-CD8 hinge-CD8 TM-41BB-CD3z |
| TN-OF-B20-L2 (TOBL2) | OF($V_H$-$V_L$)-B20($V_L$-$V_H$) | SP-OF $V_H$-linker 1-OF $V_L$-linker 2-B20 $V_L$-linker 3-B20$V_H$-CD8 hinge-CD8 TM-41BB-CD3z |
| TN-OF-B20-L3 (TOBL3) | OF($V_H$-$V_L$)-B20($V_H$-$V_L$) | SP-OF $V_H$-linker 1-OF $V_L$-linker 2-B20 $V_H$-linker 3-B20$V_L$-CD8 hinge-CD8 TM-41BB-CD3z |
| TN-OF-B20-L4 (TOBL4) | OF($V_L$-$V_H$)-B20($V_H$-$V_L$) | SP-OF $V_L$-linker 1-OF $V_H$-linker 2-B20 $V_H$-linker 3-B20$V_L$-CD8 hinge-CD8 TM-41BB-CD3z |
| TN-OF-B20-1 (TOB1) | OF($V_L$-$V_H$)-B20($V_H$-$V_L$) | SP-OF $V_L$-linker 1-OF $V_H$-linker 2-B20 $V_H$-linker 3-B20$V_L$-IgG4 hinge-CD28 TM-41BB-CD3z |
| TN-OF-B20-2 (TOB2) | OF($V_L$-$V_H$)-B20($V_L$-$V_H$) | SP-OF $V_L$-linker 1-OF $V_H$-linker 2-B20 $V_L$-linker 3-B20$V_H$-IgG4 hinge-CD28 TM-41BB-CD3z |
| TN-OF-B20-3 (TOB3) | OF($V_H$-$V_L$)-B20($V_L$-$V_H$) | SP-OF $V_H$-linker 1-OF $V_L$-linker 2-B20 $V_L$-linker 3-B20$V_H$-IgG4 hinge-CD28 TM-41BB-CD3z |
| TN-OF-B20-4 (TOB4) | OF($V_H$-$V_L$)-B20($V_H$-$V_L$) | SP-OF $V_H$-linker 1-OF $V_L$-linker 2-B20 $V_H$-linker 3-B20$V_L$-IgG4 hinge-CD28 TM-41BB-CD3z |

Sequences:
TN-OF-B20-L1 (TOBL1, or C-CAR168)
CD8a SP nucleic acid sequence (63 nt)

(SEQ ID NO: 1)
atggccttaccagtgaccgccttgctcctgccgctggccttgctgctccacgccgccaggccg

CD8a SP amino acid sequence:

(SEQ ID NO: 2)
MALPVTALLLPLALLLHAARP

OF $V_L$ nucleic acid sequence (321 nt)

(SEQ ID NO: 3)
GAAATTGTGTTGACACAGTCTCCAGCCACCCTGTCTTTGTCTCCAGGGGAAAGAGCCACC

CTCTCCTGCAGGGCCAGTCAGAGTGTTAGCAGCTACTTAGCCTGGTACCAACAGAAACCT

GGCCAGGCTCCCAGGCTCCTCATCTATGATGCATCCAACAGGGCCACTGGCATCCCAGCC

AGGTTCAGTGGCAGTGGGTCTGGGACAGACTTCACTCTCACCATCAGCAGCCTAGAGCCT

GAAGATTTTGCAGTTTATTACTGTCAGCAGCGTAGCAACTGGCCGATCACCTTCGGCCAA

GGGACACGACTGGAGATTAAA

OF $V_L$ amino acid sequence:

(SEQ ID NO: 4)
EIVLTQSPATLSLSPGERATLSCRASQSVSSYLAWYQQKPGQAPRLLIYDASNRATGIPA

RFSGSGSGTDFTLTISSLEPEDFAVYYCQQRSNWPITFGQGTRLEIK

Linker-1 nucleic acid sequence (54 nt)

(SEQ ID NO: 5)
GGCAGTACTAGCGGTGGTGGCTCCGGGGGCGGTTCCGGTGGGGGCGGCAGCAGC

Linker-1 amino acid sequence:

(SEQ ID NO: 6)
GSTSGGGSGGGSGGGGSS

OF $V_H$ nucleic acid sequence (366 nt)

(SEQ ID NO: 7)
GAAGTGCAGCTGGTGGAGTCTGGGGGAGGCTTGGTACAGCCTGGCAGGTCCCTGAGACTC

TCCTGTGCAGCCTCTGGATTCACCTTTAATGATTATGCCATGCACTGGGTCCGGCAAGCT

CCAGGGAAGGGCCTGGAGTGGGTCTCAACTATTAGTTGGAATAGTGGTTCCATAGGCTAT

GCGGACTCTGTGAAGGGCCGATTCACCATCTCCAGAGACAACGCCAAGAAGTCCCTGTAT

CTGCAAATGAACAGTCTGAGAGCTGAGGACACGGCCTTGTATTACTGTGCAAAAGATATA

CAGTACGGCAACTACTACTACGGTATGGACGTCTGGGGCCAAGGGACCACGGTCACCGTC

TCCTCA

OF $V_H$ amino acid sequence:

(SEQ ID NO: 8)
EVQLVESGGGLVQPGRSLRLSCAASGFTFNDYAMHWVRQAPGKGLEWVSTISWNSGSIGY

ADSVKGRFTISRDNAKKSLYLQMNSLRAEDTALYYCAKDIQYGNYYYGMDVWGQGTTVTV

SS

Linker-2 nucleic acid sequence (15 nt)

(SEQ ID NO: 9)
GGAGGTGGTGGATCC

Linker-2 amino acid sequence:

(SEQ ID NO: 10)
GGGGS

B20 $V_L$ nucleic acid sequence (321 nt)

(SEQ ID NO: 11)
Gacatccagatgacccagtccccctcctccctgtccgcctccgtgggcgaccgggtgacc atcacctgccgggcctcccagggcatctccaactacctgaactggtaccagcagaagccc ggcaaggcccccaagcccctgatctactacacctccaacctgcagtccggcgtgccctcc -continued cggttctccggctccggctccggcaccgactacaccctgaccatctcctccctgcagccc gaggacttcgccacctactactgcatgggccagaccatctcctcctacaccttcggccag ggcaccaagctggagatcaag B20 $V_L$ amino acid sequence:

(SEQ ID NO: 12)

DIQMTQSPSSLSASVGDRVTITCRASQGISNYLNWYQQKPGKAPKPLIYYTSNLQSGVPS

RFSGSGSGTDYTLTISSLQPEDFATYYCMGQTISSYTFGQGTKLEIK

Linker-3 nucleic acid sequence (45 nt)

(SEQ ID NO: 13)

Ggtggcggtggctcgggcggtggtgggtcgggtggcggcggatct

Linker-3 amino acid sequence:

(SEQ ID NO: 14)

GGGGSGGGGSGGGGS

B20 $V_H$ nucleic acid sequence (363 nt)

(SEQ ID NO: 15)

Gaggtgcagctggtggagtccggcggcggcctggtgcagcccggcggctccctgcggctg tcctgcgccgcctccggcttcaccttctccaacttcgacatggcctgggtgcggcaggcc cccggcaagggcctggtgtgggtgtcctccatcaccaccggcgccgaccacgccatctac gccgactccgtgaagggccggttcaccatctcccgggacaacgccaagaacaccctgtac ctgcagatgaactccctgcgggccgaggacaccgccgtgtactactgcgtgcggcacggc tactacgacggctaccacctgttcgactactggggccagggcaccctggtgaccgtgtcc tcc B20 $V_H$ amino acid sequence:

(SEQ ID NO: 16)

EVQLVESGGGLVQPGGSLRLSCAASGFTFSNFDMAWVRQAPGKGLVWVSSITTGADHAIY

ADSVKGRFTISRDNAKNTLYLQMNSLRAEDTAVYYCVRHGYYDGYHLFDYWGQGTLVTVS

S

CD8a hinge nucleic acid sequence (165 nt)

(SEQ ID NO: 17)

Ttcgtgccggtcttcctgccagcgaagcccaccacgacgccagcgccgcgaccaccaaca ccggcgcccaccatcgcgtcgcagcccctgtccctgcgcccagaggcgtgccggccagcg gcggggggcgcagtgcacacgagggggctggacttcgcctgtgat CD8a hinge amino acid sequence:

(SEQ ID NO: 18)

FVPVFLPAKPTTTPAPRPPTPAPTIASQPLSLRPEACRPAAGGAVHTRGLDFACD

CD8a TM nucleic acid sequence (72 nt)

(SEQ ID NO: 19)

Atctacatctgggcgcccttggccgggacttgtggggtccttctcctgtcactggt tatcaccctttactgc

CD8a TM amino acid sequence:

(SEQ ID NO: 20)

IYIWAPLAGTCGVLLLSLVITLYC

4-1BB nucleic acid sequence (126 nt)

(SEQ ID NO: 21)

Aaacggggcagaaagaaactcctgtatatattcaaacaaccatttatgagaccagtacaa actactcaagaggaagatggctgtagctgccgatttccagaagaagaagaaggaggatgt gaactg -continued 4-1BB amino acid sequence:

(SEQ ID NO: 22)
KRGRKKLLYIFKQPFMRPVQTTQEEDGCSCRFPEEEEGGCEL

CD3z nucleic acid sequence (336 nt)

(SEQ ID NO: 23)
Agagtgaagttcagcaggagcgcagacgcccccgcgtaccagcagggccagaaccagctc tataacgagctcaatctaggacgaagagaggagtacgatgttttggacaagagacgtggc cgggaccctgagatggggggaaagccgagaaggaagaaccctcaggaaggcctgtacaat gaactgcagaaagataagatggcggaggcctacagtgagattgggatgaaaggcgagcgc cggaggggcaaggggcacgatggcctttaccagggtctcagtacagccaccaaggacacc tacgacgcccttcacatgcaggccctgccccctcgctaa CD3z amino acid sequence:

(SEQ ID NO: 24)
RVKFSRSADAPAYQQGQNQLYNELNLGRREEYDVLDKRRGRDPEMGGKPRRKNPQEGLYN

ELQKDKMAEAYSEIGMKGERRRGKGHDGLYQGLSTATKDTYDALHMQALPPR

TOBL1 nucleic acid sequence (2247 nt)

(SEQ ID NO: 25)
atggccttaccagtgaccgccttgctcctgccgctggccttgctgctccacgccgccagg ccgGAAATTGTGTTGACACAGTCTCCAGCCACCCTGTCTTTGTCTCCAGGGGAAAGAGCC

ACCCTCTCCTGCAGGGCCAGTCAGAGTGTTAGCAGCTACTTAGCCTGGTACCAACAGAAA

CCTGGCCAGGCTCCCAGGCTCCTCATCTATGATGCATCCAACAGGGCCACTGGCATCCCA

GCCAGGTTCAGTGGCAGTGGGTCTGGGACAGACTTCACTCTCACCATCAGCAGCCTAGAG

CCTGAAGATTTTGCAGTTTATTACTGTCAGCAGCGTAGCAACTGGCCGATCACCTTCGGC

CAAGGGACACGACTGGAGATTAAAGGCAGTACTAGCGGTGGTGGCTCCGGGGGCGGTTCC

GGTGGGGGCGGCAGCAGCGAAGTGCAGCTGGTGGAGTCTGGGGGAGGCTTGGTACAGCCT

GGCAGGTCCCTGAGACTCTCCTGTGCAGCCTCTGGATTCACCTTTAATGATTATGCCATG

CACTGGGTCCGGCAAGCTCCAGGGAAGGGCCTGGAGTGGGTCTCAACTATTAGTTGGAAT

AGTGGTTCCATAGGCTATGCGGACTCTGTGAAGGGCCGATTCACCATCTCCAGAGACAAC

GCCAAGAAGTCCCTGTATCTGCAAATGAACAGTCTGAGAGCTGAGGACACGGCCTTGTAT

TACTGTGCAAAAGATATACAGTACGGCAACTACTACTACGGTATGGACGTCTGGGGCCAA

GGGACCACGGTCACCGTCTCCTCAGGAGGTGGTGGATCCGacatccagatgacccagtcc ccctcctccctgtccgcctccgtgggcgaccgggtgaccatcacctgccgggcctcccag ggcatctccaactacctgaactggtaccagcagaagcccggcaaggcccccaagcccctg atctactacacctccaacctgcagtccggcgtgccctcccggttctccggctccggctcc ggcaccgactacaccctgaccatctcctccctgcagcccgaggacttcgccacctactac tgcatgggccagaccatctcctcctacaccttcggccagggcaccaagctggagatcaag Ggtggcggtggctcgggcggtggtgggtcgggtggcggcggatctgaggtgcagctggtg gagtccggcggcggcctggtgcagcccggcggctccctgcggctgtcctgcgccgcctcc ggcttcaccttctccaacttcgacatggcctgggtgcggcaggcccccggcaagggcctg gtgtgggtgtcctccatcaccaccggcgccgaccacgccatctacgccgactccgtgaag ggccggttcaccatctcccgggacaacgccaagaacaccctgtacctgcagatgaactcc ctgcgggccgaggacaccgccgtgtactactgcgtgcggcacggctactacgacggctac cacctgttcgactactggggccagggcaccctggtgaccgtgtcctccttcgtgccggtc ttcctgccagcgaagcccaccacgacgccagcgccgcgaccaccaacaccggcgcccacc atcgcgtcgcagcccctgtccctgcgcccagaggcgtgccggccagcggggggggcgcag -continued tgcacacgagggggctggacttcgcctgtgatatctacatctgggcgcccttggccggga cttgtggggtccttctcctgtcactggttatcaccctttactgcaaacggggcagaaaga aactcctgtatatattcaaacaaccatttatgagaccagtacaaactactcaagaggaag atggctgtagctgccgatttccagaagaagaagaaggaggatgtgaactgagagtgaagt tcagcaggagcgcagacgcccccgcgtaccagcagggccagaaccagctctataacgagc tcaatctaggacgaagagaggagtacgatgttttggacaagagacgtggccgggaccctg agatggggggaaagccgagaaggaagaaccctcaggaaggcctgtacaatgaactgcaga aagataagatggcggaggcctacagtgagattgggatgaaaggcgagcgccggaggggca aggggcacgatggcctttaccagggtctcagtacagccaccaaggacacctacgacgccc ttcacatgcaggccctgccccctcgctaa TOBL1 amino acid sequence:

(SEQ ID NO: 26)

MALPVTALLLPLALLLHAARPEIVLTQSPATLSLSPGERATLSCRASQSVSSYLAWYQQK

PGQAPRLLIYDASNRATGIPARFSGSGSGTDFTLTISSLEPEDFAVYYCQQRSNWPITFG

QGTRLEIKGSTSGGGSGGGSGGGGSSEVQLVESGGGLVQPGRSLRLSCAASGFTFNDYAM

HWVRQAPGKGLEWVSTISWNSGSIGYADSVKGRFTISRDNAKKSLYLQMNSLRAEDTALY

YCAKDIQYGNYYYGMDVWGQGTTVTVSSGGGGSDIQMTQSPSSLSASVGDRVTITCRASQ

GISNYLNWYQQKPGKAPKPLIYYTSNLQSGVPSRFSGSGSGTDYTLTISSLQPEDFATYY

CMGQTISSYTFGQGTKLEIKGGGGSGGGGSGGGGSEVQLVESGGGLVQPGGSLRLSCAAS

GFTFSNFDMAWVRQAPGKGLVWVSSITTGADHAIYADSVKGRFTISRDNAKNTLYLQMNS

LRAEDTAVYYCVRHGYYDGYHLFDYWGQGTLVTVSSFVPVFLPAKPTTTPAPRPPTPAPT

IASQPLSLRPEACRPAAGGAVHTRGLDFACDIYIWAPLAGTCGVLLLSLVITLYCKRGRK

KLLYIFKQPFMRPVQTTQEEDGCSCRFPEEEEGGCELRVKFSRSADAPAYQQGQNQLYNE

LNLGRREEYDVLDKRRGRDPEMGGKPRRKNPQEGLYNELQKDKMAEAYSEIGMKGERRRG

KGHDGLYQGLSTATKDTYDALHMQALPPR

TN-OF-B20-L2 (TOBL2)
CD8a SP nucleic acid sequence (63 nt)

(SEQ ID NO: 27)

Atggccttaccagtgaccgccttgctcctgccgctggccttgctgctccacgccgccaggccg

OF $V_H$ nucleic acid sequence (SEQ ID NO: 28)

GAAGTGCAGCTGGTGGAGTCTGGGGGAGGCTTGGTACAGCCTGGCAGGTCCCTGAGACTC

TCCTGTGCAGCCTCTGGATTCACCTTTAATGATTATGCCATGCACTGGGTCCGGCAAGCT

CCAGGGAAGGGCCTGGAGTGGGTCTCAACTATTAGTTGGAATAGTGGTTCCATAGGCTAT

GCGGACTCTGTGAAGGGCCGATTCACCATCTCCAGAGACAACGCCAAGAAGTCCCTGTAT

CTGCAAATGAACAGTCTGAGAGCTGAGGACACGGCCTTGTATTACTGTGCAAAAGATATA

CAGTACGGCAACTACTACTACGGTATGGACGTCTGGGGCCAAGGGACCACGGTCACCGTC

TCCTCA

Linker-1 nucleic acid sequence (SEQ ID NO: 29)

GGCAGTACTAGCGGTGGTGGCTCCGGGGGCGGTTCCGGTGGGGGCGGCAGCAGC

OF $V_L$ nucleic acid sequence (SEQ ID NO: 30)

GAAATTGTGTTGACACAGTCTCCAGCCACCCTGTCTTTGTCTCCAGGGGAAAGAGCCAC

CCTCTCCTGCAGGGCCAGTCAGAGTGTTAGCAGCTACTTAGCCTGGTACCAACAGAAAC

CTGGCCAGGCTCCCAGGCTCCTCATCTATGATGCATCCAACAGGGCCACTGGCATCCCA

-continued

GCCAGGTTCAGTGGCAGTGGGTCTGGGACAGACTTCACTCTCACCATCAGCAGCCTAGA

GCCTGAAGATTTTGCAGTTTATTACTGTCAGCAGCGTAGCAACTGGCCGATCACCTTCG

GCCAAGGGACACGACTGGAGATTAAA

Linker-2 nucleic acid sequence (SEQ ID NO: 31)

GGAGGTGGTGGATCC

BCMA-20 scFv (729 nt):

B20 $V_L$ nucleic acid sequence (321 nt)

(SEQ ID NO: 32)

gacatccagatgacccagtcccccctcctccctgtccgcctccgtggggaccgggtgacca tcacctgccgggcctcccagggcatctccaactacctgaactggtaccagcagaagcccg gcaaggcccccaagcccctgatctactacacctccaacctgcagtccggcgtgccctccc ggttctccggctccggctccggcaccgactacaccctgaccatctcctccctgcagcccg aggacttcgccacctactactgcatgggccagaccatctcctcctacaccttcggccagg gcaccaagctggagatcaag Linker-3 nucleic acid sequence (45 nt)

(SEQ ID NO: 33)

ggtggcggtggctcgggcggtggtgggtcgggtggcggcggatct

B20 $V_H$ nucleic acid sequence (363 nt)

(SEQ ID NO: 34)

gaggtgcagctggtggagtccggcggcggcctggtgcagcccggcggctccctgcggctg tcctgcgccgcctccggcttcaccttctccaacttcgacatggcctgggtgcggcaggcc cccggcaagggcctggtgtgggtgtcctccatcaccaccggcgccgaccacgccatctac gccgactccgtgaagggccggttcaccatctcccgggacaacgccaagaacaccctgtac ctgcagatgaactccctgcgggccgaggacaccgccgtgtactactgcgtgcggcacggc tactacgacggctaccacctgttcgactactggggccagggcaccctggtgaccgtgtcc tcc CD8a hinge nucleic acid sequence (165 nt)

(SEQ ID NO: 35)

Ttcgtgccggtcttcctgccagcgaagcccaccacgacgccagcgccgcgaccaccaaca ccggcgcccaccatcgcgtcgcagcccctgtccctgcgcccagaggcgtgccggccagcg gggggggcgcagtgcacacgagggggctggacttcgcctgtgat CD8a TM nucleic acid sequence (72 nt)

(SEQ ID NO: 36)

Atctacatctgggcgcccttggccgggacttgtggggtccttctcctgtcactggttatc accctttactgc 4-1BB nucleic acid sequence (126 nt)

(SEQ ID NO: 37)

Aaacggggcagaaagaaactcctgtatatattcaaacaaccatttatgagaccagtacaa actactcaagaggaagatggctgtagctgccgatttccagaagaagaagaaggaggatgt gaactg CD3z nucleic acid sequence (336 nt)

(SEQ ID NO: 38)

Agagtgaagttcagcaggagcgcagacgcccccgcgtaccagcagggccagaaccagctc tataacgagctcaatctaggacgaagagaggagtacgatgttttggacaagagacgtggc cgggaccctgagatggggggaaagccgagaaggaagaaccctcaggaaggcctgtacaat -continued gaactgcagaaagataagatggcggaggcctacagtgagattgggatgaaaggcgagcgc cggaggggcaaggggcacgatggcctttaccagggtctcagtacagccaccaaggacacc tacgacgcccttcacatgcaggccctgccccctogctaa TOBL2 nucleic acid sequence (2247 nt)

(SEQ ID NO: 39)

atggccttaccagtgaccgccttgctcctgccgctggccttgctgctccacgccgccagg ccgGAAGTGCAGCTGGTGGAGTCTGGGGGAGGCTTGGTACAGCCTGGCAGGTCCCTGAGA

CTCTCCTGTGCAGCCTCTGGATTCACCTTTAATGATTATGCCATGCACTGGGTCCGGCAA

GCTCCAGGGAAGGGCCTGGAGTGGGTCTCAACTATTAGTTGGAATAGTGGTTCCATAGGC

TATGCGGACTCTGTGAAGGGCCGATTCACCATCTCCAGAGACAACGCCAAGAAGTCCCTG

TATCTGCAAATGAACAGTCTGAGAGCTGAGGACACGGCCTTGTATTACTGTGCAAAAGAT

ATACAGTACGGCAACTACTACTACGGTATGGACGTCTGGGGCCAAGGGACCACGGTCACC

GTCTCCTCAGGCAGTACTAGCGGTGGTGGCTCCGGGGGCGGTTCCGGTGGGGGCGGCAGC

AGCGAAATTGTGTTGACACAGTCTCCAGCCACCCTGTCTTTGTCTCCAGGGGAAAGAGCC

ACCCTCTCCTGCAGGGCCAGTCAGAGTGTTAGCAGCTACTTAGCCTGGTACCAACAGAAA

CCTGGCCAGGCTCCCAGGCTCCTCATCTATGATGCATCCAACAGGGCCACTGGCATCCCA

GCCAGGTTCAGTGGCAGTGGGTCTGGGACAGACTTCACTCTCACCATCAGCAGCCTAGAG

CCTGAAGATTTTGCAGTTTATTACTGTCAGCAGCGTAGCAACTGGCCGATCACCTTCGGC

CAAGGGACACGACTGGAGATTAAAGGAGGTGGTGGATCCGacatccagatgacccagtcc ccctcctccctgtccgcctccgtgggcgaccgggtgaccatcacctgccgggcctcccag ggcatctccaactacctgaactggtaccagcagaagcccggcaaggcccccaagcccctg atctactacacctccaacctgcagtccggcgtgccctcccggttctccggctccggctcc ggcaccgactacaccctgaccatctcctccctgcagcccgaggacttcgccacctactac tgcatgggccagaccatctcctcctacaccttcggccagggcaccaagctggagatcaag Ggtggcggtggctcgggcggtggtgggtcgggtggcggcggatctgaggtgcagctggtg gagtccggcggcggcctggtgcagcccggcggctccctgcggctgtcctgcgccgcctcc ggcttcaccttctccaacttcgacatggcctgggtgcggcaggcccccggcaagggcctg gtgtgggtgtcctccatcaccaccggcgccgaccacgccatctacgccgactccgtgaag ggccggttcaccatctcccgggacaacgccaagaacaccctgtacctgcagatgaactcc ctgcgggccgaggacaccgccgtgtactactgcgtgcggcacggctactacgacggctac cacctgttcgactactggggccagggcaccctggtgaccgtgtcctccttcgtgccggtc ttcctgccagcgaagcccaccacgacgccagcgccgcgaccaccaacaccggcgcccacc atcgcgtcgcagcccctgtccctgcgcccagaggcgtgccggccagcggggggggcgcag tgcacacgagggggctggacttcgcctgtgatatctacatctgggcgcccttggccggga cttgtggggtccttctcctgtcactggttatcaccctttactgcaaacggggcagaaaga aactcctgtatatattcaaacaaccatttatgagaccagtacaaactactcaagaggaag atggctgtagctgccgatttccagaagaagaagaaggaggatgtgaactgAgagtgaagt tcagcaggagcgcagacgcccccgcgtaccagcagggccagaaccagctctataacgagc tcaatctaggacgaagagaggagtacgatgttttggacaagagacgtggccgggaccctg agatgggggggaaagccgagaaggaagaaccctcaggaaggcctgtacaatgaactgcaga aagataagatggcggaggcctacagtgagattgggatgaaaggcgagcgccggaggggca aggggcacgatggcctttaccagggtctcagtacagccaccaaggacacctacgacgccc -continued ttcacatgcaggccctgccccctcgctaa TOBL2 amino acid sequence:

(SEQ ID NO: 40)

MALPVTALLLPLALLLHAARPEVQLVESGGGLVQPGRSLRLSCAASGFTENDYAMHWVRQ

APGKGLEWVSTISWNSGSIGYADSVKGRFTISRDNAKKSLYLQMNSLRAEDTALYYCAKD

IQYGNYYYGMDVWGQGTTVTVSSGSTSGGGSGGGSGGGGSSEIVLTQSPATLSLSPGERA

TLSCRASQSVSSYLAWYQQKPGQAPRLLIYDASNRATGIPARFSGSGSGTDFTLTISSLE

PEDFAVYYCQQRSNWPITFGQGTRLEIKGGGGSDIQMTQSPSSLSASVGDRVTITCRASQ

GISNYLNWYQQKPGKAPKPLIYYTSNLQSGVPSRFSGSGSGTDYTLTISSLQPEDFATYY

CMGQTISSYTFGQGTKLEIKGGGGSGGGGSGGGGSEVQLVESGGGLVQPGGSLRLSCAAS

GFTFSNFDMAWVRQAPGKGLVWVSSITTGADHAIYADSVKGRFTISRDNAKNTLYLQMNS

LRAEDTAVYYCVRHGYYDGYHLFDYWGQGTLVTVSSFVPVFLPAKPTTTPAPRPPTPAPT

IASQPLSLRPEACRPAAGGAVHTRGLDFACDIYIWAPLAGTCGVLLLSLVITLYCKRGRK

KLLYIFKQPFMRPVQTTQEEDGCSCRFPEEEEGGCELRVKFSRSADAPAYQQGQNQLYNE

LNLGRREEYDVLDKRRGRDPEMGGKPRRKNPQEGLYNELQKDKMAEAYSEIGMKGERRRG

KGHDGLYQGLSTATKDTYDALHMQALPPR

TN-OF-B20-L3 (TOBL3)
CD8a SP (63 nt) nucleic acid sequence (SEQ ID NO: 41)

Atggccttaccagtgaccgccttgctcctgccgctggccttgctgctccacgccgccaggccg

OF $V_H$ nucleic acid sequence (SEQ ID NO: 42)

GAAGTGCAGCTGGTGGAGTCTGGGGGAGGCTTGGTACAGCCTGGCAGGTCCCTGAGACTC

TCCTGTGCAGCCTCTGGATTCACCTTTAATGATTATGCCATGCACTGGGTCCGGCAAGCT

CCAGGGAAGGGCCTGGAGTGGGTCTCAACTATTAGTTGGAATAGTGGTTCCATAGGCTAT

GCGGACTCTGTGAAGGGCCGATTCACCATCTCCAGAGACAACGCCAAGAAGTCCCTGTAT

CTGCAAATGAACAGTCTGAGAGCTGAGGACACGGCCTTGTATTACTGTGCAAAAGATATA

CAGTACGGCAACTACTACTACGGTATGGACGTCTGGGGCCAAGGGACCACGGTCACCGTC

TCCTCA

Linker-1 nucleic acid sequence (SEQ ID NO: 43)

GGCAGTACTAGCGGTGGTGGCTCCGGGGGCGGTTCCGGTGGGGGCGGCAGCAGC

OF $V_L$ nucleic acid sequence (SEQ ID NO: 44)

GAAATTGTGTTGACACAGTCTCCAGCCACCCTGTCTTTGTCTCCAGGGGAAAGAGCCACC

CTCTCCTGCAGGGCCAGTCAGAGTGTTAGCAGCTACTTAGCCTGGTACCAACAGAAACCT

GGCCAGGCTCCCAGGCTCCTCATCTATGATGCATCCAACAGGGCCACTGGCATCCCAGCC

AGGTTCAGTGGCAGTGGGTCTGGGACAGACTTCACTCTCACCATCAGCAGCCTAGAGCCT

GAAGATTTTGCAGTTTATTACTGTCAGCAGCGTAGCAACTGGCCGATCACCTTCGGCCAA

GGGACACGACTGGAGATTAAA

Linker-2 nucleic acid sequence (SEQ ID NO: 45)

GGAGGTGGTGGATCC

BCMA-20 scFv (729 nt):
B20 $V_H$ nucleic acid sequence (363 nt)

(SEQ ID NO: 46)

Gaggtgcagctggtggagtccggcggcggcctggtgcagcccggcggctccctgcggctg tcctgcgccgcctccggcttcaccttctccaacttcgacatggcctgggtgcggcaggcc -continued cccggcaagggcctggtgtgggtgtcctccatcaccaccggcgccgaccacgccatctac gccgactccgtgaagggccggttcaccatctcccgggacaacgccaagaacaccctgtac ctgcagatgaactccctgcgggccgaggacaccgccgtgtactactgcgtgcggcacggc tactacgacggctaccacctgttcgactactggggccagggcaccctggtgaccgtgtcc tcc Linker-3 nucleic acid sequence (45 nt)

(SEQ ID NO: 47)

Ggtggcggtggctcgggcggtggtgggtcgggtggcggcggatct

B20 $V_L$ nucleic acid sequence (321 nt)

(SEQ ID NO: 48)

Gacatccagatgacccagtccccctcctccctgtccgcctccgtgggcgaccgggtgacc atcacctgccgggcctcccagggcatctccaactacctgaactggtaccagcagaagccc ggcaaggcccccaagcccctgatctactacacctccaacctgcagtccggcgtgccctcc cggttctccggctccggctccggcaccgactacaccctgaccatctcctccctgcagccc gaggacttcgccacctactactgcatgggccagaccatctcctcctacaccttcggccag ggcaccaagctggagatcaag CD8a hinge nucleic acid sequence (165 nt)

(SEQ ID NO: 49)

Ttcgtgccggtcttcctgccagcgaagcccaccacgacgccagcgccgcgaccaccaaca ccggcgcccaccatcgcgtcgcagcccctgtccctgcgcccagaggcgtgccggccagcg gggggggcgcagtgcacacgagggggctggacttcgcctgtgat CD8a TM nucleic acid sequence (72 nt)

(SEQ ID NO: 50)

Atctacatctgggcgcccttggccgggacttgtggggtccttctcctgtcactggttatc accctttactgc 4-1BB nucleic acid sequence (126 nt)

(SEQ ID NO: 51)

Aaacggggcagaaagaaactcctgtatatattcaaacaaccatttatgagaccagtacaa actactcaagaggaagatggctgtagctgccgatttccagaagaagaagaaggaggatgt gaactg CD3z nucleic acid sequence (336 nt)

(SEQ ID NO: 52)

Agagtgaagttcagcaggagcgcagacgcccccgcgtaccagcagggccagaaccagctc tataacgagctcaatctaggacgaagagaggagtacgatgttttggacaagagacgtggc cgggaccctgagatggggggaaagccgagaaggaagaaccctcaggaaggcctgtacaat gaactgcagaaagataagatggcggaggcctacagtgagattgggatgaaaggcgagcgc cggaggggcaaggggcacgatggcctttaccagggtctcagtacagccaccaaggacacc tacgacgcccttcacatgcaggccctgccccctcgctaa TOBL3 nucleic acid sequence (SEQ ID NO: 53)

atggccttaccagtgaccgccttgctcctgccgctggccttgctgctccacgccgccagg ccgGAAGTGCAGCTGGTGGAGTCTGGGGGAGGCTTGGTACAGCCTGGCAGGTCCCTGAGA

CTCTCCTGTGCAGCCTCTGGATTCACCTTTAATGATTATGCCATGCACTGGGTCCGGCAA

GCTCCAGGGAAGGGCCTGGAGTGGGTCTCAACTATTAGTTGGAATAGTGGTTCCATAGGC

TATGCGGACTCTGTGAAGGGCCGATTCACCATCTCCAGAGACAACGCCAAGAAGTCCCTG

TATCTGCAAATGAACAGTCTGAGAGCTGAGGACACGGCCTTGTATTACTGTGCAAAAGAT

ATACAGTACGGCAACTACTACTACGGTATGGACGTCTGGGGCCAAGGGACCACGGTCACC

GTCTCCTCAGGCAGTACTAGCGGTGGTGGCTCCGGGGGCGGTTCCGGTGGGGGCGGCAGC

-continued

AGCGAAATTGTGTTGACACAGTCTCCAGCCACCCTGTCTTTGTCTCCAGGGGAAAGAGCC

ACCCTCTCCTGCAGGGCCAGTCAGAGTGTTAGCAGCTACTTAGCCTGGTACCAACAGAAA

CCTGGCCAGGCTCCCAGGCTCCTCATCTATGATGCATCCAACAGGGCCACTGGCATCCCA

GCCAGGTTCAGTGGCAGTGGGTCTGGGACAGACTTCACTCTCACCATCAGCAGCCTAGAG

CCTGAAGATTTTGCAGTTTATTACTGTCAGCAGCGTAGCAACTGGCCGATCACCTTCGGC

CAAGGGACACGACTGGAGATTAAAGGAGGTGGTGGATCCgaggtgcagctggtggagtcc ggcggcggcctggtgcagcccggcggctccctgcggctgtcctgcgccgcctccggcttc accttctccaacttcgacatggcctgggtgcggcaggcccccggcaagggcctggtgtgg gtgtcctccatcaccaccggcgccgaccacgccatctacgccgactccgtgaagggccgg ttcaccatctcccgggacaacgccaagaacaccctgtacctgcagatgaactccctgcgg gccgaggacaccgccgtgtactactgcgtgcggcacggctactacgacggctaccacctg ttcgactactggggccagggcaccctggtgaccgtgtcctccGgtggcggtggctcgggc ggtggtgggtcgggtggcggcggatctGacatccagatgacccagtcccccctcctccctg tccgcctccgtgggcgaccgggtgaccatcacctgccgggcctcccagggcatctccaac tacctgaactggtaccagcagaagcccggcaaggcccccaagcccctgatctactacacc tccaacctgcagtccggcgtgccctcccggttctccggctccggctccggcaccgactac accctgaccatctcctccctgcagcccgaggacttcgccacctactactgcatgggccag accatctcctcctacaccttcggccagggcaccaagctggagatcaagttcgtgccggtc ttcctgccagcgaagcccaccacgacgccagcgccgcgaccaccaacaccggcgcccacc atcgcgtcgcagcccctgtccctgcgcccagaggcgtgccggccagcgggggggggcgcag tgcacacgagggggctggacttcgcctgtgatatctacatctgggcgcccttggccggga cttgtggggtccttctcctgtcactggttatcaccctttactgcaaacggggcagaaaga aactcctgtatatattcaaacaaccatttatgagaccagtacaaactactcaagaggaag atggctgtagctgccgatttccagaagaagaagaaggaggatgtgaactgAgagtgaagt tcagcaggagcgcagacgcccccgcgtaccagcagggccagaaccagctctataacgagc tcaatctaggacgaagagaggagtacgatgttttggacaagagacgtggccgggaccctg agatgggggggaaagccgagaaggaagaaccctcaggaaggcctgtacaatgaactgcaga aagataagatggcggaggcctacagtgagattgggatgaaaggcgagcgccggaggggca aggggcacgatggcctttaccagggtctcagtacagccaccaaggacacctacgacgccc ttcacatgcaggccctgccccctcgctaa TOBL3 amino acid sequence:

(SEQ ID NO: 54)

MALPVTALLLPLALLLHAARPEVQLVESGGGLVQPGRSLRLSCAASGFTENDYAMHWVRQ

APGKGLEWVSTISWNSGSIGYADSVKGRFTISRDNAKKSLYLQMNSLRAEDTALYYCAKD

IQYGNYYYGMDVWGQGTTVTVSSGSTSGGGSGGGSGGGGSSEIVLTQSPATLSLSPGERA

TLSCRASQSVSSYLAWYQQKPGQAPRLLIYDASNRATGIPARFSGSGSGTDFTLTISSLE

PEDFAVYYCQQRSNWPITFGQGTRLEIKGGGGSEVQLVESGGGLVQPGGSLRLSCAASGF

TFSNFDMAWVRQAPGKGLVWVSSITTGADHAIYADSVKGRFTISRDNAKNTLYLQMNSLR

AEDTAVYYCVRHGYYDGYHLFDYWGQGTLVTVSSGGGGSGGGGSGGGGSDIQMTQSPSSL

SASVGDRVTITCRASQGISNYLNWYQQKPGKAPKPLIYYTSNLQSGVPSRFSGSGSGTDY

TLTISSLQPEDFATYYCMGQTISSYTFGQGTKLEIKFVPVFLPAKPTTTPAPRPPTPAPT

-continued

IASQPLSLRPEACRPAAGGAVHTRGLDFACDIYIWAPLAGTCGVLLLSLVITLYCKRGRK

KLLYIFKQPFMRPVQTTQEEDGCSCRFPEEEEGGCELRVKFSRSADAPAYQQGQNQLYNE

LNLGRREEYDVLDKRRGRDPEMGGKPRRKNPQEGLYNELQKDKMAEAYSEIGMKGERRRG

KGHDGLYQGLSTATKDTYDALHMQALPPR

TN-OF-B20-L4 (TOBL4)
CD8a SP nucleic acid sequence (63 nt)

(SEQ ID NO: 55)

Atggccttaccagtgaccgccttgctcctgccgctggccttgctgctccacgccgccagg ccg

OF $V_L$ nucleic acid sequence (SEQ ID NO: 56)

GAAATTGTGTTGACACAGTCTCCAGCCACCCTGTCTTTGTCTCCAGGGGAAAGAGCCACC

CTCTCCTGCAGGGCCAGTCAGAGTGTTAGCAGCTACTTAGCCTGGTACCAACAGAAACCT

GGCCAGGCTCCCAGGCTCCTCATCTATGATGCATCCAACAGGGCCACTGGCATCCCAGCC

AGGTTCAGTGGCAGTGGGTCTGGGACAGACTTCACTCTCACCATCAGCAGCCTAGAGCCT

GAAGATTTTGCAGTTTATTACTGTCAGCAGCGTAGCAACTGGCCGATCACCTTCGGCCAA

GGGACACGACTGGAGATTAAA

Linker-1 nucleic acid sequence (SEQ ID NO: 57)

GGCAGTACTAGCGGTGGTGGCTCCGGGGGCGGTTCCGGTGGGGGCGGCAGCAGC

OF $V_H$ nucleic acid sequence (SEQ ID NO: 58)

GAAGTGCAGCTGGTGGAGTCTGGGGGAGGCTTGGTACAGCCTGGCAGGTCCCTGAGACTC

TCCTGTGCAGCCTCTGGATTCACCTTTAATGATTATGCCATGCACTGGGTCCGGCAAGCT

CCAGGGAAGGGCCTGGAGTGGGTCTCAACTATTAGTTGGAATAGTGGTTCCATAGGCTAT

GCGGACTCTGTGAAGGGCCGATTCACCATCTCCAGAGACAACGCCAAGAAGTCCCTGTAT

CTGCAAATGAACAGTCTGAGAGCTGAGGACACGGCCTTGTATTACTGTGCAAAAGATATA

CAGTACGGCAACTACTACTACGGTATGGACGTCTGGGGCCAAGGGACCACGGTCACCGTC

TCCTCA

Linker-2 nucleic acid sequence (SEQ ID NO: 59)

GGAGGTGGTGGATCC

BCMA-20 scFv (729 nt):
B20 $V_H$ nucleic acid sequence (363 nt)

(SEQ ID NO: 60)

Gaggtgcagctggtggagtccggcggcggcctggtgcagcccggcggctccctgcggctg tcctgcgccgcctccggcttcaccttctccaacttcgacatggcctgggtgcggcaggcc cccggcaagggcctggtgtgggtgtcctccatcaccaccggcgccgaccacgccatctac gccgactccgtgaagggccggttcaccatctcccgggacaacgccaagaacaccctgtac ctgcagatgaactccctgcgggccgaggacaccgccgtgtactactgcgtgcggcacggc tactacgacggctaccacctgttcgactactggggccagggcaccctggtgaccgtgtcc tcc Linker-3 nucleic acid sequence (45 nt)

(SEQ ID NO: 61)

Ggtggcggtggctcgggcggtggtgggtcgggtggcggcggatct

B20 $V_L$ nucleic acid sequence (321 nt)

(SEQ ID NO: 62)

Gacatccagatgacccagtccccctcctccctgtccgcctccgtgggcgaccgggtgacc atcacctgccgggcctcccagggcatctccaactacctgaactggtaccagcagaagccc ggcaaggcccccaagcccctgatctactacacctccaacctgcagtccggcgtgccctcc -continued cggttctccggctccggctccggcaccgactacaccctgaccatctcctccctgcagccc gaggacttcgccacctactactgcatgggccagaccatctcctcctacaccttcggccag ggcaccaagctggagatcaag CD8a hinge nucleic acid sequence (165 nt)

(SEQ ID NO: 63)

Ttcgtgccggtcttcctgccagcgaagcccaccacgacgccagcgccgcgaccaccaaca ccggcgcccaccatcgcgtcgcagcccctgtccctgcgcccagaggcgtgccggccagcg gggggggcgcagtgcacacgagggggctggacttcgcctgtgat CD8a TM nucleic acid sequence (72 nt)

(SEQ ID NO: 64)

Atctacatctgggcgcccttggccgggacttgtggggtccttctcctgtcactggttatc accctttactgc 4-1BB nucleic acid sequence (126 nt)

(SEQ ID NO: 65)

Aaacggggcagaaagaaactcctgtatatattcaaacaaccatttatgagaccagtacaa actactcaagaggaagatggctgtagctgccgatttccagaagaagaagaaggaggatgt gaactg CD3z nucleic acid sequence (336 nt)

(SEQ ID NO: 66)

Agagtgaagttcagcaggagcgcagacgcccccgcgtaccagcagggccagaaccagctc tataacgagctcaatctaggacgaagagaggagtacgatgttttggacaagagacgtggc cgggaccctgagatgggggggaaagccgagaaggaagaaccctcaggaaggcctgtacaat gaactgcagaaagataagatggcggaggcctacagtgagattgggatgaaaggcgagcgc cggaggggcaaggggcacgatggcctttaccagggtctcagtacagccaccaaggacacc tacgacgcccttcacatgcaggccctgccccctcgctaa TOBL4 nucleic acid sequence (2247 nt)

(SEQ ID NO: 67)

atggccttaccagtgaccgccttgctcctgccgctggccttgctgctccacgccgccagg ccgGAAATTGTGTTGACACAGTCTCCAGCCACCCTGTCTTTGTCTCCAGGGGAAAGAGCC

ACCCTCTCCTGCAGGGCCAGTCAGAGTGTTAGCAGCTACTTAGCCTGGTACCAACAGAAA

CCTGGCCAGGCTCCCAGGCTCCTCATCTATGATGCATCCAACAGGGCCACTGGCATCCCA

GCCAGGTTCAGTGGCAGTGGGTCTGGGACAGACTTCACTCTCACCATCAGCAGCCTAGAG

CCTGAAGATTTTGCAGTTTATTACTGTCAGCAGCGTAGCAACTGGCCGATCACCTTCGGC

CAAGGGACACGACTGGAGATTAAAGGCAGTACTAGCGGTGGTGGCTCCGGGGGCGGTTCC

GGTGGGGGCGGCAGCAGCGAAGTGCAGCTGGTGGAGTCTGGGGGAGGCTTGGTACAGCCT

GGCAGGTCCCTGAGACTCTCCTGTGCAGCCTCTGGATTCACCTTTAATGATTATGCCATG

CACTGGGTCCGGCAAGCTCCAGGGAAGGGCCTGGAGTGGGTCTCAACTATTAGTTGGAAT

AGTGGTTCCATAGGCTATGCGGACTCTGTGAAGGGCCGATTCACCATCTCCAGAGACAAC

GCCAAGAAGTCCCTGTATCTGCAAATGAACAGTCTGAGAGCTGAGGACACGGCCTTGTAT

TACTGTGCAAAAGATATACAGTACGGCAACTACTACTACGGTATGGACGTCTGGGGCCAA

GGGACCACGGTCACCGTCTCCTCAGGAGGTGGTGGATCCgaggtgcagctggtggagtcc ggcggcggcctggtgcagcccggcggctccctgcggctgtcctgcgccgcctccggcttc accttctccaacttcgacatggcctgggtgcggcaggcccccggcaagggcctggtgtgg gtgtcctccatcaccaccggcgccgaccacgccatctacgccgactccgtgaagggccgg ttcaccatctcccgggacaacgccaagaacaccctgtacctgcagatgaactccctgcgg -continued gccgaggacaccgccgtgtactactgcgtgcggcacggctactacgacggctaccacctg ttcgactactggggccagggcaccctggtgaccgtgtcctccGgtggcggtggctcgg gcggtggtgggtcgggtggggcggatctGacatccagatgacccagtccccctcctcc ctgtccgcctccgtgggcgaccgggtgaccatcacctgccgggcctcccagggcatctcc aactacctgaactggtaccagcagaagcccggcaaggcccccaagcccctgatctactac acctccaacctgcagtccggcgtgccctcccggttctccggctccggctccggcaccgac tacaccctgaccatctcctccctgcagcccgaggacttcgccacctactactgcatgggc cagaccatctcctcctacaccttcggccagggcaccaagctggagatcaagttcgtgccg gtcttcctgccagcgaagcccaccacgacgccagcgccgcgaccaccaacaccggcgccc accatcgcgtcgcagcccctgtccctgcgcccagaggcgtgccggccagcggggggggcg cagtgcacacgagggggctggacttcgcctgtgatatctacatctgggcgcccttggccg ggacttgtggggtccttctcctgtcactggttatcaccctttactgcaaacggggcagaa agaaactcctgtatatattcaaacaaccatttatgagaccagtacaaactactcaagagg aagatggctgtagctgccgatttccagaagaagaagaaggaggatgtgaactgAgagtga agttcagcaggagcgcagacgcccccgcgtaccagcagggccagaaccagctctataacg agctcaatctaggacgaagagaggagtacgatgttttggacaagagacgtggccgggacc ctgagatggggggaaagccgagaaggaagaaccctcaggaaggcctgtacaatgaactgc agaaagataagatggcggaggcctacagtgagattgggatgaaaggcgagcgccggaggg gcaaggggcacgatggcctttaccagggtctcagtacagccaccaaggacacctacgacg cccttcacatgcaggccctgccccctcgctaa TOBL4 amino acid sequence:

(SEQ ID NO: 68)

MALPVTALLLPLALLLHAARPEIVLTQSPATLSLSPGERATLSCRASQSVSSYLAWYQQK

PGQAPRLLIYDASNRATGIPARFSGSGSGTDFTLTISSLEPEDFAVYYCQQRSNWPITFG

QGTRLEIKGSTSGGGSGGGSGGGGSSEVQLVESGGGLVQPGRSLRLSCAASGFTFNDYAM

HWVRQAPGKGLEWVSTISWNSGSIGYADSVKGRFTISRDNAKKSLYLQMNSLRAEDTALY

YCAKDIQYGNYYYGMDVWGQGTTVTVSSGGGGSEVQLVESGGGLVQPGGSLRLSCAASGF

TFSNFDMAWVRQAPGKGLVWVSSITTGADHAIYADSVKGRFTISRDNAKNTLYLQMNSLR

AEDTAVYYCVRHGYYDGYHLFDYWGQGTLVTVSSGGGGSGGGGSGGGGSDIQMTQSPSSL

SASVGDRVTITCRASQGISNYLNWYQQKPGKAPKPLIYYTSNLQSGVPSRFSGSGSGTDY

TLTISSLQPEDFATYYCMGQTISSYTFGQGTKLEIKFVPVFLPAKPTTTPAPRPPTPAPT

IASQPLSLRPEACRPAAGGAVHTRGLDFACDIYIWAPLAGTCGVLLLSLVITLYCKRGRK

KLLYIFKQPFMRPVQTTQEEDGCSCRFPEEEEGGCELRVKFSRSADAPAYQQGQNQLYNE

LNLGRREEYDVLDKRRGRDPEMGGKPRRKNPQEGLYNELQKDKMAEAYSEIGMKGERRRG

KGHDGLYQGLSTATKDTYDALHMQALPPR

TN-OF-B20-1(TOB1)
CD8a SP nucleic acid sequence (SEQ ID NO: 69)

ATGGCCTTACCAGTGACCGCCTTGCTCCTGCCGCTGGCCTTGCTGCTCCACGCCGCCAGG

CCG

OF $V_L$ nucleic acid sequence (SEQ ID NO: 70)

GAAATTGTGTTGACACAGTCTCCAGCCACCCTGTCTTTGTCTCCAGGGGAAAGAGCCACC

CTCTCCTGCAGGGCCAGTCAGAGTGTTAGCAGCTACTTAGCCTGGTACCAACAGAAACCT

-continued

GGCCAGGCTCCCAGGCTCCTCATCTATGATGCATCCAACAGGGCCACTGGCATCCCAGCC

AGGTTCAGTGGCAGTGGGTCTGGGACAGACTTCACTCTCACCATCAGCAGCCTAGAGCCT

GAAGATTTTGCAGTTTATTACTGTCAGCAGCGTAGCAACTGGCCGATCACCTTCGGCCAA

GGGACACGACTGGAGATTAAA

Linker-1 nucleic acid sequence (SEQ ID NO: 71)

GGCAGTACTAGCGGTGGTGGCTCCGGGGGCGGTTCCGGTGGGGGCGGCAGCAGC

OF $V_H$ nucleic acid sequence (SEQ ID NO: 72)

GAAGTGCAGCTGGTGGAGTCTGGGGGAGGCTTGGTACAGCCTGGCAGGTCCCTGAGACTC

TCCTGTGCAGCCTCTGGATTCACCTTTAATGATTATGCCATGCACTGGGTCCGGCAAGCT

CCAGGGAAGGGCCTGGAGTGGGTCTCAACTATTAGTTGGAATAGTGGTTCCATAGGCTAT

GCGGACTCTGTGAAGGGCCGATTCACCATCTCCAGAGACAACGCCAAGAAGTCCCTGTAT

CTGCAAATGAACAGTCTGAGAGCTGAGGACACGGCCTTGTATTACTGTGCAAAAGATATA

CAGTACGGCAACTACTACTACGGTATGGACGTCTGGGGCCAAGGGACCACGGTCACCGTC

TCCTCA

Linker-2 nucleic acid sequence (SEQ ID NO: 73)

GGAGGTGGTGGATCC

B20 $V_H$ nucleic acid sequence (SEQ ID NO: 74)

Gaggtgcagctggtggagtccggcggcggcctggtgcagcccggcggctccctgcggctg tcctgcgccgcctccggcttcaccttctccaacttcgacatggcctgggtgcggcaggcc cccggcaagggcctggtgtgggtgtcctccatcaccaccggcgccgaccacgccatctac gccgactccgtgaagggccggttcaccatctcccgggacaacgccaagaacaccctgtac ctgcagatgaactccctgcgggccgaggacaccgccgtgtactactgcgtgcggcacggc tactacgacggctaccacctgttcgactactggggccagggcaccctggtgaccgtgtcc tcc Linker-3 nucleic acid sequence (SEQ ID NO: 75)

ggtggcggtggctcgggcggtggtgggtcgggtggcggcggatct

B20 $V_L$ nucleic acid sequence (SEQ ID NO: 76)

Gacatccagatgacccagtcccctcctccctgtccgcctccgtgggcgaccgggtgacc atcacctgccgggcctcccagggcatctccaactacctgaactggtaccagcagaagccc ggcaaggcccccaagcccctgatctactacacctccaacctgcagtccggcgtgccctcc cggttctccggctccggctccggcaccgactacaccctgaccatctcctccctgcagccc gaggacttcgccacctactactgcatgggccagaccatctcctcctacaccttcggccag ggcaccaagctggagatcaag LgG4 hinge nucleic acid sequence (36 nt)

(SEQ ID NO: 77)

GAGAGCAAGTACGGACCGCCCTGCCCCCCTTGCCCT

IgG4 hinge amino acid sequence:

(SEQ ID NO: 78)

ESKYGPPCPPCP

-continued

CD28 TM nucleic acid sequence (84 nt)

(SEQ ID NO: 79)

ATGTTCTGGGTGCTGGTGGTGGTCGGAGGCGTGCTGGCCTGCTACAGCCTGCTGGTCACC

GTGGCCTTCATCATCTTTTGGGTG

CD28 TM amino acid sequence:

(SEQ ID NO: 80)

MFWVLVVVGGVLACYSLLVTVAFIIFWV

4-1BB nucleic acid sequence (SEQ ID NO: 81)

AAACGGGGCAGAAAGAAACTCCTGTATATATTCAAACAACCATTTATGAGACCAGTACAA

ACTACTCAAGAGGAAGATGGCTGTAGCTGCCGATTTCCAGAAGAAGAAGAAGGAGGATGT

GAACTG

CD3z nucleic acid sequence (SEQ ID NO: 82)

CGGGTGAAGTTCAGCAGAAGCGCCGACGCCCCTGCCTACCAGCAGGGCCAGAATCAGCTG

TACAACGAGCTGAACCTGGGCAGAAGGGAAGAGTACGACGTCCTGGATAAGCGGAGAGGC

CGGGACCCTGAGATGGGCGGCAAGCCTCGGCGGAAGAACCCCCAGGAAGGCCTGTATAAC

GAACTGCAGAAAGACAAGATGGCCGAGGCCTACAGCGAGATCGGCATGAAGGGCGAGCGG

AGGCGGGGCAAGGGCCACGACGGCCTGTATCAGGGCCTGTCCACCGCCACCAAGGATACC

TACGACGCCCTGCACATGCAGGCCCTGCCCCCAAGG

TOB1 nucleic acid sequence (2130 nt)

(SEQ ID NO: 83)

ATGGCCTTACCAGTGACCGCCTTGCTCCTGCCGCTGGCCTTGCTGCTCCACGCCGCCAGG

CCGGAAATTGTGTTGACACAGTCTCCAGCCACCCTGTCTTTGTCTCCAGGGGAAAGAGCC

ACCCTCTCCTGCAGGGCCAGTCAGAGTGTTAGCAGCTACTTAGCCTGGTACCAACAGAAA

CCTGGCCAGGCTCCCAGGCTCCTCATCTATGATGCATCCAACAGGGCCACTGGCATCCCA

GCCAGGTTCAGTGGCAGTGGGTCTGGGACAGACTTCACTCTCACCATCAGCAGCCTAGAG

CCTGAAGATTTTGCAGTTTATTACTGTCAGCAGCGTAGCAACTGGCCGATCACCTTCGGC

CAAGGGACACGACTGGAGATTAAAGGCAGTACTAGCGGTGGTGGCTCCGGGGGCGGTTCC

GGTGGGGGCGGCAGCAGCGAAGTGCAGCTGGTGGAGTCTGGGGGAGGCTTGGTACAGCCT

GGCAGGTCCCTGAGACTCTCCTGTGCAGCCTCTGGATTCACCTTTAATGATTATGCCATG

CACTGGGTCCGGCAAGCTCCAGGGAAGGGCCTGGAGTGGGTCTCAACTATTAGTTGGAAT

AGTGGTTCCATAGGCTATGCGGACTCTGTGAAGGGCCGATTCACCATCTCCAGAGACAAC

GCCAAGAAGTCCCTGTATCTGCAAATGAACAGTCTGAGAGCTGAGGACACGGCCTTGTAT

TACTGTGCAAAAGATATACAGTACGGCAACTACTACTACGGTATGGACGTCTGGGGCCAA

GGGACCACGGTCACCGTCTCCTCAGGAGGTGGTGGATCCgaggtgcagctggtggagtcc ggcggcggcctggtgcagcccggcggctccctgcggctgtcctgcgccgcctccggcttc accttctccaacttcgacatggcctgggtgcggcaggcccccggcaagggcctggtgtgg gtgtcctccatcaccaccggcgccgaccacgccatctacgccgactccgtgaagggccgg ttcaccatctcccgggacaacgccaagaacaccctgtacctgcagatgaactccctgcgg gccgaggacaccgccgtgtactactgcgtgcggcacggctactacgacggctaccacctg ttcgactactggggccagggcaccctggtgaccgtgtcctccggtggcggtggctcgggc ggtggtgggtcgggtggcggcggatctgacatccagatgacccagtccccctcctccctg tccgcctccgtgggcgaccgggtgaccatcacctgccgggcctcccagggcatctccaac tacctgaactggtaccagcagaagcccggcaaggcccccaagcccctgatctactacacc tccaacctgcagtccggcgtgccctcccggttctccggctccggctccggcaccgactac -continued accctgaccatctcctccctgcagcccgaggacttcgccacctactactgcatgggccag accatctcctcctacaccttcggccagggcaccaagctggagatcaagGAGAGCAAGTAC

GGACCGCCCTGCCCCCCTTGCCCTATGTTCTGGGTGCTGGTGGTGGTCGGAGGCGTGCTG

GCCTGCTACAGCCTGCTGGTCACCGTGGCCTTCATCATCTTTTGGGTGAAACGGGGCAGA

AAGAAACTCCTGTATATATTCAAACAACCATTTATGAGACCAGTACAAACTACTCAAGAG

GAAGATGGCTGTAGCTGCCGATTTCCAGAAGAAGAAGAAGGAGGATGTGAACTGCGGGTG

AAGTTCAGCAGAAGCGCCGACGCCCCTGCCTACCAGCAGGGCCAGAATCAGCTGTACAAC

GAGCTGAACCTGGGCAGAAGGGAAGAGTACGACGTCCTGGATAAGCGGAGAGGCCGGGAC

CCTGAGATGGGCGGCAAGCCTCGGCGGAAGAACCCCCAGGAAGGCCTGTATAACGAACTG

CAGAAAGACAAGATGGCCGAGGCCTACAGCGAGATCGGCATGAAGGGCGAGCGGAGGCGG

GGCAAGGGCCACGACGGCCTGTATCAGGGCCTGTCCACCGCCACCAAGGATACCTACGAC

GCCCTGCACATGCAGGCCCTGCCCCCAAGGTAA

TOB1 amino acid sequence:

(SEQ ID NO: 84)

MALPVTALLLPLALLLHAARPEIVLTQSPATLSLSPGERATLSCRASQSVSSYLAWYQQK

PGQAPRLLIYDASNRATGIPARFSGSGSGTDFTLTISSLEPEDFAVYYCQQRSNWPITFG

QGTRLEIKGSTSGGGSGGGSGGGGSSEVQLVESGGGLVQPGRSLRLSCAASGFTFNDYAM

HWVRQAPGKGLEWVSTISWNSGSIGYADSVKGRFTISRDNAKKSLYLQMNSLRAEDTALY

YCAKDIQYGNYYYGMDVWGQGTTVTVSSGGGGSEVQLVESGGGLVQPGGSLRLSCAASGF

TFSNFDMAWVRQAPGKGLVWVSSITTGADHAIYADSVKGRFTISRDNAKNTLYLQMNSLR

AEDTAVYYCVRHGYYDGYHLFDYWGQGTLVTVSSGGGGSGGGGSGGGGSDIQMTQSPSSL

SASVGDRVTITCRASQGISNYLNWYQQKPGKAPKPLIYYTSNLQSGVPSRFSGSGSGTDY

TLTISSLQPEDFATYYCMGQTISSYTFGQGTKLEIKESKYGPPCPPCPMFWVLVVVGGVL

ACYSLLVTVAFIIFWVKRGRKKLLYIFKQPFMRPVQTTQEEDGCSCRFPEEEEGGCELRV

KFSRSADAPAYQQGQNQLYNELNLGRREEYDVLDKRRGRDPEMGGKPRRKNPQEGLYNEL

QKDKMAEAYSEIGMKGERRRGKGHDGLYQGLSTATKDTYDALHMQALPPR

TN-OF-B20-2 (TOB2)
CD8a SP nucleic acid sequence (SEQ ID NO: 85)

ATGGCCTTACCAGTGACCGCCTTGCTCCTGCCGCTGGCCTTGCTGCTCCACGCCGCCAGG

CCG

OF $V_L$ nucleic acid sequence (SEQ ID NO: 86)

GAAATTGTGTTGACACAGTCTCCAGCCACCCTGTCTTTGTCTCCAGGGGAAAGAGCCACC

CTCTCCTGCAGGGCCAGTCAGAGTGTTAGCAGCTACTTAGCCTGGTACCAACAGAAACCT

GGCCAGGCTCCCAGGCTCCTCATCTATGATGCATCCAACAGGGCCACTGGCATCCCAGCC

AGGTTCAGTGGCAGTGGGTCTGGGACAGACTTCACTCTCACCATCAGCAGCCTAGAGCCT

GAAGATTTTGCAGTTTATTACTGTCAGCAGCGTAGCAACTGGCCGATCACCTTCGGCCAA

GGGACACGACTGGAGATTAAA

Linker-1 nucleic acid sequence (SEQ ID NO: 87)

GGCAGTACTAGCGGTGGTGGCTCCGGGGGCGGTTCCGGTGGGGGCGGCAGCAGC

OF $V_H$ nucleic acid sequence (SEQ ID NO: 88)

GAAGTGCAGCTGGTGGAGTCTGGGGGAGGCTTGGTACAGCCTGGCAGGTCCCTGAGACTC

TCCTGTGCAGCCTCTGGATTCACCTTTAATGATTATGCCATGCACTGGGTCCGGCAAGCT

-continued

CCAGGGAAGGGCCTGGAGTGGGTCTCAACTATTAGTTGGAATAGTGGTTCCATAGGCTAT
GCGGACTCTGTGAAGGGCCGATTCACCATCTCCAGAGACAACGCCAAGAAGTCCCTGTAT
CTGCAAATGAACAGTCTGAGAGCTGAGGACACGGCCTTGTATTACTGTGCAAAAGATATA
CAGTACGGCAACTACTACTACGGTATGGACGTCTGGGGCCAAGGGACCACGGTCACCGTC
TCCTCA

Linker-2 nucleic acid sequence (SEQ ID NO: 89)

GGAGGTGGTGGATCC

B20 $V_L$ nucleic acid sequence (SEQ ID NO: 90)

Gacatccagatgacccagtcccccctcctccctgtccgcctccgtgggcgaccgggtgacc
atcacctgccgggcctcccagggcatctccaactacctgaactggtaccagcagaagccc
ggcaaggcccccaagcccctgatctactacacctccaacctgcagtccggcgtgccctcc
cggttctccggctccggctccggcaccgactacaccctgaccatctcctccctgcagccc
gaggacttcgccacctactactgcatgggccagaccatctcctcctacaccttcggccag
ggcaccaagctggagatcaag Linker-3 nucleic acid sequence (SEQ ID NO: 91)

ggtggcggtggctcgggcggtggtgggtcgggtggcggcggatct

B20 $V_H$ nucleic acid sequence (SEQ ID NO: 92)

Gaggtgcagctggtggagtccggcggcggcctggtgcagcccggggctccctgcggctgt
cctgcgccgcctccggcttcaccttctccaacttcgacatggcctgggtgcggcaggccc
ccggcaagggcctggtgtgggtgtcctccatcaccaccggcgccgaccacgccatctacg
ccgactccgtgaagggccggttcaccatctcccgggacaacgccaagaacaccctgtacc
tgcagatgaactccctgcgggccgaggacaccgccgtgtactactgcgtgcggcacggct
actacgacggctaccacctgttcgactactggggccagggcaccctggtgaccgtgtcct
cc hinge nucleic acid sequence (SEQ ID NO: 93)

GAGAGCAAGTACGGACCGCCCTGCCCCCCTTGCCCT

CD28 TM nucleic acid sequence (SEQ ID NO: 94)

ATGTTCTGGGTGCTGGTGGTGGTCGGAGGCGTGCTGGCCTGCTACAGCCTGCTGGTCACC
GTGGCCTTCATCATCTTTTGGGTG 4-1BB nucleic acid sequence (SEQ ID NO: 95)

AAACGGGGCAGAAAGAAACTCCTGTATATATTCAAACAACCATTTATGAGACCAGTACAA
ACTACTCAAGAGGAAGATGGCTGTAGCTGCCGATTTCCAGAAGAAGAAGAAGGAGGATGT
GAACTG

CD3z nucleic acid sequence (SEQ ID NO: 96)

CGGGTGAAGTTCAGCAGAAGCGCCGACGCCCCTGCCTACCAGCAGGGCCAGAATCAGCTG
TACAACGAGCTGAACCTGGGCAGAAGGGAAGAGTACGACGTCCTGGATAAGCGGAGAGGC
CGGGACCCTGAGATGGGCGGCAAGCCTCGGCGGAAGAACCCCCAGGAAGGCCTGTATAAC
GAACTGCAGAAAGACAAGATGGCCGAGGCCTACAGCGAGATCGGCATGAAGGGCGAGCGG
AGGCGGGGCAAGGGCCACGACGGCCTGTATCAGGGCCTGTCCACCGCCACCAAGGATACC
TACGACGCCCTGCACATGCAGGCCCTGCCCCCAAGG

-continued

TOB2 nucleic acid sequence (2130 nt)

(SEQ ID NO: 97)

ATGGCCTTACCAGTGACCGCCTTGCTCCTGCCGCTGGCCTTGCTGCTCCACGCCGCCAGG

CCGGAAATTGTGTTGACACAGTCTCCAGCCACCCTGTCTTTGTCTCCAGGGGAAAGAGCC

ACCCTCTCCTGCAGGGCCAGTCAGAGTGTTAGCAGCTACTTAGCCTGGTACCAACAGAAA

CCTGGCCAGGCTCCCAGGCTCCTCATCTATGATGCATCCAACAGGGCCACTGGCATCCCA

GCCAGGTTCAGTGGCAGTGGGTCTGGGACAGACTTCACTCTCACCATCAGCAGCCTAGAG

CCTGAAGATTTTGCAGTTTATTACTGTCAGCAGCGTAGCAACTGGCCGATCACCTTCGGC

CAAGGGACACGACTGGAGATTAAAGGCAGTACTAGCGGTGGTGGCTCCGGGGGCGGTTCC

GGTGGGGGCGGCAGCAGCGAAGTGCAGCTGGTGGAGTCTGGGGGAGGCTTGGTACAGCCT

GGCAGGTCCCTGAGACTCTCCTGTGCAGCCTCTGGATTCACCTTTAATGATTATGCCATG

CACTGGGTCCGGCAAGCTCCAGGGAAGGGCCTGGAGTGGGTCTCAACTATTAGTTGGAAT

AGTGGTTCCATAGGCTATGCGGACTCTGTGAAGGGCCGATTCACCATCTCCAGAGACAAC

GCCAAGAAGTCCCTGTATCTGCAAATGAACAGTCTGAGAGCTGAGGACACGGCCTTGTAT

TACTGTGCAAAAGATATACAGTACGGCAACTACTACTACGGTATGGACGTCTGGGGCCAA

GGGACCACGGTCACCGTCTCCTCAGGAGGTGGTGGATCCGacatccagatgacccagtcc ccctcctccctgtccgcctccgtgggcgaccgggtgaccatcacctgccgggcctcccag ggcatctccaactacctgaactggtaccagcagaagcccggcaaggcccccaagcccctg atctactacacctccaacctgcagtccggcgtgccctcccggttctccggctccggctcc ggcaccgactacaccctgaccatctcctccctgcagcccgaggacttcgccacctactac tgcatgggccagaccatctcctcctacaccttcggccagggcaccaagctggagatcaag ggtggcggtggctcgggcggtggtgggtcgggtggcggcggatctgaggtgcagctggtg gagtccggcggcggcctggtgcagcccggcggctccctgcggctgtcctgcgccgcctcc ggcttcaccttctccaacttcgacatggcctgggtgcggcaggcccccggcaagggcctg gtgtgggtgtcctccatcaccaccggcgccgaccacgccatctacgccgactccgtgaag ggccggttcaccatctcccgggacaacgccaagaacaccctgtacctgcagatgaactcc ctgcgggccgaggacaccgccgtgtactactgcgtgcggcacggctactacgacggctac cacctgttcgactactggggccagggcaccctggtgaccgtgtcctccGAGAGCAAGTAC

GGACCGCCCTGCCCCCCTTGCCCTATGTTCTGGGTGCTGGTGGTGGTCGGAGGCGTGCTG

GCCTGCTACAGCCTGCTGGTCACCGTGGCCTTCATCATCTTTTGGGTGAAACGGGGCAGA

AAGAAACTCCTGTATATATTCAAACAACCATTTATGAGACCAGTACAAACTACTCAAGAG

GAAGATGGCTGTAGCTGCCGATTTCCAGAAGAAGAAGAAGGAGGATGTGAACTGCGGGTG

AAGTTCAGCAGAAGCGCCGACGCCCCTGCCTACCAGCAGGGCCAGAATCAGCTGTACAAC

GAGCTGAACCTGGGCAGAAGGGAAGAGTACGACGTCCTGGATAAGCGGAGAGGCCGGGAC

CCTGAGATGGGCGGCAAGCCTCGGCGGAAGAACCCCCAGGAAGGCCTGTATAACGAACTG

CAGAAAGACAAGATGGCCGAGGCCTACAGCGAGATCGGCATGAAGGGCGAGCGGAGGCGG

GGCAAGGGCCACGACGGCCTGTATCAGGGCCTGTCCACCGCCACCAAGGATACCTACGAC

GCCCTGCACATGCAGGCCCTGCCCCCAAGGTAA

TOB2 amino acid sequence:

(SEQ ID NO: 98)

MALPVTALLLPLALLLHAARPEIVLTQSPATLSLSPGERATLSCRASQSVSSYLAWYQQK

PGQAPRLLIYDASNRATGIPARFSGSGSGTDFTLTISSLEPEDFAVYYCQQRSNWPITFG

QGTRLEIKGSTSGGGSGGGSGGGGSSEVQLVESGGGLVQPGRSLRLSCAASGFTFNDYAM

-continued

HWVRQAPGKGLEWVSTISWNSGSIGYADSVKGRFTISRDNAKKSLYLQMNSLRAEDTALY

YCAKDIQYGNYYYGMDVWGQGTTVTVSSGGGGSDIQMTQSPSSLSASVGDRVTITCRASQ

GISNYLNWYQQKPGKAPKPLIYYTSNLQSGVPSRFSGSGSGTDYTLTISSLQPEDFATYY

CMGQTISSYTFGQGTKLEIKGGGGSGGGGSGGGGSEVQLVESGGGLVQPGGSLRLSCAAS

GFTFSNFDMAWVRQAPGKGLVWVSSITTGADHAIYADSVKGRFTISRDNAKNTLYLQMNS

LRAEDTAVYYCVRHGYYDGYHLFDYWGQGTLVTVSSESKYGPPCPPCPMFWVLVVVGGVL

ACYSLLVTVAFIIFWVKRGRKKLLYIFKQPFMRPVQTTQEEDGCSCRFPEEEEGGCELRV

KFSRSADAPAYQQGQNQLYNELNLGRREEYDVLDKRRGRDPEMGGKPRRKNPQEGLYNEL

QKDKMAEAYSEIGMKGERRRGKGHDGLYQGLSTATKDTYDALHMQALPPR

TN-OF-B20-3 (TOB3)
CD8a SP nucleic acid sequence (SEQ ID NO: 99)

ATGGCCTTACCAGTGACCGCCTTGCTCCTGCCGCTGGCCTTGCTGCTCCACGCCGCCAGG

CCG

OF $V_H$ nucleic acid sequence (SEQ ID NO: 100)

GAAGTGCAGCTGGTGGAGTCTGGGGGAGGCTTGGTACAGCCTGGCAGGTCCCTGAGACTC

TCCTGTGCAGCCTCTGGATTCACCTTTAATGATTATGCCATGCACTGGGTCCGGCAAGCT

CCAGGGAAGGGCCTGGAGTGGGTCTCAACTATTAGTTGGAATAGTGGTTCCATAGGCTAT

GCGGACTCTGTGAAGGGCCGATTCACCATCTCCAGAGACAACGCCAAGAAGTCCCTGTAT

CTGCAAATGAACAGTCTGAGAGCTGAGGACACGGCCTTGTATTACTGTGCAAAAGATATA

CAGTACGGCAACTACTACTACGGTATGGACGTCTGGGGCCAAGGGACCACGGTCACCGTC

TCCTCA

Linker-1 nucleic acid sequence (SEQ ID NO: 101)

GGCAGTACTAGCGGTGGTGGCTCCGGGGGCGGTTCCGGTGGGGGCGGCAGCAGC

OF $V_L$ nucleic acid sequence (SEQ ID NO: 102)

GAAATTGTGTTGACACAGTCTCCAGCCACCCTGTCTTTGTCTCCAGGGGAAAGAGCCACC

CTCTCCTGCAGGGCCAGTCAGAGTGTTAGCAGCTACTTAGCCTGGTACCAACAGAAACCT

GGCCAGGCTCCCAGGCTCCTCATCTATGATGCATCCAACAGGGCCACTGGCATCCCAGCC

AGGTTCAGTGGCAGTGGGTCTGGGACAGACTTCACTCTCACCATCAGCAGCCTAGAGCCT

GAAGATTTTGCAGTTTATTACTGTCAGCAGCGTAGCAACTGGCCGATCACCTTCGGCCAA

GGGACACGACTGGAGATTAAA

Linker-2 nucleic acid sequence (SEQ ID NO: 103)

GGAGGTGGTGGATCC

B20 $V_L$ nucleic acid sequence (SEQ ID NO: 104)

Gacatccagatgacccagtcccccctcctccctgtccgcctccgtgggcgaccgggtgacc atcacctgccgggcctcccagggcatctccaactacctgaactggtaccagcagaagccc ggcaaggcccccaagcccctgatctactacacctccaacctgcagtccggcgtgccctcc -continued cggttctccggctccggctccggcaccgactacaccctgaccatctcctccctgcagccc gaggacttcgccacctactactgcatgggccagaccatctcctcctacaccttcggccag ggcaccaagctggagatcaag Linker-3 nucleic acid sequence (SEQ ID NO: 105)

ggtggcggtggctcgggcggtggtgggtcgggtggcggcggatct

B20 $V_H$ nucleic acid sequence (SEQ ID NO: 106)

Gaggtgcagctggtggagtccggcggcggcctggtgcagcccggcggctccctgcggctg tcctgcgccgcctccggcttcaccttctccaacttcgacatggcctgggtgcggcaggcc cccggcaagggcctggtgtgggtgtcctccatcaccaccggcgccgaccacgccatctac gccgactccgtgaagggccggttcaccatctcccgggacaacgccaagaacaccctgtac ctgcagatgaactccctgcgggccgaggacaccgccgtgtactactgcgtgcggcacggc tactacgacggctaccacctgttcgactactggggccagggcaccctggtgaccgtgtcc tcc hinge nucleic acid sequence (SEQ ID NO: 107)

GAGAGCAAGTACGGACCGCCCTGCCCCCCTTGCCCT

CD28 TM nucleic acid sequence (SEQ ID NO: 108)

ATGTTCTGGGTGCTGGTGGTGGTCGGAGGCGTGCTGGCCTGCTACAGCCTGCTGGTCACC

GTGGCCTTCATCATCTTTTGGGTG 4-1BB nucleic acid sequence (SEQ ID NO: 109)

AAACGGGGCAGAAAGAAACTCCTGTATATATTCAAACAACCATTTATGAGACCAGTACAA

ACTACTCAAGAGGAAGATGGCTGTAGCTGCCGATTTCCAGAAGAAGAAGAAGGAGGATGT

GAACTG

CD3z nucleic acid sequence (SEQ ID NO: 110)

CGGGTGAAGTTCAGCAGAAGCGCCGACGCCCCTGCCTACCAGCAGGGCCAGAATCAGCTG

TACAACGAGCTGAACCTGGGCAGAAGGGAAGAGTACGACGTCCTGGATAAGCGGAGAGGC

CGGGACCCTGAGATGGGCGGCAAGCCTCGGCGGAAGAACCCCCAGGAAGGCCTGTATAAC

GAACTGCAGAAAGACAAGATGGCCGAGGCCTACAGCGAGATCGGCATGAAGGGCGAGCGG

AGGCGGGGCAAGGGCCACGACGGCCTGTATCAGGGCCTGTCCACCGCCACCAAGGATACC

TACGACGCCCTGCACATGCAGGCCCTGCCCCCAAGG

TOB3 nucleic acid sequence (2130 nt)

(SEQ ID NO: 111)

ATGGCCTTACCAGTGACCGCCTTGCTCCTGCCGCTGGCCTTGCTGCTCCACGCCGCCAGG

CCGGAAGTGCAGCTGGTGGAGTCTGGGGGAGGCTTGGTACAGCCTGGCAGGTCCCTGAGA

CTCTCCTGTGCAGCCTCTGGATTCACCTTTAATGATTATGCCATGCACTGGGTCCGGCAA

GCTCCAGGGAAGGGCCTGGAGTGGGTCTCAACTATTAGTTGGAATAGTGGTTCCATAGGC

TATGCGGACTCTGTGAAGGGCCGATTCACCATCTCCAGAGACAACGCCAAGAAGTCCCTG

TATCTGCAAATGAACAGTCTGAGAGCTGAGGACACGGCCTTGTATTACTGTGCAAAAGAT

ATACAGTACGGCAACTACTACTACGGTATGGACGTCTGGGGCCAAGGGACCACGGTCACC

GTCTCCTCAGGCAGTACTAGCGGTGGTGGCTCCGGGGGCGGTTCCGGTGGGGGCGGCAGC

AGCGAAATTGTGTTGACACAGTCTCCAGCCACCCTGTCTTTGTCTCCAGGGGAAAGAGCC

ACCCTCTCCTGCAGGGCCAGTCAGAGTGTTAGCAGCTACTTAGCCTGGTACCAACAGAAA

CCTGGCCAGGCTCCCAGGCTCCTCATCTATGATGCATCCAACAGGGCCACTGGCATCCCA

-continued

GCCAGGTTCAGTGGCAGTGGGTCTGGGACAGACTTCACTCTCACCATCAGCAGCCTAGAG

CCTGAAGATTTTGCAGTTTATTACTGTCAGCAGCGTAGCAACTGGCCGATCACCTTCGGC

CAAGGGACACGACTGGAGATTAAAGGAGGTGGTGGATCCGacatccagatgacccagtcc ccctcctccctgtccgcctccgtgggcgaccgggtgaccatcacctgccgggcctcccag ggcatctccaactacctgaactggtaccagcagaagcccggcaaggcccccaagcccctg atctactacacctccaacctgcagtccggcgtgccctcccggttctccggctccggctcc ggcaccgactacaccctgaccatctcctccctgcagcccgaggacttcgccacctactac tgcatgggccagaccatctcctcctacaccttcggccagggcaccaagctggagatcaag ggtggcggtggctcgggcggtggtgggtcgggtggcggcggatctgaggtgcagctggtg gagtccggcggcggcctggtgcagcccggcggctccctgcggctgtcctgcgccgcctcc ggcttcaccttctccaacttcgacatggcctgggtgcggcaggcccccggcaagggcctg gtgtgggtgtcctccatcaccaccggcgccgaccacgccatctacgccgactccgtgaag ggccggttcaccatctcccgggacaacgccaagaacaccctgtacctgcagatgaactcc ctgcgggccgaggacaccgccgtgtactactgcgtgcggcacggctactacgacggctac cacctgttcgactactggggccagggcaccctggtgaccgtgtcctccGAGAGCAAGTAC

GGACCGCCCTGCCCCCCTTGCCCTATGTTCTGGGTGCTGGTGGTGGTCGGAGGCGTGCTG

GCCTGCTACAGCCTGCTGGTCACCGTGGCCTTCATCATCTTTTGGGTGAAACGGGGCAGA

AAGAAACTCCTGTATATATTCAAACAACCATTTATGAGACCAGTACAAACTACTCAAGAG

GAAGATGGCTGTAGCTGCCGATTTCCAGAAGAAGAAGAAGGAGGATGTGAACTGCGGGTG

AAGTTCAGCAGAAGCGCCGACGCCCCTGCCTACCAGCAGGGCCAGAATCAGCTGTACAAC

GAGCTGAACCTGGGCAGAAGGGAAGAGTACGACGTCCTGGATAAGCGGAGAGGCCGGGAC

CCTGAGATGGGCGGCAAGCCTCGGCGGAAGAACCCCCAGGAAGGCCTGTATAACGAACTG

CAGAAAGACAAGATGGCCGAGGCCTACAGCGAGATCGGCATGAAGGGCGAGCGGAGGCGG

GGCAAGGGCCACGACGGCCTGTATCAGGGCCTGTCCACCGCCACCAAGGATACCTACGAC

GCCCTGCACATGCAGGCCCTGCCCCCAAGGTAA

TOB3 amino acid sequence:

(SEQ ID NO: 112)

MALPVTALLLPLALLLHAARPEVQLVESGGGLVQPGRSLRLSCAASGFTFNDYAMHWVRQ

APGKGLEWVSTISWNSGSIGYADSVKGRFTISRDNAKKSLYLQMNSLRAEDTALYYCAKD

IQYGNYYYGMDVWGQGTTVTVSSGSTSGGGSGGGSGGGGSSEIVLTQSPATLSLSPGERA

TLSCRASQSVSSYLAWYQQKPGQAPRLLIYDASNRATGIPARFSGSGSGTDFTLTISSLE

PEDFAVYYCQQRSNWPITFGQGTRLEIKGGGGSDIQMTQSPSSLSASVGDRVTITCRASQ

GISNYLNWYQQKPGKAPKPLIYYTSNLQSGVPSRFSGSGSGTDYTLTISSLQPEDFATYY

CMGQTISSYTFGQGTKLEIKGGGGSGGGGSGGGGSEVQLVESGGGLVQPGGSLRLSCAAS

GFTFSNFDMAWVRQAPGKGLVWVSSITTGADHAIYADSVKGRFTISRDNAKNTLYLQMNS

LRAEDTA VYYCVRHGYYDGYHLFDYWGQGTLVTVSSESKYGPPCPPCPMFWVLVVV

-continued

GGVLACYSLLVTVAFIIFWVKRGRKKLLYIFKQPFMRPVQTTQEEDGCSCRFPEEEEGGC

ELRVKFSRSADAPAYQQGQNQLYNELNLGRREEYDVLDKRRGRDPEMGGKPRRKNPQEGL

YNELQKDKMAEAYSEIGMKGERRRGKGHDGLYQGLSTATKDTYDALHMQALPPR

TN-OF-B20-4 (TOB4)
CD8a SP nucleic acid sequence
(SEQ ID NO: 113)
ATGGCCTTACCAGTGACCGCCTTGCTCCTGCCGCTGGCCTTGCTGCTCCACGCCGCCAGG

CCG

OF $V_H$ nucleic acid sequence
(SEQ ID NO: 114)
GAAGTGCAGCTGGTGGAGTCTGGGGGAGGCTTGGTACAGCCTGGCAGGTCCCTGAGACTC

TCCTGTGCAGCCTCTGGATTCACCTTTAATGATTATGCCATGCACTGGGTCCGGCAAGCT

CCAGGGAAGGGCCTGGAGTGGGTCTCAACTATTAGTTGGAATAGTGGTTCCATAGGCTAT

GCGGACTCTGTGAAGGGCCGATTCACCATCTCCAGAGACAACGCCAAGAAGTCCCTGTAT

CTGCAAATGAACAGTCTGAGAGCTGAGGACACGGCCTTGTATTACTGTGCAAAAGATATA

CAGTACGGCAACTACTACTACGGTATGGACGTCTGGGGCCAAGGGACCACGGTCACCGTC

TCCTCA

Linker-1 nucleic acid sequence
(SEQ ID NO: 115)
GGCAGTACTAGCGGTGGTGGCTCCGGGGGCGGTTCCGGTGGGGGCGGCAGCAGC OF $V_L$ nucleic acid sequence
(SEQ ID NO: 116)
GAAATTGTGTTGACACAGTCTCCAGCCACCCTGTCTTTGTCTCCAGGGGAAAGAGCCACC

CTCTCCTGCAGGGCCAGTCAGAGTGTTAGCAGCTACTTAGCCTGGTACCAACAGAAACCT

GGCCAGGCTCCCAGGCTCCTCATCTATGATGCATCCAACAGGGCCACTGGCATCCCAGCC

AGGTTCAGTGGCAGTGGGTCTGGGACAGACTTCACTCTCACCATCAGCAGCCTAGAGCCT

GAAGATTTTGCAGTTTATTACTGTCAGCAGCGTAGCAACTGGCCGATCACCTTCGGCCAA

GGGACACGACTGGAGATTAAA

Linker-2 nucleic acid sequence
(SEQ ID NO: 117)
GGAGGTGGTGGATCC

B20 $V_H$ nucleic acid sequence
(SEQ ID NO: 118)
Gaggtgcagctggtggagtccggcggcggcctggtgcagcccggcggctccctgcggctg tcctgcgccgcctccggcttcaccttctccaacttcgacatggcctgggtgcggcaggcc cccggcaagggcctggtgtgggtgtcctccatcaccaccggcgccgaccacgccatctac gccgactccgtgaagggccggttcaccatctcccgggacaacgccaagaacaccctgtac ctgcagatgaactccctgcgggccgaggacaccgccgtgtactactgcgtgcggcacggc tactacgacggctaccacctgttcgactactggggccagggcaccctggtgaccgtgtcc tcc Linker-3 nucleic acid sequence
(SEQ ID NO: 119)
ggtggcggtggctcgggcggtggtgggtcgggtggcggcggatct B20 $V_L$ nucleic acid sequence
(SEQ ID NO: 120)
Gacatccagatgacccagtccccctcctccctgtccgcctccgtgggcgaccgggtgacc atcacctgccgggcctcccagggcatctccaactacctgaactggtaccagcagaagccc ggcaaggcccccaagcccctgatctactacacctccaacctgcagtccggcgtgccctcc cggttctccggctccggctccggcaccgactacaccctgaccatctcctccctgcagccc -continued gaggacttcgccacctactactgcatgggccagaccatctcctcctacaccttcggccag ggcaccaagctggagatcaag hinge nucleic acid sequence (SEQ ID NO: 121)

GAGAGCAAGTACGGACCGCCCTGCCCCCCTTGCCCT

CD28 TM nucleic acid sequence (SEQ ID NO: 122)

ATGTTCTGGGTGCTGGTGGTGGTCGGAGGCGTGCTGGCCTGCTACAGCCTGCTGGTCACC

GTGGCCTTCATCATCTTTTGGGTG 4-1BB nucleic acid sequence (SEQ ID NO: 123)

AAACGGGGCAGAAAGAAACTCCTGTATATATTCAAACAACCATTTATGAGACCAGTACAA

ACTACTCAAGAGGAAGATGGCTGTAGCTGCCGATTTCCAGAAGAAGAAGAAGGAGGATGT

GAACTG

CD3z nucleic acid sequence (SEQ ID NO: 124)

CGGGTGAAGTTCAGCAGAAGCGCCGACGCCCCTGCCTACCAGCAGGGCCAGAATCAGCTG

TACAACGAGCTGAACCTGGGCAGAAGGGAAGAGTACGACGTCCTGGATAAGCGGAGAGGC

CGGGACCCTGAGATGGGCGGCAAGCCTCGGCGGAAGAACCCCCAGGAAGGCCTGTATAAC

GAACTGCAGAAAGACAAGATGGCCGAGGCCTACAGCGAGATCGGCATGAAGGGCGAGCGG

AGGCGGGGCAAGGGCCACGACGGCCTGTATCAGGGCCTGTCCACCGCCACCAAGGATACC

TACGACGCCCTGCACATGCAGGCCCTGCCCCCAAGG

TOB4 nucleic acid sequence (2130 nt)

(SEQ ID NO: 125)

ATGGCCTTACCAGTGACCGCCTTGCTCCTGCCGCTGGCCTTGCTGCTCCACGCCGCCAGG

CCGGAAGTGCAGCTGGTGGAGTCTGGGGGAGGCTTGGTACAGCCTGGCAGGTCCCTGAGA

CTCTCCTGTGCAGCCTCTGGATTCACCTTTAATGATTATGCCATGCACTGGGTCCGGCAA

GCTCCAGGGAAGGGCCTGGAGTGGGTCTCAACTATTAGTTGGAATAGTGGTTCCATAGGC

TATGCGGACTCTGTGAAGGGCCGATTCACCATCTCCAGAGACAACGCCAAGAAGTCCCTG

TATCTGCAAATGAACAGTCTGAGAGCTGAGGACACGGCCTTGTATTACTGTGCAAAAGAT

ATACAGTACGGCAACTACTACTACGGTATGGACGTCTGGGGCCAAGGGACCACGGTCACC

GTCTCCTCAGGCAGTACTAGCGGTGGTGGCTCCGGGGGCGGTTCCGGTGGGGGCGGCAGC

AGCGAAATTGTGTTGACACAGTCTCCAGCCACCCTGTCTTTGTCTCCAGGGGAAAGAGCC

ACCCTCTCCTGCAGGGCCAGTCAGAGTGTTAGCAGCTACTTAGCCTGGTACCAACAGAAA

CCTGGCCAGGCTCCCAGGCTCCTCATCTATGATGCATCCAACAGGGCCACTGGCATCCCA

GCCAGGTTCAGTGGCAGTGGGTCTGGGACAGACTTCACTCTCACCATCAGCAGCCTAGAG

CCTGAAGATTTTGCAGTTTATTACTGTCAGCAGCGTAGCAACTGGCCGATCACCTTCGGC

CAAGGGACACGACTGGAGATTAAAGGAGGTGGTGGATCCgaggtgcagctggtggagtcc ggcggcggcctggtgcagcccggcggctccctgcggctgtcctgcgccgcctccggcttc accttctccaacttcgacatggcctgggtgcggcaggcccccggcaagggcctggtgtgg gtgtcctccatcaccaccggcgccgaccacgccatctacgccgactccgtgaagggccgg ttcaccatctcccgggacaacgccaagaacaccctgtacctgcagatgaactccctgcgg -continued gccgaggacaccgccgtgtactactgcgtgcggcacggctactacgacggctaccacctg ttcgactactggggccagggcaccctggtgaccgtgtcctccggtggcggtggctcgggc ggtggtgggtcgggtggcggcggatctGacatccagatgacccagtccccctcctccctg tccgcctccgtgggcgaccgggtgaccatcacctgccgggcctcccagggcatctccaac tacctgaactggtaccagcagaagcccggcaaggcccccaagcccctgatctactacacc tccaacctgcagtccggcgtgccctcccggttctccggctccggctccggcaccgactac accctgaccatctcctccctgcagcccgaggacttcgccacctactactgcatgggccag accatctcctcctacaccttcggccagggcaccaagctggagatcaagGAGAGCAAGTAC

GGACCGCCCTGCCCCCCTTGCCCTATGTTCTGGGTGCTGGTGGTGGTCGGAGGCGTGCTG

GCCTGCTACAGCCTGCTGGTCACCGTGGCCTTCATCATCTTTTGGGTGAAACGGGGCAGA

AAGAAACTCCTGTATATATTCAAACAACCATTTATGAGACCAGTACAAACTACTCAAGAG

GAAGATGGCTGTAGCTGCCGATTTCCAGAAGAAGAAGAAGGAGGATGTGAACTGCGGGTG

AAGTTCAGCAGAAGCGCCGACGCCCCTGCCTACCAGCAGGGCCAGAATCAGCTGTACAAC

GAGCTGAACCTGGGCAGAAGGGAAGAGTACGACGTCCTGGATAAGCGGAGAGGCCGGGAC

CCTGAGATGGGCGGCAAGCCTCGGCGGAAGAACCCCCAGGAAGGCCTGTATAACGAACTG

CAGAAAGACAAGATGGCCGAGGCCTACAGCGAGATCGGCATGAAGGGCGAGCGGAGGCGG

GGCAAGGGCCACGACGGCCTGTATCAGGGCCTGTCCACCGCCACCAAGGATACCTACGAC

GCCCTGCACATGCAGGCCCTGCCCCCAAGGTAA

TOB4 amino acid sequence:

(SEQ ID NO: 126)

MALPVTALLLPLALLLHAARPEVQLVESGGGLVQPGRSLRLSCAASGFTENDYAMHWVRQ

APGKGLEWVSTISWNSGSIGYADSVKGRFTISRDNAKKSLYLQMNSLRAEDTALYYCAKD

IQYGNYYYGMDVWGQGTTVTVSSGSTSGGGSGGGSGGGGSSEIVLTQSPATLSLSPGERA

TLSCRASQSVSSYLAWYQQKPGQAPRLLIYDASNRATGIPARFSGSGSGTDFTLTISSLE

PEDFAVYYCQQRSNWPITFGQGTRLEIKGGGGSEVQLVESGGGLVQPGGSLRLSCAASGF

TFSNFDMAWVRQAPGKGLVWVSSITTGADHAIYADSVKGRFTISRDNAKNTLYLQMNSLR

AEDTAVYYCVRHGYYDGYHLFDYWGQGTLVTVSSGGGGSGGGGSGGGGSDIQMTQSPSSL

SASVGDRVTITCRASQGISNYLNWYQQKPGKAPKPLIYYTSNLQSGVPSRFSGSGSGTDY

TLTISSLQPEDFATYYCMGQTISSYTFGQGTKLEIKESKYGPPCPPCPMFWVLVVVGGVL

ACYSLLVTVAFIIFWVKRGRKKLLYIFKQPFMRPVQTTQEEDGCSCRFPEEEEGGCELRV

KFSRSADAPAYQQGQNQLYNELNLGRREEYDVLDKRRGRDPEMGGKPRRKNPQEGLYNEL

QKDKMAEAYSEIGMKGERRRGKGHDGLYQGLSTATKDTYDALHMQALPPR

OF-$V_H$-CDR1:

(SEQ ID NO: 127)

NDYAMH

OF-$V_H$-CDR2:

(SEQ ID NO: 128)

TISWNSGSIGYADSVKG

OF-$V_H$-CDR3:

(SEQ ID NO: 129)

DIQYGNYYYGMDV

OF-$V_L$-CDR1:

(SEQ ID NO: 130)

RASQSVSSYLA

-continued

OF-$V_L$-CDR2:

DASNRAT (SEQ ID NO: 131)

OF-$V_L$-CDR3:

QQRSNWPIT (SEQ ID NO: 132)

BCMA-20 VL

| Region | Sequence Fragment | Residues of SEQ ID No: 12 | Length | SEQ ID No: |
|---|---|---|---|---|
| LFR1 | DIQMTQSPSSLS ASVGDRVTITC | 1-23 | 23 | SEQ ID No: 133 |
| CDR-L1 | RASQGISNYLN | 24-34 | 11 | SEQ ID No: 134 |
| LFR2 | WYQQKPGKAPK PLIY | 35-49 | 15 | SEQ ID No: 135 |
| CDR-L2 | YTSNLQS | 50-56 | 7 | SEQ ID No: 136 |
| LFR3 | GVPSRFSGSGSG TDYTLTISSLQP EDFATYYC | 57-88 | 32 | SEQ ID No: 137 |
| CDR-L3 | MGQTISSYT | 89-97 | 9 | SEQ ID No: 138 |
| LFR4 | FGQGTKLEIK | 98-107 | 10 | SEQ ID No: 139 |

BCMA-20 VH

| Region | Sequence Fragment | Residues of SEQ ID No: 16 | Length | SEQ ID No: |
|---|---|---|---|---|
| HFR1 | EVQLVESGGGL VQPGGSLRLSC AASGFTFS | 1-30 | 30 | SEQ ID No: 140 |
| CDR-H1 | NFDMA | 31-35 | 5 | SEQ ID No: 141 |
| HFR2 | WVRQAPGKGLV WVS | 36-49 | 14 | SEQ ID No: 142 |
| CDR-H2 | SITTGADHAIY ADSVKG | 50-66 | 17 | SEQ ID No: 143 |
| HFR3 | RFTISRDNAKN TLYLQMNSLRA EDTAVYYCVR | 67-98 | 32 | SEQ ID No: 144 |
| CDR-H3 | HGYYDGYHLFD Y | 99-110 | 12 | SEQ ID No: 145 |
| HFR4 | WGQGTLVTVSS | 111-121 | 11 | SEQ ID No: 146 |

The scope of the present invention is not limited by what has been specifically shown and described hereinabove. Those skilled in the art will recognize that there are suitable alternatives to the depicted examples of materials, configurations, constructions and dimensions. Numerous references, including patents and various publications, are cited and discussed in the description of this invention. The citation and discussion of such references is provided merely to clarify the description of the present invention and is not an admission that any reference is prior art to the invention described herein. All references cited and discussed in this specification are incorporated herein by reference in their entirety. Variations, modifications and other implementations of what is described herein will occur to those of ordinary skill in the art without departing from the spirit and scope of the invention. While certain embodiments of the present invention have been shown and described, it will be obvious to those skilled in the art that changes and modifications may be made without departing from the spirit and scope of the invention. The matter set forth in the foregoing description and accompanying drawings is offered by way of illustration only and not as a limitation.

The invention claimed is:

1. A bispecific chimeric antigen receptor (CAR), comprising:

(1) an anti-CD20 antigen-binding region which comprises a light chain variable region ($V_L1$) and a heavy chain variable region ($V_H1$), wherein $V_L1$ is located at the N-terminus of $V_H1$, wherein $V_L1$ and $V_H1$ comprise the amino acid sequences set forth in SEQ ID NO: 4 and SEQ ID NO: 8, respectively; and (ii) an anti-BCMA antigen-binding region which comprises a light chain variable region ($V_L2$) and a heavy chain variable region ($V_H2$), wherein $V_L2$ is located at the N-terminus of $V_H2$, wherein $V_L2$ and $V_H2$ comprise the amino acid sequences set forth in SEQ ID NO: 12 and SEQ ID NO: 16, respectively, wherein the anti-CD20 antigen-binding region is located at the N-terminus of the anti-BCMA antigen-binding region.

2. The bispecific CAR of claim 1, wherein the anti-CD20 antigen-binding region is a single-chain variable fragment (scFv) that specifically binds CD20, and wherein the anti-BCMA antigen-binding region is a scFv that specifically binds BCMA.

3. The bispecific CAR of claim 1, wherein the bispecific CAR further comprises one or more of the following:

(a) a signal peptide, (b) a hinge region, (c) a transmembrane domain, (d) a co-stimulatory region, and (e) a cytoplasmic signaling domain.

4. The bispecific CAR of claim 3, wherein the co-stimulatory region comprises a co-stimulatory region of 4-1BB (CD137), CD28, OX40, CD2, CD7, CD27, CD30, CD40, CD70, CD134, PD1, Dap10, CDS, ICAM-1, LFA-1 (CD11a/CD18), ICOS (CD278), NKG2D, GITR, TLR2, or combinations thereof.

5. The bispecific CAR of claim 3, wherein the cytoplasmic signaling domain comprises a cytoplasmic signaling domain of CD3ζ.

6. The bispecific CAR of claim 3, wherein the hinge region comprises a hinge region of IgG4, CD8, CD28, CD137, or combinations thereof.

7. The bispecific CAR of claim 3, wherein the hinge region comprises a hinge region of CD8.

8. The bispecific CAR of claim 3, wherein the transmembrane domain comprises a transmembrane domain of CD8, CD28, CD3ε, CD45, CD4, CD5, CD9, CD16, CD22, CD33, CD37, CD64, CD80, CD86, CD134, CD137, CD154, or combinations thereof.

9. The bispecific CAR of claim 3, wherein the transmembrane domain comprises a transmembrane domain of CD8.

10. An immune cell comprising the bispecific CAR of claim 1.

11. The immune cell of claim 10, wherein the immune cell is a T cell or a natural killer (NK) cell.

12. A pharmaceutical composition, comprising the immune cell of claim 10.

* * * * *

SEQUENCE LISTING

```
Sequence total quantity: 146
SEQ ID NO: 1            moltype = DNA  length = 63
FEATURE                 Location/Qualifiers
source                  1..63
                        mol_type = other DNA
                        organism = synthetic construct
SEQUENCE: 1
atggccttac cagtgaccgc cttgctcctg ccgctggcct tgctgctcca cgccgccagg  60
ccg                                                                63

SEQ ID NO: 2            moltype = AA  length = 21
FEATURE                 Location/Qualifiers
source                  1..21
                        mol_type = protein
                        organism = synthetic construct
SEQUENCE: 2
```

```
MALPVTALLL PLALLLHAAR P                                      21

SEQ ID NO: 3            moltype = DNA  length = 321
FEATURE                 Location/Qualifiers
source                  1..321
                        mol_type = other DNA
                        organism = synthetic construct
SEQUENCE: 3
gaaattgtgt tgacacagtc tccagccacc ctgtctttgt ctccagggga aagagccacc  60
ctctcctgca gggccagtca gagtgttagc agctacttag cctggtacca acagaaacct  120
ggccaggctc ccaggctcct catctatgat gcatccaaca gggccactgg catcccagcc  180
aggttcagtg gcagtgggtc tgggacagac ttcactctca ccatcagcag cctagagcct  240
gaagattttg cagtttatta ctgtcagcag cgtagcaact ggccgatcac cttcggccaa  300
gggacacgac tggagattaa a                                      321

SEQ ID NO: 4            moltype = AA  length = 107
FEATURE                 Location/Qualifiers
source                  1..107
                        mol_type = protein
                        organism = synthetic construct
SEQUENCE: 4
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ RSNWPITFGQ GTRLEIK            107

SEQ ID NO: 5            moltype = DNA  length = 54
FEATURE                 Location/Qualifiers
source                  1..54
                        mol_type = other DNA
                        organism = synthetic construct
SEQUENCE: 5
ggcagtacta gcggtggtgg ctccgggggc ggttccggtg gggcggcag cagc       54

SEQ ID NO: 6            moltype = AA  length = 18
FEATURE                 Location/Qualifiers
source                  1..18
                        mol_type = protein
                        organism = synthetic construct
SEQUENCE: 6
GSTSGGGSGG GSGGGGSS                                          18

SEQ ID NO: 7            moltype = DNA  length = 366
FEATURE                 Location/Qualifiers
source                  1..366
                        mol_type = other DNA
                        organism = synthetic construct
SEQUENCE: 7
gaagtgcagc tggtggagtc tgggggaggc ttggtacagc ctggcaggtc cctgagactc  60
tcctgtgcag cctctggatt cacctttaat gattatgcca tgcactgggt ccggcaagct  120
ccagggaagg gcctggagtg ggtctcaact attagttgga atagtggttc cataggctat  180
gcggactctg tgaagggccg attcaccatc tccagagaca acgccaagaa gtccctgtat  240
ctgcaaatga acagtctgag agctgaggac acggccttgt attactgtgc aaaagatata  300
cagtacggca actactacta cggtatggac gtctggggcc aagggaccac ggtcaccgtc  360
tcctca                                                       366

SEQ ID NO: 8            moltype = AA  length = 122
FEATURE                 Location/Qualifiers
source                  1..122
                        mol_type = protein
                        organism = synthetic construct
SEQUENCE: 8
EVQLVESGGG LVQPGRSLRL SCAASGFTFN DYAMHWVRQA PGKGLEWVST ISWNSGSIGY  60
ADSVKGRFTI SRDNAKKSLY LQMNSLRAED TALYYCAKDI QYGNYYYGMD VWGQGTTVTV  120
SS                                                           122

SEQ ID NO: 9            moltype = DNA  length = 15
FEATURE                 Location/Qualifiers
source                  1..15
                        mol_type = other DNA
                        organism = synthetic construct
SEQUENCE: 9
ggaggtggtg gatcc                                             15

SEQ ID NO: 10           moltype = AA  length = 5
FEATURE                 Location/Qualifiers
source                  1..5
                        mol_type = protein
                        organism = synthetic construct
SEQUENCE: 10
GGGGS                                                        5
```

```
SEQ ID NO: 11          moltype = DNA  length = 321
FEATURE                Location/Qualifiers
source                 1..321
                       mol_type = other DNA
                       organism = synthetic construct
SEQUENCE: 11
gacatccaga tgacccagtc cccctcctcc ctgtccgcct ccgtgggcga ccgggtgacc  60
atcacctgcc gggcctccca gggcatctcc aactacctga actggtacca gcagaagccc  120
ggcaaggccc ccaagcccct gatctactac acctccaacc tgcagtccgg cgtgccctcc  180
cggttctccg gctccggctc cggcaccgac tacaccctga ccatctcctc cctgcagccc  240
gaggacttcg ccacctacta ctgcatgggc cagaccatct cctcctacac cttcggccag  300
ggcaccaagc tggagatcaa g                                            321

SEQ ID NO: 12          moltype = AA  length = 107
FEATURE                Location/Qualifiers
source                 1..107
                       mol_type = protein
                       organism = synthetic construct
SEQUENCE: 12
DIQMTQSPSS LSASVGDRVT ITCRASQGIS NYLNWYQQKP GKAPKPLIYY TSNLQSGVPS  60
RFSGSGSGTD YTLTISSLQP EDFATYYCMG QTISSYTFGQ GTKLEIK                107

SEQ ID NO: 13          moltype = DNA  length = 45
FEATURE                Location/Qualifiers
source                 1..45
                       mol_type = other DNA
                       organism = synthetic construct
SEQUENCE: 13
ggtggcggtg gctcgggcgg tggtgggtcg ggtggcggcg gatct                 45

SEQ ID NO: 14          moltype = AA  length = 15
FEATURE                Location/Qualifiers
source                 1..15
                       mol_type = protein
                       organism = synthetic construct
SEQUENCE: 14
GGGGSGGGGS GGGGS                                                   15

SEQ ID NO: 15          moltype = DNA  length = 363
FEATURE                Location/Qualifiers
source                 1..363
                       mol_type = other DNA
                       organism = synthetic construct
SEQUENCE: 15
gaggtgcagc tggtggagtc cggcggcggc ctggtgcagc ccggcggctc cctgcggctg  60
tcctgcgccg cctccggctt caccttctcc aacttcgaca tggcctgggt gcggcaggcc  120
cccggcaagg gcctggtgtg ggtgtcctcc atcaccaccg gcgccgacca cgccatctac  180
gccgactccg tgaagggccg gttcaccatc tcccgggaca acgccaagaa caccctgtac  240
ctgcagatga actccctgcg ggccgaggac accgccgtgt actactgcgt gcggcacggc  300
tactacgacg gctaccacct gttcgactac tggggccagg gcaccctggt gaccgtgtcc  360
tcc                                                                363

SEQ ID NO: 16          moltype = AA  length = 121
FEATURE                Location/Qualifiers
source                 1..121
                       mol_type = protein
                       organism = synthetic construct
SEQUENCE: 16
EVQLVESGGG LVQPGGSLRL SCAASGFTFS NFDMAWVRQA PGKGLVWVSS ITTGADHAIY  60
ADSVKGRFTI SRDNAKNTLY LQMNSLRAED TAVYYCVRHG YYDGYHLFDY WGQGTLVTVS  120
S                                                                  121

SEQ ID NO: 17          moltype = DNA  length = 165
FEATURE                Location/Qualifiers
source                 1..165
                       mol_type = other DNA
                       organism = synthetic construct
SEQUENCE: 17
ttcgtgccgg tcttcctgcc agcgaagccc accacgacgc cagcgccgcg accaccaaca  60
ccggcgccca ccatcgcgtc gcagcccctg tccctgcgcc cagaggcgtg ccggccagcg  120
gcggggggcg cagtgcacac gagggggctg gacttcgcct gtgat                 165

SEQ ID NO: 18          moltype = AA  length = 55
FEATURE                Location/Qualifiers
source                 1..55
                       mol_type = protein
                       organism = synthetic construct
SEQUENCE: 18
```

```
FVPVFLPAKP TTTPAPRPPT PAPTIASQPL SLRPEACRPA AGGAVHTRGL DFACD       55

SEQ ID NO: 19          moltype = DNA  length = 72
FEATURE                Location/Qualifiers
source                 1..72
                       mol_type = other DNA
                       organism = synthetic construct
SEQUENCE: 19
atctacatct gggcgccctt ggccgggact tgtggggtcc ttctcctgtc actggttatc  60
accctttact gc                                                      72

SEQ ID NO: 20          moltype = AA  length = 24
FEATURE                Location/Qualifiers
source                 1..24
                       mol_type = protein
                       organism = synthetic construct
SEQUENCE: 20
IYIWAPLAGT CGVLLLSLVI TLYC                                         24

SEQ ID NO: 21          moltype = DNA  length = 126
FEATURE                Location/Qualifiers
source                 1..126
                       mol_type = other DNA
                       organism = synthetic construct
SEQUENCE: 21
aaacggggca gaaagaaact cctgtatata ttcaaacaac catttatgag accagtacaa  60
actactcaag aggaagatgg ctgtagctgc cgatttccag aagaagaaga aggaggatgt  120
gaactg                                                             126

SEQ ID NO: 22          moltype = AA  length = 42
FEATURE                Location/Qualifiers
source                 1..42
                       mol_type = protein
                       organism = synthetic construct
SEQUENCE: 22
KRGRKKLLYI FKQPFMRPVQ TTQEEDGCSC RFPEEEEGGC EL                     42

SEQ ID NO: 23          moltype = DNA  length = 339
FEATURE                Location/Qualifiers
source                 1..339
                       mol_type = other DNA
                       organism = synthetic construct
SEQUENCE: 23
agagtgaagt tcagcaggag cgcagacgcc cccgcgtacc agcagggcca gaaccagctc  60
tataacgagc tcaatctagg acgaagagag gagtacgatg ttttggacaa gagacgtggc  120
cgggaccctg agatgggggg aaagccgaga aggaagaacc ctcaggaagg cctgtacaat  180
gaactgcaga aagataagat ggcggaggcc tacagtgaga ttgggatgaa aggcgagcgc  240
cggaggggca aggggcacga tggcctttac cagggtctca gtacagccac caaggacacc  300
tacgacgccc ttcacatgca ggccctgccc cctcgctaa                         339

SEQ ID NO: 24          moltype = AA  length = 112
FEATURE                Location/Qualifiers
source                 1..112
                       mol_type = protein
                       organism = synthetic construct
SEQUENCE: 24
RVKFSRSADA PAYQQGQNQL YNELNLGRRE EYDVLDKRRG RDPEMGGKPR RKNPQEGLYN  60
ELQKDKMAEA YSEIGMKGER RRGKGHDGLY QGLSTATKDT YDALHMQALP PR          112

SEQ ID NO: 25          moltype = DNA  length = 2250
FEATURE                Location/Qualifiers
source                 1..2250
                       mol_type = other DNA
                       organism = synthetic construct
SEQUENCE: 25
atggccttac cagtgaccgc cttgctcctg ccgctggcct tgctgctcca cgccgccagg  60
ccggaaattg tgttgacaca gtctccagcc accctgtctt tgtctccagg ggaaagagcc  120
accctctcct gcagggccag tcagagtgtt agcagctact tagcctggta ccaacagaaa  180
cctggccagg ctcccaggct cctcatctat gatgcatcca acagggccac tggcatccca  240
gccaggttca gtggcagtgg gtctgggaca gacttcactc tcaccatcag cagcctagag  300
cctgaagatt ttgcagttta ttactgtcag cagcgtagca actggccgat caccttcggc  360
caagggacac gactggagat taaaggcagt actagcggtg gtggctccgg gggcggttcc  420
ggtgggggcg gcagcagcga agtgcagctg gtggagtctg gggggaggctt ggtacagcct  480
ggcaggtccc tgagactctc ctgtgcagcc tctggattca cctttaatga ttatgccatg  540
cactgggtcc ggcaagctcc agggaagggc ctggagtggg tctcaactat tagttggaat  600
agtggttcca taggctatgc ggactctgtg aagggccgat tcaccatctc cagagacaac  660
gccaagaagt ccctgtatct gcaaatgaac agtctgagag ctgaggacac ggccttgtat  720
tactgtgcaa aagatataca gtacggcaac tactactacg gtatggacgt ctggggccaa  780
gggaccacgg tcaccgtctc ctcaggaggt ggtggatccg acatccagat gacccagtcc  840
```

```
ccctcctccc tgtccgcctc cgtgggcgac cgggtgacca tcacctgccg ggcctcccag  900
ggcatctcca actacctgaa ctggtaccag cagaagcccg gcaaggcccc caagcccctg  960
atctactaca cctccaacct gcagtccggc gtgccctccc ggttctccgg ctccggctcc  1020
ggcaccgact acaccctgac catctcctcc ctgcagcccg aggacttcgc cacctactac  1080
tgcatgggcc agaccatctc ctcctacacc ttcggccagg gcaccaagct ggagatcaag  1140
ggtggcggtg gctcgggcgg tggtgggtcg ggtggcggcg gatctgaggt gcagctggtg  1200
gagtccggcg gcggcctggt gcagcccggc ggctccctgc ggctgtcctg cgccgcctcc  1260
ggcttcacct tctccaactt cgacatggcc tgggtgcggc aggcccccgg caagggcctg  1320
gtgtgggtgt cctccatcac caccggcgcc gaccacgcca tctacgccga ctccgtgaag  1380
ggccggttca ccatctcccg ggacaacgcc aagaacaccc tgtacctgca gatgaactcc  1440
ctgcgggccg aggacaccgc cgtgtactac tgcgtgcggc acggctacta cgacggctac  1500
cacctgttcg actactgggg ccagggcacc ctggtgaccg tgtcctcctt cgtgccggtc  1560
ttcctgccag cgaagcccac cacgacgcca gcgccgcgac caccaacacc ggcgcccacc  1620
atcgcgtcgc agcccctgtc cctgcgccca gaggcgtgcc ggccagcggc ggggggcgca  1680
gtgcacacga gggggctgga cttcgcctgt gatatctaca tctgggcgcc cttggccggg  1740
acttgtgggg tccttctcct gtcactggtt atcacccttt actgcaaacg gggcagaaag  1800
aaactcctgt atatattcaa acaaccattt atgagaccag tacaaactac tcaagaggaa  1860
gatggctgta gctgccgatt tccagaagaa gaagaaggag gatgtgaact gagagtgaag  1920
ttcagcagga gcgcagacgc ccccgcgtac cagcagggcc agaaccagct ctataacgag  1980
ctcaatctag gacgaagaga ggagtacgat gttttggaca agagacgtgg ccgggaccct  2040
gagatggggg gaaagccgag aaggaagaac cctcaggaag gcctgtacaa tgaactgcag  2100
aaagataaga tggcggaggc ctacagtgag attgggatga aaggcgagcg ccggaggggc  2160
aaggggcacg atggccttta ccagggtctc agtacagcca ccaaggacac ctacgacgcc  2220
cttcacatgc aggccctgcc ccctcgctaa                                   2250

SEQ ID NO: 26           moltype = AA  length = 749
FEATURE                 Location/Qualifiers
source                  1..749
                        mol_type = protein
                        organism = synthetic construct
SEQUENCE: 26
MALPVTALLL PLALLLHAAR PEIVLTQSPA TLSLSPGERA TLSCRASQSV SSYLAWYQQK  60
PGQAPRLLIY DASNRATGIP ARFSGSGSGT DFTLTISSLE PEDFAVYYCQ QRSNWPITFG  120
QGTRLEIKGS TSGGGSGGGS GGGGSSEVQL VESGGGLVQP GRSLRLSCAA SGFTFNDYAM  180
HWVRQAPGKG LEWVSTISWN SGSIGYADSV KGRFTISRDN AKKSLYLQMN SLRAEDTALY  240
YCAKDIQYGN YYYGMDVWGQ GTTVTVSSGG GGSDIQMTQS PSSLSASVGD RVTITCRASQ  300
GISNYLNWYQ QKPGKAPKPL IYYTSNLQSG VPSRFSGSGS GTDYTLTISS LQPEDFATYY  360
CMGQTISSYT FGQGTKLEIK GGGGSGGGGS GGGGSEVQLV ESGGGLVQPG GSLRLSCAAS  420
GFTFSNFDMA WVRQAPGKGL VWVSSITTGA DHAIYADSVK GRFTISRDNA KNTLYLQMNS  480
LRAEDTAVYY CVRHGYYDGY HLFDYWGQGT LVTVSSFVPV FLPAKPTTTP APRPPTPAPT  540
IASQPLSLRP EACRPAAGGA VHTRGLDFAC DIYIWAPLAG TCGVLLLSLV ITLYCKRGRK  600
KLLYIFKQPF MRPVQTTQEE DGCSCRFPEE EEGGCELRVK FSRSADAPAY QQGQNQLYNE  660
LNLGRREEYD VLDKRRGRDP EMGGKPRRKN PQEGLYNELQ KDKMAEAYSE IGMKGERRRG  720
KGHDGLYQGL STATKDTYDA LHMQALPPR                                   749

SEQ ID NO: 27           moltype = DNA  length = 63
FEATURE                 Location/Qualifiers
source                  1..63
                        mol_type = other DNA
                        organism = synthetic construct
SEQUENCE: 27
atggccttac cagtgaccgc cttgctcctg ccgctggcct tgctgctcca cgccgccagg  60
ccg                                                                63

SEQ ID NO: 28           moltype = DNA  length = 366
FEATURE                 Location/Qualifiers
source                  1..366
                        mol_type = other DNA
                        organism = synthetic construct
SEQUENCE: 28
gaagtgcagc tggtggagtc tgggggaggc ttggtacagc ctggcaggtc cctgagactc  60
tcctgtgcag cctctggatt cacctttaat gattatgcca tgcactgggt ccggcaagct  120
ccagggaagg gcctggagtg ggtctcaact attagttgga atagtggttc cataggctat  180
gcggactctg tgaagggccg attcaccatc tccagagaca acgccaagaa gtccctgtat  240
ctgcaaatga acagtctgag agctgaggac acggccttgt attactgtgc aaaagatata  300
cagtacggca actactacta cggtatggac gtctggggcc aagggaccac ggtcaccgtc  360
tcctca                                                             366

SEQ ID NO: 29           moltype = DNA  length = 54
FEATURE                 Location/Qualifiers
source                  1..54
                        mol_type = other DNA
                        organism = synthetic construct
SEQUENCE: 29
ggcagtacta gcggtggtgg ctccgggggc ggttccggtg ggggcggcag cagc        54

SEQ ID NO: 30           moltype = DNA  length = 321
FEATURE                 Location/Qualifiers
source                  1..321
```

```
                        mol_type = other DNA
                        organism = synthetic construct
SEQUENCE: 30
gaaattgtgt tgacacagtc tccagccacc ctgtctttgt ctccagggga aagagccacc  60
ctctcctgca gggccagtca gagtgttagc agctacttag cctggtacca acagaaacct  120
ggccaggctc ccaggctcct catctatgat gcatccaaca gggccactgg catcccagcc  180
aggttcagtg gcagtgggtc tgggacagac ttcactctca ccatcagcag cctagagcct  240
gaagattttg cagtttatta ctgtcagcag cgtagcaact ggccgatcac cttcggccaa  300
gggacacgac tggagattaa a                                            321

SEQ ID NO: 31           moltype = DNA  length = 15
FEATURE                 Location/Qualifiers
source                  1..15
                        mol_type = other DNA
                        organism = synthetic construct
SEQUENCE: 31
ggaggtggtg gatcc                                                   15

SEQ ID NO: 32           moltype = DNA  length = 321
FEATURE                 Location/Qualifiers
source                  1..321
                        mol_type = other DNA
                        organism = synthetic construct
SEQUENCE: 32
gacatccaga tgacccagtc cccctcctcc ctgtccgcct ccgtgggcga ccgggtgacc  60
atcacctgcc gggcctccca gggcatctcc aactacctga actggtacca gcagaagccc  120
ggcaaggccc ccaagcccct gatctactac acctccaacc tgcagtccgg cgtgccctcc  180
cggttctccg gctccggctc cggcaccgac tacaccctga ccatctcctc cctgcagccc  240
gaggacttcg ccacctacta ctgcatgggc cagaccatct cctcctacac cttcggccag  300
ggcaccaagc tggagatcaa g                                            321

SEQ ID NO: 33           moltype = DNA  length = 45
FEATURE                 Location/Qualifiers
source                  1..45
                        mol_type = other DNA
                        organism = synthetic construct
SEQUENCE: 33
ggtggcggtg gctcgggcgg tggtgggtcg ggtggcggcg gatct                  45

SEQ ID NO: 34           moltype = DNA  length = 363
FEATURE                 Location/Qualifiers
source                  1..363
                        mol_type = other DNA
                        organism = synthetic construct
SEQUENCE: 34
gaggtgcagc tggtggagtc cggcggcggc ctggtgcagc ccggcggctc cctgcggctg  60
tcctgcgccg cctccggctt caccttctcc aacttcgaca tggcctgggt gcggcaggcc  120
cccggcaagg gcctggtgtg ggtgtcctcc atcaccaccg gcgccgacca cgccatctac  180
gccgactccg tgaagggccg gttcaccatc tcccgggaca acgccaagaa caccctgtac  240
ctgcagatga actccctgcg ggccgaggac accgccgtgt actactgcgt gcggcacggc  300
tactacgacg gctaccacct gttcgactac tggggccagg gcaccctggt gaccgtgtcc  360
tcc                                                                363

SEQ ID NO: 35           moltype = DNA  length = 165
FEATURE                 Location/Qualifiers
source                  1..165
                        mol_type = other DNA
                        organism = synthetic construct
SEQUENCE: 35
ttcgtgccgg tcttcctgcc agcgaagccc accacgacgc cagcgccgcg accaccaaca  60
ccggcgccca ccatcgcgtc gcagcccctg tccctgcgcc cagaggcgtg ccggccagcg  120
gcggggggcg cagtgcacac gagggggctg gacttcgcct gtgat                  165

SEQ ID NO: 36           moltype = DNA  length = 72
FEATURE                 Location/Qualifiers
source                  1..72
                        mol_type = other DNA
                        organism = synthetic construct
SEQUENCE: 36
atctacatct gggcgccctt ggccgggact tgtggggtcc ttctcctgtc actggttatc  60
accctttact gc                                                      72

SEQ ID NO: 37           moltype = DNA  length = 126
FEATURE                 Location/Qualifiers
source                  1..126
                        mol_type = other DNA
                        organism = synthetic construct
SEQUENCE: 37
aaacggggca gaaagaaact cctgtatata ttcaaacaac catttatgag accagtacaa  60
```

-continued

```
actactcaag aggaagatgg ctgtagctgc cgatttccag aagaagaaga aggaggatgt  120
gaactg                                                             126

SEQ ID NO: 38          moltype = DNA  length = 339
FEATURE                Location/Qualifiers
source                 1..339
                       mol_type = other DNA
                       organism = synthetic construct
SEQUENCE: 38
agagtgaagt tcagcaggag cgcagacgcc cccgcgtacc agcagggcca gaaccagctc  60
tataacgagc tcaatctagg acgaagagag gagtacgatg ttttggacaa gagacgtggc  120
cgggaccctg agatgggggg aaagccgaga aggaagaacc ctcaggaagg cctgtacaat  180
gaactgcaga aagataagat ggcggaggcc tacagtgaga ttgggatgaa aggcgagcgc  240
cggaggggca aggggcacga tggcctttac cagggtctca gtacagccac caaggacacc  300
tacgacgccc ttcacatgca ggccctgccc cctcgctaa                         339

SEQ ID NO: 39          moltype = DNA  length = 2250
FEATURE                Location/Qualifiers
source                 1..2250
                       mol_type = other DNA
                       organism = synthetic construct
SEQUENCE: 39
atggccttac cagtgaccgc cttgctcctg ccgctggcct tgctgctcca cgccgccagg  60
ccggaagtgc agctggtgga gtctggggga ggcttggtac agcctggcag gtccctgaga  120
ctctcctgtg cagcctctgg attcaccttt aatgattatg ccatgcactg ggtccggcaa  180
gctccaggga agggcctgga gtgggtctca actattagtt ggaatagtgg ttccataggc  240
tatgcggact ctgtgaaggg ccgattcacc atctccagag acaacgccaa gaagtccctg  300
tatctgcaaa tgaacagtct gagagctgag gacacggcct tgtattactg tgcaaaagat  360
atacagtacg gcaactacta ctacggtatg gacgtctggg gccaagggac cacggtcacc  420
gtctcctcag gcagtactag cggtggtggc tccgggggcg gttccggtgg gggcggcagc  480
agcgaaattg tgttgacaca gtctccagcc accctgtctt tgtctccagg ggaaagagcc  540
accctctcct gcagggccag tcagagtgtt agcagctact tagcctggta ccaacagaaa  600
cctggccagg ctcccaggct cctcatctat gatgcatcca acagggccac tggcatccca  660
gccaggttca gtggcagtgg gtctgggaca gacttcactc tcaccatcag cagcctagag  720
cctgaagatt ttgcagttta ttactgtcag cagcgtagca actggccgat caccttcggc  780
caagggacac gactggagat taaaggaggt ggtggatccg acatccagat gacccagtcc  840
ccctcctccc tgtccgcctc cgtgggcgac cgggtgacca tcacctgccg ggcctcccag  900
ggcatctcca actacctgaa ctggtaccag cagaagcccg gcaaggcccc caagcccctg  960
atctactaca cctccaacct gcagtccggc gtgccctccc ggttctccgg ctccggctcc  1020
ggcaccgact acaccctgac catctcctcc ctgcagcccg aggacttcgc cacctactac  1080
tgcatgggcc agaccatctc ctcctacacc ttcggccagg gcaccaagct ggagatcaag  1140
ggtggcggtg gctcgggcgg tggtgggtcg ggtggcggcg gatctgaggt gcagctggtg  1200
gagtccggcg gcggcctggt gcagcccggc ggctccctgc ggctgtcctg cgccgcctcc  1260
ggcttcacct tctccaactt cgacatggcc tgggtgcggc aggcccccgg caagggcctg  1320
gtgtgggtgt cctccatcac caccggcgcc gaccacgcca tctacgccga ctccgtgaag  1380
ggccggttca ccatctcccg ggacaacgcc aagaacaccc tgtacctgca gatgaactcc  1440
ctgcgggccg aggacaccgc cgtgtactac tgcgtgcggc acggctacta cgacggctac  1500
cacctgttcg actactgggg ccagggcacc ctggtgaccg tgtcctcctt cgtgccggtc  1560
ttcctgccag cgaagcccac cacgacgcca gcgccgcgac caccaacacc ggcgcccacc  1620
atcgcgtcgc agcccctgtc cctgcgccca gaggcgtgcc ggccagcggc ggggggcgca  1680
gtgcacacga gggggctgga cttcgcctgt gatatctaca tctgggcgcc cttggccggg  1740
acttgtgggg tccttctcct gtcactggtt atcacccttt actgcaaacg gggcagaaag  1800
aaactcctgt atatattcaa acaaccattt atgagaccag tacaaactac tcaagaggaa  1860
gatggctgta gctgccgatt tccagaagaa gaagaaggag gatgtgaact gagagtgaag  1920
ttcagcagga gcgcagacgc ccccgcgtac cagcagggcc agaaccagct ctataacgag  1980
ctcaatctag gacgaagaga ggagtacgat gttttggaca agagacgtgg ccgggaccct  2040
gagatggggg gaaagccgag aaggaagaac cctcaggaag gcctgtacaa tgaactgcag  2100
aaagataaga tggcggaggc ctacagtgag attgggatga aaggcgagcg ccggaggggc  2160
aaggggcacg atggccttta ccagggtctc agtacagcca ccaaggacac ctacgacgcc  2220
cttcacatgc aggccctgcc ccctcgctaa                                   2250

SEQ ID NO: 40          moltype = AA  length = 749
FEATURE                Location/Qualifiers
source                 1..749
                       mol_type = protein
                       organism = synthetic construct
SEQUENCE: 40
MALPVTALLL PLALLLHAAR PEVQLVESGG GLVQPGRSLR LSCAASGFTF NDYAMHWVRQ  60
APGKGLEWVS TISWNSGSIG YADSVKGRFT ISRDNAKKSL YLQMNSLRAE DTALYYCAKD  120
IQYGNYYYGM DVWGQGTTVT VSSGSTSGGG SGGGSGGGGS SEIVLTQSPA TLSLSPGERA  180
TLSCRASQSV SSYLAWYQQK PGQAPRLLIY DASNRATGIP ARFSGSGSGT DFTLTISSLE  240
PEDFAVYYCQ QRSNWPITFG QGTRLEIKGG GGSDIQMTQS PSSLSASVGD RVTITCRASQ  300
GISNYLNWYQ QKPGKAPKPL IYYTSNLQSG VPSRFSGSGS GTDYTLTISS LQPEDFATYY  360
CMGQTISSYT FGQGTKLEIK GGGGSGGGGS GGGGSEVQLV ESGGGLVQPG GSLRLSCAAS  420
GFTFSNFDMA WVRQAPGKGL VWVSSITTGA DHAIYADSVK GRFTISRDNA KNTLYLQMNS  480
LRAEDTAVYY CVRHGYYDGY HLFDYWGQGT LVTVSSFVPV FLPAKPTTTP APRPPTPAPT  540
IASQPLSLRP EACRPAAGGA VHTRGLDFAC DIYIWAPLAG TCGVLLLSLV ITLYCKRGRK  600
KLLYIFKQPF MRPVQTTQEE DGCSCRFPEE EEGGCELRVK FSRSADAPAY QQGQNQLYNE  660
LNLGRREEYD VLDKRRGRDP EMGGKPRRKN PQEGLYNELQ KDKMAEAYSE IGMKGERRRG  720
```

```
KGHDGLYQGL STATKDTYDA LHMQALPPR                              749

SEQ ID NO: 41          moltype = DNA  length = 63
FEATURE                Location/Qualifiers
source                 1..63
                       mol_type = other DNA
                       organism = synthetic construct
SEQUENCE: 41
atggccttac cagtgaccgc cttgctcctg ccgctggcct tgctgctcca cgccgccagg  60
ccg                                                                 63

SEQ ID NO: 42          moltype = DNA  length = 366
FEATURE                Location/Qualifiers
source                 1..366
                       mol_type = other DNA
                       organism = synthetic construct
SEQUENCE: 42
gaagtgcagc tggtggagtc tgggggaggc ttggtacagc ctggcaggtc cctgagactc  60
tcctgtgcag cctctggatt cacctttaat gattatgcca tgcactgggt ccggcaagct  120
ccagggaagg gcctggagtg ggtctcaact attagttgga atagtggttc cataggctat  180
gcggactctg tgaagggccg attcaccatc tccagagaca acgccaagaa gtccctgtat  240
ctgcaaatga acagtctgag agctgaggac acggccttgt attactgtgc aaaagatata  300
cagtacggca actactacta cggtatggac gtctggggcc aagggaccac ggtcaccgtc  360
tcctca                                                              366

SEQ ID NO: 43          moltype = DNA  length = 54
FEATURE                Location/Qualifiers
source                 1..54
                       mol_type = other DNA
                       organism = synthetic construct
SEQUENCE: 43
ggcagtacta gcggtggtgg ctccgggggc ggttccggtg gggggcggcag cagc        54

SEQ ID NO: 44          moltype = DNA  length = 321
FEATURE                Location/Qualifiers
source                 1..321
                       mol_type = other DNA
                       organism = synthetic construct
SEQUENCE: 44
gaaattgtgt tgacacagtc tccagccacc ctgtctttgt ctccagggga aagagccacc  60
ctctcctgca gggccagtca gagtgttagc agctacttag cctggtacca acagaaacct  120
ggccaggctc ccaggctcct catctatgat gcatccaaca gggccactgg catcccagcc  180
aggttcagtg gcagtgggtc tgggacagac ttcactctca ccatcagcag cctagagcct  240
gaagattttg cagtttatta ctgtcagcag cgtagcaact ggccgatcac cttcggccaa  300
gggacacgac tggagattaa a                                             321

SEQ ID NO: 45          moltype = DNA  length = 15
FEATURE                Location/Qualifiers
source                 1..15
                       mol_type = other DNA
                       organism = synthetic construct
SEQUENCE: 45
ggaggtggtg gatcc                                                    15

SEQ ID NO: 46          moltype = DNA  length = 363
FEATURE                Location/Qualifiers
source                 1..363
                       mol_type = other DNA
                       organism = synthetic construct
SEQUENCE: 46
gaggtgcagc tggtggagtc cggcggcggc ctggtgcagc ccggcggctc cctgcggctg  60
tcctgcgccg cctccggctt caccttctcc aacttcgaca tggcctgggt gcggcaggcc  120
cccggcaagg gcctggtgtg ggtgtcctcc atcaccaccg gcgccgacca cgccatctac  180
gccgactccg tgaagggccg gttcaccatc tcccgggaca acgccaagaa caccctgtac  240
ctgcagatga actccctgcg ggccgaggac accgccgtgt actactgcgt gcggcacggc  300
tactacgacg gctaccacct gttcgactac tggggccagg gcaccctggt gaccgtgtcc  360
tcc                                                                 363

SEQ ID NO: 47          moltype = DNA  length = 45
FEATURE                Location/Qualifiers
source                 1..45
                       mol_type = other DNA
                       organism = synthetic construct
SEQUENCE: 47
ggtggcggtg gctcgggcgg tggtgggtcg ggtggcggcg gatct                   45

SEQ ID NO: 48          moltype = DNA  length = 321
FEATURE                Location/Qualifiers
source                 1..321
```

```
                         mol_type = other DNA
                         organism = synthetic construct
SEQUENCE: 48
gacatccaga tgacccagtc cccctcctcc ctgtccgcct ccgtgggcga ccgggtgacc  60
atcacctgcc gggcctccca gggcatctcc aactacctga actggtacca gcagaagccc  120
ggcaaggccc ccaagcccct gatctactac acctccaacc tgcagtccgg cgtgccctcc  180
cggttctccg gctccggctc cggcaccgac tacaccctga ccatctcctc cctgcagccc  240
gaggacttcg ccacctacta ctgcatgggc cagaccatct cctcctacac cttcggccag  300
ggcaccaagc tggagatcaa g                                            321

SEQ ID NO: 49            moltype = DNA  length = 165
FEATURE                  Location/Qualifiers
source                   1..165
                         mol_type = other DNA
                         organism = synthetic construct
SEQUENCE: 49
ttcgtgccgg tcttcctgcc agcgaagccc accacgacgc cagcgccgcg accaccaaca  60
ccggcgccca ccatcgcgtc gcagcccctg tccctgcgcc cagaggcgtg ccggccagcg  120
gcggggggcg cagtgcacac gagggggctg gacttcgcct gtgat                  165

SEQ ID NO: 50            moltype = DNA  length = 72
FEATURE                  Location/Qualifiers
source                   1..72
                         mol_type = other DNA
                         organism = synthetic construct
SEQUENCE: 50
atctacatct gggcgccctt ggccgggact tgtggggtcc ttctcctgtc actggttatc  60
accctttact gc                                                      72

SEQ ID NO: 51            moltype = DNA  length = 126
FEATURE                  Location/Qualifiers
source                   1..126
                         mol_type = other DNA
                         organism = synthetic construct
SEQUENCE: 51
aaacggggca gaaagaaact cctgtatata ttcaaacaac catttatgag accagtacaa  60
actactcaag aggaagatgg ctgtagctgc cgatttccag aagaagaaga aggaggatgt  120
gaactg                                                             126

SEQ ID NO: 52            moltype = DNA  length = 339
FEATURE                  Location/Qualifiers
source                   1..339
                         mol_type = other DNA
                         organism = synthetic construct
SEQUENCE: 52
agagtgaagt tcagcaggag cgcagacgcc cccgcgtacc agcagggcca gaaccagctc  60
tataacgagc tcaatctagg acgaagagag gagtacgatg ttttggacaa gagacgtggc  120
cgggaccctg agatgggggg aaagccgaga aggaagaacc ctcaggaagg cctgtacaat  180
gaactgcaga aagataagat ggcggaggcc tacagtgaga ttgggatgaa aggcgagcgc  240
cggaggggca aggggcacga tggcctttac cagggtctca gtacagccac caaggacacc  300
tacgacgccc ttcacatgca ggccctgccc cctcgctaa                         339

SEQ ID NO: 53            moltype = DNA  length = 2250
FEATURE                  Location/Qualifiers
source                   1..2250
                         mol_type = other DNA
                         organism = synthetic construct
SEQUENCE: 53
atggccttac cagtgaccgc cttgctcctg ccgctggcct tgctgctcca cgccgccagg  60
ccggaagtgc agctggtgga gtctggggga ggcttggtac agcctggcag gtccctgaga  120
ctctcctgtg cagcctctgg attcaccttt aatgattatg ccatgcactg ggtccggcaa  180
gctccaggga agggcctgga gtgggtctca actattagtt ggaatagtgg ttccataggc  240
tatgcggact ctgtgaaggg ccgattcacc atctccagag acaacgccaa gaagtccctg  300
tatctgcaaa tgaacagtct gagagctgag gacacggcct tgtattactg tgcaaaagat  360
atacagtacg gcaactacta ctacggtatg gacgtctggg gccaagggac cacggtcacc  420
gtctcctcag gcagtactag cggtggtggc tccgggggcg gttccggtgg gggcggcagc  480
agcgaaattg tgttgacaca gtctccagcc accctgtctt tgtctccagg ggaaagagcc  540
accctctcct gcagggccag tcagagtgtt agcagctact tagcctggta ccaacagaaa  600
cctggccagg ctcccaggct cctcatctat gatgcatcca acagggccac tggcatccca  660
gccaggttca gtggcagtgg gtctgggaca gacttcactc tcaccatcag cagcctagag  720
cctgaagatt ttgcagttta ttactgtcag cagcgtagca actggccgat caccttcggc  780
caagggacac gactggagat taaaggaggt ggtggatccg aggtgcagct ggtggagtcc  840
ggcggcggcc tggtgcagcc cggcggctcc ctgcggctgt cctgcgccgc ctccggcttc  900
accttctcca acttcgacat ggcctgggtg cggcaggccc ccggcaaggg cctggtgtgg  960
gtgtcctcca tcaccaccgg cgccgaccac gccatctacg ccgactccgt gaagggccgg  1020
ttcaccatct cccgggacaa cgccaagaac accctgtacc tgcagatgaa ctccctgcgg  1080
gccgaggaca ccgccgtgta ctactgcgtg cggcacggct actacgacgg ctaccacctg  1140
ttcgactact ggggccaggg caccctggtg accgtgtcct ccggtggcgg tggctcgggc  1200
ggtggtgggt cgggtggcgg cggatctgac atccagatga cccagtcccc ctcctccctg  1260
```

```
tccgcctccg tgggcgaccg ggtgaccatc acctgccggg cctcccaggg catctccaac  1320
tacctgaact ggtaccagca gaagcccggc aaggccccca agcccctgat ctactacacc  1380
tccaacctgc agtccggcgt gccctcccgg ttctccggct ccggctccgg caccgactac  1440
accctgacca tctcctccct gcagcccgag gacttcgcca cctactactg catgggccag  1500
accatctcct cctacacctt cggccagggc accaagctgg agatcaagtt cgtgccggtc  1560
ttcctgccag cgaagcccac cacgacgcca gcgccgcgac caccaacacc ggcgcccacc  1620
atcgcgtcgc agcccctgtc cctgcgccca gaggcgtgcc ggccagcggc ggggggcgca  1680
gtgcacacga gggggctgga cttcgcctgt gatatctaca tctgggcgcc cttggccggg  1740
acttgtgggg tccttctcct gtcactggtt atcacccttt actgcaaacg gggcagaaag  1800
aaactcctgt atatattcaa acaaccattt atgagaccag tacaaactac tcaagaggaa  1860
gatggctgta gctgccgatt tccagaagaa gaagaaggag gatgtgaact gagagtgaag  1920
ttcagcagga gcgcagacgc ccccgcgtac cagcagggcc agaaccagct ctataacgag  1980
ctcaatctag gacgaagaga ggagtacgat gttttggaca agagacgtgg ccgggaccct  2040
gagatggggg gaaagccgag aaggaagaac cctcaggaag gcctgtacaa tgaactgcag  2100
aaagataaga tggcggaggc ctacagtgag attgggatga aaggcgagcg ccggaggggc  2160
aaggggcacg atggccttta ccagggtctc agtacagcca ccaaggacac ctacgacgcc  2220
cttcacatgc aggccctgcc ccctcgctaa                                    2250

SEQ ID NO: 54           moltype = AA  length = 749
FEATURE                 Location/Qualifiers
source                  1..749
                        mol_type = protein
                        organism = synthetic construct
SEQUENCE: 54
MALPVTALLL PLALLLHAAR PEVQLVESGG GLVQPGRSLR LSCAASGFTF NDYAMHWVRQ  60
APGKGLEWVS TISWNSGSIG YADSVKGRFT ISRDNAKKSL YLQMNSLRAE DTALYYCAKD  120
IQYGNYYYGM DVWGQGTTVT VSSGSTSGGG SGGGSGGGGS SEIVLTQSPA TLSLSPGERA  180
TLSCRASQSV SSYLAWYQQK PGQAPRLLIY DASNRATGIP ARFSGSGSGT DFTLTISSLE  240
PEDFAVYYCQ QRSNWPITFG QGTRLEIKGG GGSEVQLVES GGGLVQPGGS LRLSCAASGF  300
TFSNFDMAWV RQAPGKGLVW VSSITTGADH AIYADSVKGR FTISRDNAKN TLYLQMNSLR  360
AEDTAVYYCV RHGYYDGYHL FDYWGQGTLV TVSSGGGGSG GGGSGGGGSD IQMTQSPSSL  420
SASVGDRVTI TCRASQGISN YLNWYQQKPG KAPKPLIYYT SNLQSGVPSR FSGSGSGTDY  480
TLTISSLQPE DFATYYCMGQ TISSYTFGQG TKLEIKFVPV FLPAKPTTTP APRPPTPAPT  540
IASQPLSLRP EACRPAAGGA VHTRGLDFAC DIYIWAPLAG TCGVLLLSLV ITLYCKRGRK  600
KLLYIFKQPF MRPVQTTQEE DGCSCRFPEE EEGGCELRVK FSRSADAPAY QQGQNQLYNE  660
LNLGRREEYD VLDKRRGRDP EMGGKPRRKN PQEGLYNELQ KDKMAEAYSE IGMKGERRRG  720
KGHDGLYQGL STATKDTYDA LHMQALPPR                                     749

SEQ ID NO: 55           moltype = DNA  length = 63
FEATURE                 Location/Qualifiers
source                  1..63
                        mol_type = other DNA
                        organism = synthetic construct
SEQUENCE: 55
atggccttac cagtgaccgc cttgctcctg ccgctggcct tgctgctcca cgccgccagg  60
ccg                                                                 63

SEQ ID NO: 56           moltype = DNA  length = 321
FEATURE                 Location/Qualifiers
source                  1..321
                        mol_type = other DNA
                        organism = synthetic construct
SEQUENCE: 56
gaaattgtgt tgacacagtc tccagccacc ctgtctttgt ctccagggga aagagccacc  60
ctctcctgca gggccagtca gagtgttagc agctacttag cctggtacca acagaaacct  120
ggccaggctc ccaggctcct catctatgat gcatccaaca gggccactgg catcccagcc  180
aggttcagtg gcagtgggtc tgggacagac ttcactctca ccatcagcag cctagagcct  240
gaagattttg cagtttatta ctgtcagcag cgtagcaact ggccgatcac cttcggccaa  300
gggacacgac tggagattaa a                                             321

SEQ ID NO: 57           moltype = DNA  length = 54
FEATURE                 Location/Qualifiers
source                  1..54
                        mol_type = other DNA
                        organism = synthetic construct
SEQUENCE: 57
ggcagtacta gcggtggtgg ctccgggggc ggttccggtg ggggcggcag cagc        54

SEQ ID NO: 58           moltype = DNA  length = 366
FEATURE                 Location/Qualifiers
source                  1..366
                        mol_type = other DNA
                        organism = synthetic construct
SEQUENCE: 58
gaagtgcagc tggtggagtc tgggggaggc ttggtacagc ctggcaggtc cctgagactc  60
tcctgtgcag cctctggatt cacctttaat gattatgcca tgcactgggt ccggcaagct  120
ccagggaagg gcctggagtg ggtctcaact attagttgga atagtggttc cataggctat  180
gcggactctg tgaagggccg attcaccatc tccagagaca acgccaagaa gtccctgtat  240
ctgcaaatga acagtctgag agctgaggac acggccttgt attactgtgc aaaagatata  300
```

```
cagtacggca actactacta cggtatggac gtctggggcc aagggaccac ggtcaccgtc  360
tcctca                                                             366

SEQ ID NO: 59          moltype = DNA  length = 15
FEATURE                Location/Qualifiers
source                 1..15
                       mol_type = other DNA
                       organism = synthetic construct
SEQUENCE: 59
ggaggtggtg gatcc                                                   15

SEQ ID NO: 60          moltype = DNA  length = 363
FEATURE                Location/Qualifiers
source                 1..363
                       mol_type = other DNA
                       organism = synthetic construct
SEQUENCE: 60
gaggtgcagc tggtggagtc cggcggcggc ctggtgcagc ccggcggctc cctgcggctg  60
tcctgcgccg cctccggctt caccttctcc aacttcgaca tggcctgggt gcggcaggcc  120
cccggcaagg gcctggtgtg ggtgtcctcc atcaccaccg gcgccgacca cgccatctac  180
gccgactccg tgaagggccg gttcaccatc tcccgggaca acgccaagaa caccctgtac  240
ctgcagatga actccctgcg ggccgaggac accgccgtgt actactgcgt gcggcacggc  300
tactacgacg gctaccacct gttcgactac tggggccagg gcaccctggt gaccgtgtcc  360
tcc                                                                363

SEQ ID NO: 61          moltype = DNA  length = 45
FEATURE                Location/Qualifiers
source                 1..45
                       mol_type = other DNA
                       organism = synthetic construct
SEQUENCE: 61
ggtggcggtg gctcgggcgg tggtgggtcg ggtggcggcg gatct                  45

SEQ ID NO: 62          moltype = DNA  length = 321
FEATURE                Location/Qualifiers
source                 1..321
                       mol_type = other DNA
                       organism = synthetic construct
SEQUENCE: 62
gacatccaga tgacccagtc cccctcctcc ctgtccgcct ccgtgggcga ccgggtgacc  60
atcacctgcc gggcctccca gggcatctcc aactacctga actggtacca gcagaagccc  120
ggcaaggccc ccaagcccct gatctactac acctccaacc tgcagtccgg cgtgccctcc  180
cggttctccg gctccggctc cggcaccgac tacaccctga ccatctcctc cctgcagccc  240
gaggacttcg ccacctacta ctgcatgggc cagaccatct cctcctacac cttcggccag  300
ggcaccaagc tggagatcaa g                                            321

SEQ ID NO: 63          moltype = DNA  length = 165
FEATURE                Location/Qualifiers
source                 1..165
                       mol_type = other DNA
                       organism = synthetic construct
SEQUENCE: 63
ttcgtgccgg tcttcctgcc agcgaagccc accacgacgc cagcgccgcg accaccaaca  60
ccggcgccca ccatcgcgtc gcagcccctg tccctgcgcc cagaggcgtg ccggccagcg  120
gcggggggcg cagtgcacac gagggggctg gacttcgcct gtgat                  165

SEQ ID NO: 64          moltype = DNA  length = 72
FEATURE                Location/Qualifiers
source                 1..72
                       mol_type = other DNA
                       organism = synthetic construct
SEQUENCE: 64
atctacatct gggcgccctt ggccgggact tgtggggtcc ttctcctgtc actggttatc  60
accctttact gc                                                      72

SEQ ID NO: 65          moltype = DNA  length = 126
FEATURE                Location/Qualifiers
source                 1..126
                       mol_type = other DNA
                       organism = synthetic construct
SEQUENCE: 65
aaacggggca gaaagaaact cctgtatata ttcaaacaac catttatgag accagtacaa  60
actactcaag aggaagatgg ctgtagctgc cgatttccag aagaagaaga aggaggatgt  120
gaactg                                                             126

SEQ ID NO: 66          moltype = DNA  length = 339
FEATURE                Location/Qualifiers
source                 1..339
                       mol_type = other DNA
```

```
                         organism = synthetic construct
SEQUENCE: 66
agagtgaagt tcagcaggag cgcagacgcc cccgcgtacc agcagggcca gaaccagctc  60
tataacgagc tcaatctagg acgaagagag gagtacgatg ttttggacaa gagacgtggc  120
cgggaccctg agatgggggg aaagccgaga aggaagaacc ctcaggaagg cctgtacaat  180
gaactgcaga aagataagat ggcggaggcc tacagtgaga ttgggatgaa aggcgagcgc  240
cggaggggca aggggcacga tggcctttac cagggtctca gtacagccac caaggacacc  300
tacgacgccc ttcacatgca ggccctgccc cctcgctaa                         339

SEQ ID NO: 67            moltype = DNA  length = 2250
FEATURE                  Location/Qualifiers
source                   1..2250
                         mol_type = other DNA
                         organism = synthetic construct
SEQUENCE: 67
atggccttac cagtgaccgc cttgctcctg ccgctggcct tgctgctcca cgccgccagg  60
ccggaaattg tgttgacaca gtctccagcc accctgtctt tgtctccagg ggaaagagcc  120
accctctcct gcagggccag tcagagtgtt agcagctact tagcctggta ccaacagaaa  180
cctggccagg ctcccaggct cctcatctat gatgcatcca acagggccac tggcatccca  240
gccaggttca gtggcagtgg gtctgggaca gacttcactc tcaccatcag cagcctagag  300
cctgaagatt ttgcagttta ttactgtcag cagcgtagca actggccgat caccttcggc  360
caagggacac gactggagat taaaggcagt actagcggtg gtggctccgg gggcggttcc  420
ggtgggggcg gcagcagcga agtgcagctg gtggagtctg ggggaggctt ggtacagcct  480
ggcaggtccc tgagactctc ctgtgcagcc tctggattca cctttaatga ttatgccatg  540
cactgggtcc ggcaagctcc agggaagggc ctggagtggg tctcaactat tagttggaat  600
agtggttcca taggctatgc ggactctgtg aagggccgat tcaccatctc cagagacaac  660
gccaagaagt ccctgtatct gcaaatgaac agtctgagag ctgaggacac ggccttgtat  720
tactgtgcaa aagatataca gtacggcaac tactactacg gtatggacgt ctggggccaa  780
gggaccacgg tcaccgtctc ctcaggaggt ggtggatccg aggtgcagct ggtggagtcc  840
ggcggcggcc tggtgcagcc cggcggctcc ctgcggctgt cctgcgccgc ctccggcttc  900
accttctcca acttcgacat ggcctgggtg cggcaggccc ccggcaaggg cctggtgtgg  960
gtgtcctcca tcaccaccgg cgccgaccac gccatctacg ccgactccgt gaagggccgg  1020
ttcaccatct cccgggacaa cgccaagaac accctgtacc tgcagatgaa ctccctgcgg  1080
gccgaggaca ccgccgtgta ctactgcgtg cggcacggct actacgacgg ctaccacctg  1140
ttcgactact ggggccaggg caccctggtg accgtgtcct ccggtggcgg tggctcgggc  1200
ggtggtgggt cgggtggcgg cggatctgac atccagatga cccagtcccc ctcctccctg  1260
tccgcctccg tgggcgaccg ggtgaccatc acctgccggg cctcccaggg catctccaac  1320
tacctgaact ggtaccagca gaagcccggc aaggccccca agcccctgat ctactacacc  1380
tccaacctgc agtccggcgt gccctcccgg ttctccggct ccggctccgg caccgactac  1440
accctgacca tctcctccct gcagcccgag gacttcgcca cctactactg catgggccag  1500
accatctcct cctacacctt cggccagggc accaagctgg agatcaagtt cgtgccggtc  1560
ttcctgccag cgaagcccac cacgacgcca gcgccgcgac caccaacacc ggcgcccacc  1620
atcgcgtcgc agcccctgtc cctgcgccca gaggcgtgcc ggccagcggc ggggggcgca  1680
gtgcacacga gggggctgga cttcgcctgt gatatctaca tctgggcgcc cttggccggg  1740
acttgtgggg tccttctcct gtcactggtt atcacccttt actgcaaacg gggcagaaag  1800
aaactcctgt atatattcaa acaaccattt atgagaccag tacaaactac tcaagaggaa  1860
gatggctgta gctgccgatt tccagaagaa gaagaaggag gatgtgaact gagagtgaag  1920
ttcagcagga gcgcagacgc ccccgcgtac cagcagggcc agaaccagct ctataacgag  1980
ctcaatctag gacgaagaga ggagtacgat gttttggaca agagacgtgg ccgggaccct  2040
gagatggggg gaaagccgag aaggaagaac cctcaggaag gcctgtacaa tgaactgcag  2100
aaagataaga tggcggaggc ctacagtgag attgggatga aaggcgagcg ccggaggggc  2160
aaggggcacg atggccttta ccagggtctc agtacagcca ccaaggacac ctacgacgcc  2220
cttcacatgc aggccctgcc ccctcgctaa                                   2250

SEQ ID NO: 68            moltype = AA  length = 749
FEATURE                  Location/Qualifiers
source                   1..749
                         mol_type = protein
                         organism = synthetic construct
SEQUENCE: 68
MALPVTALLL PLALLLHAAR PEIVLTQSPA TLSLSPGERA TLSCRASQSV SSYLAWYQQK  60
PGQAPRLLIY DASNRATGIP ARFSGSGSGT DFTLTISSLE PEDFAVYYCQ QRSNWPITFG  120
QGTRLEIKGS TSGGGSGGGS GGGGSSEVQL VESGGGLVQP GRSLRLSCAA SGFTFNDYAM  180
HWVRQAPGKG LEWVSTISWN SGSIGYADSV KGRFTISRDN AKKSLYLQMN SLRAEDTALY  240
YCAKDIQYGN YYYGMDVWGQ GTTVTVSSGG GGSEVQLVES GGGLVQPGGS LRLSCAASGF  300
TFSNFDMAWV RQAPGKGLVW VSSITTGADH AIYADSVKGR FTISRDNAKN TLYLQMNSLR  360
AEDTAVYYCV RHGYYDGYHL FDYWGQGTLV TVSSGGGGSG GGGSGGGGSD IQMTQSPSSL  420
SASVGDRVTI TCRASQGISN YLNWYQQKPG KAPKPLIYYT SNLQSGVPSR FSGSGSGTDY  480
TLTISSLQPE DFATYYCMGQ TISSYTFGQG TKLEIKFVPV FLPAKPTTTP APRPPTPAPT  540
IASQPLSLRP EACRPAAGGA VHTRGLDFAC DIYIWAPLAG TCGVLLLSLV ITLYCKRGRK  600
KLLYIFKQPF MRPVQTTQEE DGCSCRFPEE EEGGCELRVK FSRSADAPAY QQGQNQLYNE  660
LNLGRREEYD VLDKRRGRDP EMGGKPRRKN PQEGLYNELQ KDKMAEAYSE IGMKGERRRG  720
KGHDGLYQGL STATKDTYDA LHMQALPPR                                    749

SEQ ID NO: 69            moltype = DNA  length = 63
FEATURE                  Location/Qualifiers
source                   1..63
                         mol_type = other DNA
                         organism = synthetic construct
```

```
SEQUENCE: 69
atggccttac cagtgaccgc cttgctcctg ccgctggcct tgctgctcca cgccgccagg  60
ccg                                                                63

SEQ ID NO: 70          moltype = DNA  length = 321
FEATURE                Location/Qualifiers
source                 1..321
                       mol_type = other DNA
                       organism = synthetic construct
SEQUENCE: 70
gaaattgtgt tgacacagtc tccagccacc ctgtctttgt ctccagggga aagagccacc  60
ctctcctgca gggccagtca gagtgttagc agctacttag cctggtacca acagaaacct  120
ggccaggctc ccaggctcct catctatgat gcatccaaca gggccactgg catcccagcc  180
aggttcagtg gcagtgggtc tgggacagac ttcactctca ccatcagcag cctagagcct  240
gaagattttg cagtttatta ctgtcagcag cgtagcaact ggccgatcac cttcggccaa  300
gggacacgac tggagattaa a                                            321

SEQ ID NO: 71          moltype = DNA  length = 54
FEATURE                Location/Qualifiers
source                 1..54
                       mol_type = other DNA
                       organism = synthetic construct
SEQUENCE: 71
ggcagtacta gcggtggtgg ctccgggggc ggttccggtg gggggcggcag cagc       54

SEQ ID NO: 72          moltype = DNA  length = 366
FEATURE                Location/Qualifiers
source                 1..366
                       mol_type = other DNA
                       organism = synthetic construct
SEQUENCE: 72
gaagtgcagc tggtggagtc tgggggaggc ttggtacagc ctggcaggtc cctgagactc  60
tcctgtgcag cctctggatt cacctttaat gattatgcca tgcactgggt ccggcaagct  120
ccagggaagg gcctggagtg ggtctcaact attagttgga atagtggttc cataggctat  180
gcggactctg tgaagggccg attcaccatc tccagagaca acgccaagaa gtccctgtat  240
ctgcaaatga acagtctgag agctgaggac acggccttgt attactgtgc aaaagatata  300
cagtacggca actactacta cggtatggac gtctggggcc aagggaccac ggtcaccgtc  360
tcctca                                                             366

SEQ ID NO: 73          moltype = DNA  length = 15
FEATURE                Location/Qualifiers
source                 1..15
                       mol_type = other DNA
                       organism = synthetic construct
SEQUENCE: 73
ggaggtggtg gatcc                                                   15

SEQ ID NO: 74          moltype = DNA  length = 363
FEATURE                Location/Qualifiers
source                 1..363
                       mol_type = other DNA
                       organism = synthetic construct
SEQUENCE: 74
gaggtgcagc tggtggagtc cggcggcggc ctggtgcagc ccggcggctc cctgcggctg  60
tcctgcgccg cctccggctt caccttctcc aacttcgaca tggcctgggt gcggcaggcc  120
cccggcaagg gcctggtgtg ggtgtcctcc atcaccaccg gcgccgacca cgccatctac  180
gccgactccg tgaagggccg gttcaccatc tcccgggaca acgccaagaa caccctgtac  240
ctgcagatga actccctgcg ggccgaggac accgccgtgt actactgcgt gcggcacggc  300
tactacgacg gctaccacct gttcgactac tggggccagg gcaccctggt gaccgtgtcc  360
tcc                                                                363

SEQ ID NO: 75          moltype = DNA  length = 45
FEATURE                Location/Qualifiers
source                 1..45
                       mol_type = other DNA
                       organism = synthetic construct
SEQUENCE: 75
ggtggcggtg gctcgggcgg tggtgggtcg ggtggcggcg gatct                  45

SEQ ID NO: 76          moltype = DNA  length = 321
FEATURE                Location/Qualifiers
source                 1..321
                       mol_type = other DNA
                       organism = synthetic construct
SEQUENCE: 76
gacatccaga tgacccagtc cccctcctcc ctgtccgcct ccgtgggcga ccgggtgacc  60
atcacctgcc gggcctccca gggcatctcc aactacctga actggtacca gcagaagccc  120
ggcaaggccc ccaagcccct gatctactac acctccaacc tgcagtccgg cgtgccctcc  180
cggttctccg gctccggctc cggcaccgac tacaccctga ccatctcctc cctgcagccc  240
```

```
gaggacttcg ccacctacta ctgcatgggc cagaccatct cctcctacac cttcggccag  300
ggcaccaagc tggagatcaa g                                            321

SEQ ID NO: 77          moltype = DNA  length = 36
FEATURE                Location/Qualifiers
source                 1..36
                       mol_type = other DNA
                       organism = synthetic construct
SEQUENCE: 77
gagagcaagt acggaccgcc ctgccccccct tgccct                            36

SEQ ID NO: 78          moltype = AA  length = 12
FEATURE                Location/Qualifiers
source                 1..12
                       mol_type = protein
                       organism = synthetic construct
SEQUENCE: 78
ESKYGPPCPP CP                                                      12

SEQ ID NO: 79          moltype = DNA  length = 84
FEATURE                Location/Qualifiers
source                 1..84
                       mol_type = other DNA
                       organism = synthetic construct
SEQUENCE: 79
atgttctggg tgctggtggt ggtcggaggc gtgctggcct gctacagcct gctggtcacc  60
gtggccttca tcatcttttg ggtg                                         84

SEQ ID NO: 80          moltype = AA  length = 28
FEATURE                Location/Qualifiers
source                 1..28
                       mol_type = protein
                       organism = synthetic construct
SEQUENCE: 80
MFWVLVVVGG VLACYSLLVT VAFIIFWV                                     28

SEQ ID NO: 81          moltype = DNA  length = 126
FEATURE                Location/Qualifiers
source                 1..126
                       mol_type = other DNA
                       organism = synthetic construct
SEQUENCE: 81
aaacggggca gaaagaaact cctgtatata ttcaaacaac catttatgag accagtacaa  60
actactcaag aggaagatgg ctgtagctgc cgatttccag aagaagaaga aggaggatgt  120
gaactg                                                             126

SEQ ID NO: 82          moltype = DNA  length = 336
FEATURE                Location/Qualifiers
source                 1..336
                       mol_type = other DNA
                       organism = synthetic construct
SEQUENCE: 82
cgggtgaagt tcagcagaag cgccgacgcc cctgcctacc agcagggcca gaatcagctg  60
tacaacgagc tgaacctggg cagaagggaa gagtacgacg tcctggataa gcggagaggc  120
cgggaccctg agatgggcgg caagcctcgg cggaagaacc cccaggaagg cctgtataac  180
gaactgcaga aagacaagat ggccgaggcc tacagcgaga tcggcatgaa gggcgagcgg  240
aggcggggca agggccacga cggcctgtat cagggcctgt ccaccgccac caaggatacc  300
tacgacgccc tgcacatgca ggccctgccc ccaagg                            336

SEQ ID NO: 83          moltype = DNA  length = 2133
FEATURE                Location/Qualifiers
source                 1..2133
                       mol_type = other DNA
                       organism = synthetic construct
SEQUENCE: 83
atggccttac cagtgaccgc cttgctcctg ccgctggcct tgctgctcca cgccgccagg  60
ccggaaattg tgttgacaca gtctccagcc accctgtctt tgtctccagg ggaaagagcc  120
accctctcct gcagggccag tcagagtgtt agcagctact tagcctggta ccaacagaaa  180
cctggccagg ctcccaggct cctcatctat gatgcatcca acagggccac tggcatccca  240
gccaggttca gtggcagtgg gtctgggaca gacttcactc tcaccatcag cagcctagag  300
cctgaagatt ttgcagttta ttactgtcag cagcgtagca actggccgat caccttcggc  360
caagggacac gactggagat taaaggcagt actagcggtg gtggctccgg gggcggttcc  420
ggtgggggcg gcagcagcga agtgcagctg gtggagtctg ggggaggctt ggtacagcct  480
ggcaggtccc tgagactctc ctgtgcagcc tctggattca cctttaatga ttatgccatg  540
cactgggtcc ggcaagctcc agggaagggc ctggagtggg tctcaactat tagttggaat  600
agtggttcca taggctatgc ggactctgtg aagggccgat tcaccatctc cagagacaac  660
gccaagaagt ccctgtatct gcaaatgaac agtctgagag ctgaggacac ggccttgtat  720
tactgtgcaa aagatataca gtacggcaac tactactacg gtatggacgt ctggggccaa  780
gggaccacgg tcaccgtctc ctcaggaggt ggtggatccg aggtgcagct ggtggagtcc  840
```

```
ggcggcggcc tggtgcagcc cggcggctcc ctgcggctgt cctgcgccgc ctccggcttc  900
accttctcca acttcgacat ggcctgggtg cggcaggccc ccggcaaggg cctggtgtgg  960
gtgtcctcca tcaccaccgg cgccgaccac gccatctacg ccgactccgt gaagggccgg  1020
ttcaccatct cccgggacaa cgccaagaac accctgtacc tgcagatgaa ctccctgcgg  1080
gccgaggaca ccgccgtgta ctactgcgtg cggcacggct actacgacgg ctaccacctg  1140
ttcgactact ggggccaggg caccctggtg accgtgtcct ccggtggcgg tggctcgggc  1200
ggtggtgggt cgggtggcgg cggatctgac atccagatga cccagtcccc ctcctccctg  1260
tccgcctccg tgggcgaccg ggtgaccatc acctgccggg cctcccaggg catctccaac  1320
tacctgaact ggtaccagca gaagcccggc aaggccccca agcccctgat ctactacacc  1380
tccaacctgc agtccggcgt gccctcccgg ttctccggct ccggctccgg caccgactac  1440
accctgacca tctcctccct gcagcccgag gacttcgcca cctactactg catgggccag  1500
accatctcct cctacacctt cggccagggc accaagctgg agatcaagga gagcaagtac  1560
ggaccgccct gccccccttg ccctatgttc tgggtgctgg tggtggtcgg aggcgtgctg  1620
gcctgctaca gcctgctggt caccgtggcc ttcatcatct tttgggtgaa acggggcaga  1680
aagaaactcc tgtatatatt caaacaacca tttatgagac cagtacaaac tactcaagag  1740
gaagatggct gtagctgccg atttccagaa gaagaagaag gaggatgtga actgcgggtg  1800
aagttcagca gaagcgccga cgcccctgcc taccagcagg gccagaatca gctgtacaac  1860
gagctgaacc tgggcagaag ggaagagtac gacgtcctgg ataagcggag aggccgggac  1920
cctgagatgg gcggcaagcc tcggcggaag aacccccagg aaggcctgta taacgaactg  1980
cagaaagaca agatggccga ggcctacagc gagatcggca tgaagggcga gcggaggcgg  2040
ggcaagggcc acgacggcct gtatcagggc ctgtccaccg ccaccaagga tacctacgac  2100
gccctgcaca tgcaggccct gcccccaagg taa                              2133

SEQ ID NO: 84          moltype = AA  length = 710
FEATURE                Location/Qualifiers
source                 1..710
                       mol_type = protein
                       organism = synthetic construct
SEQUENCE: 84
MALPVTALLL PLALLLHAAR PEIVLTQSPA TLSLSPGERA TLSCRASQSV SSYLAWYQQK  60
PGQAPRLLIY DASNRATGIP ARFSGSGSGT DFTLTISSLE PEDFAVYYCQ QRSNWPITFG  120
QGTRLEIKGS TSGGGSGGGS GGGGSSEVQL VESGGGLVQP GRSLRLSCAA SGFTFNDYAM  180
HWVRQAPGKG LEWVSTISWN SGSIGYADSV KGRFTISRDN AKKSLYLQMN SLRAEDTALY  240
YCAKDIQYGN YYYGMDVWGQ GTTVTVSSGG GGSEVQLVES GGGLVQPGGS LRLSCAASGF  300
TFSNFDMAWV RQAPGKGLVW VSSITTGADH AIYADSVKGR FTISRDNAKN TLYLQMNSLR  360
AEDTAVYYCV RHGYYDGYHL FDYWGQGTLV TVSSGGGGSG GGGSGGGGSD IQMTQSPSSL  420
SASVGDRVTI TCRASQGISN YLNWYQQKPG KAPKPLIYYT SNLQSGVPSR FSGSGSGTDY  480
TLTISSLQPE DFATYYCMGQ TISSYTFGQG TKLEIKESKY GPPCPPCPMF WVLVVVGGVL  540
ACYSLLVTVA FIIFWVKRGR KKLLYIFKQP FMRPVQTTQE EDGCSCRFPE EEEGGCELRV  600
KFSRSADAPA YQQGQNQLYN ELNLGRREEY DVLDKRRGRD PEMGGKPRRK NPQEGLYNEL  660
QKDKMAEAYS EIGMKGERRR GKGHDGLYQG LSTATKDTYD ALHMQALPPR             710

SEQ ID NO: 85          moltype = DNA  length = 63
FEATURE                Location/Qualifiers
source                 1..63
                       mol_type = other DNA
                       organism = synthetic construct
SEQUENCE: 85
atggccttac cagtgaccgc cttgctcctg ccgctggcct tgctgctcca cgccgccagg  60
ccg                                                               63

SEQ ID NO: 86          moltype = DNA  length = 321
FEATURE                Location/Qualifiers
source                 1..321
                       mol_type = other DNA
                       organism = synthetic construct
SEQUENCE: 86
gaaattgtgt tgacacagtc tccagccacc ctgtctttgt ctccagggga aagagccacc  60
ctctcctgca gggccagtca gagtgttagc agctacttag cctggtacca acagaaacct  120
ggccaggctc ccaggctcct catctatgat gcatccaaca gggccactgg catcccagcc  180
aggttcagtg gcagtgggtc tgggacagac ttcactctca ccatcagcag cctagagcct  240
gaagattttg cagtttatta ctgtcagcag cgtagcaact ggccgatcac cttcggccaa  300
gggacacgac tggagattaa a                                           321

SEQ ID NO: 87          moltype = DNA  length = 54
FEATURE                Location/Qualifiers
source                 1..54
                       mol_type = other DNA
                       organism = synthetic construct
SEQUENCE: 87
ggcagtacta gcggtggtgg ctccgggggc ggttccggtg gggcggcag cagc        54

SEQ ID NO: 88          moltype = DNA  length = 366
FEATURE                Location/Qualifiers
source                 1..366
                       mol_type = other DNA
                       organism = synthetic construct
SEQUENCE: 88
gaagtgcagc tggtggagtc tgggggaggc ttggtacagc ctggcaggtc cctgagactc  60
```

```
tcctgtgcag cctctggatt cacctttaat gattatgcca tgcactgggt ccggcaagct  120
ccagggaagg gcctggagtg ggtctcaact attagttgga atagtggttc cataggctat  180
gcggactctg tgaagggccg attcaccatc tccagagaca acgccaagaa gtccctgtat  240
ctgcaaatga acagtctgag agctgaggac acggccttgt attactgtgc aaaagatata  300
cagtacggca actactacta cggtatggac gtctggggcc aagggaccac ggtcaccgtc  360
tcctca                                                             366

SEQ ID NO: 89          moltype = DNA  length = 15
FEATURE                Location/Qualifiers
source                 1..15
                       mol_type = other DNA
                       organism = synthetic construct
SEQUENCE: 89
ggaggtggtg gatcc                                                   15

SEQ ID NO: 90          moltype = DNA  length = 321
FEATURE                Location/Qualifiers
source                 1..321
                       mol_type = other DNA
                       organism = synthetic construct
SEQUENCE: 90
gacatccaga tgacccagtc cccctcctcc ctgtccgcct ccgtgggcga ccgggtgacc  60
atcacctgcc gggcctccca gggcatctcc aactacctga actggtacca gcagaagccc  120
ggcaaggccc ccaagcccct gatctactac acctccaacc tgcagtccgg cgtgccctcc  180
cggttctccg gctccggctc cggcaccgac tacaccctga ccatctcctc cctgcagccc  240
gaggacttcg ccacctacta ctgcatgggc cagaccatct cctcctacac cttcggccag  300
ggcaccaagc tggagatcaa g                                            321

SEQ ID NO: 91          moltype = DNA  length = 45
FEATURE                Location/Qualifiers
source                 1..45
                       mol_type = other DNA
                       organism = synthetic construct
SEQUENCE: 91
ggtggcggtg gctcgggcgg tggtgggtcg ggtggcggcg gatct                  45

SEQ ID NO: 92          moltype = DNA  length = 363
FEATURE                Location/Qualifiers
source                 1..363
                       mol_type = other DNA
                       organism = synthetic construct
SEQUENCE: 92
gaggtgcagc tggtggagtc cggcggcggc ctggtgcagc ccggcggctc cctgcggctg  60
tcctgcgccg cctccggctt caccttctcc aacttcgaca tggcctgggt gcggcaggcc  120
cccggcaagg gcctggtgtg ggtgtcctcc atcaccaccg gcgccgacca cgccatctac  180
gccgactccg tgaagggccg gttcaccatc tcccgggaca acgccaagaa caccctgtac  240
ctgcagatga actccctgcg ggccgaggac accgccgtgt actactgcgt gcggcacggc  300
tactacgacg gctaccacct gttcgactac tggggccagg gcaccctggt gaccgtgtcc  360
tcc                                                                363

SEQ ID NO: 93          moltype = DNA  length = 36
FEATURE                Location/Qualifiers
source                 1..36
                       mol_type = other DNA
                       organism = synthetic construct
SEQUENCE: 93
gagagcaagt acggaccgcc ctgccccccct tgccct                            36

SEQ ID NO: 94          moltype = DNA  length = 84
FEATURE                Location/Qualifiers
source                 1..84
                       mol_type = other DNA
                       organism = synthetic construct
SEQUENCE: 94
atgttctggg tgctggtggt ggtcggaggc gtgctggcct gctacagcct gctggtcacc  60
gtggccttca tcatcttttg ggtg                                         84

SEQ ID NO: 95          moltype = DNA  length = 126
FEATURE                Location/Qualifiers
source                 1..126
                       mol_type = other DNA
                       organism = synthetic construct
SEQUENCE: 95
aaacggggca gaaagaaact cctgtatata ttcaaacaac catttatgag accagtacaa  60
actactcaag aggaagatgg ctgtagctgc cgatttccag aagaagaaga aggaggatgt  120
gaactg                                                             126

SEQ ID NO: 96          moltype = DNA  length = 336
FEATURE                Location/Qualifiers
```

```
source                  1..336
                        mol_type = other DNA
                        organism = synthetic construct
SEQUENCE: 96
cgggtgaagt tcagcagaag cgccgacgcc cctgcctacc agcagggcca gaatcagctg  60
tacaacgagc tgaacctggg cagaagggaa gagtacgacg tcctggataa gcggagaggc  120
cgggaccctg agatgggcgg caagcctcgg cggaagaacc cccaggaagg cctgtataac  180
gaactgcaga aagacaagat ggccgaggcc tacagcgaga tcggcatgaa gggcgagcgg  240
aggcggggca agggccacga cggcctgtat cagggcctgt ccaccgccac caaggatacc  300
tacgacgccc tgcacatgca ggccctgccc ccaagg                            336

SEQ ID NO: 97           moltype = DNA  length = 2133
FEATURE                 Location/Qualifiers
source                  1..2133
                        mol_type = other DNA
                        organism = synthetic construct
SEQUENCE: 97
atggccttac cagtgaccgc cttgctcctg ccgctggcct tgctgctcca cgccgccagg  60
ccggaaattg tgttgacaca gtctccagcc accctgtctt tgtctccagg ggaaagagcc  120
accctctcct gcagggccag tcagagtgtt agcagctact tagcctggta ccaacagaaa  180
cctggccagg ctcccaggct cctcatctat gatgcatcca acagggccac tggcatccca  240
gccaggttca gtggcagtgg gtctgggaca gacttcactc tcaccatcag cagcctagag  300
cctgaagatt ttgcagttta ttactgtcag cagcgtagca actggccgat caccttcggc  360
caagggacac gactggagat taaaggcagt actagcggtg gtggctccgg gggcggttcc  420
ggtgggggcg gcagcagcga agtgcagctg gtggagtctg gggggaggctt ggtacagcct  480
ggcaggtccc tgagactctc ctgtgcagcc tctggattca cctttaatga ttatgccatg  540
cactgggtcc ggcaagctcc agggaagggc ctggagtggg tctcaactat tagttggaat  600
agtggttcca taggctatgc ggactctgtg aagggccgat tcaccatctc cagagacaac  660
gccaagaagt ccctgtatct gcaaatgaac agtctgagag ctgaggacac ggccttgtat  720
tactgtgcaa aagatataca gtacggcaac tactactacg gtatggacgt ctggggccaa  780
gggaccacgg tcaccgtctc ctcaggaggt ggtggatccg acatccagat gacccagtcc  840
ccctcctccc tgtccgcctc cgtgggcgac cgggtgacca tcacctgccg ggcctcccag  900
ggcatctcca actacctgaa ctggtaccag cagaagcccg gcaaggcccc caagcccctg  960
atctactaca cctccaacct gcagtccggc gtgccctccc ggttctccgg ctccggctcc  1020
ggcaccgact acaccctgac catctcctcc ctgcagcccg aggacttcgc cacctactac  1080
tgcatgggcc agaccatctc ctcctacacc ttcggccagg gcaccaagct ggagatcaag  1140
ggtggcggtg gctcgggcgg tggtgggtcg ggtggcggcg gatctgaggt gcagctggtg  1200
gagtccggcg gcggcctggt gcagcccggc ggctccctgc ggctgtcctg cgccgcctcc  1260
ggcttcacct tctccaactt cgacatggcc tgggtgcggc aggcccccgg caagggcctg  1320
gtgtgggtgt cctccatcac caccggcgcc gaccacgcca tctacgccga ctccgtgaag  1380
ggccggttca ccatctcccg ggacaacgcc aagaacaccc tgtacctgca gatgaactcc  1440
ctgcgggccg aggacaccgc cgtgtactac tgcgtgcggc acggctacta cgacggctac  1500
cacctgttcg actactgggg ccagggcacc ctggtgaccg tgtcctccga gagcaagtac  1560
ggaccgccct gccccccttg ccctatgttc tgggtgctgg tggtggtcgg aggcgtgctg  1620
gcctgctaca gcctgctggt caccgtggcc ttcatcatct tttgggtgaa acggggcaga  1680
aagaaactcc tgtatatatt caaacaacca tttatgagac cagtacaaac tactcaagag  1740
gaagatggct gtagctgccg atttccagaa gaagaagaag gaggatgtga actgcgggtg  1800
aagttcagca gaagcgccga cgcccctgcc taccagcagg gccagaatca gctgtacaac  1860
gagctgaacc tgggcagaag ggaagagtac gacgtcctgg ataagcggag aggccgggac  1920
cctgagatgg gcggcaagcc tcggcggaag aacccccagg aaggcctgta taacgaactg  1980
cagaaagaca agatggccga ggcctacagc gagatcggca tgaagggcga gcggaggcgg  2040
ggcaagggcc acgacggcct gtatcagggc ctgtccaccg ccaccaagga tacctacgac  2100
gccctgcaca tgcaggccct gcccccaagg taa                               2133

SEQ ID NO: 98           moltype = AA  length = 710
FEATURE                 Location/Qualifiers
source                  1..710
                        mol_type = protein
                        organism = synthetic construct
SEQUENCE: 98
MALPVTALLL PLALLLHAAR PEIVLTQSPA TLSLSPGERA TLSCRASQSV SSYLAWYQQK  60
PGQAPRLLIY DASNRATGIP ARFSGSGSGT DFTLTISSLE PEDFAVYYCQ QRSNWPITFG  120
QGTRLEIKGS TSGGGSGGGS GGGGSSEVQL VESGGGLVQP GRSLRLSCAA SGFTFNDYAM  180
HWVRQAPGKG LEWVSTISWN SGSIGYADSV KGRFTISRDN AKKSLYLQMN SLRAEDTALY  240
YCAKDIQYGN YYYGMDVWGQ GTTVTVSSGG GGSDIQMTQS PSSLSASVGD RVTITCRASQ  300
GISNYLNWYQ QKPGKAPKPL IYYTSNLQSG VPSRFSGSGS GTDYTLTISS LQPEDFATYY  360
CMGQTISSYT FGQGTKLEIK GGGGSGGGGS GGGGSEVQLV ESGGGLVQPG GSLRLSCAAS  420
GFTFSNFDMA WVRQAPGKGL VWVSSITTGA DHAIYADSVK GRFTISRDNA KNTLYLQMNS  480
LRAEDTAVYY CVRHGYYDGY HLFDYWGQGT LVTVSSESKY GPPCPPCPMF WVLVVVGGVL  540
ACYSLLVTVA FIIFWVKRGR KKLLYIFKQP FMRPVQTTQE EDGCSCRFPE EEEGGCELRV  600
KFSRSADAPA YQQGQNQLYN ELNLGRREEY DVLDKRRGRD PEMGGKPRRK NPQEGLYNEL  660
QKDKMAEAYS EIGMKGERRR GKGHDGLYQG LSTATKDTYD ALHMQALPPR             710

SEQ ID NO: 99           moltype = DNA  length = 63
FEATURE                 Location/Qualifiers
source                  1..63
                        mol_type = other DNA
                        organism = synthetic construct
SEQUENCE: 99
```

```
atggccttac cagtgaccgc cttgctcctg ccgctggcct tgctgctcca cgccgccagg  60
ccg                                                                63

SEQ ID NO: 100         moltype = DNA  length = 366
FEATURE                Location/Qualifiers
source                 1..366
                       mol_type = other DNA
                       organism = synthetic construct
SEQUENCE: 100
gaagtgcagc tggtggagtc tgggggaggc ttggtacagc ctggcaggtc cctgagactc  60
tcctgtgcag cctctggatt cacctttaat gattatgcca tgcactgggt ccggcaagct  120
ccagggaagg gcctggagtg ggtctcaact attagttgga atagtggttc cataggctat  180
gcggactctg tgaagggccg attcaccatc tccagagaca acgccaagaa gtccctgtat  240
ctgcaaatga acagtctgag agctgaggac acggccttgt attactgtgc aaaagatata  300
cagtacggca actactacta cggtatggac gtctggggcc aagggaccac ggtcaccgtc  360
tcctca                                                             366

SEQ ID NO: 101         moltype = DNA  length = 54
FEATURE                Location/Qualifiers
source                 1..54
                       mol_type = other DNA
                       organism = synthetic construct
SEQUENCE: 101
ggcagtacta gcggtggtgg ctccgggggc ggttccggtg gggcggcag cagc        54

SEQ ID NO: 102         moltype = DNA  length = 321
FEATURE                Location/Qualifiers
source                 1..321
                       mol_type = other DNA
                       organism = synthetic construct
SEQUENCE: 102
gaaattgtgt tgacacagtc tccagccacc ctgtctttgt ctccagggga aagagccacc  60
ctctcctgca gggccagtca gagtgttagc agctacttag cctggtacca acagaaacct  120
ggccaggctc ccaggctcct catctatgat gcatccaaca gggccactgg catcccagcc  180
aggttcagtg gcagtgggtc tgggacagac ttcactctca ccatcagcag cctagagcct  240
gaagattttg cagtttatta ctgtcagcag cgtagcaact ggccgatcac cttcggccaa  300
gggacacgac tggagattaa a                                            321

SEQ ID NO: 103         moltype = DNA  length = 15
FEATURE                Location/Qualifiers
source                 1..15
                       mol_type = other DNA
                       organism = synthetic construct
SEQUENCE: 103
ggaggtggtg gatcc                                                   15

SEQ ID NO: 104         moltype = DNA  length = 321
FEATURE                Location/Qualifiers
source                 1..321
                       mol_type = other DNA
                       organism = synthetic construct
SEQUENCE: 104
gacatccaga tgacccagtc cccctcctcc ctgtccgcct ccgtgggcga ccgggtgacc  60
atcacctgcc gggcctccca gggcatctcc aactacctga actggtacca gcagaagccc  120
ggcaaggccc ccaagcccct gatctactac acctccaacc tgcagtccgg cgtgccctcc  180
cggttctccg gctccggctc cggcaccgac tacaccctga ccatctcctc cctgcagccc  240
gaggacttcg ccacctacta ctgcatgggc cagaccatct cctcctacac cttcggccag  300
ggcaccaagc tggagatcaa g                                            321

SEQ ID NO: 105         moltype = DNA  length = 45
FEATURE                Location/Qualifiers
source                 1..45
                       mol_type = other DNA
                       organism = synthetic construct
SEQUENCE: 105
ggtggcggtg gctcgggcgg tggtgggtcg ggtggcggcg gatct                  45

SEQ ID NO: 106         moltype = DNA  length = 363
FEATURE                Location/Qualifiers
source                 1..363
                       mol_type = other DNA
                       organism = synthetic construct
SEQUENCE: 106
gaggtgcagc tggtggagtc cggcggcggc ctggtgcagc ccggcggctc cctgcggctg  60
tcctgcgccg cctccggctt caccttctcc aacttcgaca tggcctgggt gcggcaggcc  120
cccggcaagg gcctggtgtg ggtgtcctcc atcaccaccg gcgccgacca cgccatctac  180
gccgactccg tgaagggccg gttcaccatc tcccgggaca acgccaagaa caccctgtac  240
ctgcagatga actccctgcg ggccgaggac accgccgtgt actactgcgt gcggcacggc  300
tactacgacg gctaccacct gttcgactac tggggccagg gcaccctggt gaccgtgtcc  360
```

```
tcc                                                                363

SEQ ID NO: 107         moltype = DNA  length = 36
FEATURE                Location/Qualifiers
source                 1..36
                       mol_type = other DNA
                       organism = synthetic construct
SEQUENCE: 107
gagagcaagt acggaccgcc ctgcccccct tgccct                            36

SEQ ID NO: 108         moltype = DNA  length = 84
FEATURE                Location/Qualifiers
source                 1..84
                       mol_type = other DNA
                       organism = synthetic construct
SEQUENCE: 108
atgttctggg tgctggtggt ggtcggaggc gtgctggcct gctacagcct gctggtcacc  60
gtggccttca tcatcttttg ggtg                                         84

SEQ ID NO: 109         moltype = DNA  length = 126
FEATURE                Location/Qualifiers
source                 1..126
                       mol_type = other DNA
                       organism = synthetic construct
SEQUENCE: 109
aaacggggca gaaagaaact cctgtatata ttcaaacaac catttatgag accagtacaa  60
actactcaag aggaagatgg ctgtagctgc cgatttccag aagaagaaga aggaggatgt  120
gaactg                                                             126

SEQ ID NO: 110         moltype = DNA  length = 336
FEATURE                Location/Qualifiers
source                 1..336
                       mol_type = other DNA
                       organism = synthetic construct
SEQUENCE: 110
cgggtgaagt tcagcagaag cgccgacgcc cctgcctacc agcagggcca gaatcagctg  60
tacaacgagc tgaacctggg cagaagggaa gagtacgacg tcctggataa gcggagaggc  120
cgggaccctg agatgggcgg caagcctcgg cggaagaacc cccaggaagg cctgtataac  180
gaactgcaga aagacaagat ggccgaggcc tacagcgaga tcggcatgaa gggcgagcgg  240
aggcggggca agggccacga cggcctgtat cagggcctgt ccaccgccac caaggatacc  300
tacgacgccc tgcacatgca ggccctgccc ccaagg                            336

SEQ ID NO: 111         moltype = DNA  length = 2133
FEATURE                Location/Qualifiers
source                 1..2133
                       mol_type = other DNA
                       organism = synthetic construct
SEQUENCE: 111
atggccttac cagtgaccgc cttgctcctg ccgctggcct tgctgctcca cgccgccagg  60
ccggaagtgc agctggtgga gtctggggga ggcttggtac agcctggcag gtccctgaga  120
ctctcctgtg cagcctctgg attcaccttt aatgattatg ccatgcactg ggtccggcaa  180
gctccaggga agggcctgga gtgggtctca actattagtt ggaatagtgg ttccataggc  240
tatgcggact ctgtgaaggg ccgattcacc atctccagag acaacgccaa gaagtccctg  300
tatctgcaaa tgaacagtct gagagctgag gacacggcct tgtattactg tgcaaaagat  360
atacagtacg gcaactacta ctacggtatg gacgtctggg gccaagggac cacggtcacc  420
gtctcctcag gcagtactag cggtggtggc tccgggggcg gttccggtgg gggcggcagc  480
agcgaaattg tgttgacaca gtctccagcc accctgtctt tgtctccagg ggaaagagcc  540
accctctcct gcagggccag tcagagtgtt agcagctact tagcctggta ccaacagaaa  600
cctggccagg ctcccaggct cctcatctat gatgcatcca acagggccac tggcatccca  660
gccaggttca gtggcagtgg gtctgggaca gacttcactc tcaccatcag cagcctagag  720
cctgaagatt ttgcagttta ttactgtcag cagcgtagca actggccgat caccttcggc  780
caagggacac gactggagat taaaggaggt ggtggatccg acatccagat gacccagtcc  840
ccctcctccc tgtccgcctc cgtgggcgac cgggtgacca tcacctgccg ggcctcccag  900
ggcatctcca actacctgaa ctggtaccag cagaagcccg gcaaggcccc caagcccctg  960
atctactaca cctccaacct gcagtccggc gtgccctccc ggttctccgg ctccggctcc  1020
ggcaccgact acaccctgac catctcctcc ctgcagcccg aggacttcgc cacctactac  1080
tgcatgggcc agaccatctc ctcctacacc ttcggccagg gcaccaagct ggagatcaag  1140
ggtggcggtg gctcgggcgg tggtgggtcg ggtggcggcg gatctgaggt gcagctggtg  1200
gagtccggcg gcggcctggt gcagcccggc ggctccctgc ggctgtcctg cgccgcctcc  1260
ggcttcacct tctccaactt cgacatggcc tgggtgcggc aggcccccgg caagggcctg  1320
gtgtgggtgt cctccatcac caccggcgcc gaccacgcca tctacgccga ctccgtgaag  1380
ggccggttca ccatctcccg ggacaacgcc aagaacaccc tgtacctgca gatgaactcc  1440
ctgcgggccg aggacaccgc cgtgtactac tgcgtgcggc acggctacta cgacggctac  1500
cacctgttcg actactgggg ccagggcacc ctggtgaccg tgtcctccga gagcaagtac  1560
ggaccgccct gccccccttg ccctatgttc tgggtgctgg tggtggtcgg aggcgtgctg  1620
gcctgctaca gcctgctggt caccgtggcc ttcatcatct tttgggtgaa acggggcaga  1680
aagaaactcc tgtatatatt caaacaacca tttatgagac cagtacaaac tactcaagag  1740
gaagatggct gtagctgccg atttccagaa gaagaagaag gaggatgtga actgcgggtg  1800
aagttcagca gaagcgccga cgcccctgcc taccagcagg gccagaatca gctgtacaac  1860
```

```
gagctgaacc tgggcagaag ggaagagtac gacgtcctgg ataagcggag aggccgggac  1920
cctgagatgg gcggcaagcc tcggcggaag aacccccagg aaggcctgta taacgaactg  1980
cagaaagaca agatggccga ggcctacagc gagatcggca tgaagggcga gcggaggcgg  2040
ggcaagggcc acgacggcct gtatcagggc ctgtccaccg ccaccaagga tacctacgac  2100
gccctgcaca tgcaggccct gcccccaagg taa                              2133

SEQ ID NO: 112          moltype = AA  length = 710
FEATURE                 Location/Qualifiers
source                  1..710
                        mol_type = protein
                        organism = synthetic construct
SEQUENCE: 112
MALPVTALLL PLALLLHAAR PEVQLVESGG GLVQPGRSLR LSCAASGFTF NDYAMHWVRQ  60
APGKGLEWVS TISWNSGSIG YADSVKGRFT ISRDNAKKSL YLQMNSLRAE DTALYYCAKD  120
IQYGNYYYGM DVWGQGTTVT VSSGSTSGGG SGGGSGGGGS SEIVLTQSPA TLSLSPGERA  180
TLSCRASQSV SSYLAWYQQK PGQAPRLLIY DASNRATGIP ARFSGSGSGT DFTLTISSLE  240
PEDFAVYYCQ QRSNWPITFG QGTRLEIKGG GGSDIQMTQS PSSLSASVGD RVTITCRASQ  300
GISNYLNWYQ QKPGKAPKPL IYYTSNLQSG VPSRFSGSGS GTDYTLTISS LQPEDFATYY  360
CMGQTISSYT FGQGTKLEIK GGGGSGGGGS GGGGSEVQLV ESGGGLVQPG GSLRLSCAAS  420
GFTFSNFDMA WVRQAPGKGL VWVSSITTGA DHAIYADSVK GRFTISRDNA KNTLYLQMNS  480
LRAEDTAVYY CVRHGYYDGY HLFDYWGQGT LVTVSSESKY GPPCPPCPMF WVLVVVGGVL  540
ACYSLLVTVA FIIFWVKRGR KKLLYIFKQP FMRPVQTTQE EDGCSCRFPE EEEGGCELRV  600
KFSRSADAPA YQQGQNQLYN ELNLGRREEY DVLDKRRGRD PEMGGKPRRK NPQEGLYNEL  660
QKDKMAEAYS EIGMKGERRR GKGHDGLYQG LSTATKDTYD ALHMQALPPR            710

SEQ ID NO: 113          moltype = DNA  length = 63
FEATURE                 Location/Qualifiers
source                  1..63
                        mol_type = other DNA
                        organism = synthetic construct
SEQUENCE: 113
atggccttac cagtgaccgc cttgctcctg ccgctggcct tgctgctcca cgccgccagg  60
ccg                                                               63

SEQ ID NO: 114          moltype = DNA  length = 366
FEATURE                 Location/Qualifiers
source                  1..366
                        mol_type = other DNA
                        organism = synthetic construct
SEQUENCE: 114
gaagtgcagc tggtggagtc tgggggaggc ttggtacagc ctggcaggtc cctgagactc  60
tcctgtgcag cctctggatt cacctttaat gattatgcca tgcactgggt ccggcaagct  120
ccagggaagg gcctggagtg ggtctcaact attagttgga atagtggttc cataggctat  180
gcggactctg tgaagggccg attcaccatc tccagagaca acgccaagaa gtccctgtat  240
ctgcaaatga acagtctgag agctgaggac acggccttgt attactgtgc aaaagatata  300
cagtacggca actactacta cggtatggac gtctggggcc aagggaccac ggtcaccgtc  360
tcctca                                                            366

SEQ ID NO: 115          moltype = DNA  length = 54
FEATURE                 Location/Qualifiers
source                  1..54
                        mol_type = other DNA
                        organism = synthetic construct
SEQUENCE: 115
ggcagtacta gcggtggtgg ctccgggggc ggttccggtg ggggcggcag cagc       54

SEQ ID NO: 116          moltype = DNA  length = 321
FEATURE                 Location/Qualifiers
source                  1..321
                        mol_type = other DNA
                        organism = synthetic construct
SEQUENCE: 116
gaaattgtgt tgacacagtc tccagccacc ctgtctttgt ctccagggga aagagccacc  60
ctctcctgca gggccagtca gagtgttagc agctacttag cctggtacca acagaaacct  120
ggccaggctc ccaggctcct catctatgat gcatccaaca gggccactgg catcccagcc  180
aggttcagtg gcagtgggtc tgggacagac ttcactctca ccatcagcag cctagagcct  240
gaagattttg cagtttatta ctgtcagcag cgtagcaact ggccgatcac cttcggccaa  300
gggacacgac tggagattaa a                                           321

SEQ ID NO: 117          moltype = DNA  length = 15
FEATURE                 Location/Qualifiers
source                  1..15
                        mol_type = other DNA
                        organism = synthetic construct
SEQUENCE: 117
ggaggtggtg gatcc                                                  15

SEQ ID NO: 118          moltype = DNA  length = 363
FEATURE                 Location/Qualifiers
```

```
source                  1..363
                        mol_type = other DNA
                        organism = synthetic construct
SEQUENCE: 118
gaggtgcagc tggtggagtc cggcggcggc ctggtgcagc ccggcggctc cctgcggctg  60
tcctgcgccg cctccggctt caccttctcc aacttcgaca tggcctgggt gcggcaggcc  120
cccggcaagg gcctggtgtg ggtgtcctcc atcaccaccg gcgccgacca cgccatctac  180
gccgactccg tgaagggccg gttcaccatc tcccgggaca acgccaagaa caccctgtac  240
ctgcagatga actccctgcg ggccgaggac accgccgtgt actactgcgt gcggcacggc  300
tactacgacg gctaccacct gttcgactac tggggccagg gcaccctggt gaccgtgtcc  360
tcc                                                                363

SEQ ID NO: 119          moltype = DNA  length = 45
FEATURE                 Location/Qualifiers
source                  1..45
                        mol_type = other DNA
                        organism = synthetic construct
SEQUENCE: 119
ggtggcggtg gctcgggcgg tggtgggtcg ggtggcggcg gatct                 45

SEQ ID NO: 120          moltype = DNA  length = 321
FEATURE                 Location/Qualifiers
source                  1..321
                        mol_type = other DNA
                        organism = synthetic construct
SEQUENCE: 120
gacatccaga tgacccagtc cccctcctcc ctgtccgcct ccgtgggcga ccgggtgacc  60
atcacctgcc gggcctccca gggcatctcc aactacctga actggtacca gcagaagccc  120
ggcaaggccc ccaagcccct gatctactac acctccaacc tgcagtccgg cgtgccctcc  180
cggttctccg gctccggctc cggcaccgac tacaccctga ccatctcctc cctgcagccc  240
gaggacttcg ccacctacta ctgcatgggc cagaccatct cctcctacac cttcggccag  300
ggcaccaagc tggagatcaa g                                            321

SEQ ID NO: 121          moltype = DNA  length = 36
FEATURE                 Location/Qualifiers
source                  1..36
                        mol_type = other DNA
                        organism = synthetic construct
SEQUENCE: 121
gagagcaagt acggaccgcc ctgccccccct tgccct                           36

SEQ ID NO: 122          moltype = DNA  length = 84
FEATURE                 Location/Qualifiers
source                  1..84
                        mol_type = other DNA
                        organism = synthetic construct
SEQUENCE: 122
atgttctggg tgctggtggt ggtcggaggc gtgctggcct gctacagcct gctggtcacc  60
gtggccttca tcatcttttg ggtg                                         84

SEQ ID NO: 123          moltype = DNA  length = 126
FEATURE                 Location/Qualifiers
source                  1..126
                        mol_type = other DNA
                        organism = synthetic construct
SEQUENCE: 123
aaacggggca gaaagaaact cctgtatata ttcaaacaac catttatgag accagtacaa  60
actactcaag aggaagatgg ctgtagctgc cgatttccag aagaagaaga aggaggatgt  120
gaactg                                                             126

SEQ ID NO: 124          moltype = DNA  length = 336
FEATURE                 Location/Qualifiers
source                  1..336
                        mol_type = other DNA
                        organism = synthetic construct
SEQUENCE: 124
cgggtgaagt tcagcagaag cgccgacgcc cctgcctacc agcagggcca gaatcagctg  60
tacaacgagc tgaacctggg cagaagggaa gagtacgacg tcctggataa gcggagaggc  120
cgggaccctg agatgggcgg caagcctcgg cggaagaacc cccaggaagg cctgtataac  180
gaactgcaga aagacaagat ggccgaggcc tacagcgaga tcggcatgaa gggcgagcgg  240
aggcggggca agggccacga cggcctgtat cagggcctgt ccaccgccac caaggatacc  300
tacgacgccc tgcacatgca ggccctgccc ccaagg                            336

SEQ ID NO: 125          moltype = DNA  length = 2133
FEATURE                 Location/Qualifiers
source                  1..2133
                        mol_type = other DNA
                        organism = synthetic construct
SEQUENCE: 125
```

```
atggccttac cagtgaccgc cttgctcctg ccgctggcct tgctgctcca cgccgccagg  60
ccggaagtgc agctggtgga gtctgggggga ggcttggtac agcctggcag gtccctgaga  120
ctctcctgtg cagcctctgg attcaccttt aatgattatg ccatgcactg ggtccggcaa  180
gctccaggga agggcctgga gtgggtctca actattagtt ggaatagtgg ttccataggc  240
tatgcggact ctgtgaaggg ccgattcacc atctccagag acaacgccaa gaagtccctg  300
tatctgcaaa tgaacagtct gagagctgag gacacggcct tgtattactg tgcaaaagat  360
atacagtacg gcaactacta ctacggtatg gacgtctggg gccaagggac cacggtcacc  420
gtctcctcag gcagtactag cggtggtggc tccgggggcg gttccggtgg gggcggcagc  480
agcgaaattg tgttgacaca gtctccagcc accctgtctt tgtctccagg ggaaagagcc  540
accctctcct gcagggccag tcagagtgtt agcagctact tagcctggta ccaacagaaa  600
cctggccagg ctcccaggct cctcatctat gatgcatcca acagggccac tggcatccca  660
gccaggttca gtggcagtgg gtctgggaca gacttcactc tcaccatcag cagcctagag  720
cctgaagatt ttgcagttta ttactgtcag cagcgtagca actggccgat caccttcggc  780
caagggacac gactggagat taaaggaggt ggtggatccg aggtgcagct ggtggagtcc  840
ggcggcggcc tggtgcagcc cggcggctcc ctgcggctgt cctgcgccgc ctccggcttc  900
accttctcca acttcgacat ggcctgggtg cggcaggccc ccggcaaggg cctggtgtgg  960
gtgtcctcca tcaccaccgg cgccgaccac gccatctacg ccgactccgt gaagggccgg  1020
ttcaccatct cccgggacaa cgccaagaac accctgtacc tgcagatgaa ctccctgcgg  1080
gccgaggaca ccgccgtgta ctactgcgtg cggcacggct actacgacgg ctaccacctg  1140
ttcgactact ggggccaggg caccctggtg accgtgtcct ccggtggcgg tggctcgggc  1200
ggtggtgggt cgggtggcgg cggatctgac atccagatga cccagtcccc ctcctccctg  1260
tccgcctccg tgggcgaccg ggtgaccatc acctgccggg cctcccaggg catctccaac  1320
tacctgaact ggtaccagca gaagcccggc aaggccccca agcccctgat ctactacacc  1380
tccaacctgc agtccggcgt gccctcccgg ttctccggct ccggctccgg caccgactac  1440
accctgacca tctcctccct gcagcccgag gacttcgcca cctactactg catgggccag  1500
accatctcct cctacacctt cggccagggc accaagctgg agatcaagga gagcaagtac  1560
ggaccgccct gccccccttg ccctatgttc tgggtgctgg tggtggtcgg aggcgtgctg  1620
gcctgctaca gcctgctggt caccgtggcc ttcatcatct tttgggtgaa acggggcaga  1680
aagaaactcc tgtatatatt caaacaacca tttatgagac cagtacaaac tactcaagag  1740
gaagatggct gtagctgccg atttccagaa gaagaagaag gaggatgtga actgcgggtg  1800
aagttcagca gaagcgccga cgcccctgcc taccagcagg gccagaatca gctgtacaac  1860
gagctgaacc tgggcagaag ggaagagtac gacgtcctgg ataagcggag aggccgggac  1920
cctgagatgg gcggcaagcc tcggcggaag aacccccagg aaggcctgta taacgaactg  1980
cagaaagaca agatggccga ggcctacagc gagatcggca tgaagggcga gcggaggcgg  2040
ggcaagggcc acgacggcct gtatcagggc ctgtccaccg ccaccaagga tacctacgac  2100
gccctgcaca tgcaggccct gcccccaagg taa                              2133
```

```
SEQ ID NO: 126          moltype = AA  length = 710
FEATURE                 Location/Qualifiers
source                  1..710
                        mol_type = protein
                        organism = synthetic construct
SEQUENCE: 126
MALPVTALLL PLALLLHAAR PEVQLVESGG GLVQPGRSLR LSCAASGFTF NDYAMHWVRQ  60
APGKGLEWVS TISWNSGSIG YADSVKGRFT ISRDNAKKSL YLQMNSLRAE DTALYYCAKD  120
IQYGNYYYGM DVWGQGTTVT VSSGSTSGGG SGGGSGGGGS SEIVLTQSPA TLSLSPGERA  180
TLSCRASQSV SSYLAWYQQK PGQAPRLLIY DASNRATGIP ARFSGSGSGT DFTLTISSLE  240
PEDFAVYYCQ QRSNWPITFG QGTRLEIKGG GGSEVQLVES GGGLVQPGGS LRLSCAASGF  300
TFSNFDMAWV RQAPGKGLVW VSSITTGADH AIYADSVKGR FTISRDNAKN TLYLQMNSLR  360
AEDTAVYYCV RHGYYDGYHL FDYWGQGTLV TVSSGGGGSG GGGSGGGGSD IQMTQSPSSL  420
SASVGDRVTI TCRASQGISN YLNWYQQKPG KAPKPLIYYT SNLQSGVPSR FSGSGSGTDY  480
TLTISSLQPE DFATYYCMGQ TISSYTFGQG TKLEIKESKY GPPCPPCPMF WVLVVVGGVL  540
ACYSLLVTVA FIIFWVKRGR KKLLYIFKQP FMRPVQTTQE EDGCSCRFPE EEEGGCELRV  600
KFSRSADAPA YQQGQNQLYN ELNLGRREEY DVLDKRRGRD PEMGGKPRRK NPQEGLYNEL  660
QKDKMAEAYS EIGMKGERRR GKGHDGLYQG LSTATKDTYD ALHMQALPPR             710

SEQ ID NO: 127          moltype = AA  length = 6
FEATURE                 Location/Qualifiers
source                  1..6
                        mol_type = protein
                        organism = synthetic construct
SEQUENCE: 127
NDYAMH                                                             6

SEQ ID NO: 128          moltype = AA  length = 17
FEATURE                 Location/Qualifiers
source                  1..17
                        mol_type = protein
                        organism = synthetic construct
SEQUENCE: 128
TISWNSGSIG YADSVKG                                                 17

SEQ ID NO: 129          moltype = AA  length = 13
FEATURE                 Location/Qualifiers
source                  1..13
                        mol_type = protein
                        organism = synthetic construct
SEQUENCE: 129
DIQYGNYYYG MDV                                                     13
```

```
SEQ ID NO: 130          moltype = AA  length = 11
FEATURE                 Location/Qualifiers
source                  1..11
                        mol_type = protein
                        organism = synthetic construct
SEQUENCE: 130
RASQSVSSYL A                                                            11

SEQ ID NO: 131          moltype = AA  length = 7
FEATURE                 Location/Qualifiers
source                  1..7
                        mol_type = protein
                        organism = synthetic construct
SEQUENCE: 131
DASNRAT                                                                 7

SEQ ID NO: 132          moltype = AA  length = 9
FEATURE                 Location/Qualifiers
source                  1..9
                        mol_type = protein
                        organism = synthetic construct
SEQUENCE: 132
QQRSNWPIT                                                               9

SEQ ID NO: 133          moltype = AA  length = 23
FEATURE                 Location/Qualifiers
source                  1..23
                        mol_type = protein
                        organism = synthetic construct
SEQUENCE: 133
DIQMTQSPSS LSASVGDRVT ITC                                               23

SEQ ID NO: 134          moltype = AA  length = 11
FEATURE                 Location/Qualifiers
source                  1..11
                        mol_type = protein
                        organism = synthetic construct
SEQUENCE: 134
RASQGISNYL N                                                            11

SEQ ID NO: 135          moltype = AA  length = 15
FEATURE                 Location/Qualifiers
source                  1..15
                        mol_type = protein
                        organism = synthetic construct
SEQUENCE: 135
WYQQKPGKAP KPLIY                                                        15

SEQ ID NO: 136          moltype = AA  length = 7
FEATURE                 Location/Qualifiers
source                  1..7
                        mol_type = protein
                        organism = synthetic construct
SEQUENCE: 136
YTSNLQS                                                                 7

SEQ ID NO: 137          moltype = AA  length = 32
FEATURE                 Location/Qualifiers
source                  1..32
                        mol_type = protein
                        organism = synthetic construct
SEQUENCE: 137
GVPSRFSGSG SGTDYTLTIS SLQPEDFATY YC                                     32

SEQ ID NO: 138          moltype = AA  length = 9
FEATURE                 Location/Qualifiers
source                  1..9
                        mol_type = protein
                        organism = synthetic construct
SEQUENCE: 138
MGQTISSYT                                                               9

SEQ ID NO: 139          moltype = AA  length = 10
FEATURE                 Location/Qualifiers
source                  1..10
                        mol_type = protein
                        organism = synthetic construct
SEQUENCE: 139
```

-continued

```
FGQGTKLEIK                                                          10

SEQ ID NO: 140          moltype = AA  length = 30
FEATURE                 Location/Qualifiers
source                  1..30
                        mol_type = protein
                        organism = synthetic construct
SEQUENCE: 140
EVQLVESGGG LVQPGGSLRL SCAASGFTFS                                    30

SEQ ID NO: 141          moltype = AA  length = 5
FEATURE                 Location/Qualifiers
source                  1..5
                        mol_type = protein
                        organism = synthetic construct
SEQUENCE: 141
NFDMA                                                               5

SEQ ID NO: 142          moltype = AA  length = 14
FEATURE                 Location/Qualifiers
source                  1..14
                        mol_type = protein
                        organism = synthetic construct
SEQUENCE: 142
WVRQAPGKGL VWVS                                                     14

SEQ ID NO: 143          moltype = AA  length = 17
FEATURE                 Location/Qualifiers
source                  1..17
                        mol_type = protein
                        organism = synthetic construct
SEQUENCE: 143
SITTGADHAI YADSVKG                                                  17

SEQ ID NO: 144          moltype = AA  length = 32
FEATURE                 Location/Qualifiers
source                  1..32
                        mol_type = protein
                        organism = synthetic construct
SEQUENCE: 144
RFTISRDNAK NTLYLQMNSL RAEDTAVYYC VR                                 32

SEQ ID NO: 145          moltype = AA  length = 12
FEATURE                 Location/Qualifiers
source                  1..12
                        mol_type = protein
                        organism = synthetic construct
SEQUENCE: 145
HGYYDGYHLF DY                                                       12

SEQ ID NO: 146          moltype = AA  length = 11
FEATURE                 Location/Qualifiers
source                  1..11
                        mol_type = protein
                        organism = synthetic construct
SEQUENCE: 146
WGQGTLVTVS S                                                        11
```